United States Patent
Abellera et al.

(10) Patent No.: US 12,065,706 B2
(45) Date of Patent: Aug. 20, 2024

(54) METHODS FOR PRODUCING CORN PLANTS WITH DOWNY MILDEW RESISTANCE AND COMPOSITIONS THEREOF

(71) Applicant: Monsanto Technology LLC, St. Louis, MO (US)

(72) Inventors: Jorgen Costes Abellera, General Santos (PH); Romain Fouquet, Saint-Palais (FR); Vincent Lombard, Ballwin, MO (US); Yule Pan, Chesterfield, MO (US); Jean Jose Somera, General Santos (PH); Xianghai Ye, O'Fallon, MO (US)

(73) Assignee: Monsanto Technology LLC, St. Louis, MO (US)

( * ) Notice: Subject to any disclaimer, the term of this patent is extended or adjusted under 35 U.S.C. 154(b) by 92 days.

(21) Appl. No.: 17/822,615

(22) Filed: Aug. 26, 2022

(65) Prior Publication Data

US 2023/0135707 A1    May 4, 2023

Related U.S. Application Data

(62) Division of application No. 17/082,851, filed on Oct. 28, 2020, now Pat. No. 11,459,622, which is a division of application No. 15/261,286, filed on Sep. 9, 2016, now Pat. No. 10,858,709.

(60) Provisional application No. 62/216,593, filed on Sep. 10, 2015.

(51) Int. Cl.
  *A01H 5/10*     (2018.01)
  *A01H 1/04*     (2006.01)
  *A01H 6/46*     (2018.01)
  *C12Q 1/6895*   (2018.01)

(52) U.S. Cl.
  CPC ........... *C12Q 1/6895* (2013.01); *A01H 1/045* (2021.01); *A01H 5/10* (2013.01); *A01H 6/4684* (2018.05); *C12Q 2600/13* (2013.01); *C12Q 2600/156* (2013.01)

(58) Field of Classification Search
  None
  See application file for complete search history.

(56) References Cited

U.S. PATENT DOCUMENTS

| | | |
|---|---|---|
| 5,210,015 A | 5/1993 | Gelfand |
| 5,217,863 A | 6/1993 | Campbell et al. |
| 5,468,613 A | 11/1995 | Erlich et al. |
| 5,563,055 A | 10/1996 | Townsend et al. |
| 5,595,890 A | 1/1997 | Newton et al. |
| 5,616,464 A | 4/1997 | Albagli et al. |
| 5,762,876 A | 6/1998 | Lincoln et al. |
| 5,800,944 A | 9/1998 | Blonsky et al. |
| 5,876,930 A | 3/1999 | Livak et al. |
| 5,945,283 A | 8/1999 | Kwok et al. |
| 6,004,744 A | 12/1999 | Goelet et al. |
| 6,013,431 A | 1/2000 | Soederlund et al. |
| 6,030,787 A | 2/2000 | Livak et al. |
| 6,090,558 A | 7/2000 | Butler et al. |
| 6,503,710 B2 | 1/2003 | Gut et al. |
| 6,613,509 B1 | 9/2003 | Chen |
| 6,799,122 B2 | 9/2004 | Benson |
| 6,913,879 B1 | 7/2005 | Schena |
| 6,996,476 B2 | 2/2006 | Najarian |
| 7,238,476 B2 | 7/2007 | Mckeown et al. |
| 7,250,252 B2 | 7/2007 | Katz et al. |
| 7,270,981 B2 | 9/2007 | Armes et al. |
| 7,282,355 B2 | 10/2007 | Shi |
| 7,297,485 B2 | 11/2007 | Bornarth et al. |
| 7,312,039 B2 | 12/2007 | Barany et al. |
| 10,858,709 B2 | 12/2020 | Abellera et al. |
| 11,459,622 B2 | 10/2022 | Abellera et al. |
| 2009/0064360 A1 | 3/2009 | Kerns et al. |
| 2010/0037342 A1 | 2/2010 | Johnson |
| 2011/0008793 A1 | 1/2011 | Butruille |

FOREIGN PATENT DOCUMENTS

WO    WO 2009/029771 A2    3/2009

OTHER PUBLICATIONS

Agrama, H. A. et al. (Aug. 1999). "Mapping of QTL for Downy Mildew Resistance in Maize," Theoretical and Applied Genetics, 99(3-4):519-523.
Arus, P. et al. (1993). "Marker-assisted Selection," Plant Breeding 314-331.
Borevitz, J. O. et al. (Mar. 2003). "Large-Scale Identification of Single-Feature Polymorphisms in Complex Genomes," Genome Research 13(3):513-523.
Churchill, G. A. et al. (Nov. 1994). "Empirical Threshold Values for Quantitative Trait Mapping," Genetics, 138(3):963-971.
Cui, X. et al. (Oct. 15, 2005). "Detecting Single-Feature Polymorphisms Using Oligonucleotide Arrays and Robusti," Bioinformatics 21(20):3852-3858.
Dalmacio, S. C. et al. (2000) "Importance of and Growing Concerns for Maize Diseases in the Asian Region," *Proceedings of 7th Asian Regional Maize Workshop*, 267-276.
Flint-Garcia, S. A. et al. (2003). "Structure of Linkage Disequilibrium in Plants, " Annual Review of Plant Biology 54:357-374.
Gaj, T. et al. (Jul. 2013, e-pub. May 9, 2013). "ZFN, TALEN, and CRISPR/Cas-Based Methods for Genome Engineering," Trends Biotechnol. 31(7):397-405.

(Continued)

*Primary Examiner* — Brent T Page
(74) *Attorney, Agent, or Firm* — Morrison & Foerster LLP

(57) ABSTRACT

The present disclosure is in the field of plant breeding and disease resistance. The disclosure provides methods for breeding corn plants having downy mildew (DM) resistance using marker-assisted selection. The disclosure further provides corn germplasm resistant to DM. The disclosure also provides markers associated with DM resistance loci for introgressing these loci into elite germplasm in a breeding program, thus producing novel DM resistant germplasm.

6 Claims, No Drawings

Specification includes a Sequence Listing.

(56) References Cited

OTHER PUBLICATIONS

Ganal, M. W. et al. (2011). "A Large Maize (*Zea mays* L.) SNP Genotyping Array: Development and Germplasm Genotyping, and Genetic Mapping to Compare with the B73 Reference Genome," PLoS One 6(12): e28334:1-15.

GenBank Accession No. AC212457, last updated Feb. 18, 2018, located at < https://www.ncbi.nlm.nih.gov/gene/103629872>, two pages.

Gruber, M. Y. et al. (1993). "Vectors for Plant Transformation," Methods in Plant Molecular Biology and Biotechnology 89-119.

Hedrick, P. W. (Oct. 1987). "Gametic Disequilibrium Measures: Proceed with Caution," Genetics 117(2):331-341.

Horsch, R. B. et al. (Mar. 8, 1985). "A Simple and General Method for Transferring Genes into Plants," Science 227(4691):1229-1231.

International Search Report and Written Opinion issued Feb. 27, 2017, for PCT Application No. PCT/US16/50946, filed Sep. 9, 2016, 14 pages.

Invitation to Pay Additional Fees dated Dec. 8, 2016, for International Application No. PCT/US2016/050946, 3 pages.

Jampatong, C. et al. (2010). "QTL Mapping for Downy Mildew (*Peronosclerospora sorghi*) Resistance in Maize," Proceedings of the 10th Asian Regional Maize Workshop 291-298.

Jampatong, C. et al. (2013). "Mapping of QTL Affecting Resistance Against Sorghum Downy Mildew (*Peronosclerospora sorghi*) in Maize (*Zea Mays* L)," Maydica 58:119-126.

Jannink, J. L. et al. (2002). "Association Mapping in Plant Populations," Quantitative Genetics, Genomics and Plant Breeding 59-68.

Jansen, J. et al. (1994). "Biometrics in Plant Breeding: Applications of Molecular Markers," Proceedings of the Ninth Meeting of the EUCARPIA Section Biometrics in Plant Breeding 19-31.

Jansen, R. C. et al. (Jul. 1995). "Genotype-by-Environment Interaction in Genetic Mapping of Multiple Quantitative Trait Loci," Theoretical and Applied Genetics 91:33-37.

Jansen, R.C. et al. (Apr. 1994). "High Resolution of Quantitative Traits into Multiple Loci Via Interval Mapping," Genetics 136:1447-1455.

Jeffers, D. et al. (2000). "Status in Breeding for Resistance to Maize Diseases at CIMMYT," Proceedings of $7^{th}$ Asian Regional Maize Workshop 257-266.

Jeger, M. J. et al.(1998). "The Epidemiology, Variability and Control of the Downy Mildews of Pearl Millet and Sorghum, with Particular Reference to Africa," Plant Pathology 47:544-569.

Jones, E. S. et al. (Jul. 1, 2002). "Mapping Quantitative Train Loci for Resistance to Downy Mildew in Pearl Millet: Field and Glasshouse Screens Detect the Same QTL," Crop Science 42(4):1316-1323.

Kruglyak, L. et al. (Mar. 1995). "A Nonparametric Approach for Mapping Quantitative Trait Loci," Genetics 139 (3):1421-1428.

Lander, E. S. et al. (Jan. 1989). "Mapping Mendelian Factors Underlying Quantitative Traits Using RFLP Linkage Maps," Genetics 121(1):185-199.

Lincoln, S. E. et al. (1990). "Mapping Genes Controlling Quantitative Traits Using MAPMAKER/QTL Version 1.1: A Tutorial and Reference Manual," Whitehead Institute for Biomedical Research 7-43.

Miki, B. L. et al. (1993). "Procedures for Introducing Foreign DNA into Plants," Methods in Plant Molecular Biology and Biotechnology 67-88.

Mueller, D. et al. (Jul. 2014). "Corn Disease Loss Estimates from the United Sates and Ontario, Canada—2012," Purdue Extension Publication BP-96-12-W: 1-5, 5 pages.

Nair, S. K. et al. (May 2005). "Identification and Validation of QTLs Conferring Resistance to Sorghum Downy Mildew (*Peronosclerospora sorghi*) and Rajasthan Downy Mildew (*P. heteropogoni*) in Maize," Theoretical and Applied Genetics 110(8):1384-1392.

Nelson, J. C. (Jun. 1997). "QGENE: Software for Marker-Based Genomic Analysis and Breeding," Molecular Breeding 3(3):239-245.

Openshaw, S. J. et al. (1994). "Marker-assisted Selection in Backcross Breeding," Analysis of Molecular Marker Data 41-43.

Ragot, M. et al. (1995). "Marker-Assisted Backcrossing: Practical Example," INRA 72:45-56.

Reich, D. E. et al. (May 10, 2001). "Linkage Disequilibrium in the Human Genome," Nature 411:199-204.

Sabry, A. et al. (Jul. 2006). "A Region of Maize Chromosome 2 Affects Response to Downy Mildew Pathogens," Theoretical and Applied Genetics 113(2):321-330.

Service, R.F. (2006). "Gene Sequencing. The Race for the $1000 Genome," Science 311(5767):1544-1546.

Singh, P. et al. (2010). "Graphical Genotyping of Genomic Resources (QTL-NILs and RILs) and Transcriptome Profiling of Maize Genotypes in Response to Sorghum Downy Mildew (*Peronosclerospora sorghi*) in India," Proceedings of the $10^{th}$ Asian Regional Maize Workshop 220-223.

Telle, S. et al. (2011). "Molecular Phylogenetic Analysis of Peronosclerospora (Oomycetes) Reveals Cryptic Species and Genetically Distinct Species Parasitic to Maize," Eur. J Plant Pathol. 130:521-528.

Utz et al. (1994). "Comparison of Different Approaches to Interval Mapping of Quantitative Trait Loci," Proceedings of the Ninth Meeting of the Eucarpia Section Biometrics in Plant Breeding, Wageningen, Netherlands, Jul. 6-8, 195-204.

Zeng, Z. B. (Apr. 1994). "Precision Mapping of Quantitative Trait Loci," Genetics 136(4):1457-1468.

METHODS FOR PRODUCING CORN PLANTS WITH DOWNY MILDEW RESISTANCE AND COMPOSITIONS THEREOF

CROSS-REFERENCE TO RELATED APPLICATIONS

This application is a divisional of U.S. patent application Ser. No. 17/082,851, filed Oct. 28, 2020, now U.S. Pat. No. 11,459,622, which is a divisional of U.S. patent application Ser. No. 15/261,286, filed Sep. 9, 2016, now U.S. Pat. No. 10,858,709, which claims the benefit and priority of U.S. Provisional Application No. 62/216,593, filed on Sep. 10, 2015, all of which are incorporated by reference in their entireties herein.

FIELD

The present disclosure relates to the field of agricultural biotechnology. More specifically, this disclosure relates to methods for producing corn plants or seeds with improved downy mildew resistance.

INCORPORATION OF SEQUENCE LISTING

The content of the electronic sequence listing (file name: 777052056511SubSeqList.xml, date recorded: Sep. 30, 2022, size: 928,795 bytes) is herein incorporated by reference in its entirety.

BACKGROUND

Corn (*Zea mays* L.) is one of the most important commercial crops in the world. Like many commercial crops, corn is subjected to numerous potentially detrimental environmental conditions (e.g., moisture availability, temperature stresses, soil conditions, pests, disease) that can reduce, or entirely eliminate, crop yield. Crop disease alone accounted for the loss of more than 1.3 billion bushels of corn in the United States and Ontario, Canada in 2012. See Mueller, Corn Disease Loss Estimates from the United States and Ontario, Canada—2012. Purdue Extension Publication BP-96-12-W (2014).

Downy mildew (DM) is a crop disease caused by several oomycete pathogens of the genera *Peronosclerospora*, *Sclerophthora*, and *Sclerospora*. Some DM pathogens are known to be host-species specific. For instance, *Sclerospora graminicola* infects *Setaria* sp., but not pearl millet (*Pennisetum glaucum*). Young corn plants infected by DM often die prematurely. Plants that do not die prematurely from DM infection are often stunted in growth. Corn plants infected by DM often exhibit leaf chlorosis, and leaves that are more narrow and erect than is typical. DM infected fields routinely see yield reductions of about 40-60%, but up to 100% yield loss has been documented. Yield loss in surviving plants is primarily due to a failure to form cobs, which hold the seed, and replacement of parts of the pollen-bearing tassel with vegetative tissues (e.g., leaves). See Jeger et al, The epidemiology, variability and control of the downy mildews of pearl millet and sorghum, with particular reference to Africa. *Plant Pathology*, 47:544-569 (1998).

Currently, there are few effective control measures to combat DM infection in corn fields. The fungicide metalaxyl can be used in reducing DM infection for about 42 days, but it can be prohibitively expensive and it is most useful when applied to seed prior to planting. Additionally, at least some oomycetes that cause DM infection show signs of being resistant to fungicides, including metalaxyl. See Dalmacio, Importance of and Growing Concerns for Maize Diseases in the Asian Region. In: Vasal et al. eds. (2000) *Proceedings of 7$^{th}$ Asian Regional Maize Workshop. The 7$^{th}$ Asian Regional Maize Workshop: Strengthening hybrid maize technology and public-private partnership to accelerate maize production in the Asian region*. Los Baños, Philippines, 23-27 Feb. 1998, Laguna, Philippines: PCARRD, p 267-276.

Genetic resistance to DM presents an attractive option for combating DM infection. Studies describing DM resistance quantitative trait loci (QTLs) have been reported, although commercialization of these genetic resistance has been lacking. See Agrama et al., Mapping of QTL for downy mildew resistance in maize. *Theoretical and Applied Genetics*, 99:519-523 (1999); Nair et al., Identification and validation of QTLs conferring resistance to sorghum downy mildew (*Peronosclerospora sorghi*) and Rajasthan downy mildew (*P. heteropogoni*) in maize. *Theoretical and Applied Genetics*, 110:1384-1392 (2005); Sabry et al. A region of maize chromosome 2 affects response to downy mildew pathogens. *Theoretical and Applied Genetics*, 113:321-330 (2006); Singh et al. Graphical Genotyping of Genomic Resources (QTL-NILs and RILs) and Transcriptome Profiling of Maize Genotypes in Response to Sorghum Downy Mildew (*Peronosclerospora sorghi*) in India. In: Zaidi et al. eds. (2010) *Maize for Asia: Emerging Trends and Technologies. Proceedings of The 10$^{th}$ Asian Regional Maize Workshop*. Makassar, Indonesia, 20-23 Oct. 2008, Mexico D.F.: CIMMYT, p 220-223; Jampatong et al., QTL mapping for downy mildew (*Peronosclerospora sorghi*) resistance in maize. In: Zaidi et al. eds. (2010) *Maize for Asia: Emerging Trends and Technologies. Proceedings of The 10$^{th}$ Asian Regional Maize Workshop*. Makassar, Indonesia, 20-23 Oct. 2008, Mexico D.F.: CIMMYT, p 291-298; Jampatong et al., Mapping of QTL affecting resistance against sorghum downy mildew (*Peronosclerospora sorghi*) in maize (*Zea mays* L). Maydica, 58:119-126 (2013).

There is a need in corn breeding to identify corn germplasm that provides resistance to DM infection. There is also a need to develop polymorphic markers for monitoring and introgressing DM resistance alleles, and further develop agronomically elite corn lines comprising DM resistance for enhancing plant productivity.

SUMMARY

The present disclosure identifies genetic loci conferring downy mildew (DM) resistance in corn, and provides molecular markers linked to these resistance loci. This disclosure further provides methods for introgressing resistance alleles of genetic loci conferring DM resistance into plant varieties previously lacking such alleles, thereby providing plants with DM resistance. The genetic loci, markers, and methods provided herein therefore allow for production of new varieties with enhanced DM resistance.

In an aspect, this disclosure provides a method of creating a population of corn plants or seeds, where the method comprises the steps of: (a) genotyping a first population of corn plants or seeds at one or more marker loci associated with and within about 20 cM of a DM resistance QTL selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01; (b) selecting from the first population one or more corn plants or seeds comprising one or more DM resistance alleles of the marker loci; and (c)

producing from the selected one or more corn plants or seeds a second population of corn plants or seeds comprising one or more DM QTLs.

In an aspect, this disclosure provides a method of creating a population of corn plants or seeds comprising at least one allele associated with DM resistance, where the method comprises the steps of: (a) genotyping a first population of corn plants, the population comprising at least one allele associated with DM resistance, wherein the at least one DM resistance allele is associated with a marker selected from the group consisting of SEQ ID NOs: 1-114; (b) selecting from the first population one or more corn plants or seeds comprising the at least one DM resistance allele; and (c) producing from the selected corn plants or seeds a second population of corn plants or seeds comprising the at least one DM resistance allele.

In an aspect, this disclosure provides a method for introgressing a resistance allele of a locus conferring DM resistance, where the method comprises the steps of: (a) crossing a first corn plant with a second corn plant, wherein the first corn plant comprises the resistance allele wherein the at least one DM resistance allele is associated with a marker selected from the group consisting of SEQ ID NOs: 1-114; (b) genotyping a progeny corn plant or seed from the cross using a marker associated with the resistance allele; and (c) selecting a progeny plant or seed comprising the resistance allele.

In an aspect, this disclosure provides a method of introgressing a DM resistance QTL, where the method comprises the steps of: (a) crossing a first corn plant comprising a DM resistance QTL selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01, with a second corn plant of a different genotype to produce one or more progeny plants or seeds; (b) assaying the one or more progeny plants or seeds at a marker locus associated with the DM resistance QTL; and (c) selecting a progeny plant or seed comprising the DM resistance QTL.

In an aspect, this disclosure provides a method for creating a population of corn plants or seeds with DM resistance, where the method comprises the steps of: (a) concurrently detecting in a first population of corn plants or seeds the presence of a combination of two or more, three or more, four or more, five or more, six or more, seven or more, eight or more, nine or more, ten or more, or eleven or more introgressed DM resistance loci selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01; (b) selecting from the first population one or more corn plants or seed comprising the one or more, two or more, three or more, four or more, five or more, six or more, seven or more, eight or more, nine or more, ten or more, or eleven or more introgressed DM resistance QTLs; and (c) producing a population of offspring from the selected one or more corn plants or seeds.

In an aspect, this disclosure provides a method of producing a corn plant with enhanced DM resistance, where the method comprises the steps of: (a) crossing a first corn plant comprising a DM resistance QTL with a second corn plant of a different genotype to produce one or more progeny plants or seeds; and (b) selecting a progeny plant or seed comprising a DM resistance allele of a polymorphic locus linked to the DM resistance QTL, wherein the polymorphic locus is in a chromosomal segment flanked by: any two of marker loci SEQ ID NOs: 1 to 11; any two of marker loci SEQ ID NOs: 12 to 22; any two of marker loci SEQ ID NOs: 23 to 28; any two of marker loci SEQ ID NOs: 29 to 32; any two of marker loci SEQ ID NOs: 33 to 38; any two of marker loci SEQ ID NOs: 39 to 45; any two of marker loci SEQ ID NOs: 46 to 55, and 57; any two of marker loci SEQ ID NOs: 56, and 58 to 62; marker loci SEQ ID NOs: 63 and 64; any two of marker loci SEQ ID NOs: 65 to 90; or any two of marker loci SEQ ID NOs: 91 to 114.

In an aspect, this disclosure provides a method of obtaining a corn plant or seed with enhanced DM resistance, where the method comprises the steps of: (a) detecting in a population of corn plants or seeds a plant or seed comprising a DM resistance allele at a polymorphic locus in a chromosomal segment flanked by: any two of marker loci SEQ ID NOs: 1 to 11; any two of marker loci SEQ ID NOs: 12 to 22; any two of marker loci SEQ ID NOs: 23 to 28; any two of marker loci SEQ ID NOs: 29 to 32; any two of marker loci SEQ ID NOs: 33 to 38; any two of marker loci SEQ ID NOs: 39 to 45; any two of marker loci SEQ ID NOs: 46 to 57; any two of marker loci SEQ ID NOs: 54 to 62; marker loci SEQ ID NOs: 63 and 64; any two of marker loci SEQ ID NOs: 65 to 90; or any two of marker loci SEQ ID NOs: 91 to 114; and (b) selecting the plant or seed from the population based on the presence of the DM resistance allele.

In an aspect, this disclosure provides a method of obtaining a corn plant or seed with enhanced DM resistance, where the method comprises the steps of: (a) detecting in a population of corn plants or seeds a plant or seed comprising a DM resistance allele at a polymorphic locus in a chromosomal segment flanked by: any two of marker loci SEQ ID NOs: 1 to 11; any two of marker loci SEQ ID NOs: 12 to 22; any two of marker loci SEQ ID NOs: 23 to 28; any two of marker loci SEQ ID NOs: 29 to 32; any two of marker loci SEQ ID NOs: 33 to 38; any two of marker loci SEQ ID NOs: 39 to 45; any two of marker loci SEQ ID NOs: 46 to 55, and 57; any two of marker loci SEQ ID NOs: 56, and 58 to 62; marker loci SEQ ID NOs: 63 and 64; any two of marker loci SEQ ID NOs: 65 to 90; or any two of marker loci SEQ ID NOs: 91 to 114; and (b) selecting the plant or seed from the population based on the presence of the DM resistance allele.

In an aspect, this disclosure provides a method of producing a corn plant with enhanced DM resistance, where the method comprises the steps of: (a) crossing a first corn plant comprising a DM resistance haplotype with a second corn plant of a different genotype to produce one or more progeny plants or seeds; and (b) selecting a progeny plant or seed based on the presence of the DM resistance haplotype, wherein the haplotype comprises resistance alleles of two or more polymorphic loci in a chromosomal interval flanked by: any two marker loci selected from the group consisting of SEQ ID NOs: 1 to 11; any two marker loci selected from the group consisting of SEQ ID NOs: 12 to 22; any two marker loci selected from the group consisting of SEQ ID NOs: 23 to 28; any two marker loci selected from the group consisting of SEQ ID NOs: 29 to 32; any two marker loci selected from the group consisting of SEQ ID NOs: 33 to 38; any two marker loci selected from the group consisting of SEQ ID NOs: 39 to 45; any two marker loci selected from the group consisting of SEQ ID NOs: 46 to 57; any two marker loci selected from the group consisting of SEQ ID NOs: 54 to 62; SEQ ID NOs: 63 and 64; any two marker loci selected from the group consisting of SEQ ID NOs: 65 to 90; or any two marker loci selected from the group consisting of SEQ ID NOs: 91 to 114.

In an aspect, this disclosure provides a method of producing a corn plant with enhanced DM resistance, where the method comprises the steps of: (a) crossing a first corn plant comprising a DM resistance haplotype with a second corn plant of a different genotype to produce one or more progeny plants or seeds; and (b) selecting a progeny plant or seed based on the presence of the DM resistance haplotype, wherein the haplotype comprises resistance alleles of two or more polymorphic loci in a chromosomal interval flanked by: any two marker loci selected from the group consisting of SEQ ID NOs: 1 to 11; any two marker loci selected from the group consisting of SEQ ID NOs: 12 to 22; any two marker loci selected from the group consisting of SEQ ID NOs: 23 to 28; any two marker loci selected from the group consisting of SEQ ID NOs: 29 to 32; any two marker loci selected from the group consisting of SEQ ID NOs: 33 to 38; any two marker loci selected from the group consisting of SEQ ID NOs: 39 to 45; any two marker loci selected from the group consisting of SEQ ID NOs: 46 to 55, and 57; any two marker loci selected from the group consisting of SEQ ID NOs: 56, and 58 to 62; SEQ ID NOs: 63 and 64; any two marker loci selected from the group consisting of SEQ ID NOs: 65 to 90; or any two marker loci selected from the group consisting of SEQ ID NOs: 91 to 114.

In an aspect, this disclosure provides a method of obtaining a corn plant or seed with enhanced DM resistance, where the method comprises the steps of: (a) detecting in a population of corn plants or seeds a plant or seed comprising a DM resistance haplotype, wherein the haplotype comprises resistance alleles of two or more polymorphic loci in a chromosomal interval flanked by: any two marker loci selected from the group consisting of SEQ ID NOs: 5 to 8; SEQ ID NOs: 7 and 8; any two marker loci selected from the group consisting of SEQ ID NOs: 12 to 14; any two marker loci selected from the group consisting of SEQ ID NOs: 18 to 20; any two marker loci selected from the group consisting of SEQ ID NOs: 25 to 27; any two marker loci selected from the group consisting of SEQ ID NOs: 29 to 31; any two marker loci selected from the group consisting of SEQ ID NOs: 34 to 36; any two marker loci selected from the group consisting of SEQ ID NOs: 39 to 45; any two marker loci selected from the group consisting of SEQ ID NOs: 49 to 51; SEQ ID NOs: 58 and 59; SEQ ID NOs: 63 and 64; any two marker loci selected from the group consisting of SEQ ID NOs: 77 to 80; or any two marker loci selected from the group consisting of SEQ ID NOs: 99 to 106; and (b) selecting the plant or seed from the population based on the presence of the DM resistance haplotype.

In an aspect, this disclosure provides a method for selecting a corn plant or seed comprising the steps of: (a) genotyping a population of corn plants or seeds at a polymorphic locus associated with a marker selected from the group consisting of SEQ ID NOs: 1-114; and (b) selecting a corn plant or seed comprising a DM resistance allele at the polymorphic locus.

In an aspect, this disclosure provides a method for selecting a corn plant or seed comprising the steps of: (a) isolating nucleic acids from a corn plant or seed; (b) analyzing the nucleic acids to detect a polymorphic marker associated with a DM resistance QTL selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01; and (c) selecting a corn plant or seed comprising the DM resistance QTL.

In an aspect, this disclosure provides a method for selecting a corn plant or seed comprising the steps of: (a) detecting in a population of corn plants or seeds a corn plant or seed comprising a DM resistance allele of a marker locus associated with a DM resistance QTL selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01; and (b) selecting the corn plant or seed comprising the DM resistance allele.

In an aspect, this disclosure provides a method for evaluating a collection of corn germplasm comprising the steps of: (a) obtaining a collection of corn germplasm; (b) isolating nucleic acids from each germplasm; (c) assaying the nucleic acids for one or more markers linked to a DM resistance QTL selected from the group consisting of DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01; and (d) selecting germplasm comprising a DM resistance QTL based on the marker assay.

In an aspect, this disclosure provides a method comprising providing a set of corn seeds comprising one or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01, to a person desirous of planting the set of corn seeds in a field plot.

In an aspect, this disclosure provides a method of growing a population of corn plants in a field plot, wherein the method comprises planting a population of corn seeds comprising one or more, two or more, three or more, four or more, five or more, six or more, seven or more, eight or more, nine or more, ten or more, or eleven or more introgressed DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 in the field plot.

In an aspect, this disclosure provides a corn plant or seed comprising DM resistance and one or more, two or more, three or more, four or more, five or more, six or more, seven or more, eight or more, nine or more, ten or more, or eleven or more introgressed DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01.

BRIEF DESCRIPTION OF THE SEQUENCES

SEQ ID NOs: 1-114 list sequences of exemplary SNP marker loci associated with a DM resistance QTL. Example resistant and susceptible alleles of these marker loci are listed in Table 8. SEQ ID NOs: 115 to 570 list the sequences of exemplary primers and probes which can be used to detect the SNP marker loci of SEQ ID NOs: 1-114.

DETAILED DESCRIPTION

Unless defined otherwise herein, terms are to be understood according to conventional usage by those of ordinary skill in the relevant art. Examples of resources describing many of the terms related to molecular biology used herein can be found in Alberts et al., Molecular Biology of The Cell, 5$^{th}$ Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed., Oxford University Press: New York, 2002; and Lewin, Genes IX, Oxford University Press: New York, 2007. The nomenclature for DNA bases as set forth at 37 C.F.R. § 1.822 is used.

As used herein, terms in the singular and the singular forms "a," "an," and "the," for example, include plural referents unless the content clearly dictates otherwise. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

As used herein, "plant" refers to a whole plant, any part thereof, or a cell or tissue culture derived from a plant, comprising any of: whole plants, plant components or organs (e.g., leaves, stems, roots, etc.), plant tissues, seeds, plant cells, and/or progeny of the same. A progeny plant can be from any filial generation, e.g., $F_1$, $F_2$, $F_3$, $F_4$, $F_5$, $F_6$, $F_7$, etc. A plant cell is a biological cell of a plant, taken from a plant or derived through culture from a cell taken from a plant.

As used herein, a "corn plant" or "maize plant" refers to a plant of species *Zea mays* L and includes all plant varieties that can be bred with corn, including wild maize species.

As used herein, "germplasm" refers to living sources of genetic material. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed, or tissues from which new plants may be grown, or plant parts, such as leaves, stems, pollen, or cells that can be cultured into a whole plant.

As used herein, the phrase "associated with" or "linked to" refers to a recognizable and/or assayable relationship between two entities. For example, the phrase "associated with DM resistance" refers to a trait, locus, gene, allele, marker, phenotype, etc., or the expression thereof, the presence or absence of which can influence an extent, degree, and/or rate at which a plant or a part of interest thereof that has a DM resistance trait. As such, a marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with a resistance allele" refers to a marker whose presence or absence can be used to predict whether and to what extent a plant will display a DM resistance phenotype.

As used herein, a centimorgan ("cM") is a unit of measure of recombination frequency and genetic distance between two loci. One cM is equal to a 1% chance that a marker at one genetic locus will be separated from a marker at, a second locus due to crossing over in a single generation.

As used herein, "closely linked" means that the marker or locus is within about 20 cM, 15 cM, 10 cM, 5 cM, 4 cM, 3 cM, 2 cM, 1 cM, 0.5 cM or less than 0.5 cM of another marker or locus. For example, 20 cM means that recombination occurs between the marker and the locus with a frequency of equal to or less than about 20%.

As used herein, "locus" is a chromosome region or chromosomal region where a polymorphic nucleic acid, trait determinant, gene, or marker is located. A locus may represent a single nucleotide, a few nucleotides or a large number of nucleotides in a genomic region. The loci of this disclosure comprise one or more polymorphisms in a population; e.g., alternative alleles are present in some individuals. A "gene locus" is a specific chromosome location in the genome of a species where a specific gene can be found.

As used herein, "allele" refers to an alternative nucleic acid sequence at a particular locus. The length of an allele can be as small as one nucleotide base. For example, a first allele can occur on one chromosome, while a second allele occurs on a second homologous chromosome, e.g., as occurs for different chromosomes of a heterozygous individual, or between different homozygous or heterozygous individuals in a population.

As used herein, "crossed" or "cross" means to produce progeny via fertilization (e.g. cells, seeds or plants) and includes crosses between plants (sexual) and self-fertilization (selfing).

As used herein, "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot et al., Marker-assisted Backcrossing: A Practical Example, in *Techniques Et Utilisations Des Marqueurs Moleculaires Les Colloques,* 72:45-56 (1995); and Openshaw et al., Marker-assisted Selection in Backcross Breeding, in Proceedings Of The Symposium "Analysis Of Molecular Marker Data," pp. 41-43 (1994). The initial cross gives rise to the $F_1$ generation. The term "BC1" refers to the second use of the recurrent parent, "BC2" refers to the third use of the recurrent parent, and so on. In an aspect, a backcross is performed repeatedly, with a progeny individual of each successive backcross generation being itself backcrossed to the same parental genotype.

As used herein, "agronomically elite background" means any line that has resulted from breeding and selection for superior agronomic performance. Similarly, an "elite germplasm" or elite strain of germplasm is an agronomically superior germplasm. Numerous elite lines are available and known to those of skill in the art of corn breeding.

As used herein, "genotype" is the genetic constitution of an individual (or group of individuals) at one or more genetic loci, as contrasted with the observable trait (phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome. The term genotype can also refer to determining the genetic constitution of an individual (or group of individuals) at one or more genetic loci.

As used herein, a "haplotype" is the genotype of an individual at a plurality of genetic loci. Typically, the genetic loci described by a haplotype are physically and genetically linked, e.g., in the same chromosome interval. A haplotype can also refer to a combination of SNP alleles located within a single gene.

As used herein, "marker assay" means a method for detecting a polymorphism at a particular locus using a particular method, e.g. measurement of at least one phenotype (such as seed color, flower color, or other visually detectable traits), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc.

As used herein, "marker assisted selection" (MAS) is a process by which phenotypes are selected based on marker genotypes. "Marker assisted selection breeding" refers to the process of selecting a desired trait or traits in a plant or plants by detecting one or more nucleic acids from the plant, where the nucleic acid is linked to the desired trait, and then selecting the plant or germplasm possessing those one or more nucleic acids.

As used herein, "polymorphism" means the presence of one or more variations in a population. A polymorphism may manifest as a variation in the nucleotide sequence of a nucleic acid or as a variation in the amino acid sequence of a protein. Polymorphisms include the presence of one or more variations of a nucleic acid sequence or nucleic acid feature at one or more loci in a population of one or more individuals. The variation may comprise but is not limited to one or more nucleotide base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs), a restriction fragment length polymorphism, and a tag SNP. A genetic marker, a gene, a DNA-derived sequence, a RNA-derived sequence, a promoter, a 5' untranslated region of a gene, a 3' untranslated region of a gene, microRNA, siRNA, a tolerance locus, a satellite marker, a transgene, mRNA, ds mRNA, a transcriptional profile, and a methylation pattern may also comprise polymorphisms. In addition, the presence, absence, or variation in copy number of the preceding may comprise polymorphisms.

As used herein, "SNP" or "single nucleotide polymorphism" means a sequence variation that occurs when a single nucleotide (A, T, C, or G) in the genome sequence is altered or variable. "SNP markers" exist when SNPs are mapped to sites on the genome.

As used herein, "marker," or "molecular marker," or "marker locus" is a term used to denote a nucleic acid or amino acid sequence that is sufficiently unique to characterize a specific locus on the genome. Any detectable polymorphic trait can be used as a marker so long as it is inherited differentially and exhibits linkage disequilibrium with a phenotypic trait of interest. A number of markers and integrated genetic maps have been developed for corn, e.g., the UMC 98 map, the Nested Association Mapping (NAM) map, the Intermated B73/Mol7 (IBM2) Neighbors 2008 genetic map, and the LHRF Gnp2004 map. See maizegdb.org/data_Center/map for more. All markers are used to define a specific locus in corn genomes. Large numbers of these markers have been mapped. See maizegdb.org/data_center/marker. Each marker is therefore an indicator of a specific segment of DNA, having a unique nucleotide sequence. The map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage and/or under environmental conditions where the trait can be expressed. Molecular markers have been widely used to determine genetic composition in corn. In an aspect, markers used herein exhibit LOD scores of 2 or greater, 3 or greater, 4 or greater, 5 or greater, 6 or greater, 7 or greater, 8 or greater, or 9 or greater with an associated trait of interest (e.g., DM resistance), measuring using a method known in the art such as Qgene Version 2.23 (1996) and default parameters.

As used herein, "linkage disequilibrium" (LD) refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Linked loci co-segregate more than 50% of the time, e.g., from about 51% to about 100% of the time. Linkage disequilibrium can be measured using any one of the methods provided in Hedrick, Gametic disequilibrium measures: proceed with caution. *Genetics*, 117:331-41(1987). The term "physically linked" is sometimes used to indicate that two loci, e.g., two marker loci, are physically present on the same chromosome. Advantageously, the two linked loci are located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time.

As used herein, a "genetic map" is the relationship of genetic linkage among loci on one or more chromosomes (or linkage groups) within a given species, generally depicted in a diagrammatic or tabular form. "Genetic mapping" is the process of defining the linkage relationships of loci through the use of genetic markers, populations segregating for the markers, and standard genetic principles of recombination frequency. A "genetic map location" is a location on a genetic map relative to surrounding genetic markers on the same linkage group where a specified marker can be found within a given species. In contrast, a "physical map" of the genome refers to absolute distances (for example, measured in base pairs or isolated and overlapping contiguous genetic fragments, e.g., contigs). In general, the closer two markers or genomic loci are on the genetic map, the closer they lie to one another on the physical map. A physical map of the genome does not take into account the genetic behavior (e.g., recombination frequencies) between different points on the physical map. A lack of precise proportionality between genetic distances and physical distances can exist due to the fact that the likelihood of genetic recombination is not uniform throughout the genome; some chromosome regions are cross-over "hot spots," while other regions demonstrate only rare recombination events, if any. Genetic mapping variability can also be observed between different populations of the same crop species. In spite of this variability in the genetic map that may occur between populations, genetic map and marker information derived from one population generally remains useful across multiple populations in identification of plants with desired traits, counter-selection of plants with undesirable traits and in MAS breeding. As one of skill in the art will recognize, recombination frequencies (and as a result, genetic map positions) in any particular population are not static. The genetic distances separating two markers (or a marker and a QTL) can vary depending on how the map positions are determined. For example, variables such as the parental mapping populations used, the software used in the marker mapping or QTL mapping, and the parameters input by the user of the mapping software can contribute to the QTL marker genetic map relationships. However, it is not intended that this disclosure be limited to any particular mapping populations, use of any particular software, or any particular set of software parameters to determine linkage of a particular marker or haplotypes with a desired phenotype. It is well within the ability of one of ordinary skill in the art to extrapolate the novel features described herein to any gene pool or population of interest, and using any particular software and software parameters. Indeed, observations regarding genetic markers and haplotypes in populations in addition to those described herein are readily made using the teaching of the present disclosure.

As used herein, "selecting" or "selection" in the context of marker-assisted selection or breeding refer to the act of picking or choosing desired individuals, normally from a population, based on certain pre-determined criteria.

As used herein, "primer" refers to an oligonucleotide (synthetic or occurring naturally), which is capable of acting as a point of initiation of nucleic acid synthesis or replication along a complementary strand when placed under conditions in which synthesis of a complementary strand is catalyzed by a polymerase. Typically, primers are about 10 to 30 nucleotides in length, but longer or shorter sequences can be employed. Primers may be provided in double-stranded form, though the single-stranded form is more typically used. A primer can further contain a detectable label, for example a 5' end label.

As used herein, "probe" refers to an oligonucleotide (synthetic or occurring naturally) that is complementary (though not necessarily fully complementary) to a polynucleotide of interest and forms a duplex structure by hybridization with at least one strand of the polynucleotide of interest. Typically, probes are oligonucleotides from 10 to 50 nucleotides in length, but longer or shorter sequences can be employed. A probe can further contain a detectable label.

As used herein, a "population of plants," "population of seeds", "plant population", or "seed population" means a set comprising any number, including one, of individuals, objects, or data from which samples are taken for evaluation. Most commonly, the terms relate to a breeding population of plants from which members are selected and crossed to produce progeny in a breeding program. A population of plants can include the progeny of a single breeding cross or a plurality of breeding crosses, and can be either actual plants or plant derived material, or in silico representations of the plants or seeds. The population members need not be identical to the population members selected for use in subsequent cycles of analyses or those ultimately selected to obtain final progeny plants or seeds. Often, a plant or seed population is derived from a single biparental cross, but may also derive from two or more crosses between the same or different parents. Although a population of plants or seeds may comprise any number of individuals, those of skill in the art will recognize that plant breeders commonly use population sizes ranging from one or two hundred individuals to several thousand, and that the highest performing 5-20% of a population is what is commonly selected to be used in subsequent crosses in order to improve the performance of subsequent generations of the population.

As used herein, "cultivar" and "variety" are used synonymously and mean a group of plants within a species (e.g., Z. mays L.) that share certain genetic traits that separate them from other possible varieties within that species. Corn cultivars can be inbreds or hybrids, though commercial corn cultivars are mostly hybrids to take advantage of hybrid vigor. Individuals within a corn hybrid cultivar are homogeneous, nearly genetically identical, with most loci in the heterozygous state.

As used herein, the term "inbred" means a line that has been bred for genetic homogeneity.

As used herein, the term "hybrid" means a progeny of mating between at least two genetically dissimilar parents. Without limitation, examples of mating schemes include single crosses, modified single cross, double modified single cross, three-way cross, modified three-way cross, and double cross wherein at least one parent in a modified cross is the progeny of a cross between sister lines.

As used herein, "introgression" refers to the transmission of a desired allele of a genetic locus from one genetic background to another.

As used herein, the term "chromosome interval" or "chromosomal interval" designates a contiguous linear span of genomic DNA that resides on a single chromosome.

As used herein, "flanked by," when used to describe a chromosomal interval, refers to two loci physically surrounding the chromosomal interval, with one locus on each side of the chromosomal interval. As referenced herein, a chromosomal interval flanked by two marker loci includes the two marker loci.

As used herein, a "resistant allele" is an allele at a particular locus that confers, or contributes to, DM resistance, or alternatively, is an allele that allows the identification of plants that comprise DM resistance. A resistant allele of a marker is a marker allele that segregates with DM resistance, or alternatively, segregates with DM susceptibility, therefore providing the benefit of identifying plants having DM susceptibility. A resistant allelic form of a chromosome interval is a chromosome interval that includes a nucleotide sequence that contributes to DM resistance at one or more genetic loci physically located in the chromosome interval.

As used herein, "genetic element" or "gene" refers to a heritable sequence of DNA, e.g., a genomic sequence, with functional significance. The term "gene" can also be used to refer to, e.g., a cDNA and/or an mRNA encoded by a genomic sequence, as well as to that genomic sequence.

As used herein, the terms "phenotype," or "phenotypic trait," or "trait" refers to one or more detectable characteristics of a cell or organism which can be influenced by genotype. The phenotype can be observable to the naked eye, or by any other means of evaluation known in the art, e.g., microscopy, biochemical analysis, genomic analysis, an assay for a particular disease tolerance, etc. In some cases, a phenotype is directly controlled by a single gene or genetic locus, e.g., a "single gene trait." In other cases, a phenotype is the result of several genes.

As used herein, "resistance" and "enhanced resistance" are used interchangeably herein and refer to any type of increase in resistance, or any type of decrease in susceptibility. A "resistant plant" or "resistant plant variety" need not possess absolute or complete resistance. Instead, a "resistant plant," "resistant plant variety," or a plant or plant variety with "enhanced resistance" will have a level of resistance which is higher than that of a comparable susceptible plant or variety. The level of downy mildew resistance can be determined based on disease ratings as determined in Example 1. Specifically, resistance to DM infection of corn plants is scored using a DM resistance scale, wherein DM resistance is measured by counting the percentage of plants infected by DM in a field plot 40 days after planting. A DM resistance scale comprises ratings of highly resistant (e.g., fewer than 5% of plants infected); moderately resistant (e.g., 5 to 15% of plants infected); intermediate (e.g., 15-35% of plants infected); moderately susceptible (e.g., 35-45% of plants infected); and highly susceptible (e.g., greater than 45% of plants infected).

As used herein, "quantitative trait locus" (QTL) or "quantitative trait loci" (QTLs) refer to a genetic domain that effects a phenotype that can be described in quantitative terms and can be assigned a "phenotypic value" which corresponds to a quantitative value for the phenotypic trait.

As used herein, "adjacent", when used to describe a nucleic acid molecule that hybridizes to DNA containing a polymorphism, refers to a nucleic acid that hybridizes to DNA sequences that directly abut the polymorphic nucleotide base position. For example, a nucleic acid molecule that can be used in a single base extension assay is "adjacent" to the polymorphism.

As used herein, "downy mildew" refers to a plant disease caused by oomycete species in the genera *Peronosclerospora, Sclerophthora,* and *Sclerospora.*

As used herein, a "low downy mildew stress condition" refers to a condition where very few to no DM susceptible corn plants in a field plot (e.g., fewer than 10%) exhibit signs of DM infection. Signs of DM infection can include: premature death, stunted growth, chlorotic leaves, narrow leaves, erect leaves, shredded leaves, failed cob formation, and vegetative tissue within the tassel.

As used herein, a "high downy mildew stress condition" refers to a condition where a plurality of DM susceptible corn plants in a field plot (e.g., more than 30%) exhibit signs of DM infection.

As used herein, "field plot" refers to a location that is suitable for growing corn. The location may be indoors (e.g., a greenhouse or growth chamber) or outdoors; irrigated or non-irrigated; in the ground or in a container that holds soil.

As used herein, a "planting season" is the length of time, typically about 90-120 days, in which corn may be grown from seed to maturity. One skilled in the art would recognize that a "planting season" could be significantly shorter or longer than about 90-120 days depending on the corn variety being grown and environmental conditions.

As used herein, "staggered planting" refers to planting a crop in a single field plot multiple times during the same planting season, with each planting separated by at least 1 day. For instance, planting corn seeds in a field plot on day 1 and again on day 15 would comprise a staggered planting.

As used herein, "transgenic" means a plant or seed whose genome has been altered by the stable integration of recombinant DNA. A transgenic line includes a plant regenerated from an originally-transformed plant cell and progeny transgenic plants from later generations or crosses of a transformed plant.

As used herein, "haploid" means a line that has had its normal chromosome complement reduced by half, typically by pollinating an ear with pollen from a haploid inducing line. In corn, haploid refers to an individual plant or seed that has a haploid chromosome complement where n=10, instead of the normal diploid chromosome complement where 2n=20. A "doubled haploid" refers to a haploid line (n=10) that has been induced, typically via chemical means, to double its chromosome complement and return to a diploid state (2n=20) that is homozygous at all loci within the genome.

As used herein, "yield penalty" refers to a reduction of seed yield in a line correlated with or caused by the presence of a DM resistance allele or DM resistance QTL as compared to a line that does not contain that DM resistance allele or DM resistance QTL.

As used herein, "seed yield" can refer to a measure of crop production such as test weight, seed number per plant, seed weight, seed number per unit area (i.e. seeds, or weight of seeds, per acre), bushels per acre, tons per acre, kilograms per hectare, or quintals per hectare.

Downy mildew is a plant disease caused by oomycete species of several genera, such as *Peronosclerospora, Sclerophthora,* and *Sclerospora.* Due to poor understanding of downy mildew systematics, it is not always possible to identify members of *Peronosclerospora, Sclerospora,* and *Sclerophthora* to species. However, species known to cause downy mildew include, but are not limited to: *P. eriochloae, P. graminicola, P. heteropogoni, P. maydis, P. miscanthi, P. philippinensis, P. sacchari, P. sorghi, P. spontanea, P. zeae, Sclerophthora macrospora, Scleropthora rayssiae* var. *zeae,* and *Sclerospora graminicola.* Downy mildew afflicts corn worldwide, with particularly devastating effects in Africa and Asia. About 29-31% of total areas growing tropical lowland, subtropical, mid-altitude, transition zone, and highland corn report economic losses due to downy mildew. See Jeffers et al. Status in Breeding for Resistance to Maize Diseases at CIMMYT. In: In: Vasal et al. eds. (2000) *Proceedings of 7th Asian Regional Maize Workshop. The 7th Asian Regional Maize Workshop: Strengthening hybrid maize technology and public-private partnership to accelerate maize production in the Asian region.* Los Baños, Philippines, 23-27 Feb. 1998, Laguna, Philippines: PCARRD, p 257-266.

Corn plants are at risk of contracting downy mildew infection as they emerge from the ground as seedlings; downy mildew oospores can persist in soil for at least up to 10 years. If corn plants are infected at the seedling stage they often die prematurely. Older corn plants may be infected by wind-blown downy mildew spores. Typical symptoms of corn afflicted by downy mildew include stunted growth, chlorotic leaves, narrow leaves, and erect leaves. More rarely, infected corn leaves exhibit a shredded phenotype. Corn seed yields are reduced by downy mildew due to a failure of cob formation and a replacement of tassels by vegetative structures such as leaves. See Jeger et al, The epidemiology, variability and control of the downy mildews of pearl millet and sorghum, with particular reference to Africa. *Plant Pathology,* 47:544-569 (1998). Varieties of corn that are highly susceptible to downy mildew can experience up to 50-100% yield loss, although up to 40-60% yield loss is more typical. When staggered planting is used, late-plantings suffer the greatest yield losses.

Several systemic fungicides, including metalaxyl, fosetyl-Al, furalaxyl, Patafol, and benalaxyl are used to combat downy mildew. See Dalmacio, Importance of and Growing Concerns for Maize Diseases in the Asian Region. In: Vasal et al. eds. (2000) *Proceedings of 7th Asian Regional Maize Workshop. The 7th Asian Regional Maize Workshop: Strengthening hybrid maize technology and public-private*

*partnership to accelerate maize production in the Asian region.* Los Baños, Philippines, 23-27 Feb. 1998, Laguna, Philippines: PCARRD, p 267-276. However, reliance on chemical agents to reduce DM incidence is unreliable, because DM may develop resistance to the chemical agents. Indeed, incidences of DM occurring in fields planted with metalaxyl-treated seeds and causing yield loss have been reported. Id. A corn plant or seed disclosed herein possesses one or more DM resistance QTLs and/or DM resistance alleles that confer enhanced resistance to downy mildew compared to a corn plant or seed that lacks the one or more DM resistance QTLs or DM resistance alleles. Further, a corn plant or seed disclosed herein provides increased yield in high DM pressure conditions, while suffering no yield penalties in low DM pressure conditions.

In an aspect, a corn plant or seed provided in this disclosure is *Zea mays* L. In another aspect, a corn plant or seed provided in this disclosure is *Zea mays* ssp. mays. In yet another aspect, a corn plant or seed provided herein is a domesticated line or variety. In an aspect, a corn plant or seed provided herein is not *Zea diploperennis*. In an aspect, a corn plant or seed provided herein is not *Zea perennis*. In an aspect, a corn plant or seed provided herein is not *Zea luxurians*. In an aspect, a corn plant or seed provided herein is not *Zea nicaraguensis*. In an aspect, a corn plant or seed provided herein is not *Zea mays* ssp. *huehuetenangensis*. In an aspect, a corn plant or seed provided herein is not *Zea mays* ssp. *mexicana*. In an aspect, a corn plant or seed provided herein is not *Zea mays* ssp. *parviglumis*.

In an aspect, this disclosure provides quantitative trait loci (QTLs) that exhibit significant co-segregation with DM resistance. The QTLs of this disclosure can be tracked during plant breeding or introgressed into a desired genetic background in order to provide plants exhibiting enhanced DM resistance and one or more other beneficial traits. In an aspect, this disclosure identifies QTL intervals that are associated with DM resistance in corn varieties CV357626 and CV368354.

In an aspect, this disclosure provides molecular markers linked to the QTLs disclosed herein and methods of using these markers for detection of and selection for DM resistance. An aspect of this disclosure includes specific markers and their resistance alleles, chromosome intervals comprising the markers, and methods of detecting markers genetically linked to DM resistance to identify plant lines with enhanced DM resistance. For example, one aspect of this disclosure provides a chromosome interval associated with DM resistance which is flanked by any two of marker loci SEQ ID NOs: 5 to 8. Another aspect of this disclosure provides a chromosome interval associated with DM resistance, where the interval is flanked by marker loci SEQ ID NOs: 7 and 8. Another aspect of this disclosure provides a chromosome interval associated with DM resistance which is flanked by any two of marker loci SEQ ID NOs: 12 to 14. Another aspect of this disclosure provides a chromosome interval associated with DM resistance which is flanked by any two of marker loci SEQ ID NOs: 18 to 20. Another aspect of this disclosure provides a chromosome interval associated with DM resistance which is flanked by any two of marker loci SEQ ID NOs: 25 to 27. Another aspect of this disclosure provides a chromosome interval associated with DM resistance which is flanked by any two of marker loci SEQ ID NOs: 29 to 31. Another aspect of this disclosure provides a chromosome interval associated with DM resistance which is flanked by any two of marker loci SEQ ID NOs: 34 to 36. Another aspect of this disclosure provides a chromosome interval associated with DM resistance which is flanked by any two of marker loci SEQ ID NOs: 39 to 45. Another aspect of this disclosure provides a chromosome interval associated with DM resistance which is flanked by any two of marker loci SEQ ID NOs: 49 to 51. Another aspect of this disclosure provides a chromosome interval associated with DM resistance, where the interval is flanked by marker loci SEQ ID NOs: 58 and 59. Another aspect of this disclosure provides a chromosome interval associated with DM resistance, where the interval is flanked by marker loci SEQ ID NOs: 63 and 64. Another aspect of this disclosure provides a chromosome interval associated with DM resistance which is flanked by any two of marker loci SEQ ID NOs: 77 to 80. Another aspect of this disclosure provides a chromosome interval associated with DM resistance which is flanked by any two of marker loci SEQ ID NOs: 99 to 106. Also provided herein are markers, e.g., SEQ ID NOs: 1-114, that are useful for tracking DM resistant alleles and can be used in marker assisted selection (MAS) breeding programs to produce plants with enhanced DM resistance.

This disclosure further provides methods of using the markers identified herein to introgress loci associated with DM resistance into DM susceptible plants. Thus, one skilled in the art can use this disclosure to create a novel corn plant or seed with DM resistance by crossing a donor line comprising a QTL disclosed herein with any desired recipient line, with or without MAS.

In another aspect, this disclosure further provides methods for introgressing multiple DM resistance QTLs identified herein to generate an enhanced DM resistant population of corn plants or seeds.

In an aspect, this disclosure provides a method of creating a population of corn plants or seeds, where the method comprises the steps of: (a) genotyping a first population of corn plants or seeds at one or more marker loci associated with one or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01; (b) selecting from the first population one or more corn plants or seeds comprising one or more DM resistance alleles of the one or more marker loci; and (c) producing from the selected one or more corn plants or seeds a second population of corn plants or seeds comprising one or more DM QTLs.

In an aspect, this disclosure provides a method of creating a population of corn plants or seeds, which method comprising the steps of: (a) genotyping a first population of corn plants, the population comprising at least one allele associated with DM resistance, wherein the DM resistance allele is associated with a marker selected from the group consisting of SEQ ID NOs: 1-114; (b) selecting from the first population one or more corn plants or seeds comprising the DM resistance allele; and (c) producing from the selected corn plants or seeds a second population of corn plants or seeds comprising the at least one DM resistance allele.

In an aspect, this disclosure provides a method for introgressing a resistance allele of a locus conferring DM resistance, which method comprising the steps of: (a) crossing a first corn plant with a second corn plant, wherein the first corn plant comprises the resistance allele, wherein the DM resistance allele is associated with a marker selected from the group consisting of SEQ ID NOs: 1-114; (b) genotyping a progeny corn plant or seed from the cross using a marker associated with the resistance allele; and (c) selecting a progeny plant or seed comprising the resistance allele.

In an aspect, this disclosure provides a method for introgressing a DM resistance QTL, which method comprising the steps of: (a) crossing a first corn plant comprising a DM resistance QTL selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01, with a second corn plant of a different genotype to produce one or more progeny plants or seeds; (b) assaying the one or more progeny plants or seeds at a marker locus associated with the DM resistance QTL; and (c) selecting a progeny plant or seed comprising the DM resistance QTL.

In an aspect, this disclosure provides a method for creating a population of corn plants or seeds with DM resistance, which method comprising the steps of: (a) concurrently detecting in a first population of corn plants or seeds the presence of a combination of two or more, three or more, four or more, five or more, six or more, seven or more, eight or more, nine or more, ten or more, or eleven or more introgressed DM resistance loci selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01; (b) selecting from the first population one or more corn plants or seed comprising the one or more, two or more, three or more, four or more, five or more, six or more, seven or more, eight or more, nine or more, ten or more, or eleven or more introgressed DM resistance QTLs; and (c) producing a population of offspring from the selected one or more corn plants or seeds. In an aspect, a method comprises concurrent detection of one or more molecular markers located in at least one chromosome interval flanked by any two of marker loci SEQ ID NOs: 1 to 11, any two of marker loci SEQ ID NOs: 12 to 22, any two of marker loci SEQ ID NOs: 23 to 28, any two of marker loci SEQ ID NOs: 29 to 32, any two of marker loci SEQ ID NOs: 33 to 38, any two of marker loci SEQ ID NOs: 39 to 45, any two of marker loci SEQ ID NOs: 46 to 57, any two of marker loci SEQ ID NOs: 54 to 62, any two of marker loci SEQ ID NOs: 65 to 90, or any two of marker loci SEQ ID NOs: 91-114. In another aspect, a method comprises concurrent detection of one or more molecular markers located in at least one chromosome interval flanked by any two of marker loci SEQ ID NOs: 5 to 8, marker loci SEQ ID NOs: 7 and 8, any two of marker loci SEQ ID NOs: 12 to 14, any two of marker loci SEQ ID NOs: 18 to 20, any two of marker loci SEQ ID NOs: 25 to 27, any two of marker loci SEQ ID NOs: 29 to 31, any two of marker loci SEQ ID NOs: 34 to 36, any two of marker loci SEQ ID NOs: 39 to 45, any two of marker loci SEQ ID NOs: 49 to 51, marker loci SEQ ID NOs: 58 and 59, marker loci SEQ ID NOs: 63 and 64, any two of marker loci SEQ ID NOs: 77 to 80, or any two of marker loci SEQ ID NOs: 99 to 106.

In an aspect, a method comprises concurrently detecting DM resistance QTLs DM_5.01, DM_6.02, and DM_7.01. In an aspect, a method comprises concurrently detecting DM resistance QTLs DM_5.01, DM_6.02, DM_7.01, and DM_8.01. In an aspect, a method comprises concurrently detecting DM resistance QTLs DM_5.01, DM_6.02, and DM_8.01. In an aspect, a method comprises concurrently detecting DM resistance QTLs DM_6.02, DM_7.01, and DM_8.01. In an aspect, a method comprises concurrently detecting DM resistance QTLs DM_1.01, DM_2.03, and DM_6.01. In an aspect, a method comprises concurrently detecting DM resistance QTLs DM_1.01, DM_4.01, and DM_6.01.

In another aspect, a method comprises concurrently detecting DM resistance QTL 1.01 and at least one or more, two or more, three or more, five or more, six or more, seven or more, eight or more, nine or more, ten or more, eleven or more, or twelve DM resistance QTLs selected from the group consisting of DM_1.02, DM_2.01, DM_2.02, DM_2.03, DM_3.01, DM_4.01, DM_5.01, DM_6.01, DM_6.02, DM_7.01, DM_8.01, and DM_9.01.

In another aspect, a method comprises concurrently detecting DM resistance QTL 1.02 and at least one or more, two or more, three or more, five or more, six or more, seven or more, eight or more, nine or more, ten or more, eleven or more, or twelve DM resistance QTLs selected from the group consisting of DM_1.01, DM_2.01, DM_2.02, DM_2.03, DM_3.01, DM_4.01, DM_5.01, DM_6.01, DM_6.02, DM_7.01, DM_8.01, and DM_9.01.

In another aspect, a method comprises concurrently detecting DM resistance QTL 2.01 and at least one or more, two or more, three or more, five or more, six or more, seven or more, eight or more, nine or more, ten or more, eleven or more, or twelve DM resistance QTLs selected from the group consisting of DM_1.01, DM_2.02, DM_2.02, DM_2.03, DM_3.01, DM_4.01, DM_5.01, DM_6.01, DM_6.02, DM_7.01, DM_8.01, and DM_9.01.

In another aspect, a method comprises concurrently detecting DM resistance QTL 2.02 and at least one or more, two or more, three or more, five or more, six or more, seven or more, eight or more, nine or more, ten or more, eleven or more, or twelve DM resistance QTLs selected from the group consisting of DM_1.01, DM_1.02, DM_2.01, DM_2.03, DM_3.01, DM_4.01, DM_5.01, DM_6.01, DM_6.02, DM_7.01, DM_8.01, and DM_9.01.

In another aspect, a method comprises concurrently detecting DM resistance QTL 2.03 and at least one or more, two or more, three or more, five or more, six or more, seven or more, eight or more, nine or more, ten or more, eleven or more, or twelve DM resistance QTLs selected from the group consisting of DM_1.01, DM_1.02, DM_2.01, DM_2.02, DM_3.01, DM_4.01, DM_5.01, DM_6.01, DM_6.02, DM_7.01, DM_8.01, and DM_9.01.

In another aspect, a method comprises concurrently detecting DM resistance QTL 3.01 and at least one or more, two or more, three or more, five or more, six or more, seven or more, eight or more, nine or more, ten or more, eleven or more, or twelve DM resistance QTLs selected from the group consisting of DM_1.01, DM_1.02, DM_2.01, DM_2.02 DM_2.03, DM_4.01, DM_5.01, DM_6.01, DM_6.02, DM_7.01, DM_8.01, and DM_9.01.

In another aspect, a method comprises concurrently detecting DM resistance QTL 4.01 and at least one or more, two or more, three or more, five or more, six or more, seven or more, eight or more, nine or more, ten or more, eleven or more, or twelve DM resistance QTLs selected from the group consisting of DM_1.01, DM_1.02, DM_2.01, DM_2.02 DM_2.03, DM_3.01, DM_5.01, DM_6.01, DM_6.02, DM_7.01, DM_8.01, and DM_9.01.

In another aspect, a method comprises concurrently detecting DM resistance QTL 5.01 and at least one or more, two or more, three or more, five or more, six or more, seven or more, eight or more, nine or more, ten or more, eleven or more, or twelve DM resistance QTLs selected from the group consisting of DM_1.01, DM_1.02, DM_2.01, DM_2.02 DM_2.03, DM_3.01, DM_4.01, DM_6.01, DM_6.02, DM_7.01, DM_8.01, and DM_9.01.

In another aspect, a method comprises concurrently detecting DM resistance QTL 6.01 and at least one or more, two or more, three or more, five or more, six or more, seven or more, eight or more, nine or more, ten or more, eleven or more, or twelve DM resistance QTLs selected from the group consisting of DM_1.01, DM_1.02, DM_2.01, DM_2.02 DM_2.03, DM_3.01, DM_4.01, DM_5.01, DM_6.02, DM_7.01, DM_8.01, and DM_9.01.

In another aspect, a method comprises concurrently detecting DM resistance QTL DM_6.02 and at least one or more, two or more, three or more, five or more, six or more, seven or more, eight or more, nine or more, ten or more, eleven or more, or twelve DM resistance QTLs from the group consisting of DM_1.01, DM_1.02, DM_2.01, DM_2.02, DM_2.03, DM_3.01, DM_4.01, DM_5.01, DM_6.01, DM_7.01, DM_8.01, and DM_9.01.

In another aspect, a method comprises concurrently detecting DM resistance QTL 7.01 and at least one or more, two or more, three or more, five or more, six or more, seven or more, eight or more, nine or more, ten or more, eleven or more, or twelve DM resistance QTLs selected from the group consisting of DM_1.01, DM_1.02, DM_2.01, DM_2.02 DM_2.03, DM_3.01, DM_4.01, DM_5.01, DM_6.01, DM_6.02, DM_8.01, and DM_9.01.

In another aspect, a method comprises concurrently detecting DM resistance QTL 8.01 and at least one or more, two or more, three or more, five or more, six or more, seven or more, eight or more, nine or more, ten or more, eleven or more, or twelve DM resistance QTLs selected from the group consisting of DM_1.01, DM_1.02, DM_2.01, DM_2.02 DM_2.03, DM_3.01, DM_4.01, DM_5.01, DM_6.01, DM_6.02, DM_7.01, and DM_9.01.

In another aspect, a method comprises concurrently detecting DM resistance QTL 9.01 and at least one or more, two or more, three or more, five or more, six or more, seven or more, eight or more, nine or more, ten or more, eleven or more, or twelve DM resistance QTLs selected from the group consisting of DM_1.01, DM_1.02, DM_2.01, DM_2.02 DM_2.03, DM_3.01, DM_4.01, DM_5.01, DM_6.01, DM_6.02, DM_7.01, and DM_8.01.

In an aspect, this disclosure provides a method of producing a corn plant with enhanced DM resistance, which method comprising the steps of: (a) crossing a first corn plant comprising a DM resistance QTL with a second corn plant of a different genotype to produce one or more progeny plants or seeds; (b) selecting a progeny plant or seed comprising a DM resistance allele of a polymorphic locus linked to a DM resistance QTL, wherein a polymorphic locus is in a chromosomal segment flanked by any two of marker loci SEQ ID NOs: 1 to 11, any two of marker loci SEQ ID NOs: 12 to 22, any two of marker loci SEQ ID NOs: 23 to 28, any two of marker loci SEQ ID NOs: 29 to 32, any two of marker loci SEQ ID NOs: 33 to 38, any two of marker loci SEQ ID NOs: 39 to 45, any two of marker loci SEQ ID NOs: 46 to 57, any two of marker loci SEQ ID NOs: 54 to 62, any two of marker loci SEQ ID NOs: 63 and 64, any two of marker loci SEQ ID NOs: 65 to 90, or any two of marker loci SEQ ID NOs: 91-114; (c) crossing the selected progeny plant with itself or the second corn plant to produce one or more further progeny plants or seeds; and (d) selecting a further progeny plant or seed comprising the DM resistance allele. In an aspect, the further progeny plant in step (d) is an $F_2$ to $F_7$ progeny plant. In another aspect, the further progeny plant in step (d) comprises 2 to 7 generations of backcrossing. In yet another aspect, a method comprises using marker-assisted selection to select a DM resistance allele in at least one polymorphic locus selected from the group consisting of SEQ ID NOs: 1-114.

In an aspect, this disclosure provides a method of obtaining a corn plant or seed with enhanced DM resistance, which method comprises the steps of: (a) detecting in a population of corn plants or seeds a plant or seed comprising a DM resistance allele at a polymorphic locus in a chromosomal segment flanked by SEQ ID NOs: 1 to 11, any two of marker loci SEQ ID NOs: 12 to 22, any two of marker loci SEQ ID NOs: 23 to 28, any two of marker loci SEQ ID NOs: 29 to 32, any two of marker loci SEQ ID NOs: 33 to 38, any two of marker loci SEQ ID NOs: 39 to 45, any two of marker loci SEQ ID NOs: 46 to 57, any two of marker loci SEQ ID NOs: 54 to 62, any two of marker loci SEQ ID NOs: 63 and 64, any two of marker loci SEQ ID NOs: 65 to 90, or any two of marker loci SEQ ID NOs: 91-114; and (b) selecting the plant or seed from the population based on the presence of the DM resistance allele.

In an aspect, this disclosure provides a method of producing a corn plant with enhanced DM resistance, which method comprising the steps of: (a) crossing a first corn plant comprising a DM resistance haplotype with a second corn plant of a different genotype to produce one or more progeny plants or seeds; (b) selecting a progeny plant or seed based on the presence of the DM resistance haplotype, wherein the haplotype comprises resistance alleles of two or more polymorphic loci in a chromosomal interval flanked by: any two marker loci selected from the group consisting of SEQ ID NOs: 1 to 11; any two marker loci selected from the group consisting of SEQ ID NOs: 12 to 22; any two marker loci selected from the group consisting of SEQ ID NOs: 23 to 28; any two marker loci selected from the group consisting of SEQ ID NOs: 29 to 32; any two marker loci selected from the group consisting of SEQ ID NOs: 33 to 38; any two marker loci selected from the group consisting of SEQ ID NOs: 39 to 45; any two marker loci selected from the group consisting of SEQ ID NOs: 46 to 57; any two marker loci selected from the group consisting of SEQ ID NOs: 54 to 62; SEQ ID NO: 63 and SEQ ID NO: 64; any two marker loci selected from the group consisting of SEQ ID NOs: 65 to 90; or any two marker loci selected from the group consisting of SEQ ID NOs: 91-114.

In an aspect, this disclosure provides a method of obtaining a corn plant or seed with enhanced DM resistance, which method comprising the steps of: (a) detecting in a population of corn plants or seeds a plant or seed comprising a DM resistance haplotype, wherein the haplotype comprises resistance alleles of two or more polymorphic loci in a chromosomal interval flanked by: any two marker loci selected from the group consisting of SEQ ID NOs: 5 to 8; SEQ ID NO: 7 and SEQ ID NO: 8; any two marker loci selected from the group consisting of SEQ ID NOs: 12 to 14; any two marker loci selected from the group consisting of SEQ ID NOs: 18 to 20; any two marker loci selected from the group consisting of SEQ ID NOs: 25 to 27; any two marker loci selected from the group consisting of SEQ ID NOs: 29 to 31; any two marker loci selected from the group consisting of SEQ ID NOs: 34 to 36; any two marker loci selected from the group consisting of SEQ ID NOs: 39 to 45; any two marker loci selected from the group consisting of SEQ ID NOs: 49 to 51; SEQ ID NO: 58 and SEQ ID NO: 59; SEQ ID NO: 63 and SEQ ID NO: 64; any two marker loci selected from the group consisting of SEQ ID NOs: 66 to 76; or any two marker loci selected from the group consisting of SEQ ID NOs: 99 to 106; and (b) selecting a plant or seed from the population based on the presence of the DM resistance haplotype. In yet another aspect, a DM resistance haplotype comprises resistance alleles of two or more polymorphic loci selected from the group consisting of SEQ ID NOs: 5-8, 12-14, 18-20, 25-27, 29-31, 34-36, 39-45, 49-51, 58, 59, 63, 64, 66-76, and 99-106.

In an aspect, this disclosure provides a method for selecting a corn plant or seed, which method comprising the steps of: (a) isolated nucleic acids from a corn plant or seed; (b) analyzing the nucleic acids to detect a polymorphic marker associated with a DM resistance QTL selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01; and (c) selecting a corn plant or seed comprising the DM resistance QTL.

In an aspect, this disclosure provides a method for selecting a corn plant or seed, which method comprising the steps of: (a) detecting in a population of corn plants or seeds a corn plant or seed comprising a DM resistance allele of a marker locus associated with a DM resistance QTL selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01; and (b) selecting a corn plant or seed comprising the DM resistance allele.

In an aspect, this disclosure provides a method for evaluating a collection of corn germplasm, which method comprising the steps of: (a) obtaining a collection of corn germplasm; (b) isolating nucleic acids from each germplasm; (c) assaying the nucleic acids for one or more markers linked to a DM resistance QTL selected from the group consisting of DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01; and (d) selecting germplasm comprising a DM resistance QTL based on the marker assay.

In an aspect, a method disclosed herein comprises genotyping by a marker assay. In an aspect, a method disclosed herein comprises marker-assisted selection. In another aspect, a method disclosed herein comprises assaying a SNP marker. In yet another aspect, a method disclosed herein comprises the use of an oligonucleotide probe. In a further aspect, a method disclosed herein comprises using an oligonucleotide probe adjacent to a polymorphic nucleotide position in a marker locus being genotyped.

In an aspect, a corn plant or seed disclosed herein may be an inbred, a hybrid, a transgenic, a haploid, a doubled haploid, or in an agronomically elite background. These groups are not mutually exclusive, and a corn plant or seed could be in two or more groups (e.g., a plant could be a transgenic hybrid, another plant could be an inbred doubled haploid, etc.).

In an aspect, a method disclosed herein comprises genotyping a corn plant or seed at a polymorphic marker locus within about 20 cM, 15 cM, 10 cM, 5 cM, 4 cM, 3 cM, 2 cM, 1 cM, 0.5 cM or less than 0.5 cM of any one of marker loci SEQ ID NOs: 1-114. In an aspect, this disclosure provides a method comprising genotyping a polymorphic locus selected from the group consisting of SEQ ID NOs: 1-114.

In an aspect, a method disclosed herein comprises genotyping a corn plant or seed at a marker locus associated with DM resistance QTL DM_1.01, which DM resistance QTL DM_1.01 is located in a chromosomal interval flanked by any two of the marker loci selected from the group consisting of SEQ ID NOs: 1 to 8. In another aspect, a method disclosed herein comprises genotyping a corn plant or seed at a marker locus associated with DM resistance QTL DM_1.01, which DM resistance QTL DM_1.01 is located in a chromosomal interval flanked by any two of the marker loci selected from the group consisting of SEQ ID NOs: 5 to 8.

In an aspect, a method disclosed herein comprises genotyping a corn plant or seed at a marker locus associated with DM resistance QTL DM_1.02 which DM resistance QTL DM_1.02 is located in a chromosomal interval flanked by any two of the marker loci selected from the group consisting of SEQ ID NOs: 6 to 11. In another aspect, a method disclosed herein comprises genotyping a corn plant or seed at a marker locus associated with DM resistance QTL DM_1.02 which DM resistance QTL DM_1.02 is located in a chromosomal interval flanked by marker loci SEQ ID NO: 7 and SEQ ID NO: 8.

In an aspect, a method disclosed herein comprises genotyping a corn plant or seed at a marker locus associated with DM resistance QTL DM_2.01, which DM resistance QTL DM_2.01 is located in a chromosomal interval flanked by any two of the marker loci selected from the group consisting of SEQ ID NOs: 12 to 22. In another aspect, a method disclosed herein comprises genotyping a corn plant or seed at a marker locus associated with DM resistance QTL DM_2.01, which DM resistance QTL DM_2.01 is located in a chromosomal interval flanked by any two of the marker loci selected from the group consisting of SEQ ID NOs: 18 to 20.

In an aspect, a method disclosed herein comprises genotyping a corn plant or seed at a marker locus associated with DM resistance QTL DM_2.02, which DM resistance QTL DM_2.02 is located in a chromosomal interval flanked by any two of the marker loci selected from the group consisting of SEQ ID NOs: 23 to 28. In another aspect, a method disclosed herein comprises genotyping a corn plant or seed at a marker locus associated with DM resistance QTL DM_2.02, which DM resistance QTL DM_2.02 is located in a chromosomal interval flanked by any two of the marker loci selected from the group consisting of SEQ ID NOs: 25 to 27.

In an aspect, a method disclosed herein comprises genotyping a corn plant or seed at a marker locus associated with DM resistance QTL DM_2.03, which DM resistance QTL DM_2.03 is located in a chromosomal interval flanked by any two of the marker loci selected from the group consisting of SEQ ID NOs: 12 to 14.

In an aspect, a method disclosed herein comprises genotyping a corn plant or seed at a marker locus associated with DM resistance QTL DM_3.01, which DM resistance QTL DM_3.01 is located in a chromosomal interval flanked by any two of the marker loci selected from the group consisting of SEQ ID NOs: 29 to 32. In an aspect, a method disclosed herein comprises genotyping a corn plant or seed at a marker locus associated with DM resistance QTL DM_3.01, which DM resistance QTL DM_3.01 is located in a chromosomal interval flanked by any two of the marker loci selected from the group consisting of SEQ ID NOs: 29 to 31.

In an aspect, a method disclosed herein comprises genotyping a corn plant or seed at a marker locus associated with DM resistance QTL DM_4.01, which DM resistance QTL DM_4.01 is located in a chromosomal interval flanked by any two of the marker loci selected from the group consisting of SEQ ID NOs: 33 to 38. In another aspect, a method disclosed herein comprises genotyping a corn plant or seed at a marker locus associated with DM resistance QTL DM_4.01, which DM resistance QTL DM_4.01 is located in a chromosomal interval flanked by any two of the marker loci selected from the group consisting of SEQ ID NOs: 34 to 36.

In an aspect, a method disclosed herein comprises genotyping a corn plant or seed at a marker locus associated with DM resistance QTL DM_5.01, which DM resistance QTL DM_5.01 is located in a chromosomal interval flanked by any two of the marker loci selected from the group consisting of SEQ ID NOs: 39 to 45.

In an aspect, a method disclosed herein comprises genotyping a corn plant or seed at a marker locus associated with DM resistance QTL DM_6.01, which DM resistance QTL DM_6.01 is located in a chromosomal interval flanked by any two of the marker loci selected from the group consisting of SEQ ID NOs: 46 to 57. In another aspect, a method disclosed herein comprises genotyping a corn plant or seed at a marker locus associated with DM resistance QTL DM_6.01, which DM resistance QTL DM_6.01 is located in a chromosomal interval flanked by any two of the marker loci selected from the group consisting of SEQ ID NOs: 49 to 51.

In an aspect, a method disclosed herein comprises genotyping a corn plant or seed at a marker locus associated with DM resistance QTL DM_6.02, which DM resistance QTL DM_6.02 is located in a chromosomal interval flanked by any two of the marker loci selected from the group consisting of SEQ ID NOs: 54 to 62. In another aspect, a method disclosed herein comprises genotyping a corn plant or seed at a marker locus associated with DM resistance QTL DM_6.02, which DM resistance QTL DM_6.02 is located in a chromosomal interval flanked by marker loci SEQ ID NO: 59 and SEQ ID NO: 59.

In an aspect, a method disclosed herein comprises genotyping a corn plant or seed at a marker locus associated with DM resistance QTL DM_7.01 which DM resistance QTL DM_7.01 is located in a chromosomal interval flanked marker loci SEQ ID NO: 63 and SEQ ID NO: 64.

In an aspect, a method disclosed herein comprises genotyping a corn plant or seed at a marker locus associated with DM resistance QTL DM_8.01, which DM resistance QTL DM_8.01 is located in a chromosomal interval flanked by any two of the marker loci selected from the group consisting of SEQ ID NOs: 65 to 90. In an aspect, a method disclosed herein comprises genotyping a corn plant or seed at a marker locus associated with DM resistance QTL DM_8.01, which DM resistance QTL DM_8.01 is located in a chromosomal interval flanked by any two of the marker loci selected from the group consisting of SEQ ID NOs: 66 to 76.

In an aspect, a method disclosed herein comprises genotyping a corn plant or seed at a marker locus associated with DM resistance QTL DM_9.01, which DM resistance QTL DM_9.01 is located in a chromosomal interval flanked by any two of the marker loci selected from the group consisting of SEQ ID NOs: 91-114. In an aspect, a method disclosed herein comprises genotyping a corn plant or seed at a marker locus associated with DM resistance QTL DM_9.01, which DM resistance QTL DM_9.01 is located in a chromosomal interval flanked by any two of the marker loci selected from the group consisting of SEQ ID NOs: 99 to 106.

In a further aspect, a method disclosed herein comprises genotyping a corn plant or seed at a marker locus located in a chromosomal interval flanked by any two of marker loci SEQ ID NOs: 1 to 11. In another aspect, a method disclosed herein comprises genotyping a corn plant or seed at a marker locus located in a chromosomal interval flanked by any two of marker loci SEQ ID NOs: 5 to 8. In yet another aspect, a method disclosed herein comprises genotyping a corn plant or seed at a marker locus located in a chromosomal interval flanked by any two of marker loci SEQ ID NO: 7 and SEQ ID NO: 8.

In a further aspect, a method disclosed herein comprises genotyping a corn plant or seed at a marker locus located in a chromosomal interval flanked by any two of marker loci SEQ ID NOs: 12 to 22. In another aspect, a method disclosed herein comprises genotyping a corn plant or seed at a marker locus located in a chromosomal interval flanked by any two of marker loci SEQ ID Nos: 12 to 14. In another aspect, a method disclosed herein comprises genotyping a corn plant or seed at a marker locus located in a chromosomal interval flanked by any two of marker loci SEQ ID NOs: 18 to 20.

In a further aspect, a method disclosed herein comprises genotyping a corn plant or seed at a marker locus located in a chromosomal interval flanked by any two of marker loci SEQ ID NOs: 23 to 28. In another aspect, a method disclosed herein comprises genotyping a corn plant or seed at a marker locus located in a chromosomal interval flanked by any two of marker loci SEQ ID NOs: 25 to 27.

In a further aspect, a method disclosed herein comprises genotyping a corn plant or seed at a marker locus located in a chromosomal interval flanked by any two of marker loci SEQ ID NOs: 29 to 32. In another aspect, a method disclosed herein comprises genotyping a corn plant or seed at a marker locus located in a chromosomal interval flanked by any two of marker loci SEQ ID NOs: 29 to 31. In yet another aspect, a method disclosed herein comprises genotyping a corn plant or seed at a marker locus located in a chromosomal interval flanked by any marker loci SEQ ID NO: 30 and SEQ ID NO: 31.

In a further aspect, a method disclosed herein comprises genotyping a corn plant or seed at a marker locus located in a chromosomal interval flanked by any two of marker loci SEQ ID NOs: 33 to 38. In another aspect, a method disclosed herein comprises genotyping a corn plant or seed at a marker locus located in a chromosomal interval flanked by any two of marker loci SEQ ID NOs: 34 to 36.

In a further aspect, a method disclosed herein comprises genotyping a corn plant or seed at a marker locus located in a chromosomal interval flanked by any two of marker loci SEQ ID NOs: 39 to 45.

In a further aspect, a method disclosed herein comprises genotyping a corn plant or seed at a marker locus located in a chromosomal interval flanked by any two of marker loci SEQ ID NOs: 46 to 57. In another aspect, a method disclosed herein comprises genotyping a corn plant or seed at a marker locus located in a chromosomal interval flanked by any two of marker loci SEQ ID NOs: 49 to 51.

In a further aspect, a method disclosed herein comprises genotyping a corn plant or seed at a marker locus located in a chromosomal interval flanked by any two of marker loci SEQ ID NOs: 54 to 62. In another aspect, a method disclosed herein comprises genotyping a corn plant or seed at a marker locus located in a chromosomal interval flanked by any two of marker loci SEQ ID NO: 58 and SEQ ID NO: 59.

In a further aspect, a method disclosed herein comprises genotyping a corn plant or seed at a marker locus located in a chromosomal interval flanked by any two of marker loci SEQ ID NO: 63 and SEQ ID NO: 64.

In a further aspect, a method disclosed herein comprises genotyping a corn plant or seed at a marker locus located in a chromosomal interval flanked by any two of marker loci SEQ ID NOs: 65 to 90. In another aspect, a method disclosed herein comprises genotyping a corn plant or seed at a marker locus located in a chromosomal interval flanked by any two of marker loci SEQ ID NOs: 66 to 76.

In a further aspect, a method disclosed herein comprises genotyping a corn plant or seed at a marker locus located in a chromosomal interval flanked by any two of marker loci SEQ ID NOs: 91-114. In another aspect, a method disclosed herein comprises genotyping a corn plant or seed at a marker locus located in a chromosomal interval flanked by any two of marker loci SEQ ID NOs: 99 to 106.

In another aspect, a method disclosed herein comprises genotyping a corn plant or seed by detecting a haplotype. In an aspect, a haplotype comprises a DM resistance allele at one or more, two or more, three or more, four or more, or five or more of marker loci SEQ ID NO: 1 to 11. In an aspect, a haplotype comprises a DM resistance allele at one or more, two or more, or three or more of marker loci SEQ ID NO: 5 to 8. In an aspect, a haplotype comprises a DM resistance allele at one or more of marker loci SEQ ID NO: 7 and SEQ ID NO: 8. In an aspect, a haplotype comprises a DM resistance allele at one or more, two or more, three or more, four or more, or five or more of marker loci SEQ ID NO: 12 to 22. In an aspect, a haplotype comprises a DM resistance allele at one or more, or two or more of marker loci SEQ ID NO: 12 to 14. In an aspect, a haplotype comprises a DM resistance allele at one or more, two or more of marker loci SEQ ID NO: 18 to 20. In an aspect, a haplotype comprises a DM resistance allele at one or more, two or more, three or more, four or more, or five or more of marker loci SEQ ID NO: 23 to 28. In an aspect, a haplotype comprises a DM resistance allele at one or more, or two or more of marker loci SEQ ID NO: 25 to 27. In an aspect, a haplotype comprises a DM resistance allele at one or more, two or more, or three or more of marker loci SEQ ID NO: 29 to 32. In an aspect, a haplotype comprises a DM resistance allele at one or more, or two or more of marker loci SEQ ID NO: 29 to 31. In an aspect, a haplotype comprises a DM resistance allele at one or more, two or more, three or more, four or more, or five or more of marker loci SEQ ID NO: 33 to 38. In an aspect, a haplotype comprises a DM resistance allele at one or more, or two or more of marker loci SEQ ID NO: 34 to 36. In an aspect, a haplotype comprises a DM resistance allele at one or more, two or more, three or more, four or more, or five or more of marker loci SEQ ID NO: 39 to 45. In an aspect, a haplotype comprises a DM resistance allele at one or more, two or more, three or more, four or more, or five or more of marker loci SEQ ID NO: 46 to 57. In an aspect, a haplotype comprises a DM resistance allele at one or more, or two or more of marker loci SEQ ID NO: 49 to 51. In an aspect, a haplotype comprises a DM resistance allele at one or more of marker loci SEQ ID NO: 58 and SEQ ID NO: 59. In an aspect, a haplotype comprises a DM resistance allele at one or more, two or more, three or more, four or more, or five or more of marker loci SEQ ID NO: 54 to 62. In an aspect, a haplotype comprises a DM resistance allele at one or more of marker loci SEQ ID NO: 63 and SEQ ID NO: 64. In an aspect, a haplotype comprises a DM resistance allele at one or more, two or more, three or more, four or more, or five or more of marker loci SEQ ID NO: 65 to 90. In an aspect, a haplotype comprises a DM resistance allele at one or more, two or more, three or more, four or more, or five or more of marker loci SEQ ID NO: 66 to 76. In an aspect, a haplotype comprises a DM resistance allele at one or more, two or more, three or more, four or more, or five or more of marker loci SEQ ID NO: 91-114. In an aspect, a haplotype comprises a DM resistance allele at one or more, two or more, three or more, four or more, or five or more of marker loci SEQ ID NO: 99 to 106.

In an aspect, a corn plant or seed comprising DM resistance QTLs or DM resistant alleles disclosed herein exhibits intermediate resistance to DM infection from oomycetes from the group consisting of *Peronosclerospora, Sclerophthora*, and *Sclerospora*. In another aspect, a corn plant or seed comprising DM resistance QTLs or DM resistant alleles disclosed herein exhibits moderate resistance to DM infection from oomycetes from the group consisting of *Peronosclerospora, Sclerophthora*, and *Sclerospora*. In a further aspect, a corn plant or seed comprising DM resistance QTLs or DM resistant alleles disclosed herein exhibits high resistance to DM infection from oomycetes from the group consisting of *Peronosclerospora, Sclerophthora*, and *Sclerospora*. In an aspect, DM infection is caused by an oomycete selected from the group consisting of *Peronosclerospora eriochloae, Peronosclerospora graminicola, Peronosclerospora heteropogoni, Peronosclerospora maydis, Peronosclerospora miscanthi, Peronosclerospora philippinensis, Peronosclerospora sacchari, Peronosclerospora sorghi, Peronosclerospora spontanea, Peronosclerospora zeae, Sclerophthora macrospora, Scleropthora rayssiae* var. *zeae*, and *Sclerospora graminicola*. In another aspect, a corn plant or seed comprising DM resistance QTLs or DM resistant alleles disclosed herein exhibits high resistance to DM infection from *P. philippinensis*. In another aspect, a corn plant or seed comprising DM resistance QTLs or DM resistant alleles disclosed herein exhibits high resistance to DM infection from *P. maydis*. In another aspect, a corn plant or seed comprising DM resistance QTLs or DM resistant alleles disclosed herein exhibits high resistance to DM infection from *P. sorghi*.

In an aspect, a DM resistance QTL or DM resistance allele disclosed herein confers no yield penalties under a low DM stress condition. In another aspect, a combination of one or more, two or more, three or more, four or more, five or more, six or more, seven or more, eight or more, nine or more, ten or more, or eleven or more DM resistance QTLs disclosed herein confer no yield penalties under a low DM stress condition.

In another aspect, a corn plant or seed disclosed herein comprising one or more, two or more, three or more, four or more, five or more, six or more, seven or more, eight or more, nine or more, ten or more, or eleven or more DM resistance QTLs or DM resistance alleles disclosed herein exhibits a reduction of DM rating score of about 0.5% or more, 1% or more, 2% or more, 3% or more, 4% or more, 5% or more, 10% or more, 15% or more, 20% or more, 30% or more, 40% or more, 50% or more, 60% or more, 70% or more, or 80% or more compared to a corn plant or seed without the one or more, two or more, three or more, four or more, five or more, six or more, seven or more, eight or more, nine or more, ten or more, or eleven or more DM resistance QTLs or DM resistance alleles under a high DM stress condition.

In another aspect, a corn plant or seed disclosed herein comprising one or more QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a reduction of DM rating score of about 0.5% or more, 1% or more, 2% or more, 3% or more, 4% or more, 5% or more, 10% or more, 15% or more, 20% or more, 30% or more, 40% or more, 50% or more, 60% or more, 70% or more, or 80% or more compared to a corn plant or seed without the one or more QTLs under a high DM stress condition.

In another aspect, a corn plant or seed disclosed herein comprising two or more QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a reduction of DM rating score of about 0.5% or more, 1% or more, 2% or more, 3% or more, 4% or more, 5% or more, 10% or more, 15% or more, 20% or more, 30% or more, 40% or more, 50% or more, 60% or more, 70% or more, or 80% or more compared to a corn plant or seed without the two or more QTLs under a high DM stress condition.

In another aspect, a corn plant or seed disclosed herein comprising three or more QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a reduction of DM rating score of about 0.5% or more, 1% or more, 2% or more, 3% or more, 4% or more, 5% or more, 10% or more, 15% or more, 20% or more, 30% or more, 40% or more, 50% or more, 60% or more, 70% or more, or 80% or more compared to a corn plant or seed without the three or more QTLs under a high DM stress condition.

In another aspect, a corn plant or seed disclosed herein comprising four or more QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a reduction of DM rating score of about 0.5% or more, 1% or more, 2% or more, 3% or more, 4% or more, 5% or more, 10% or more, 15% or more, 20% or more, 30% or more, 40% or more, 50% or more, 60% or more, 70% or more, or 80% or more compared to a corn plant or seed without the four or more QTLs under a high DM stress condition.

In another aspect, a corn plant or seed disclosed herein comprising one or more, two or more, three or more, four or more, five or more, six or more, seven or more, eight or more, nine or more, ten or more, eleven or more, twelve or more, or thirteen DM resistance QTLs or DM resistance alleles disclosed herein exhibits a reduction of DM rating score of between 0.5% and 80%, between 0.5% and 70%, between 0.5% and 60%, between 0.5% and 50%, between 0.5% and 40%, between 0.5% and 30%, between 0.5% and 20%, between 0.5% and 15%, between 1% and 10%, between 0.5% and 5%, between 0.5% and 4%, between 0.5% and 3%, between 0.5% and 2%, between 0.5% and 1%, between 1% and 70%, between 2% and 60%, between 3% and 50%, between 4% and 40%, between 5% and 30%, between 10% and 20%, or between 5% and 15% compared to a corn plant or seed without the one or more, two or more, three or more, four or more, five or more, six or more, seven or more, eight or more, nine or more, ten or more, or eleven or more DM resistance QTLs or DM resistance alleles under a high DM stress condition.

In another aspect, a corn plant or seed disclosed herein comprising one or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a reduction of DM rating score of between 0.5% and 80%, between 0.5% and 70%, between 0.5% and 60%, between 0.5% and 50%, between 0.5% and 40%, between 0.5% and 30%, between 0.5% and 20%, between 0.5% and 15%, between 1% and 10%, between 0.5% and 5%, between 0.5% and 4%, between 0.5% and 3%, between 0.5% and 2%, between 0.5% and 1%, between 1% and 70%, between 2% and 60%, between 3% and 50%, between 4% and 40%, between 5% and 30%, between 10% and 20%, or between 5% and 15% compared to a corn plant or seed without the one or more DM resistance QTLs or DM resistance alleles under a high DM stress condition.

In another aspect, a corn plant or seed disclosed herein comprising two or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a reduction of DM rating score of between 0.5% and 80%, between 0.5% and 70%, between 0.5% and 60%, between 0.5% and 50%, between 0.5% and 40%, between 0.5% and 30%, between 0.5% and 20%, between 0.5% and 15%, between 1% and 10%, between 0.5% and 5%, between 0.5% and 4%, between 0.5% and 3%, between 0.5% and 2%, between 0.5% and 1%, between 1% and 70%, between 2% and 60%, between 3% and 50%, between 4% and 40%, between 5% and 30%, between 10% and 20%, or between 5% and 15% compared to a corn plant or seed without the two or more DM resistance QTLs or DM resistance alleles under a high DM stress condition.

In another aspect, a corn plant or seed disclosed herein comprising three or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a reduction of DM rating score of between 0.5% and 80%, between 0.5% and 70%, between 0.5% and 60%, between 0.5% and 50%, between 0.5% and 40%, between 0.5% and 30%, between 0.5% and 20%, between 0.5% and 15%, between 1% and 10%, between 0.5% and 5%, between 0.5% and 4%, between 0.5% and 3%, between 0.5% and 2%, between 0.5% and 1%, between 1% and 70%, between 2% and 60%, between 3% and 50%, between 4% and 40%, between 5% and 30%, between 10% and 20%, or between 5% and 15% compared to a corn plant or seed without the three or more DM resistance QTLs or DM resistance alleles under a high DM stress condition.

In another aspect, a corn plant or seed disclosed herein comprising four or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a reduction of DM rating score of between 0.5% and 80%, between 0.5% and 70%, between 0.5% and 60%, between 0.5% and 50%, between 0.5% and 40%, between 0.5% and 30%, between 0.5% and 20%, between 0.5% and 15%, between 1% and 10%, between 0.5% and 5%, between 0.5% and 4%, between 0.5% and 3%, between 0.5% and 2%, between 0.5% and 1%, between 1% and 70%, between 2% and 60%, between 3% and 50%, between 4% and 40%, between 5% and 30%, between 10% and 20%, or between 5% and 15% compared to a corn plant or seed without the four or more DM resistance QTLs or DM resistance alleles under a high DM stress condition.

In an aspect, a corn plant or seed disclosed herein comprising one or more, two or more, three or more, four or more, five or more, six or more, seven or more, eight or more, nine or more, ten or more, eleven or more, twelve or more, or thirteen DM resistance QTLs or DM resistance alleles disclosed herein exhibits a seed yield increase of about 1% or more, 2% or more, 3% or more, 4% or more, 5% or more, 10% or more, 15% or more, 20% or more, 25% or more, 30% or more, 40% or more, 50% or more, 60% or more, 70% or more, 80% or more, 90% or more, or 100% or more than seed yield of a corn plant or seed without the one or more, two or more, three or more, four or more, five or more, six or more, seven or more, eight or more, nine or more, ten or more, or eleven or more DM resistance QTLs or DM resistance alleles under a high DM stress condition.

In an aspect, a corn plant or seed disclosed herein comprising one or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield increase of about 1% or more, 2% or more, 3% or more, 4% or more, 5% or more, 10% or more, 15% or more, 20% or more, 25% or more, 30% or more, 40% or more, 50% or more, 60% or more, 70% or more, 80% or more, 90% or more, or 100% or more than seed yield of a corn plant or seed without the one or more DM resistance QTLs or DM resistance alleles under a high DM stress condition.

In an aspect, a corn plant or seed disclosed herein comprising two or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield increase of about 1% or more, 2% or more, 3% or more, 4% or more, 5% or more, 10% or more, 15% or more, 20% or more, 25% or more, 30% or more, 40% or more, 50% or more, 60% or more, 70% or more, 80% or more, 90% or more, or 100% or more than seed yield of a corn plant or seed without the two or more DM resistance QTLs or DM resistance alleles under a high DM stress condition.

In an aspect, a corn plant or seed disclosed herein comprising three or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield increase of about 1% or more, 2% or more, 3% or more, 4% or more, 5% or more, 10% or more, 15% or more, 20% or more, 25% or more, 30% or more, 40% or more, 50% or more, 60% or more, 70% or more, 80% or more, 90% or more, or 100% or more than seed yield of a corn plant or seed without the three or more DM resistance QTLs or DM resistance alleles under a high DM stress condition.

In an aspect, a corn plant or seed disclosed herein comprising four or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield increase of about 1% or more, 2% or more, 3% or more, 4% or more, 5% or more, 10% or more, 15% or more, 20% or more, 25% or more, 30% or more, 40% or more, 50% or more, 60% or more, 70% or more, 80% or more, 90% or more, or 100% or more than seed yield of a corn plant or seed without the four or more DM resistance QTLs or DM resistance alleles under a high DM stress condition.

In another aspect, a corn plant or seed disclosed herein comprising one or more, two or more, three or more, four or more, five or more, six or more, seven or more, eight or more, nine or more, ten or more, eleven or more, twelve or more, or thirteen DM resistance QTLs or DM resistance alleles disclosed herein exhibits a seed yield increase of between 1% and 100%, between 1% and 90%, between 1% and 80%, between 1% and 70%, between 1% and 60%, between 1% and 50%, between 1% and 40%, between 1% and 30%, between 1% and 25%, between 1% and 20%, between 1% and 15%, between 1% and 10%, between 1% and 5%, between 1% and 4%, between 1% and 3%, between 1% and 2%, between 2% and 90%, between 3% and 80%, between 4% and 70%, between 5% and 60%, between 10% and 50%, between 15% and 40%, between 20% and 30%, or between 5% and 25% of seed yield of a corn plant or seed without the one or more, two or more, three or more, four or more, five or more, six or more, seven or more, eight or more, nine or more, ten or more, or eleven or more DM resistance QTLs or DM resistance alleles under a high DM stress condition.

In another aspect, a corn plant or seed disclosed herein comprising one or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield increase of between 1% and 25%, between 1% and 20%, between 1% and 15%, between 1% and 10%, between 1% and 5%, between 1% and 4%, between 1% and 3%, between 1% and 2%, between 2% and 90%, between 3% and 80%, between 4% and 70%, between 5% and 60%, between 10% and 50%, between 15% and 40%, between 20% and 30%, or between 5% and 25% of seed yield of a corn plant or seed without the one or more DM resistance QTLs or DM resistance alleles under a high DM stress condition.

In another aspect, a corn plant or seed disclosed herein comprising two or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield increase of between 1% and 25%, between 1% and 20%, between 1% and 15%, between 1% and 10%, between 1% and 5%, between 1% and 4%, between 1% and 3%, between 1% and 2%, between 2% and 90%, between 3% and 80%, between 4% and 70%, between 5% and 60%, between 10% and 50%, between 15% and 40%, between 20% and 30%, or between 5% and 25% of seed yield of a corn plant or seed without the two or more DM resistance QTLs or DM resistance alleles under a high DM stress condition.

In another aspect, a corn plant or seed disclosed herein comprising three or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield increase of between 1% and 25%, between 1% and 20%, between 1% and 15%, between 1% and 10%, between 1% and 5%, between 1% and 4%, between 1% and 3%, between 1% and 2%, between 2% and 90%, between 3% and 80%, between 4% and 70%, between 5% and 60%, between 10% and 50%, between 15% and 40%, between 20% and 30%, or between 5% and 25% of seed yield of a corn plant or seed without the three or more DM resistance QTLs or DM resistance alleles under a high DM stress condition.

In another aspect, a corn plant or seed disclosed herein comprising four or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield increase of between 1% and 25%, between 1% and 20%, between 1% and 15%, between 1% and 10%, between 1% and 5%, between 1% and 4%, between 1% and 3%, between 1% and 2%, between 2% and 90%, between 3% and 80%, between 4% and 70%, between 5% and 60%, between 10% and 50%, between 15% and 40%, between 20% and 30%, or between 5% and 25% of seed yield of a corn plant or seed without the four or more DM resistance QTLs or DM resistance alleles under a high DM stress condition.

In an aspect, a corn plant or seed disclosed herein comprising one or more, two or more, three or more, four or more, five or more, six or more, seven or more, eight or more, nine or more, ten or more, eleven or more, twelve or more, or thirteen DM resistance QTLs or DM resistance alleles disclosed herein exhibits a seed yield about 0.1 quintal/hectare or more, 0.25 quintal/hectare or more, 0.5 quintal/hectare or more, 0.75 quintal/hectare or more, 1 quintal/hectare or more, 1.5 quintal/hectare or more, 2 quintal/hectare or more, 2.5 quintal/hectare or more, 3 quintal/hectare or more, 3.5 quintal/hectare or more, 4 quintal/hectare or more, 4.5 quintal/hectare or more, 5 quintal/hectare or more, 6 quintal/hectare or more, 7 quintal/hectare or more, 8 quintal/hectare or more, 9 quintal/hectare or more, or 10 quintal/hectare or more higher than seed yield of a corn plant or seed without the one or more, two or more, three or more, four or more, five or more, six or more, seven or more, eight or more, nine or more, ten or more, eleven or more, twelve or more, or thirteen DM resistance QTLs or DM resistance alleles under a high DM stress condition.

In an aspect, a corn plant or seed disclosed herein comprising one or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield about 0.1 quintal/hectare or more, 0.25 quintal/hectare or more, 0.5 quintal/hectare or more, 0.75 quintal/hectare or more, 1 quintal/hectare or more, 1.5 quintal/hectare or more, 2 quintal/hectare or more, 2.5 quintal/hectare or more, 3 quintal/hectare or more, 3.5 quintal/hectare or more, 4 quintal/hectare or more, 4.5 quintal/hectare or more, 5 quintal/hectare or more, 6 quintal/hectare or more, 7 quintal/hectare or more, 8 quintal/hectare or more, 9 quintal/hectare or more, or 10 quintal/hectare or more higher than seed yield of a corn plant or seed without the one or more DM resistance QTLs or DM resistance alleles under a high DM stress condition.

In an aspect, a corn plant or seed disclosed herein comprising two or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield about 0.1 quintal/hectare or more, 0.25 quintal/hectare or more, 0.5 quintal/hectare or more, 0.75 quintal/hectare or more, 1 quintal/hectare or more, 1.5 quintal/hectare or more, 2 quintal/hectare or more, 2.5 quintal/hectare or more, 3 quintal/hectare or more, 3.5 quintal/hectare or more, 4 quintal/hectare or more, 4.5 quintal/hectare or more, 5 quintal/hectare or more, 6 quintal/hectare or more, 7 quintal/hectare or more, 8 quintal/hectare or more, 9 quintal/hectare or more, or 10 quintal/hectare or more higher than seed yield of a corn plant or seed without the two or more DM resistance QTLs or DM resistance alleles under a high DM stress condition.

In an aspect, a corn plant or seed disclosed herein comprising three or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield about 0.1 quintal/hectare or more, 0.25 quintal/hectare or more, 0.5 quintal/hectare or more, 0.75 quintal/hectare or more, 1 quintal/hectare or more, 1.5 quintal/hectare or more, 2 quintal/hectare or more, 2.5 quintal/hectare or more, 3 quintal/hectare or more, 3.5 quintal/hectare or more, 4 quintal/hectare or more, 4.5 quintal/hectare or more, 5 quintal/hectare or more, 6 quintal/hectare or more, 7 quintal/hectare or more, 8 quintal/hectare or more, 9 quintal/hectare or more, or 10 quintal/hectare or more higher than seed yield of a corn plant or seed without the three or more DM resistance QTLs or DM resistance alleles under a high DM stress condition.

In an aspect, a corn plant or seed disclosed herein comprising four or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield about 0.1 quintal/hectare or more, 0.25 quintal/hectare or more, 0.5 quintal/hectare or more, 0.75 quintal/hectare or more, 1 quintal/hectare or more, 1.5 quintal/hectare or more, 2 quintal/hectare or more, 2.5 quintal/hectare or more, 3 quintal/hectare or more, 3.5 quintal/hectare or more, 4 quintal/hectare or more, 4.5 quintal/hectare or more, 5 quintal/hectare or more, 6 quintal/hectare or more, 7 quintal/hectare or more, 8 quintal/hectare or more, 9 quintal/hectare or more, or 10 quintal/hectare or more higher than seed yield of a corn plant or seed without the four or more DM resistance QTLs or DM resistance alleles under a high DM stress condition.

In another aspect, a corn plant or seed disclosed herein comprising one or more, two or more, three or more, four or more, five or more, six or more, seven or more, eight or more, nine or more, ten or more, eleven or more, twelve or more, or thirteen DM resistance QTLs or DM resistance alleles disclosed herein exhibits a seed yield between 0.1 and 10 quintal/hectare, between 0.1 and 9 quintal/hectare, between 0.1 and 8 quintal/hectare, between 0.1 and 7 quintal/hectare, between 0.1 and 6 quintal/hectare, between 0.1 and 5 quintal/hectare, between 0.1 and 4.5 quintal/hectare, between 0.1 and 4 quintal/hectare, between 0.1 and 3.5 quintal/hectare, between 0.1 and 3 quintal/hectare, between 0.1 and 2.5 quintal/hectare, between 0.1 and 2 quintal/hectare, between 0.1 and 1.5 quintal/hectare, between 0.1 and 1 quintal/hectare, between 0.1 and 0.75 quintal/hectare, between 0.1 and 0.5 quintal/hectare, between 0.1 and 0.25 quintal/hectare, between 0.25 and 9 quintal/hectare, between 0.5 and 8 quintal/hectare, between 0.75 and 7 quintal/hectare, between 1 and 6 quintal/hectare, between 1.5 and 5 quintal/hectare, between 2 and 4.5 quintal/hectare, between 2.5 and 4 quintal/hectare, or between 3 and 3.5 quintal/hectare higher than seed yield of a corn plant or seed without the one or more, two or more, three or more, four or more, five or more, six or more, seven or more, eight or more, nine or more, ten or more, eleven or more, twelve or more, or thirteen DM resistance QTLs or DM resistance alleles under a high DM stress condition.

In another aspect, a corn plant or seed disclosed herein comprising one or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield between 0.1 and 5 quintal/hectare, between 0.1 and 4.5 quintal/hectare, between 0.1 and 4 quintal/hectare, between 0.1 and 3.5 quintal/hectare, between 0.1 and 3 quintal/hectare, between 0.1 and 2.5 quintal/hectare, between 0.1 and 2 quintal/hectare, between 0.1 and 1.5 quintal/hectare, between 0.1 and 1 quintal/hectare, between 0.1 and 0.75 quintal/hectare, between 0.1 and 0.5 quintal/hectare, between 0.1 and 0.25 quintal/hectare, between 0.25 and 9 quintal/hectare, between 0.5 and 8 quintal/hectare, between 0.75 and 7 quintal/hectare, between 1 and 6 quintal/hectare, between 1.5 and 5 quintal/hectare, between 2 and 4.5 quintal/hectare, between 2.5 and 4 quintal/hectare, or between 3 and 3.5 quintal/hectare higher than seed yield of a corn plant or seed without the one or more DM resistance QTLs or DM resistance alleles under a high DM stress condition.

In another aspect, a corn plant or seed disclosed herein comprising two or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield between 0.1 and 5 quintal/hectare, between 0.1 and 4.5 quintal/hectare, between 0.1 and 4 quintal/hectare, between 0.1 and 3.5 quintal/hectare, between 0.1 and 3 quintal/hectare, between 0.1 and 2.5 quintal/hectare, between 0.1 and 2 quintal/hectare, between 0.1 and 1.5 quintal/hectare, between 0.1 and 1 quintal/hectare, between 0.1 and 0.75 quintal/hectare, between 0.1 and 0.5 quintal/hectare, between 0.1 and 0.25 quintal/hectare, between 0.25 and 9 quintal/hectare, between 0.5 and 8 quintal/hectare, between 0.75 and 7 quintal/hectare, between 1 and 6 quintal/hectare, between 1.5 and 5 quintal/hectare, between 2 and 4.5 quintal/hectare, between 2.5 and 4 quintal/hectare, or between 3 and 3.5 quintal/hectare higher than seed yield of a corn plant or seed without the two or more DM resistance QTLs or DM resistance alleles under a high DM stress condition.

In another aspect, a corn plant or seed disclosed herein comprising three or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield between 0.1 and 5 quintal/hectare, between 0.1 and 4.5 quintal/hectare, between 0.1 and 4 quintal/hectare, between 0.1 and 3.5 quintal/hectare, between 0.1 and 3 quintal/hectare, between 0.1 and 2.5 quintal/hectare, between 0.1 and 2 quintal/hectare, between 0.1 and 1.5 quintal/hectare, between 0.1 and 1 quintal/hectare, between 0.1 and 0.75 quintal/hectare, between 0.1 and 0.5 quintal/hectare, between 0.1 and 0.25 quintal/hectare, between 0.25 and 9 quintal/hectare, between 0.5 and 8 quintal/hectare, between 0.75 and 7 quintal/hectare, between 1 and 6 quintal/hectare, between 1.5 and 5 quintal/hectare, between 2 and 4.5 quintal/hectare, between 2.5 and 4 quintal/hectare, or between 3 and 3.5 quintal/hectare higher than seed yield of a corn plant or seed without the three or more DM resistance QTLs or DM resistance alleles under a high DM stress condition.

In another aspect, a corn plant or seed disclosed herein comprising four or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits a seed yield between 0.1 and 5 quintal/hectare, between 0.1 and 4.5 quintal/hectare, between 0.1 and 4 quintal/hectare, between 0.1 and 3.5 quintal/hectare, between 0.1 and 3 quintal/hectare, between 0.1 and 2.5 quintal/hectare, between 0.1 and 2 quintal/hectare, between 0.1 and 1.5 quintal/hectare, between 0.1 and 1 quintal/hectare, between 0.1 and 0.75 quintal/hectare, between 0.1 and 0.5 quintal/hectare, between 0.1 and 0.25 quintal/hectare, between 0.25 and 9 quintal/hectare, between 0.5 and 8 quintal/hectare, between 0.75 and 7 quintal/hectare, between 1 and 6 quintal/hectare, between 1.5 and 5 quintal/hectare, between 2 and 4.5 quintal/hectare, between 2.5 and 4 quintal/hectare, or between 3 and 3.5 quintal/hectare higher than seed yield of a corn plant or seed without the four or more DM resistance QTLs or DM resistance alleles under a high DM stress condition.

In an aspect, this disclosure provides a DM resistant corn plant or seed comprising one or more, two or more, three or more, four or more, five or more, six or more, seven or more, eight or more, nine or more, ten or more, eleven or more, twelve or more, or thirteen introgressed DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01. In an aspect, a corn plant or seed disclosed herein comprises DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, or DM_9.01 obtainable, obtained, or introgressed from any one of corn lines CV357626 and CV368354.

In an aspect, a corn plant or seed disclosed herein comprises DM resistance QTLs DM_5.01, DM_6.02, and DM_7.01. In an aspect, a corn plant or seed disclosed herein comprises DM resistance QTLs DM_5.01, DM_6.02, DM_7.01, and DM_8.01. In an aspect, a corn plant or seed disclosed herein comprises DM resistance QTLs DM_5.01, DM_6.02, and DM_8.01. In an aspect, a corn plant or seed disclosed herein comprises DM resistance QTLs DM_6.02, DM_7.01, and DM_8.01. In an aspect, a corn plant or seed disclosed herein comprises DM resistance QTLs DM_1.01, DM_2.03, and DM_6.01. In an aspect, a corn plant or seed disclosed herein comprises DM resistance QTLs DM_1.01, DM_4.01, and DM_6.01. In an aspect, a corn plant or seed disclosed herein comprises one or more QTLs selected from the group consisting of DM resistance QTLs DM_1.01, DM_4.01, DM_6.01, DM_6.02, DM_8.01, and any combination thereof.

In another aspect, a corn plant or seed disclosed herein comprises DM resistance QTL DM_1.01 and at least one or more, two or more, three or more, five or more, six or more, seven or more, eight or more, nine or more, ten or more, eleven or more, or twelve DM resistance QTLs from the group consisting of DM_1.02, DM_2.01, DM_2.02, DM_2.03, DM_3.01, DM_4.01, DM_5.01, DM_6.01, DM_6.02, DM_7.01, DM_8.01, and DM_9.01.

In another aspect, a corn plant or seed disclosed herein comprises DM resistance QTL DM_1.02 and at least one or more, two or more, three or more, five or more, six or more, seven or more, eight or more, nine or more, ten or more, eleven or more, or twelve DM resistance QTLs from the group consisting of DM_1.01, DM_2.01, DM_2.02, DM_2.03, DM_3.01, DM_4.01, DM_5.01, DM_6.01, DM_6.02, DM_7.01, DM_8.01, and DM_9.01.

In another aspect, a corn plant or seed disclosed herein comprises DM resistance QTL DM_2.01 and at least one or more, two or more, three or more, five or more, six or more, seven or more, eight or more, nine or more, ten or more, eleven or more, or twelve DM resistance QTLs from the group consisting of DM_1.01, DM_1.02, DM_2.02, DM_2.03, DM_3.01, DM_4.01, DM_5.01, DM_6.01, DM_6.02, DM_7.01, DM_8.01, and DM_9.01.

In another aspect, a corn plant or seed disclosed herein comprises DM resistance QTL DM_2.02 and at least one or more, two or more, three or more, five or more, six or more, seven or more, eight or more, nine or more, ten or more, eleven or more, or twelve DM resistance QTLs from the group consisting of DM_1.01, DM_1.02, DM_2.01, DM_2.03, DM_3.01, DM_4.01, DM_5.01, DM_6.01, DM_6.02, DM_7.01, DM_8.01, and DM_9.01.

In another aspect, a corn plant or seed disclosed herein comprises DM resistance QTL DM_2.03 and at least one or more, two or more, three or more, five or more, six or more, seven or more, eight or more, nine or more, ten or more, eleven or more, or twelve DM resistance QTLs from the group consisting of DM_1.01, DM_1.02, DM_2.01, DM_2.02, DM_3.01, DM_4.01, DM_5.01, DM_6.01, DM_6.02, DM_7.01, DM_8.01, and DM_9.01.

In another aspect, a corn plant or seed disclosed herein comprises DM resistance QTL DM_3.01 and at least one or more, two or more, three or more, five or more, six or more, seven or more, eight or more, nine or more, ten or more, eleven or more, or twelve DM resistance QTLs from the group consisting of DM_1.01, DM_1.02, DM_2.01, DM_2.02, DM_2.03, DM_4.01, DM_5.01, DM_6.01, DM_6.02, DM_7.01, DM_8.01, and DM_9.01.

In another aspect, a corn plant or seed disclosed herein comprises DM resistance QTL DM_4.01 and at least one or more, two or more, three or more, five or more, six or more, seven or more, eight or more, nine or more, ten or more, eleven or more, or twelve DM resistance QTLs from the group consisting of DM_1.01, DM_1.02, DM_2.01, DM_2.02, DM_2.03, DM_3.01, DM_5.01, DM_6.01, DM_6.02, DM_7.01, DM_8.01, and DM_9.01.

In another aspect, a corn plant or seed disclosed herein comprises DM resistance QTL DM_5.01 and at least one or more, two or more, three or more, five or more, six or more, seven or more, eight or more, nine or more, ten or more, eleven or more, or twelve DM resistance QTLs from the group consisting of DM_1.01, DM_1.02, DM_2.01, DM_2.02, DM_2.03, DM_3.01, DM_4.01, DM_6.01, DM_6.02, DM_7.01, DM_8.01, and DM_9.01.

In another aspect, a corn plant or seed disclosed herein comprises DM resistance QTL DM_6.01 and at least one or more, two or more, three or more, five or more, six or more, seven or more, eight or more, nine or more, ten or more, eleven or more, or twelve DM resistance QTLs from the group consisting of DM_1.01, DM_1.02, DM_2.01, DM_2.02, DM_2.03, DM_3.01, DM_4.01, DM_5.01, DM_6.02, DM_7.01, DM_8.01, and DM_9.01.

In another aspect, a corn plant or seed disclosed herein comprises DM resistance QTL DM_6.02 and at least one or more, two or more, three or more, five or more, six or more, seven or more, eight or more, nine or more, ten or more, eleven or more, or twelve DM resistance QTLs from the group consisting of DM_1.01, DM_1.02, DM_2.01, DM_2.02, DM_2.03, DM_3.01, DM_4.01, DM_5.01, DM_6.01, DM_7.01, DM_8.01, and DM_9.01.

In another aspect, a corn plant or seed disclosed herein comprises DM resistance QTL DM_7.01 and at least one or more, two or more, three or more, five or more, six or more, seven or more, eight or more, nine or more, ten or more, eleven or more, or twelve DM resistance QTLs from the group consisting of DM_1.01, DM_1.02, DM_2.01, DM_2.02, DM_2.03, DM_3.01, DM_4.01, DM_5.01, DM_6.01, DM_6.02, DM_8.01, and DM_9.01.

In another aspect, a corn plant or seed disclosed herein comprises DM resistance QTL DM_8.01 and at least one or more, two or more, three or more, five or more, six or more, seven or more, eight or more, nine or more, ten or more, eleven or more, or twelve DM resistance QTLs from the group consisting of DM_1.01, DM_1.02, DM_2.01, DM_2.02, DM_2.03, DM_3.01, DM_4.01, DM_5.01, DM_6.01, DM_6.02, DM_7.01, and DM_9.01.

In another aspect, a corn plant or seed disclosed herein comprises DM resistance QTL DM_9.01 and at least one or more, two or more, three or more, five or more, six or more, seven or more, eight or more, nine or more, ten or more, eleven or more, or twelve DM resistance QTLs from the group consisting of DM_1.01, DM_1.02, DM_2.01, DM_2.02, DM_2.03, DM_3.01, DM_4.01, DM_5.01, DM_6.01, DM_6.02, DM_7.01, and DM_8.01.

In an aspect, a corn plant or seed comprising one or more DM resistance QTLs disclosed herein exhibits reduced premature death compared to a corn plant or seed lacking the one or more DM resistance QTLs under a high DM stress condition. In another aspect, a corn plant or seed comprising one or more DM resistance QTLs disclosed herein exhibit reduced stunted growth, reduced leaf chlorosis, reduced number of narrow leaves, reduced number of erect leaves, reduced number of shredded leaves, reduced number of failed cobs, reduced vegetative tissue in tassels, or any combination thereof, compared to a corn plant or seed lacking the one or more DM resistance QTL under a high DM stress condition.

In an aspect, this disclosure provides a method comprising providing a set of corn seeds comprising one or more DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01, to a person desirous of planting the set of corn seeds in a field plot. In an aspect, a method comprising a field plot that exhibits DM infection in any one of the previous one or more, two or more, three or more, four or more, five or more, six or more, seven or more, eight or more, nine or more, or ten or more planting seasons.

In an aspect, this disclosure provides a method comprising growing a population of corn plants in a field plot, which method comprising planting a population of corn seeds comprising one or more, two or more, three or more, four or more, five or more, six or more, seven or more, eight or more, nine or more, ten or more, eleven or more, twelve or more, or thirteen introgressed DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 in the field plot. In an aspect, a method disclosed herein comprises staggered planting. In another aspect, a corn plant or seed comprising a combination of one or more, two or more, three or more, four or more, five or more, six or more, seven or more, eight or more, nine or more, ten or more, eleven or more, twelve or more, or thirteen introgressed DM resistance QTLs selected from the group consisting of DM resistance QTLs DM_1.01, DM_1.02, DM_2.01, DM_2.02, DM_2.03, DM_3.01, DM_4.01, DM_5.01, DM_6.01, DM_6.02, DM_7.01, DM_8.01, and DM_9.01 exhibits increased seed yield under staggered planting conditions and a high DM stress condition compared to a corn plant or seed lacking the combination of DM resistance QTLs.

In an aspect, a method, a corn plant, or a corn seed disclosed herein is used in combination with one or more pesticides including, but not limited to, herbicides, fungicides (e.g. metalaxyl, fosetyl-Al, furalaxyl, Patafol, and benalaxyl), insecticides, microbiocides, nematicides, insect repellents, bactericides, and other substances used to control pests. In another aspect, a method, a corn plant, or a corn seed disclosed herein is used in combination with one or more triazoles, strobilurins, acylamino acids, pyrimidines, pyridines, arylphenyl ketones, amides, benzanilides, imidazoles, dinitrophenols, morpholines, phenylsulfamides and organophosphorus cpds, derivatives thereof and combinations thereof which may be applied as seed, foliar, drench, or drip treatments.

In an aspect, corn seeds disclosed herein are untreated. In another aspect, corn seeds disclosed herein can be subjected to various treatments. For example, the seeds can be treated to improve germination by priming the seeds or by disinfection to protect against seed borne pathogens. In another aspect, seeds can be coated with any available coating to improve, for example, plantability, seed emergence, and protection against seed borne pathogens. Seed coating can be any form of seed coating including, but not limited to, pelleting, film coating, and encrustments.

In a further aspect, the instant disclosure provides methods to enhance DM resistance by combining two or more DM resistance QTLs disclosed herein. In an aspect, the combined DM resistance QTLs have additive effects in providing DM resistance. In another aspect, the combined DM resistance QTLs have synergistic effects in providing DM resistance. In a further aspect, the combination of two or more, three or more, four or more, five or more, six or more, seven or more, eight or more, nine or more, ten or more, eleven or more, twelve or more, or thirteen DM resistance QTLs disclosed herein has no negative effects over corn physiology, resistance, yield, or performance in general. In a further aspect, the combination of two or more, three or more, four or more, five or more, six or more, seven or more, eight or more, nine or more, ten or more, eleven or more, twelve or more, or thirteen DM resistance QTLs disclosed herein has no statistically significant negative effects over corn physiology, resistance, yield, or performance in general.

In an aspect, this disclosure provides corn plant cells, tissues, and organs that are not reproductive material and do not mediate the natural reproduction of the plant. In another aspect, this disclosure also provides corn plant cells, tissues, and organs that are reproductive material and mediate the natural reproduction of the plant. In another aspect, this disclosure provides corn plant cells, tissues, and organs that cannot maintain themselves via photosynthesis. In another aspect, this disclosure provides somatic corn plant cells. Somatic cells, contrary to germline cells, do not mediate plant reproduction.

The provided cells, tissues and organs may be from seed, fruit, leaf, cotyledon, hypocotyl, meristem, embryos, endosperm, root, shoot, stem, pod, flower, inflorescence, stalk, pedicel, style, stigma, receptacle, petal, sepal, pollen, anther, filament, ovary, ovule, pericarp, phloem, bud, or vascular tissue. In another aspect, this disclosure provides a corn plant chloroplast. In a further aspect, this disclosure provides epidermal cells, stomata cell, trichomes, root hairs, a storage root, or a tuber. In another aspect, this disclosure provides a corn protoplast.

Skilled artisans understand that corn plants naturally reproduce via seeds, not via asexual reproduction or vegetative propagation. In an aspect, this disclosure provides corn endosperm. In another aspect, this disclosure provides corn endosperm cells. In a further aspect, this disclosure provides a male or female sterile corn plant, which cannot reproduce without human intervention.

In a further aspect, this disclosure provides processed products made from a disclosed corn plant or seed. Such products include, but are not limited to, meal, oil, plant extract, starch, or fermentation or digestion products. In another aspect, this disclosure also provides a corn meal, which is substantially oil free and which is produced using the oilseed of any of the plants disclosed herein. In another aspect, this disclosure also provides a method of providing a corn meal by crushing oilseed of any of the plants disclosed herein.

A corn plants or seed disclosed herein can also be genetically engineered to express various phenotypes of agronomic interest. Exemplary genes implicated in this regard include, but are not limited to, genes that confer resistance to pests or disease, genes that confer resistance or tolerance to an herbicide, genes that control male sterility, genes that affect abiotic stress resistance, and other genes and transcription factors that affect plant growth and agronomic traits such as yield, flowering, plant growth, or plant architecture.

Corn Transformation

A corn plant or seed disclosed herein can be genetically transformed. Numerous methods for plant transformation have been developed including biological and physical plant transformation protocols. See, for example, Mild, et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber, et al., "Vectors for Plant Transformation" in *Methods in Plant Molecular Biology and Biotechnology*, Glick B. R. and Thompson, J. E. Eds. (CRC Press, Inc., Boca Raton, 1993) pages 89-119.

A. *Agrobacterium*-Mediated Transformation—One method for introducing an expression vector into plants is based on the natural transformation system of *Agrobacterium*. See, e.g., Horsch, et al., A Simple and General Method for Transferring Genes into Plants. Science, 227:1229-1231 (1985). *A. tumefaciens* and *A. rhizogenes* are plant pathogenic soil bacteria which genetically transform plant cells. Descriptions of *Agrobacterium* vector systems and methods for *Agrobacterium*-mediated gene transfer are provided by, for example, U.S. Pat. No. 5,563,055, incorporated herein by reference in its entirety.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles. The expression vector is introduced into plant tissues with a biolistic device that accelerates the microprojectiles to speeds of 300 to 600 m/s which is sufficient to penetrate plant cell walls and membranes.

Another method for physical delivery of DNA to plants is sonication of target cells. Alternatively, liposome and spheroplast fusion have been used to introduce expression vectors into plants. Electroporation of protoplasts and whole cells and tissues can also be used.

Following transformation of corn target tissues, expression of the above-described selectable marker genes allows for preferential selection of transformed cells, tissues, and/or plants, using regeneration and selection methods well-known in the art.

The foregoing methods for transformation would typically be used for producing a transgenic variety. The transgenic variety could then be crossed with another (non-transformed or transformed) variety, in order to produce a new transgenic variety. Alternatively, a genetic trait which has been engineered into a particular corn line using the foregoing transformation techniques could be moved into another line using traditional backcrossing techniques that are well-known in the plant breeding arts. For example, a backcrossing approach could be used to move an engineered trait from a public, non-elite variety into an elite variety, or from a variety containing a foreign gene in its genome into a variety or varieties which do not contain that gene.

A corn plant or seed disclosed herein can also be produced by one or more genome engineering techniques or subject to further genomic editing. For example, one or more DM resistance alleles can be introduced into a DM susceptible background. Exemplary genome engineering techniques include meganucleases, zinc-finger nucleases, TALENs, and CRISPR/Cas9 systems. See, e.g., Gaj et al., ZFN, TALEN, and CRISPR/Cas-based methods for genome engineering. *Trends in Biotechnology*, 31:397-405 (2013).

Additional Breeding

A corn plant or seed disclosed herein can also be subject to additional breeding using one or more known methods in the art, e.g., pedigree breeding, recurrent selection, mass selection, and mutation breeding. Pedigree breeding starts with the crossing of two genotypes, such as a corn variety comprising a DM resistance QTL or DM resistance allele disclosed herein and another corn variety lacking such a locus. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-fertilization and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$, etc. After a sufficient amount of inbreeding, successive filial generations will serve to increase seed of the developed variety. The developed variety may comprise homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, a corn variety may be crossed with another variety to produce a first generation progeny plant. The first generation progeny plant may then be backcrossed to one of its parent varieties to create a BC1 or BC2. Progenies are selfed and selected so that the newly developed variety has many of the attributes of the recurrent parent and yet several of the desired attributes of the non-recurrent parent. This approach leverages the value and strengths of the recurrent parent for use in new corn varieties.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic line. A synthetic line is the resultant progeny formed by the intercrossing of several selected varieties.

Mass selection is another useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self-pollination, directed pollination could be used as part of the breeding program.

Mutation breeding can also be used to introduce new traits into a corn plant or seed disclosed herein. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, gamma rays (e.g. cobalt-60 or cesium-137), neutrons (product of nuclear fission by uranium-235 in an atomic reactor), beta radiation (emitted from radioisotopes such as phosphorus-32 or carbon-14), or ultraviolet radiation (from 2500 to 2900 nm)), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines). Transposon- or T-DNA-based mutagenesis is also encompassed by the present disclosure. Once a desired trait is observed through mutagenesis the trait may then be incorporated into existing germplasm by traditional breeding techniques.

In an aspect, the instant disclosure provides a doubled haploid corn plant and seed that comprise a DM resistance QTL or DM resistance marker alleles disclosed herein. The doubled haploid (DH) approach achieves isogenic plants in a shorter time frame, and is particularly useful for generating inbred lines and quantitative genetics studies. DH plants can be produced according to methods known in the art. For example, the initial step involves the haploidization of the plant which results in the production of a population comprising haploid seed. Non-homozygous lines are crossed with an inducer parent, resulting in the production of haploid seeds. Seeds that have haploid embryos, but normal triploid endosperm, advance to the second stage. After selecting haploid seeds from the population, the selected seeds undergo chromosome doubling to produce doubled haploid seeds. A spontaneous chromosome doubling in a cell lineage will lead to normal gamete production or the production of unreduced gametes from haploid cell lineages. Application of a chemical compound, such as colchicine, can be used to increase the rate of diploidization. Colchicine binds to tubulin and prevents its polymerization into microtubules, thus arresting mitosis at metaphase, can be used to increase the rate of diploidization, i.e. doubling of the chromosome number. These chimeric plants are self-pollinated to produce diploid (doubled haploid) seed. This DH seed is cultivated and subsequently evaluated and used in hybrid testcross production.

In an aspect, this disclosure also provides methods for making a substantially homozygous corn plant by producing or obtaining a seed from a cross of a corn plant comprising a DM resistance allele and another corn plant and applying doubled haploid methods to the $F_1$ seed or $F_1$ plant or to any successive filial generation.

Hybrid Production

In an aspect, this disclosure provides a hybrid corn plant or seed, and their production. The development of a corn hybrid in a corn plant breeding program generally involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrids. During the inbreeding process in corn, the vigor of the lines decreases. Vigor is restored when two different inbred lines are crossed to produce the hybrid. An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

Combining ability of a line, as well as the performance of the line, is a factor in the selection of improved corn lines that may be used as inbreds. Combining ability refers to a line's contribution as a parent when crossed with other lines to form hybrids. The hybrids formed for the purpose of selecting superior lines are designated test crosses. One way of measuring combining ability is by using breeding values. Breeding values are based on the overall mean of a number of test crosses. This mean is then adjusted to remove environmental effects and it is adjusted for known genetic relationships among the lines.

Hybrid seed production requires inactivation of pollen produced by the female parent. A pollination control system and effective transfer of pollen from one parent to the other offers improved plant breeding and an effective method for producing hybrid corn seed and plants. For example, a male sterility system can be used to produce corn hybrids.

Male sterility genes can increase the efficiency with which hybrids are made, in that they eliminate the need to physically emasculate the plant used as a female in a given cross. Where one desires to employ male-sterility systems, it may be beneficial to also utilize one or more male-fertility restorer genes. For example, where cytoplasmic male sterility (CMS) is used, hybrid crossing requires three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

Marker Detection

In an aspect, the present disclosure provides markers that are in linkage disequilibrium with at least one DM resistance QTL or DM resistance allele and can be used to select for DM resistance. Exemplary markers comprise SEQ ID NOs: 1-114 with their DM resistance alleles shown in Table 7. Markers within approximately 20 cM, 15 cM, 10 cM, 5 cM, 4 cM, 3 cM, 2 cM, 1 cM, 0.5 cM or less than 0.5 cM of these exemplary markers can also be identified from the known art.

Genetic markers are distinguishable from each other (as well as from the plurality of alleles of any one particular marker) on the basis of polynucleotide length and/or sequence. In general, any differentially inherited polymorphic trait (including a nucleic acid polymorphism) that segregates among progeny is a potential genetic marker.

As a set, polymorphic markers serve as a useful tool for fingerprinting plants to inform the degree of identity of lines or varieties. These markers can form a basis for determining associations with phenotype and can be used to drive genetic gain. The implementation of marker-assisted selection is dependent on the ability to detect and analyze underlying genetic differences between individuals.

Herein, nucleic acid analysis methods include, but are not limited to, PCR-based detection methods, microarray methods, mass spectrometry-based methods, and/or nucleic acid sequencing methods. In an aspect, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

A method of achieving such amplification employs the polymerase chain reaction (PCR) using primer pairs that are capable of hybridizing to the proximal sequences that define a polymorphism in its double-stranded form. Methods for typing DNA based on mass spectrometry have been disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981; and 7,250,252 all of which are incorporated herein by reference in their entireties. However, the compositions and methods of the present disclosure can be used in conjunction with any polymorphism typing method to type polymorphisms in genomic DNA samples. These genomic DNA samples used include but are not limited to genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Large-scale identification of single-feature polymorphisms in complex genomes. *Genome Research*, 13:513-523 (2003); Cui et al., Detecting single-feature polymorphisms using oligonucleotide array and robustified projection pursuit. *Bioinformatics*, 21:3852-3858 (2005)). On any one microarray, it is expected there will be a plurality of target sequences, which may represent genes and/or noncoding regions wherein each target sequence is represented by a series of overlapping oligonucleotides, rather than by a single probe. This platform provides for high throughput screening a plurality of polymorphisms. A single-feature polymorphism (SFP) is a polymorphism detected by a single probe in an oligonucleotide array, wherein a feature is a probe in the array. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616,464, employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group which can form a covalent cross-link with the other side chain member of the stem.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In an aspect, the SBE method uses four synthetic oligonucleotides. Two of the oligonucleotides serve as PCR primers and are complementary to sequence of the locus of genomic DNA which flanks a region containing the polymorphism to be assayed. Following amplification of the region of the genome containing the polymorphism, the PCR product is mixed with the third and fourth oligonucleotides (called extension primers) which are designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR, forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another aspect, the locus or loci of interest can be directly sequenced using nucleic acid sequencing technologies. Methods for nucleic acid sequencing are known in the art and include technologies provided by 454 Life Sciences (Branford, CT), Agencourt Bioscience (Beverly, MA), Applied Biosystems (Foster City, CA), LI-COR Biosciences (Lincoln, NE), NimbleGen Systems (Madison, WI), Illumina (San Diego, CA), Pac-Bio (Menlo Park, CA) and VisiGen Biotechnologies (Houston, TX). Such nucleic acid sequencing technologies comprise formats such as parallel bead arrays, sequencing by ligation, capillary electrophoresis, electronic microchips, "biochips," microarrays, parallel microchips, and single-molecule arrays, as reviewed by Service, Gene sequencing: the race for the $1000 genome. Science, 311:1544-46 (2006).

In an alternative aspect, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as BLAST, or even simple word processors.

Any of the aforementioned marker types can be employed in the context of this disclosure to identify chromosome intervals encompassing genetic element that contribute to superior agronomic performance (e.g., corn DM resistance).

The markers to be used in the methods of the present disclosure should preferably be diagnostic of origin in order for inferences to be made about subsequent populations. Experience to date suggests that SNP markers may be ideal for mapping because the likelihood that a particular SNP allele is derived from independent origins in the extant populations of a particular species is very low. As such, SNP markers appear to be useful for tracking and assisting introgression of QTL, particularly in the case of genotypes.

Association Mapping

In an aspect, the present disclosure also provides chromosome intervals, marker loci, germplasm for conducting genome-wide association mapping for DM resistance. Exemplary chromosome intervals and marker loci are provided in Tables 6 and 7. Genome-wide association mapping is conducted to find signals of association for various complex traits by surveying genetic variation in the whole genome.

Association mapping relies on chromosomal recombination opportunities over a large number of generations, in the history of a species, which allows the removal of association between a QTL and any marker not tightly linked to it, thus improving the rate of discovery of true association (Jannink and Walsh, *Quantitative Genetics, Genomics and Plant Breeding*, Kang, Ed. CAB International, pp. 59-68 (2002)).

An approach used to link phenotypic variation with genetic loci is marker-trait association (MTA) mapping, also known as linkage disequilibrium (LD) mapping. LD mapping emerged as an important gene mapping tool in the early 1990's with the advent of high-throughput genotyping technology, and has been widely used in human genetics to identify genes affecting human diseases. This approach was introduced and began to be adopted in plant gene mapping studies in early 2000's (Flint-Garcia et al., Structure of linkage disequilibrium in plants. *Annual Review of Plant Biology*, 54:357-374 (2003)).

LD mapping assumes that the main cause for LD is linkage that binds loci on the same chromosome together in transmission to next generation. However, due to recombination events accumulated over many generations in a natural population, each chromosome has been shuffled deeply, so that the chromosome has been broken into many tiny regions where loci remain transmitted together, but loci from different regions tend to transmit independently as if they were from different chromosomes. Chromosomal regions where loci are bound together in transmission are commonly known as LD blocks (Reich et al., Linkage disequilibrium in the human genome. Nature, 411:199-204 (2001)). LD mapping identifies genes of interest through genetic markers on the LD blocks where the genes are located. This is done by detecting significant associations between the markers and the traits that the genes affect with a sample of unrelated individuals or a sample of unrelated pedigrees that are genotyped on a selected set of markers covering candidate gene regions or the whole genome, and phenotyped on a set of traits of interest.

Compared with traditional linkage mapping methods that are typically based on artificial biparental segregating populations (e.g., $F_2$, BC, DH, RIL, etc.), LD mapping generally produces better mapping resolution, because of the smaller sizes of LD blocks. In addition, LD mapping is useful in identifying more than two functional alleles at associated markers in a germplasm. Further, LD mapping is efficient for evaluating natural populations.

Identification of QTL

In an aspect, markers, alleles, and haplotypes provided herein can be used for identifying QTLs associated with DM resistance. The statistical principles of QTL identification include penalized regression analysis, ridge regression, single marker analysis, complex pedigree analysis, Bayesian MCMC, identity-by-descent analysis, interval mapping, composite interval mapping (CIM), joint linkage mapping, and Haseman-Elston regression.

A QTL can act through a single gene mechanism or by a polygenic mechanism. In an aspect, the present disclosure provides a DM resistance QTL interval, where a DM resistance QTL (or multiple DM resistance QTLs) that segregates with an DM resistance trait is contained in the chromosomal interval. As used herein, when a QTL (or multiple QTLs) segregates with the DM resistance trait, it is referred to herein as a "DM resistance locus" (or "DM resistance loci").

In an aspect of this disclosure, the boundaries of a DM resistance QTL interval are drawn to encompass markers that will be linked to or associated with one or more DM resistance QTLs. In other words, a DM resistance QTL interval is drawn such that any marker that lies within that interval (including the terminal markers that define the boundaries of the interval) is genetically linked to or associated with the DM resistance QTL. Each interval comprises at least one DM resistance QTL, and furthermore, may indeed comprise more than one DM resistance QTL. Close proximity of multiple QTLs in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identifying the same QTL or two different QTLs. Regardless, knowledge of how many QTLs are in a particular interval is not necessary to make or practice the claimed subject matter.

In an aspect, the present disclosure also provides the mapping of additional SNP markers associated with or linked to one or more DM resistance QTLs disclosed herein. SNP markers are ideal for mapping because the likelihood that a particular SNP allele is derived from independent origins in the extant populations of a particular species is very low. As such, SNP markers are useful for tracking and assisting introgression of DM resistance QTLs, particularly in the case of haplotypes. In an aspect, a SNP marker is selected for mapping a DM resistance QTL based on the marker's genetic map position. In another aspect, a SNP marker is selected for mapping a DM resistance QTL based on the marker's physical map position.

The genetic linkage of additional marker molecules can be established by a gene mapping model such as, without limitation, the flanking marker model reported by Lander and Botstein, (Lander and Botstein, Mapping Mendelian Factors Underlying Quantitative Traits Using RFLP Linkage Maps. Genetics, 121:185-199 (1989)), and the interval mapping, based on maximum likelihood methods described by Lander and Botstein (supra), and implemented in the software package MAPMAKER/QTL (Lincoln and Lander, *Mapping Genes Controlling Quantitative Traits Using MAPMAKER/QTL*, Whitehead Institute for Biomedical Research, Massachusetts, (1990). Additional software includes Qgene, Version 2.23 (1996), Department of Plant Breeding and Biometry, 266 Emerson Hall, Cornell University, Ithaca, NY, the manual of which is herein incorporated by reference in its entirety).

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL). The LOD score essentially indicates how much more likely the data are to have arisen assuming the presence of a QTL versus in its absence. The LOD threshold value for avoiding a false positive with a given confidence, say 95%, depends on the number of markers and the length of the genome. Graphs indicating LOD thresholds are set forth in Lander and Botstein, (Lander and Botstein, Mapping Mendelian Factors Underlying Quantitative Traits Using RFLP Linkage Maps. Genetics, 121:185-199 (1989), and further described by Arns and Moreno-González, *Plant Breeding*, Hayward, Bosemark, Romagosa (eds.) Chapman & Hall, London, pp. 314-331 (1993).

Additional models can be used. Many modifications and alternative approaches to interval mapping have been reported, including the use of non-parametric methods (Kruglyak and Lander, A Nonparametric Approach for Mapping Quantitative Trait Loci. Genetics, 139:1421-1428 (1995), the entirety of which is herein incorporated by reference). Multiple regression methods or models can be also be used, in which the trait is regressed on a large number of markers (Jansen, *Biometrics in Plant Breed*, van Oijen, Jansen (eds.) Proceedings of the Ninth Meeting of the Eucarpia Section Biometrics in Plant Breeding, The Netherlands, pp. 116-124 (1994); Weber and Wricke, *Advances in Plant Breeding*, Blackwell, Berlin, 16 (1994)). Procedures combining interval mapping with regression analysis, whereby the phenotype is regressed onto a single putative QTL at a given marker interval, and at the same time onto a number of markers that serve as 'cofactors,' have been reported by Jansen and Stam, High Resolution of Quantitative Traits Into Multiple Loci via Interval Mapping. *Genetics*, 136:1447-1455 (1994) and Zeng, Precision Mapping of Quantitative Trait Loci. *Genetics*, 136:1457-1468 (1994). Generally, the use of cofactors reduces the bias and sampling error of the estimated QTL positions (Utz and Melchinger, *Biometrics in Plant Breeding*, van Oijen, Jansen (eds.) Proceedings of the Ninth Meeting of the Eucarpia Section *Biometrics in Plant Breeding*, The Netherlands, pp. 195-204 (1994)), thereby improving the precision and efficiency of QTL mapping (Zeng, Precision Mapping of Quantitative Trait Loci. *Genetics*, 136:1457-1468 (1994)). These models can be extended to multi-environment experiments to analyze genotype-environment interactions (Jansen et al., Genotype-by-environment interaction in genetic mapping of multiple quantitative trait loci. *Theoretical and Applied Genetics*, 91:33-37 (1995)).

In an aspect, this disclosure provides chromosomal intervals comprising QTL associated with DM resistance. In an aspect, the chromosome intervals of this disclosure are characterized by genomic regions including and flanked by any two of marker loci SEQ ID NOs: 5 to 8. In another aspect, the chromosome intervals of this disclosure are characterized by genomic regions including and flanked by marker loci SEQ ID NOs: 7 and 8. In another aspect, the chromosome intervals of this disclosure are characterized by genome regions including and flanked by any two of marker loci SEQ ID NOs: 12 to 14. In another aspect, the chromosome intervals of this disclosure are characterized by genomic regions including and flanked by any two of marker loci SEQ ID NOs: 18 to 20. In another aspect, the chromosome intervals of this disclosure are characterized by genomic regions including and flanked by any two of marker loci SEQ ID NOs: 25 to 27. In another aspect, the chromosome intervals of this disclosure are characterized by genomic regions including and flanked by any two of marker loci SEQ ID NOs: 29 to 31. In another aspect, the chromosome intervals of this disclosure are characterized by genomic regions including and flanked by any two of marker loci SEQ ID NOs: 34 to 36. In another aspect, the chromosome intervals of this disclosure are characterized by genomic regions including and flanked by any two of marker loci SEQ ID NOs: 39 to 45. In another aspect, the chromosome intervals of this disclosure are characterized by genomic regions including and flanked by any two of marker loci SEQ ID NOs: 49 to 51. In another aspect, the chromosome intervals of this disclosure are characterized by genomic regions including and flanked by marker loci SEQ ID NOs: 58 and 59. In another aspect, the chromosome intervals of this disclosure are characterized by genomic regions including and flanked by marker loci SEQ ID NOs: 63 and 64. In another aspect, the chromosome intervals of this disclosure are characterized by genomic regions including and flanked by any two of marker loci SEQ ID NOs: 77 to 80. In another aspect, the chromosome intervals of this disclosure are characterized by genomic regions including and flanked by any two of marker loci SEQ ID NOs: 99 to 106.

This disclosure also provides multiple markers linked to or associated with a DM resistance QTL, for example, the markers having the sequence selected from SEQ ID NOs: 1-114. This disclosure therefore provides plants comprising a nucleic acid molecule selected from the group consisting of SEQ ID NOs: 1-114, fragments thereof, or complements thereof. The present disclosure further provides a plant comprising alleles of the chromosome interval linked to or associated with DM resistance or fragments and complements thereof as well as any plant comprising any combination of one or more DM resistance alleles of marker loci selected from the group consisting of SEQ ID NOs: 1-114. Plants provided by this disclosure may be homozygous or heterozygous for such alleles.

The compositions and methods of the present disclosure can be utilized to guide MAS or breeding corn varieties with a desired complement (set) of allelic forms of chromosome intervals associated with superior agronomic performance (e.g. DM resistance). Any of the disclosed marker alleles can be introduced into a corn line via introgression, by traditional breeding (or introduced via transformation, or both) to yield a corn plant with superior agronomic performance. The number of alleles associated with DM resistance that can be introduced or be present in a corn plant of the present disclosure ranges from 1 to the number of alleles disclosed herein, each integer of which is incorporated herein as if explicitly recited.

MAS using additional markers flanking either side of the DNA locus provide further efficiency because an unlikely double recombination event would be needed to simultaneously break linkage between the locus and both markers. Moreover, using markers tightly flanking a locus, one skilled in the art of MAS can reduce linkage drag by more accurately selecting individuals that have less of the potentially deleterious donor parent DNA. Any marker linked to or among the chromosome intervals described herein can thus find use within the scope of this disclosure.

These marker loci can be introgressed into any desired genomic background, germplasm, plant, line, variety, etc., as part of an overall MAS breeding program designed to enhance DM resistance. This disclosure also provides QTL intervals that can be used in MAS to select plants that demonstrate DM resistance. Similarly, QTL intervals can also be used to counter-select plants that are lacking DM resistance. By identifying plants lacking a desired marker locus, plants lacking DM resistance can be identified and selected or eliminated from subsequent crosses.

The present disclosure also extends to a method of making a progeny corn plant and the resulting progeny corn plants. In an aspect, the method comprises crossing a first parent corn plant with a second corn plant and growing the corn plant parent under plant growth conditions to yield corn plant progeny. Methods of crossing and growing a corn plant are well within the ability of those of ordinary skill in the art. Such corn plant progeny can be assayed for alleles associated with DM resistance as disclosed herein and, thereby, the desired progeny selected. Such progeny plants or seed thereof can be sold commercially for corn production, used for food, processed to obtain a desired constituent of the corn, or further utilized in subsequent rounds of breeding. At least one of the first or second corn plants may be a corn plant of the present disclosure in that it comprises at least one of the allelic forms of the markers of the present disclosure, such that the progeny are capable of inheriting the allele.

By providing the positions in the corn genome of QTL intervals and the associated markers within those intervals, this disclosure also allows one skilled in the art to identify and use other markers within the intervals disclosed herein or linked to or associated with the intervals disclosed herein. Having identified such markers, these intervals can be readily identified from public linkage maps.

Closely linked markers flanking the locus of interest that have alleles in linkage disequilibrium (LD) with a DM resistance allele at that locus may be effectively used to select for progeny plants with DM resistance. Thus, the markers described herein, such as those listed in Table 7, as well as other markers genetically linked to or associated with the same chromosome interval, may be used to select for a corn plant or seed with DM resistance. Often, a set of these markers will be used, (e.g., 2 or more, 3 or more, 4 or more, 5 or more) in the flanking regions of the locus. Optionally, as described above, a marker flanking or within the actual locus may also be used. The parents and their progeny may be screened for these sets of markers, and the markers that are polymorphic between the two parents used for selection. In an introgression program, this allows for selection of the gene or locus genotype at the more proximal polymorphic markers and selection for the recurrent parent genotype at the more distal polymorphic markers.

The choice of markers actually used to practice this disclosure is not limited and can be any marker that is genetically linked to or associated with the QTL intervals as described in Table 6, including markers within approximately 20 cM, 15 cM, 10 cM, 5 cM, 4 cM, 3 cM, 2 cM, 1 cM, 0.5 cM or less than 0.5 cM of the intervals provided herein. Examples include, but are not limited to, any marker selected from SEQ ID NOs: 1-114. Furthermore, since there are many different types of marker detection assays known in the art, it is not intended that the type of marker detection assay used to practice this disclosure be limited in any way.

Marker Assisted Selection (MAS) Breeding

Marker loci and their DM resistance alleles provided herein can be used in MAS breeding of DM resistance. The more tightly linked a marker is with a DNA locus influencing a phenotype (e.g., DM resistance), the more reliable the marker is in MAS, as the likelihood of a recombination event unlinking the marker and the locus decreases. Markers containing the causal mutation for a trait, or that are within the coding sequence of a causative gene, are ideal as no recombination is expected between them and the sequence of DNA responsible for the phenotype. However, markers do not need to contain or correspond to causal mutations in order to be effective in MAS. In fact, most MAS breeding only uses markers linked to or associated with a causal mutation.

Developing molecular markers in crop species can increase efficiency in plant breeding through MAS. Genetic markers are used to identify plants that contain a desired genotype at one or more loci, and that are expected to transfer the desired genotype, along with a desired phenotype to their progeny. Genetic markers can be used to identify plants containing a desired genotype at one locus, or at several unlinked or linked loci (e.g., a haplotype), and that would be expected to transfer the desired genotype, along with a desired phenotype to their progeny. The present disclosure provides the means to identify plants that exhibit DM resistance by identifying chromosomal intervals and genetic markers associated with drought tolerance.

In general, MAS uses polymorphic markers that have been identified as having a significant likelihood of co-segregation with a desired trait. Such markers are presumed to map near a gene or genes that give the plant its desired phenotype, and are considered indicators for the desired trait.

Identification of plants or germplasm that include a marker locus or marker loci linked to a desired trait or traits provides a basis for performing MAS. Plants that comprise favorable markers or favorable alleles are selected for, while plants that comprise markers or alleles that are negatively correlated with the desired trait can be selected against. Desired markers and/or alleles can be introgressed into plants having a desired (e.g., elite or exotic) genetic background to produce an introgressed plant or germplasm having the desired trait. In an aspect, it is contemplated that a plurality of markers for desired traits are sequentially or simultaneous selected and/or introgressed. The combinations of markers that are selected for in a single plant is not limited, and can include any combination of markers disclosed herein or any marker linked to the markers disclosed herein, or any markers located within the QTL intervals defined herein.

In an aspect, a first corn plant or germplasm exhibiting a desired trait (the donor, e.g., a DM resistant corn) can be crossed with a second corn plant or germplasm (the recipient, e.g., an elite or exotic corn, depending on characteristics that are desired in the progeny) to create an introgressed corn plant or germplasm as part of a breeding program. In an aspect, the recipient plant can also contain one or more loci associated with one or more desired traits, which can be qualitative or quantitative trait loci. In another aspect, the recipient plant can contain a transgene.

In an aspect, the recipient corn plant or germplasm will typically lack desired traits as compared to the first corn plant or germplasm, while the introgressed corn plant or germplasm will display improved traits as compared to the second plant or germplasm. An introgressed corn plant or germplasm produced by these methods are also a feature of this disclosure.

MAS is a powerful shortcut to select for desired phenotypes and for introgressing desired traits into cultivars (e.g., introgressing desired traits into elite lines). MAS is easily adapted to high throughput molecular analysis methods that can quickly screen large numbers of plant or germplasm genetic material for the markers of interest and is much more cost effective than cultivating and observing plants for visible traits.

Introgression of DM Resistance QTLs Using MAS

The instant disclosure provides methods and markers for introgressing a DM resistance QTL disclosed herein into a new corn variety using MAS.

Multiple methods are available to achieve the introgression. For example, introgression of a desired allele at a specified locus can be transmitted to at least one progeny via a cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background.

The introgression of one or more desired loci from a donor line into another line is achieved via repeated backcrossing to a recurrent parent accompanied by selection to retain one or more loci from the donor parent. Markers associated with drought tolerance are assayed in progeny and those progeny with one or more desired markers are selected for advancement. In another aspect, one or more markers can be assayed in the progeny to select for plants with the genotype of the agronomically elite parent.

It is generally anticipated that trait introgression activities will require more than one generation, wherein progeny are crossed to the recurrent (agronomically elite) parent or selfed. Selections are made based on the presence of one or more markers linked to drought tolerance and can also be made based on the recurrent parent genotype, wherein screening is performed on a genetic marker and/or phenotype basis. In another aspect, markers of this disclosure can be used in conjunction with other markers, ideally at least one on each chromosome of the corn genome, to track the introgression of drought tolerance into elite germplasm. In another aspect, QTL intervals associated with drought tolerance will be useful in conjunction with SNP molecular markers of the present disclosure to combine quantitative and qualitative drought tolerance in the same plant. It is within the scope of this disclosure to utilize the methods and compositions for trait integration of drought tolerance. It is contemplated by the inventors that the present disclosure will be useful for developing commercial varieties with drought tolerance and other agronomically elite phenotypes.

EXAMPLES

Example 1. Identification of QTLs Associated with Downy Mildew Resistance in Biparental Mapping Populations Biparental mapping populations are constructed to investigate the genetic basis of downy mildew (DM) resistance in corn. Plant phenotyping is performed in field plots. Plants infected with *Peronosclerospora philippinensis*, *Peronosclerospora maydis*, or *Peronosclerospora sorghi* are planted as a point source of inoculums in the field 20 days prior to planting experimental plants. Downy mildew (DM) disease resistance is measured by counting the percentage of infected experimental plants per plot at 40 days after planting (Table 1).

TABLE 1

Description of DM rating scale.

| | |
|---|---|
| <5% | Highly Resistant |
| 5-15% | Moderately Resistant |
| 15-35% | Intermediate |
| 35-45% | Moderately Susceptible |
| >45% | Highly Susceptible |

Six mapping populations are shown in Table 2. These populations include two DM resistant parent lines, CV357626 and CV368354, which are used as male and female parents, respectively. Each mapping population is measured for DM resistance in two field replicates and the basic statistics are shown in Table 3. A standard statistical model is used to estimate the variance components and to compute the heritability ($H^2$) for DM phenotype. The heritability ($H^2$) is 0.68-0.84 for all mapping populations (Table 4) indicating that the observed DM phenotype is attributed to genetic variation.

Plants from all mapping populations are genotyped using SNP markers that collectively span each chromosome in the maize genome. Marker-trait association studies are performed to identify DM resistance QTLs and their associated markers using both single-marker analysis (SMA) and composite interval mapping (CIM).

TABLE 2

Mapping populations.

| Mapping Population | Cross | DM Resistant Parent | DM Susceptible Parent | Population Type | Population Size |
|---|---|---|---|---|---|
| A | CV374702/CV357626 | CV357626 | CV374702 | $F_3$ | 182 |
| B | CV374480/CV357626 | CV357626 | CV374480 | $F_3$ | 420 |
| C | CV371812/CV357626 | CV357626 | CV371812 | $F_3$ | 350 |
| D | CV368354/CV371792 | CV368354 | CV371792 | $F_3$ | 530 |
| E | CV368354/CV364290 | CV368354 | CV364290 | $F_3$ | 721 |
| F | CV368354/CV364209 | CV368354 | CV364209 | $F_3$ | 455 |

TABLE 3

Basic statistics for each mapping population

| Mapping Population | Replicate ID | Mean DM score (%) | Number of Lines | Standard Deviation |
|---|---|---|---|---|
| A | combined | 78.7 | 422 | 25.9 |
| | 1 | 77.5 | 212 | 26.4 |
| | 2 | 79.9 | 210 | 25.3 |
| B | combined | 17.1 | 868 | 14.1 |
| | 1 | 15.3 | 434 | 13.5 |
| | 2 | 18.9 | 434 | 14.5 |
| C | combined | 29.6 | 728 | 18.5 |
| | 1 | 30.3 | 364 | 18.4 |
| | 2 | 29 | 364 | 18.7 |
| D | Combined | 46.3 | 1173 | 22.7 |
| | 1 | 46.5 | 592 | 22.7 |
| | 2 | 46.1 | 581 | 22.7 |
| E | Combined | 33 | 1614 | 22.4 |
| | 1 | 33.3 | 809 | 22.5 |
| | 2 | 32.6 | 805 | 22.3 |
| F | Combined | 43.7 | 1054 | 23.3 |
| | 1 | 44 | 536 | 22.8 |
| | 2 | 43.3 | 518 | 23.9 |

TABLE 4

Variance component estimation and heritability analysis.

| Mapping Population | Genetic variance | Residue variance | Total phenotypic variance | $H^2$ |
|---|---|---|---|---|
| A | 269.9 | 56.3 | 326.2 | 0.83 |
| B | 87.8 | 41.6 | 129.3 | 0.68 |
| C | 205.9 | 64.3 | 270.2 | 0.76 |
| D | 311.38 | 77.44 | 388.82 | 0.8 |
| E | 272.84 | 65.23 | 338.07 | 0.81 |
| F | 339.56 | 62.96 | 402.52 | 0.84 |

Example 2. Identification of DM Resistance QTLs Via Composite Interval Mapping

A composite interval mapping (CIM) approach is taken to identify DM resistance QTL intervals based on the phenotyping and genotyping data collected in Example 1. For each marker, the thresholds of likelihood ratio between full and null models for CIM are based on 1000 random permutation tests (Churchill and Doerg, *Genetics*, 138(3):963-71 (1994)). The composite interval mapping (CIM) analysis revealed several strong QTLs associated with DM resistance. The QTLs are confirmed in multiple genetic backgrounds and summarized in Table 5.

In Table 5, genetic positions are represented in cM with position zero being the first (most distal) marker known at the beginning of the chromosome on Monsanto's internal consensus genetic map. Each row of Table 5 provides mapping population ID, number of SNP markers genotyped (#Mk), resistant parent, chromosome position, the peak of the likelihood ratio corresponding to DM resistance, left and right flanking positions, p-value, additive effect, and the phenotypic variance ($R^2$) of individual QTL or Total QTLs.

TABLE 5

CIM results from all mapping populations.

| Mapping population | #Mk | Resistant Parent | Chr | QTL Positions (cM) Peak | Left Flank | Right Flank | p-value | Additive | QTL R² | Total R² |
|---|---|---|---|---|---|---|---|---|---|---|
| A | 132 | CV357626 | 6 | 96.5 | 87.2 | 102.5 | 0.05 | 7.6 | 0.1 | 0.55 |
| A | 132 | CV357626 | 3 | 90.5 | 81.2 | 100.5 | 0.01 | 12.8 | 0.27 | 0.58 |
| B | 156 | CV357626 | 1 | 74 | 63 | 79.1 | 0.01 | 3.4 | 0.061 | 0.33 |
| B | 156 | CV357626 | 2 | 43.6 | 38.6 | 52.2 | 0.01 | 3 | 0.048 | 0.363 |
| C | 143 | CV357626 | 1 | 60.1 | 51.1 | 68.1 | 0.01 | 7.1 | 0.114 | 0.625 |
| C | 143 | CV357626 | 2 | 36.6 | 24.4 | 39.6 | 0.01 | 4.7 | 0.052 | 0.602 |
| C | 143 | CV357626 | 4 | 160.1 | 152.3 | 170.8 | 0.01 | 9.7 | 0.17 | 0.6 |
| C | 143 | CV357626 | 6 | 91.2 | 81.3 | 103.2 | 0.01 | 6.4 | 0.095 | 0.613 |
| D | 186 | CV368354 | 2 | 48.8 | 35.2 | 57.3 | 0.01 | 9.9 | 0.15 | 0.24 |
| D | 186 | CV368354 | 2 | 209.3 | 195.7 | 212 | 0.01 | 6.7 | 0.07 | 0.21 |
| D | 186 | CV368354 | 5 | 138.5 | 125.4 | 142.2 | 0.05 | 4.3 | 0.05 | 0.21 |
| D | 186 | CV368354 | 8 | 98.4 | 68.1 | 108.4 | 0.01 | 8.7 | 0.12 | 0.31 |
| D | 186 | CV368354 | 9 | 75.7 | 65.7 | 80.2 | 0.01 | 6.8 | 0.06 | 0.25 |
| E | 186 | CV368354 | 2 | 207.7 | 195.7 | 211.7 | 0.01 | 8.3 | 0.12 | 0.55 |
| E | 186 | CV368354 | 2 | 50.8 | 39.2 | 57.3 | 0.01 | 5.9 | 0.05 | 0.53 |
| E | 186 | CV368354 | 8 | 84.1 | 75.3 | 102.4 | 0.01 | 8.1 | 0.11 | 0.52 |
| E | 186 | CV368354 | 9 | 87.7 | 77.2 | 97.5 | 0.01 | 8.2 | 0.11 | 0.53 |
| F | 149 | CV368354 | 2 | 63.3 | 53.3 | 72.3 | 0.05 | 7.5 | 0.08 | 0.56 |
| F | 149 | CV368354 | 6 | 58.1 | 39.3 | 59.1 | 0.01 | 11.1 | 0.14 | 0.5 |
| F | 149 | CV368354 | 8 | 102.6 | 92.6 | 112.6 | 0.01 | 8.8 | 0.11 | 0.53 |
| F | 149 | CV368354 | 9 | 75.9 | 70.9 | 80.9 | 0.1 | 5 | 0.07 | 0.57 |

*p-value is based on 1,000 permutation tests

Example 3. Fine-Mapping Downy Mildew Resistance QTLs Via Joint Linkage Mapping As shown in Examples 1 and 2, QTLs associated with DM resistance are identified from three bi-parental mapping populations (A, B, and C) by crossing one resistant line (CV357626) with three different susceptible lines. These three mapping populations are merged for joint linkage mapping. Additional QTLs associated with DM resistance are identified from three bi-parental mapping populations (D, E, and F) by crossing one resistant line (CV368354) with three different susceptible lines. These three mapping populations are also merged for joint linkage mapping. The most informative markers are selected with bootstrapping probabilities from 3000 bootstrapping samples. Thirteen QTLs are identified through the joint linkage fine mapping. These thirteen QTLs are designated as DM_1.01, DM_1.02, DM_2.03, DM_3.01, DM_4.01, DM_6.01, DM_2.01, DM_2.02, DM_5.01, DM_6.02, DM_7.01, DM_8.01 and DM_9.01 (Table 7).

TABLE 6

Fine-mapping of DM resistance QTL by JLM.

| Chr | JLM interval CV357626 (cM) | Left Flank Marker | Right Flank Marker | IBM2008 Map (IcM) | QTL Designation |
|---|---|---|---|---|---|
| 1 | 54-69 | SEQ ID NO: 5 | SEQ ID NO: 8 | 158.5-196 | DM_1.01 |
| 1 | 68.4-73.2 | SEQ ID NO: 7 | SEQ ID NO: 8 | 194.6-206.8 | DM_1.02 |
| 2 | 21.4-33.6 | SEQ ID NO: 12 | SEQ ID NO: 14 | 49.7-88.2 | DM_2.03 |
| 3 | 80.2-92.6 | SEQ ID NO: 29 | SEQ ID NO: 31 | 208.6-318.2 | DM_3.01 |
| 4 | 152.7-162.3 | SEQ ID NO: 34 | SEQ ID NO: 36 | 525.8-572.3 | DM_4.01 |
| 6 | 85.1-90.7 | SEQ ID NO: 58 | SEQ ID NO: 59 | 374.1-389.9 | DM_6.01 |

TABLE 6-continued

Fine-mapping of DM resistance QTL by JLM.

| Chr | JLM interval CV368354 (cM) | Left Flank Marker | Right Flank Marker | IBM2008 Map (IcM) | QTL Designation |
|---|---|---|---|---|---|
| 2 | 46.8-57 | SEQ ID NO: 18 | SEQ ID NO: 20 | 138.6-169.1 | DM_2.01 |
| 2 | 200.8-212 | SEQ ID NO: 25 | SEQ ID NO: 27 | 655.6-709.5 | DM_2.02 |
| 5 | 125.4-142.2 | SEQ ID NO: 39 | SEQ ID NO: 45 | 432.3-491.7 | DM_5.01 |
| 6 | 39.7-52.7 | SEQ ID NO: 49 | SEQ ID NO: 51 | 204.2-239.6 | DM_6.02 |
| 7 | 66.4-78.5 | SEQ ID NO: 63 | SEQ ID NO: 64 | 209.6-284.6 | DM_7.01 |
| 8 | 82.6-89.4 | SEQ ID NO: 77 | SEQ ID NO: 80 | 288.3-313.8 | DM_8.01 |
| 9 | 67.9-80.7 | SEQ ID NO: 99 | SEQ ID NO: 106 | 226.5-308.9 | DM_9.01 |

Example 4. Identification of Molecular Markers Associated with DM Resistance Via Single-Marker Analysis (SMA)

Single-marker analysis (SMA) is performed to identify markers associated with DM resistance using the genotypic data from Example 1. For each marker, the thresholds (p-value) for SMA are based on 10,000 random permutation tests (Churchill and Doerg, *Genetics,* 138(3):963-71 (1994)).

In total, 114 SNP markers are identified to be linked to DM resistance (Table 7). Table 7 also provides the effect estimates on DM rating score for each marker linked to DM resistance. Further provided are the SEQ ID NO of the marker, chromosome position, marker position on Monsanto's internal consensus genetic map, corresponding marker position on the Neighbors 2008 maize genetic map (publicly available at Maize GDB website), genetic source of favorable allele, resistant allele SNP, susceptible allele SNP, the estimated effect that the marker polymorphism had on the DM rating score, and p-value based on 10,000 random permutation tests. For example, SEQ ID NO: 1 is associated with a 4.28% reduction in DM rating score by one copy of the resistant allele. However, one of skill in the art recognizes that a "resistant" allele at one locus may be a "susceptible" allele in a different genetic background. Thus, this disclosure is not limited to the "resistant" and "susceptible" alleles exemplified herein.

The primer sequences for amplifying exemplary SNP marker loci linked to the DM and the probes used to genotype the corresponding SNP sequences are provided in Table 8. In an illustrative example, SNP marker SEQ ID NO: 1 can be amplified using the primers described in Table 5 as SEQ ID NO: 115 (forward primer) and SEQ ID NO: 229 (reverse primer), and detected with probes indicated as SEQ ID NO: 343 (Probe 1) and SEQ ID NO: 457 (Probe 2).

One of skill in the art recognizes that sequences to either side of the given primers can be used in place of the given primers, so long as the primers can amplify a region that includes the allele to be detected. The precise probe used for detection can vary, e.g., any probe that can identify the region of a marker amplicon to be detected can be substituted for those probes exemplified herein. Configuration of the amplification primers and detection probes can also be varied. Thus, this disclosure is not limited to the primers, probes, or marker sequences specifically listed in the tables.

TABLE 7

Estimate effects of markers linked to DM resistance from all mapping populations by SMA.

| SEQ ID NO. | Chromosome | MON Map (cM) | IBM2008 Map (IcM) | Genetic Source of Favorable Allele | Exemplary Resistant Allele | Exemplary Susceptible Allele | Single Allele Effect | Permutation Testing Probability |
|---|---|---|---|---|---|---|---|---|
| 1 | 1 | 42.8 | 124.7 | CV357626 | A | G | 4.28 | 0.001 |
| 2 | 1 | 46.7 | 137 | CV357626 | G | A | 3.04 | 0.001 |
| 3 | 1 | 47.5 | 139.8 | CV357626 | C | T | 4.95 | 0.001 |
| 4 | 1 | 50.1 | 146.9 | CV357626 | C | G | 5.58 | 0.001 |
| 5 | 1 | 54 | 158.5 | CV357626 | G | A | 3.29 | 0.001 |
| 6 | 1 | 64.1 | 184.3 | CV357626 | G | A | 3.74 | 0.001 |
| 7 | 1 | 68.4 | 194.6 | CV357626 | A | G | 7.63 | 0.001 |
| 8 | 1 | 69 | 196 | CV357626 | T | C | 3.41 | 0.001 |
| 9 | 1 | 79.3 | 223.2 | CV357626 | T | C | 2.76 | 0.001 |
| 10 | 1 | 82.7 | 242.2 | CV357626 | A | G | 7.98 | 0.001 |
| 11 | 1 | 88.2 | 270.6 | CV357626 | C | T | 2.80 | 0.001 |
| 12 | 2 | 21.4 | 49.7 | CV357626 | T | A | 3.38 | 0.001 |
| 13 | 2 | 32.2 | 82.8 | CV357626 | G | A | 5.70 | 0.001 |
| 14 | 2 | 33.6 | 88 | CV357626 | G | A | 4.21 | 0.001 |
| 15 | 2 | 40.6 | 111.8 | CV368354 | A | G | 5.18 | 0.001 |
| 16 | 2 | 43 | 122.1 | CV368354 | A | G | 5.95 | 0.001 |
| 17 | 2 | 44.2 | 127.2 | CV368354 | A | T | 4.21 | 0.001 |
| 18 | 2 | 46.8 | 138.6 | CV368354 | G | A | 7.15 | 0.001 |
| 19 | 2 | 52.3 | 156.9 | CV368354 | A | C | 6.26 | 0.001 |
| 20 | 2 | 57 | 169.1 | CV368354 | A | G | 6.23 | 0.001 |
| 21 | 2 | 58.3 | 172.6 | CV368354 | G | T | 6.23 | 0.001 |
| 22 | 2 | 60.6 | 179.5 | CV368354 | T | A | 8.43 | 0.001 |
| 23 | 2 | 184.4 | 598.4 | CV368354 | C | A | 5.58 | 0.001 |
| 24 | 2 | 195.7 | 639 | CV368354 | C | A | 6.24 | 0.001 |
| 25 | 2 | 200.8 | 655.6 | CV368354 | T | G | 5.11 | 0.001 |
| 26 | 2 | 202.3 | 659.5 | CV368354 | T | C | 5.11 | 0.001 |
| 27 | 2 | 212 | 709.5 | CV368354 | A | G | 5.51 | 0.001 |
| 28 | 2 | 212.1 | 709.6 | CV368354 | G | A | 6.80 | 0.001 |
| 29 | 3 | 80.2 | 208.6 | CV357626 | A | G | 13.13 | 0.001 |
| 30 | 3 | 86.5 | 276.6 | CV357626 | G | C | 12.67 | 0.001 |
| 31 | 3 | 92.6 | 318.2 | CV357626 | A | G | 12.94 | 0.001 |
| 32 | 3 | 110.9 | 382.6 | CV357626 | G | A | 12.33 | 0.001 |
| 33 | 4 | 145.3 | 467.1 | CV357626 | C | A | 6.30 | 0.001 |
| 34 | 4 | 153.2 | 527 | CV357626 | C | T | 6.61 | 0.001 |
| 35 | 4 | 157.1 | 550.2 | CV357626 | A | G | 7.86 | 0.001 |
| 36 | 4 | 162.3 | 572.3 | CV357626 | G | T | 8.19 | 0.001 |
| 37 | 4 | 165.8 | 579.6 | CV357626 | T | A | 8.50 | 0.001 |
| 38 | 4 | 176.7 | 615.8 | CV357626 | G | A | 5.05 | 0.001 |
| 39 | 5 | 125.4 | 432.3 | CV368354 | C | T | 2.10 | 0.049 |
| 40 | 5 | 126.5 | 437.9 | CV368354 | T | A | 2.17 | 0.044 |
| 41 | 5 | 131.3 | 460.4 | CV368354 | T | A | 3.36 | 0.007 |
| 42 | 5 | 131.9 | 462.5 | CV368354 | T | C | 3.62 | 0.003 |
| 43 | 5 | 132.1 | 463.2 | CV368354 | C | T | 4.11 | 0.001 |
| 44 | 5 | 132.8 | 465.5 | CV368354 | C | T | 3.97 | 0.002 |
| 45 | 5 | 133.1 | 466.6 | CV368354 | A | G | 4.05 | 0.001 |
| 46 | 6 | 25.2 | 147.9 | CV368354 | T | C | 5.71 | 0.001 |
| 47 | 6 | 34 | 187.7 | CV368354 | A | G | 8.03 | 0.001 |
| 48 | 6 | 38.6 | 201.1 | CV368354 | G | A | 8.95 | 0.001 |
| 49 | 6 | 39.7 | 204.2 | CV368354 | G | A | 10.40 | 0.001 |
| 50 | 6 | 39.8 | 204.5 | CV368354 | A | G | 10.12 | 0.001 |
| 51 | 6 | 52.7 | 239.7 | CV368354 | T | C | 9.27 | 0.001 |
| 52 | 6 | 53.9 | 242.7 | CV368354 | G | A | 9.25 | 0.001 |
| 53 | 6 | 54.1 | 243.2 | CV368354 | C | A | 9.32 | 0.001 |
| 54 | 6 | 59.4 | 267.1 | CV368354 | A | G | 10.04 | 0.001 |
| 55 | 6 | 70 | 324.7 | CV368354 | G | A | 8.82 | 0.001 |

TABLE 7-continued

Estimate effects of markers linked to DM resistance from all mapping populations by SMA.

| SEQ ID NO. | Chromosome | MON Map (cM) | IBM2008 Map (IcM) | Genetic Source of Favorable Allele | Exemplary Resistant Allele | Exemplary Susceptible Allele | Single Allele Effect | Permutation Testing Probability |
|---|---|---|---|---|---|---|---|---|
| 56 | 6 | 74.3 | 341.9 | CV357626 | G | A | 5.02 | 0.001 |
| 57 | 6 | 74.7 | 343.2 | CV368354 | G | A | 6.83 | 0.001 |
| 58 | 6 | 85.1 | 374.2 | CV357626 | C | A | 7.45 | 0.001 |
| 59 | 6 | 87.2 | 380.8 | CV357626 | C | G | 5.21 | 0.001 |
| 60 | 6 | 97.8 | 417.4 | CV357626 | C | T | 8.06 | 0.001 |
| 61 | 6 | 103.8 | 434.3 | CV357626 | T | A | 7.03 | 0.001 |
| 62 | 6 | 108.2 | 444.8 | CV357626 | C | T | 7.73 | 0.001 |
| 63 | 7 | 67.5 | 231.7 | CV368354 | C | T | 7.14 | 0.001 |
| 64 | 7 | 75.4 | 264.8 | CV368354 | A | G | 7.14 | 0.001 |
| 65 | 8 | 64.8 | 193.7 | CV368354 | G | A | 6.37 | 0.001 |
| 66 | 8 | 67.1 | 204 | CV368354 | C | A | 7.41 | 0.001 |
| 67 | 8 | 67.7 | 205.2 | CV368354 | G | A | 6.13 | 0.001 |
| 68 | 8 | 71.7 | 216.2 | CV368354 | C | T | 6.78 | 0.001 |
| 69 | 8 | 71.7 | 216.2 | CV368354 | A | T | 7.11 | 0.001 |
| 70 | 8 | 71.9 | 216.7 | CV368354 | T | A | 7.01 | 0.001 |
| 71 | 8 | 71.9 | 216.7 | CV368354 | A | G | 7.25 | 0.001 |
| 72 | 8 | 74.2 | 231.1 | CV368354 | G | A | 7.43 | 0.001 |
| 73 | 8 | 74.8 | 236.2 | CV368354 | G | A | 7.62 | 0.001 |
| 74 | 8 | 75.3 | 240.4 | CV368354 | A | T | 7.81 | 0.001 |
| 75 | 8 | 75.3 | 240.4 | CV368354 | T | G | 7.30 | 0.001 |
| 76 | 8 | 75.9 | 251.6 | CV368354 | C | G | 7.30 | 0.001 |
| 77 | 8 | 82.6 | 288.3 | CV368354 | A | G | 8.07 | 0.001 |
| 78 | 8 | 84.1 | 291.7 | CV368354 | C | G | 8.34 | 0.001 |
| 79 | 8 | 84.5 | 293.6 | CV368354 | C | G | 7.67 | 0.001 |
| 80 | 8 | 89.4 | 313.8 | CV368354 | A | G | 8.16 | 0.001 |
| 81 | 8 | 101.1 | 354.7 | CV368354 | G | T | 9.20 | 0.001 |
| 82 | 8 | 102.6 | 362.2 | CV368354 | G | A | 10.00 | 0.001 |
| 83 | 8 | 103.1 | 363.9 | CV368354 | G | A | 8.02 | 0.001 |
| 84 | 8 | 103.1 | 363.9 | CV368354 | A | G | 8.55 | 0.001 |
| 85 | 8 | 103.1 | 363.9 | CV368354 | G | A | 8.12 | 0.001 |
| 86 | 8 | 104 | 374.5 | CV368354 | G | T | 7.65 | 0.001 |
| 87 | 8 | 104.8 | 374.5 | CV368354 | A | G | 9.80 | 0.001 |
| 88 | 8 | 106.4 | 380.7 | CV368354 | T | G | 8.54 | 0.001 |
| 89 | 8 | 112.1 | 394.3 | CV368354 | G | A | 8.07 | 0.001 |
| 90 | 8 | 113.1 | 396.8 | CV368354 | T | C | 6.84 | 0.001 |
| 91 | 9 | 56.8 | 158.5 | CV368354 | C | T | 6.11 | 0.001 |
| 92 | 9 | 61.4 | 188.5 | CV368354 | G | A | 5.06 | 0.001 |
| 93 | 9 | 61.5 | 189.3 | CV368354 | G | C | 5.13 | 0.001 |
| 94 | 9 | 66.2 | 212.3 | CV368354 | G | A | 5.78 | 0.001 |
| 95 | 9 | 67.2 | 245.5 | CV368354 | G | C | 6.73 | 0.001 |
| 96 | 9 | 67.8 | 226.4 | CV368354 | G | A | 7.15 | 0.001 |
| 97 | 9 | 67.8 | 226.4 | CV368354 | G | A | 7.00 | 0.001 |
| 98 | 9 | 67.8 | 226.4 | CV368354 | C | A | 7.00 | 0.001 |
| 99 | 9 | 67.9 | 226.5 | CV368354 | G | A | 6.98 | 0.001 |
| 100 | 9 | 67.9 | 245.5 | CV368354 | A | C | 6.58 | 0.001 |
| 101 | 9 | 67.9 | 226.5 | CV368354 | A | G | 6.87 | 0.001 |
| 102 | 9 | 68.2 | 245.5 | CV368354 | A | G | 7.16 | 0.001 |
| 103 | 9 | 68.4 | 227 | CV368354 | G | A | 7.16 | 0.001 |
| 104 | 9 | 74.7 | 263.6 | CV368354 | C | T | 7.40 | 0.001 |
| 105 | 9 | 77.2 | 283.6 | CV368354 | A | T | 7.54 | 0.001 |
| 106 | 9 | 80.7 | 304.9 | CV368354 | T | G | 6.35 | 0.001 |
| 107 | 9 | 82.6 | 314.5 | CV368354 | G | T | 8.69 | 0.001 |
| 108 | 9 | 87.4 | 321.6 | CV368354 | C | A | 7.66 | 0.001 |
| 109 | 9 | 87.7 | 321.8 | CV368354 | A | C | 9.25 | 0.001 |
| 110 | 9 | 88.5 | 338.7 | CV368354 | C | T | 8.83 | 0.001 |
| 111 | 9 | 88.6 | 339.2 | CV368354 | A | G | 8.69 | 0.001 |
| 112 | 9 | 88.6 | 339.2 | CV368354 | G | A | 8.79 | 0.001 |
| 113 | 9 | 89.3 | 349.3 | CV368354 | C | T | 8.36 | 0.001 |
| 114 | 9 | 96.5 | 392.9 | CV368354 | A | G | 6.60 | 0.001 |

TABLE 8

Exemplary primers and probes used for genotyping representative SNP markers associated with DM resistance

| SEQ ID NO. | SNP Position | Forward Primer | Reverse Primer | Probe 1 | Probe 2 |
|---|---|---|---|---|---|
| 1 | 483 | 115 | 229 | 343 | 457 |
| 2 | 146 | 116 | 230 | 344 | 458 |
| 3 | 137 | 117 | 231 | 345 | 459 |
| 4 | 73 | 118 | 232 | 346 | 460 |
| 5 | 82 | 119 | 233 | 347 | 461 |
| 6 | 174 | 120 | 234 | 348 | 462 |
| 7 | 328 | 121 | 235 | 349 | 463 |
| 8 | 29 | 122 | 236 | 350 | 464 |
| 9 | 177 | 123 | 237 | 351 | 465 |
| 10 | 39 | 124 | 238 | 352 | 466 |
| 11 | 160 | 125 | 239 | 353 | 467 |
| 12 | 34 | 126 | 240 | 354 | 468 |
| 13 | 674 | 127 | 241 | 355 | 469 |
| 14 | 44 | 128 | 242 | 356 | 470 |
| 15 | 254 | 129 | 243 | 357 | 471 |
| 16 | 267 | 130 | 244 | 358 | 472 |
| 17 | 365 | 131 | 245 | 359 | 473 |
| 18 | 195 | 132 | 246 | 360 | 474 |
| 19 | 321 | 133 | 247 | 361 | 475 |
| 20 | 227 | 134 | 248 | 362 | 476 |
| 21 | 428 | 135 | 249 | 363 | 477 |
| 22 | 197 | 136 | 250 | 364 | 478 |
| 23 | 406 | 137 | 251 | 365 | 479 |
| 24 | 404 | 138 | 252 | 366 | 480 |
| 25 | 342 | 139 | 253 | 367 | 481 |
| 26 | 630 | 140 | 254 | 368 | 482 |
| 27 | 102 | 141 | 255 | 369 | 483 |
| 28 | 92 | 142 | 256 | 370 | 484 |
| 29 | 49 | 143 | 257 | 371 | 485 |
| 30 | 118 | 144 | 258 | 372 | 486 |
| 31 | 291 | 145 | 259 | 373 | 487 |
| 32 | 46 | 146 | 260 | 374 | 488 |
| 33 | 353 | 147 | 261 | 375 | 489 |
| 34 | 379 | 148 | 262 | 376 | 490 |
| 35 | 362 | 149 | 263 | 377 | 491 |
| 36 | 999 | 150 | 264 | 378 | 492 |
| 37 | 115 | 151 | 265 | 379 | 493 |
| 38 | 207 | 152 | 266 | 380 | 494 |
| 39 | 280 | 153 | 267 | 381 | 495 |
| 40 | 281 | 154 | 268 | 382 | 496 |
| 41 | 81 | 155 | 269 | 383 | 497 |
| 42 | 241 | 156 | 270 | 384 | 498 |
| 43 | 299 | 157 | 271 | 385 | 499 |
| 44 | 336 | 158 | 272 | 386 | 500 |
| 45 | 468 | 159 | 273 | 387 | 501 |
| 46 | 284 | 160 | 274 | 388 | 502 |
| 47 | 250 | 161 | 275 | 389 | 503 |
| 48 | 262 | 162 | 276 | 390 | 504 |
| 49 | 496 | 163 | 277 | 391 | 505 |
| 50 | 44 | 164 | 278 | 392 | 506 |
| 51 | 82 | 165 | 279 | 393 | 507 |
| 52 | 52 | 166 | 280 | 394 | 508 |
| 53 | 409 | 167 | 281 | 395 | 509 |
| 54 | 115 | 168 | 282 | 396 | 510 |
| 55 | 256 | 169 | 283 | 397 | 511 |
| 56 | 91 | 170 | 284 | 398 | 512 |
| 57 | 47 | 171 | 285 | 399 | 513 |
| 58 | 525 | 172 | 286 | 400 | 514 |
| 59 | 253 | 173 | 287 | 401 | 515 |
| 60 | 174 | 174 | 288 | 402 | 516 |
| 61 | 250 | 175 | 289 | 403 | 517 |
| 62 | 148 | 176 | 290 | 404 | 518 |
| 63 | 130 | 177 | 291 | 405 | 519 |
| 64 | 258 | 178 | 292 | 406 | 520 |
| 65 | 324 | 179 | 293 | 407 | 521 |
| 66 | 66 | 180 | 294 | 408 | 522 |
| 67 | 621 | 181 | 295 | 409 | 523 |
| 68 | 39 | 182 | 296 | 410 | 524 |
| 69 | 149 | 183 | 297 | 411 | 525 |
| 70 | 158 | 184 | 298 | 412 | 526 |
| 71 | 263 | 185 | 299 | 413 | 527 |
| 72 | 538 | 186 | 300 | 414 | 528 |
| 73 | 49 | 187 | 301 | 415 | 529 |
| 74 | 499 | 188 | 302 | 416 | 530 |
| 75 | 139 | 189 | 303 | 417 | 531 |
| 76 | 159 | 190 | 304 | 418 | 532 |
| 77 | 342 | 191 | 305 | 419 | 533 |
| 78 | 422 | 192 | 306 | 420 | 534 |
| 79 | 54 | 193 | 307 | 421 | 535 |
| 80 | 832 | 194 | 308 | 422 | 536 |
| 81 | 100 | 195 | 309 | 423 | 537 |
| 82 | 232 | 196 | 310 | 424 | 538 |
| 83 | 434 | 197 | 311 | 425 | 539 |
| 84 | 473 | 198 | 312 | 426 | 540 |
| 85 | 435 | 199 | 313 | 427 | 541 |
| 86 | 140 | 200 | 314 | 428 | 542 |
| 87 | 366 | 201 | 315 | 429 | 543 |
| 88 | 249 | 202 | 316 | 430 | 544 |
| 89 | 574 | 203 | 317 | 431 | 545 |
| 90 | 218 | 204 | 318 | 432 | 546 |
| 91 | 701 | 205 | 319 | 433 | 547 |
| 92 | 182 | 206 | 320 | 434 | 548 |
| 93 | 444 | 207 | 321 | 435 | 549 |
| 94 | 288 | 208 | 322 | 436 | 550 |
| 95 | 295 | 209 | 323 | 437 | 551 |
| 96 | 327 | 210 | 324 | 438 | 552 |
| 97 | 100 | 211 | 325 | 439 | 553 |
| 98 | 1052 | 212 | 326 | 440 | 554 |
| 99 | 204 | 213 | 327 | 441 | 555 |
| 100 | 128 | 214 | 328 | 442 | 556 |
| 101 | 242 | 215 | 329 | 443 | 557 |
| 102 | 448 | 216 | 330 | 444 | 558 |
| 103 | 560 | 217 | 331 | 445 | 559 |
| 104 | 309 | 218 | 332 | 446 | 560 |
| 105 | 58 | 219 | 333 | 447 | 561 |
| 106 | 466 | 220 | 334 | 448 | 562 |
| 107 | 363 | 221 | 335 | 449 | 563 |
| 108 | 155 | 222 | 336 | 450 | 564 |
| 109 | 436 | 223 | 337 | 451 | 565 |
| 110 | 600 | 224 | 338 | 452 | 566 |
| 111 | 418 | 225 | 339 | 453 | 567 |
| 112 | 539 | 226 | 340 | 454 | 568 |
| 113 | 382 | 227 | 341 | 455 | 569 |
| 114 | 83 | 228 | 342 | 456 | 570 |

Example 5. Validation of DM QTLs

Multiple corn populations are used to validate effects of the DM QTLs identified herein. First, effects of individual DM resistance QTLs are tested using $BC_3F_3$ inbred plants derived from CV357626/CV523685 (Table 9). Plants carrying a resistant allele of DM-4.01 show a reduction of 15.9% in DM rating score (89.6%-73.7%=15.9%) when compared to plants carrying a susceptible allele. Plants carrying a resistant allele of DM-6.01 show a reduction of 26.6% in DM rating score (83.2%-56.6%=26.6%) when compared to plants carrying a susceptible allele. $BC_3F_3$ inbred plants are also derived from or CV368354/CV358560. Plants carrying a resistant allele of DM-8.01 show a reduction of 7.5% in DM rating score (85.6%-78.1%=7.5%) when compared to plants carrying a susceptible allele (Table 9).

TABLE 9

Efficacy test of individual QTLs on BC3F3 inbred plants.

| Cross | QTL | QTL Profile | Mean (%) | p-value |
|---|---|---|---|---|
| CV357626/CV523685 | DM_4.01 | 4− | 89.6 | <0.001 |
|  |  | 4+ | 73.7 |  |
| CV357626/CV523685 | DM_6.01 | 6− | 83.2 | <0.001 |
|  |  | 6+ | 56.6 |  |
| CV368354/CV358560 | DM_8.01 | 8− | 85.6 | <0.001 |
|  |  | 8+ | 78.1 |  |

Effects of various DM resistance QTL combinations are also tested using $F_2$ lines derived from CV375547/CV357626, CV523685/CV357626, CV356987/CV357626, CV358560/CV368354, CV368354/CV356389, CV368354/CV356054, CV353840/CV368354, and CV353184/CV368354. Inbred plants carrying multiple DM resistant QTLs from CV357626 show a reduction of 16-34% in DM rating scores when compared to plants carrying susceptible alleles. Inbred plants carrying multiple DM resistant QTLs from CV368354 show a reduction of 17.2-57.5% in DM rating scores when compared to plants carrying susceptible alleles (Table 10).

TABLE 10

Test of multiple QTL model in $F_2$ plants.

| Cross | QTL model | DM rating score (%) All negative | DM rating score (%) All positive | Efficacy (%) | p-value |
|---|---|---|---|---|---|
| CV375547/CV357626 | DM_1.01-DM_4.01-DM_6.01 | 38 | 9.8 | 28.2 | <0.001 |
| CV523685/CV357626 | DM_1.01-DM_3.01-DM_4.01 | 43.8 | 9.8 | 34 | <0.001 |
| CV356987/CV357626 | DM_1.01-DM_3.01-DM_4.01 | 23.8 | 7.8 | 16 | <0.001 |
| CV358560/CV368354 | DM_2.01-DM_4.01 | 57.47 | 34.27 | 23.2 | <0.001 |
| CV368354/CV356389 | DM_6.02-DM_8.01 | 57.04 | 17.39 | 39.65 | <0.001 |
| CV368354/CV356054 | DM_6.02-DM_8.01-DM_9.01 | 78.79 | 21.26 | 57.53 | <0.001 |
| CV353840/CV368354 | DM_8.01-DM_9.01 | 37.29 | 17.92 | 19.37 | <0.001 |
| CV353184/CV368354 | DM_2.01-DM_6.02-DM_8.01 | 26.44 | 9.23 | 17.21 | <0.001 |

Effects of DM resistance QTL combinations in hybrid plants are also tested by crossing $BC_6F_4$ inbred lines derived from CV368354/CV371792 with two highly susceptible testers to generate hybrid plants. The efficacy, equivalency, and yield protection of various combinations of DM resistance QTLs are evaluated. Several combinations of DM resistant QTLs provide a reduction of 2.1-5.8% in DM rating score across testers (shown in bold text in Table 11). DM_6.02 appear shared among these QTL combinations.

TABLE 11

Efficacy trials of multiple QTL models.

| QTL model | LSM_DIFF (%) | p-value |
|---|---|---|
| Under high disease pressure | | |
| DM_5.01-DM_6.02-DM_7.01 | 0.9 | 0.330215 |
| DM_5.01-DM_6.02-DM_7.01-DM_8.01 | 4.7 | 1.13E−06 |
| DM_5.01-DM_6.02-DM_8.01 | 2.9 | 0.002377 |
| DM_5.01-DM_7.01 | −5.4 | 2.66E−08 |
| DM_5.01-DM_7.01-DM_8.01 | −2.4 | 0.014362 |
| DM_6.02-DM_7.01-DM_8.01 | 2.1 | 0.031126 |
| Under low disease pressure | | |
| DM_5.01-DM_6.02-DM_7.01 | 2.9 | 0.002548 |
| DM_5.01-DM_6.02-DM_7.01-DM_8.01 | 5.8 | 1.36E−09 |
| DM_5.01-DM_6.02-DM_8.01 | 4.4 | 4.03E−06 |
| DM_5.01-DM_7.01 | −5.4 | 2.83E−08 |
| DM_5.01-DM_7.01-DM_8.01 | −2.7 | 0.00471 |
| DM_6.02-DM_7.01-DM_8.01 | 3.4 | 0.00045 |

DM rating score differences by least-square means (LSM_DIFF) are provided (LSM_DIFF = % of infected plants without DM resistant QTL − % of infected plants with DM resistant QTLs).

Under high disease pressure as exemplified in Example 1 (e.g., a field with a DM infected corn plant as a source inoculum), hybrid plants carrying multiple DM resistant QTLs provide a yield advantage of 3.7-4.3 quintal per hectare when compared to hybrid plants carrying the susceptible QTLs (highlighted in bold text in Table 12). Under low disease pressure (e.g., a field without a DM infected corn plant as a source inoculum), there is no statistical difference in yield between hybrid plants with or without DM resistant QTLs (Table 12) indicating no yield penalty from these QTLs. It is noted in Table 12 that negative values correspond to yield increases, while positive values correspond to yield decreases.

TABLE 12

Yield protection and equivalency trials of multiple QTL model.

| QTL model | LSM_DIFF (quintal/hectare) | p-value |
|---|---|---|
| Under high disease pressure | | |
| DM_5.01-DM_6.02-DM_7.01 | −1.4 | 0.348081 |
| DM_5.01-DM_6.02-DM_7.01-DM_8.01 | −3.9 | 0.009734 |
| DM_5.01-DM_6.02-DM_8.01 | −4.3 | 0.004883 |
| DM_5.01-DM_7.01 | 3.1 | 0.039359 |
| DM_5.01-DM_7.01-DM_8.01 | 2.6 | 0.093428 |
| DM_6.02-DM_7.01-DM_8.01 | −3.7 | 0.013656 |
| Under low disease pressure | | |
| DM_5.01-DM_6.02-DM_7.01 | 0.9 | 0.495734 |
| DM_5.01-DM_6.02-DM_7.01-DM_8.01 | 1.1 | 0.382852 |
| DM_5.01-DM_6.02-DM_8.01 | 1 | 0.4349 |
| DM_5.01-DM_7.01 | 1.3 | 0.321979 |
| DM_5.01-DM_7.01-DM_8.01 | 0.9 | 0.480224 |
| DM_6.02-DM_7.01-DM_8.01 | −1.3 | 0.318478 |

Yield differences by least-squares means (LSM_DIFF) are provided (LSM_DIFF = yield from plants without DM resistant QTLs − yield from plants with DM resistant QTLs).

Example 6. Further Validation of DM QTLs

Efficacy of individual and multiple DM resistance QTLs are further tested using $BC_3F_3$ inbred plants derived from the crosses listed in Tables 13 and 14. Non-resistant plants are used as recurrent parent plants in the backcrosses to generate these $BC_3F_3$ plants. Inbred plants carrying resistant alleles of DM_4.01 show a reduction of 37.25% in DM rating score (67.75%−30.5%=37.25%) when compared to plants carrying susceptible alleles (Table 13). Inbred plants carrying multiple DM resistant QTLs (e.g., DM_1.0FDM_4.0FDM_6.01) show a reduction in DM rating scores when compared to plants carrying susceptible alleles (Table 14).

Efficacy of individual and multiple DM resistance QTLs are also tested by crossing BC₃F₃ inbred plants with two highly susceptible tester lines to generate hybrid plants. Hybrid plants carrying multiple DM resistant QTLs (e.g., DM_1.OFDM_4.OFDM_6.01) show a reduction in DM rating scores when compared to plants carrying susceptible alleles (Table 14).

These hybrid plants are also evaluated using equivalency tests (Tables 15 and 16). Hybrid plants carrying the resistant allele of DM_2.03 provide a yield advantage of 26.16 (87.77-61.61=26.16) quintal per hectare when compared to hybrid plants carrying the susceptible QTL (highlighted in bold text in Table 15). No significant yield drag was detected in equivalency tests for multiple QTLs in hybrid plants.

TABLE 15

Equivalency test of individual QTLs

| Cross | QTL | QTL Profile* | Yield (quintal/hectare) | p-value |
|---|---|---|---|---|
| CV357626/ | DM_1.01 | 1+ | 70.30 | 0.129 |
| CV375547 |  | 1− | 56.30 |  |
|  | DM_4.01 | 4+ | 80.78 | 0.761 |
|  |  | 4− | 84.53 |  |
|  | DM_6.01 | 6+ | 62.18 | 0.557 |
|  |  | 6− | 59.01 |  |
| CV523685/ | DM_4.01 | 4+ | 97.99 | 0.883 |
| CV357626 |  | 4− | 96.49 |  |
| CV343114/ | DM_1.01 | 1+ | 72.89 | 0.879 |
| CV357626 |  | 1− | 70.81 |  |
|  | DM_2.03 | 2+ | 87.77 | 0.011 |
|  |  | 2− | 61.61 |  |

(*the presence and absence of a selected resistance QTL is shown by plus (+) and minus (−), respectively).

TABLE 13

Efficacy test of individual QTLs (*the presence and absence of a selected resistance QTL is shown by plus (+) and minus (−), respectively).

| | | | INBRED TEST | | HYBRID TEST | |
|---|---|---|---|---|---|---|
| Cross | QTL | QTL Profile* | Mean(%) | p-value | Mean(%) | p-value |
| CV357626/ | DM_1.01 | 1+ | 51.30 | 0.102 | 37.67 | 0.805 |
| CV375547 |  | 1− | 77.00 |  | 44.20 |  |
|  | DM_4.01 | 4+ | 30.50 | 0.007 | 38.34 | 0.140 |
|  |  | 4− | 67.75 |  | 56.86 |  |
|  | DM_6.01 | 6+ | NA | NA | 47.21 | 0.299 |
|  |  | 6− | NA |  | 19.08 |  |
| CV523685/ | DM_6.01 | 6+ | 87.67 | 0.637 | NA | NA |
| CV357626 |  | 6− | 100.00 |  | NA |  |
| CV343114/ | DM_1.01 | 1+ | NA | NA | 53.23 | 0.244 |
| CV357626 |  | 1− | NA |  | 37.21 |  |
|  | DM_2.03 | 2+ | 89.00 | 0.723 | 50.41 | 0.711 |
|  |  | 2− | 82.83 |  | 45.74 |  |

TABLE 14

| | | INBRED TEST DM rating score (%) | | | | HYBRID TEST DM rating score (%) | | | |
|---|---|---|---|---|---|---|---|---|---|
| Cross | QTLs | All Negative | All Positive | LSM_DIFF (%) | p-value | All Negative | All Positive | LSM_DIFF (%) | p-value |
| CV339885/ | DM_1.01- | 90.20 | 85.00 | 5.20 | 0.3031 | 4.33 | 4.87 | −0.54 | 0.7066 |
| CV357626 | DM_2.03_DM_6.01 |  |  |  |  |  |  |  |  |
| CV523685/ | DM_1.01- | 79.42 | 62.23 | 17.19 | 0.0001 | 67.33 | 50.16 | 17.17 | 0.0060 |
| CV357626 | DM_4.01_DM_6.01 |  |  |  |  |  |  |  |  |
| CV338784/ |  | 74.08 | 61.00 | 13.08 | <0.0001 | 57.45 | 41.99 | 15.46 | 0.0062 |
| CV357626 |  |  |  |  |  |  |  |  |  |
| CV337135/ |  | 73.50 | 93.68 | −20.18 | 0.3996 | 43.58 | 43.53 | 0.06 | 0.9968 |
| CV357626 |  |  |  |  |  |  |  |  |  |
| CV335787/ |  | 86.67 | 76.00 | 10.67 | 0.2029 | 64.88 | 54.84 | 10.03 | 0.3744 |
| CV357626 |  |  |  |  |  |  |  |  |  |
| CV356987/ |  | 65.58 | 35.72 | 29.86 | <0.0001 | 50.54 | 28.94 | 21.59 | <0.0001 |
| CV357626 |  |  |  |  |  |  |  |  |  |
| CV357626/ |  | 97.71 | 60.64 | 37.08 | 0.0005 | NA | NA | NA | NA |
| CV375547 |  |  |  |  |  |  |  |  |  |

TABLE 16

Equivalency test of multiple QTLs.

| | | HYBRID TEST | | | |
|---|---|---|---|---|---|
| Cross | QTL model | All Negative | All Positive | LSM_DIFF | p-value |
| CV339885/ CV357626 | DM_1.01-DM_2.03_DM_6.01 | 68.4383769 | 60.84911512 | 7.59 | 0.1391 |
| CV523685/ CV357626 | DM_1.01-DM_4.01_DM_6.01 | 67.06 | 54.49 | 12.57 | 0.0965 |
| CV338784/ CV357626 | | 63.89661472 | 60.56268131 | 3.33 | <0.0001 |
| CV337135/ CV357626 | | 65.38536565 | 55.94532966 | 9.44 | 0.6530 |
| CV335787/ CV357626 | | 64.48961024 | 62.26780695 | 2.22 | 0.0001 |
| CV356987/ CV357626 | | 71.46531304 | 73.94449948 | -2.48 | <0.0001 |

Yield differences by least-squares means (LSM_DIFF) are provided (LSM_DIFF = yield from plants without DM resistance QTLs − yield from plants with DM resistance QTLs; measured in quintals/hectare).
"All Negative" refers to plants lacking each of the three resistance QTLs, while "All Positive" refers to plants having all three resistance QTLs.

Example 7: Introgression of Downy Mildew Resistance QTLs into Additional Maize Lines A maize plant comprising one or more, two or more, three or more, four or more, five or more, six or more, seven or more, eight or more, nine or more, or ten or more DM resistance QTLs is crossed with an elite maize line comprising a desirable trait (e.g., improved yield under water, temperature, or pest stress conditions), but susceptible to DM. $F_1$ progeny plants from this cross are assayed for one or more SNP markers exemplified in Tables 7 and 8 to select for DM resistance QTLs. A selected $F_1$ progeny plant is then backcrossed with the parent elite maize line comprising the desirable trait (recurrent parent). Plants from the $BC_1$ generation are also genotyped using SNP markers exemplified in Table 8 to select for DM resistance QTLs. After multiple rounds of backcrossing (e.g., 5-7 generations) with the recurrent parent line, a new elite maize line is obtained comprising both DM resistance and the desirable trait in the recurrent parent line. Using the above introgression and marker-assisted selection strategy, the pyramiding or stacking of multiple DM resistance QTLs can be achieved.

As various modifications could be made in the constructions and methods herein described and illustrated without departing from the scope of this disclosure, it is intended that all matter contained in the foregoing description or shown in the accompanying drawings shall be interpreted as illustrative rather than limiting. The breadth and scope of the present disclosure should not be limited by any of the above-described exemplary embodiments, but should be defined only in accordance with the following claims appended hereto and their equivalents. All patent and non-patent documents cited in this specification are incorporated herein by reference in their entireties.

What is claimed is:

1. A method of creating a population of corn plants or corn seeds resistant to Downy Mildew (DM), said method comprising:
   a) genotyping a first population of corn plants or corn seeds for the presence of one or more marker loci linked within about 10 centimorgans (cM) of a DM resistance allele within a DM resistance quantitative trait locus (QTL) DM_8.01;
   b) selecting from said first population one or more corn plants or corn seeds comprising said one or more marker loci linked to said DM resistance allele selected from the group consisting of:
   SEQ ID NO: 77, comprising an A at position 342;
   SEQ ID NO: 78, comprising a C at position 422;
   SEQ ID NO: 79, comprising a C at position 54; and
   SEQ ID NO: 80, comprising an A at position 832; and
   c) producing from said one or more corn plants or corn seeds a second population of corn plants or corn seeds comprising said DM resistance allele at said DM resistance QTL DM_8.01, wherein said second population of corn plants or corn seeds comprises at least one corn plant or corn seed having improved resistance to DM as compared to a corn plant or corn seed lacking said DM resistance allele at said DM resistance QTL DM_8.01.

2. The method of claim 1, wherein said DM resistance allele at said DM resistance QTL DM_8.01 is linked within about 5 cM or 1 cM of any one of said marker loci selected from the group consisting of SEQ ID NO: 77, SEQ ID NO: 78, SEQ ID NO: 79, and SEQ ID NO: 80.

3. The method of claim 1, wherein said DM resistance allele provides moderate resistance or intermediate resistance to infection by an oomycete selected from the group consisting of *Peronosclerospora philippinensis, Peronosclerospora maydis, Peronosclerospora sorghi*, and a combination thereof.

4. The method of claim 1, wherein said second population of corn plants or corn seeds exhibits reduced premature death, reduced stunted growth, reduced leaf chlorosis, reduced number of narrow leaves, reduced number of erect leaves, reduced number of shredded leaves, reduced number of failed cobs, reduced vegetative tissue in tassels, or any combination thereof compared to corn plants or corn seeds lacking said DM resistance allele at said DM resistance QTL DM_8.01 when grown under a high DM stress condition.

5. The method of claim 1, wherein said DM resistance allele at said DM resistance QTL DM_8.01 confers no yield penalty when grown under a low DM stress condition.

6. The method of claim 1, wherein said second population of corn plants or corn seeds further comprises DM resistance QTL DM_9.01.

* * * * *

```
                    SEQUENCE LISTING

Sequence total quantity: 570
SEQ ID NO: 1            moltype = DNA  length = 599
FEATURE                 Location/Qualifiers
misc_difference         8..9
                        note = n is a, c, g, or t
misc_difference         42
                        note = n is a, c, g, or t
misc_difference         55
                        note = n is a, c, g, or t
misc_difference         65
                        note = n is a, c, g, or t
misc_difference         73
                        note = n is a, c, g, or t
misc_difference         94
                        note = n is a, c, g, or t
misc_difference         102
                        note = n is a, c, g, or t
misc_difference         217
                        note = n is a, c, g, or t
misc_difference         331
                        note = n is a, c, g, or t
misc_difference         434
                        note = n is a, c, g, or t
misc_difference         483
                        note = n is a, c, g, or t
source                  1..599
                        mol_type = unassigned DNA
                        organism = Zea mays
SEQUENCE: 1
tcgttccnna ggaggtgtac tcctgatgag tgtctgtttt tntataccct ctttnccgct    60
```

-continued

```
ttaangaaag gcngagctcc tgccattttt caanaaaaaa angtgcaaag ttccagacag    120
ttttaaggta aattccaatc atgtacaagg gcttcagact cagtcagatg ccgatgtaca    180
aacatgttac attcgtgtgc tgctgtgctt tttttnagg aaagccatac gacgcacttt     240
attgattatc aaacatgtta catcgtttac cagtctgaag aataacacca gagggttcat    300
cgaccccaaa tacagtttcc tttcaagaga nagctactct gctagttcat gtgccacctg    360
tgcgtttgta aattggacac agcattctgg gagcagtgca cggcatcctc gtgaaaaatg    420
agaagaaaaa aaanggatat ttcttcactg cctccgtctc ctttcatctc cggtatacgt    480
atngctggac aagacacaca tctatacaga tcgcatcact ggtaaacttg cacagagtaa    540
atgattacac gtccagctct ttatgcggct acagctagag gtctttggct ggtctttat     599

SEQ ID NO: 2           moltype = DNA   length = 805
FEATURE                Location/Qualifiers
misc_difference        33..34
                       note = n is a, c, g, or t
misc_difference        37..38
                       note = n is a, c, g, or t
misc_difference        40..53
                       note = n is a, c, g, or t
misc_difference        146
                       note = n is a, c, g, or t
misc_difference        196..203
                       note = n is a, c, g, or t
misc_difference        206..215
                       note = n is a, c, g, or t
misc_difference        219..223
                       note = n is a, c, g, or t
misc_difference        226..232
                       note = n is a, c, g, or t
misc_difference        235..243
                       note = n is a, c, g, or t
misc_difference        245..246
                       note = n is a, c, g, or t
misc_difference        250
                       note = n is a, c, g, or t
misc_difference        254..256
                       note = n is a, c, g, or t
misc_difference        259..261
                       note = n is a, c, g, or t
misc_difference        263..270
                       note = n is a, c, g, or t
misc_difference        273
                       note = n is a, c, g, or t
misc_difference        321
                       note = n is a, c, g, or t
misc_difference        326..339
                       note = n is a, c, g, or t
misc_difference        349
                       note = n is a, c, g, or t
misc_difference        360..365
                       note = n is a, c, g, or t
misc_difference        417
                       note = n is a, c, g, or t
misc_difference        441..443
                       note = n is a, c, g, or t
misc_difference        449
                       note = n is a, c, g, or t
misc_difference        453..454
                       note = n is a, c, g, or t
misc_difference        457
                       note = n is a, c, g, or t
misc_difference        473..474
                       note = n is a, c, g, or t
misc_difference        485
                       note = n is a, c, g, or t
misc_difference        508..515
                       note = n is a, c, g, or t
misc_difference        665
                       note = n is a, c, g, or t
misc_difference        704
                       note = n is a, c, g, or t
misc_difference        710
                       note = n is a, c, g, or t
misc_difference        730..731
                       note = n is a, c, g, or t
misc_difference        747
                       note = n is a, c, g, or t
misc_difference        749
                       note = n is a, c, g, or t
misc_difference        773
```

|  |  |  |
|---|---|---|
| misc_difference | 795..797 | |
| | note = n is a, c, g, or t | |
| misc_difference | 802..803 | |
| | note = n is a, c, g, or t | |
| source | 1..805 | |
| | mol_type = unassigned DNA | |
| | organism = Zea mays | |

SEQUENCE: 2
```
cgcctgcgcg ctgctcatgt cggacgtagc cannagnncn nnnnnnnnnn nnntcaggtc   60
gtccacctcc tggtgcaagt tcctgatgta gttgcatgtc tcctgcaaca ccctcgcaga  120
tggcacctgc atggggaaga cggcanatta aagggagaac aatttaccgg accgtcggct  180
caagctcatc tcacannnnn nnnatnnnnn nnnnnttgnn nnncannnnn nngannnnnn  240
nnnanngctn catnnnatnn ntnnnnnnnn atntagtagg ggccattcaa cttttgactg  300
gaaattttgg ccaatttgat ngttgnnnnn nnnnnnnnnc aggtcggcng taggtaccan  360
nnnnnccgta tcagatcaca tttcttaggc ctcaatgtgt agcgaatgcc gccacanggt  420
aatgctaatt tttcagctaa nnncctaana acnntantag agattttgga tanncattc   480
agctnataaa gtggtaacgt acgatatnnn nnnnngaact tcagttacat actcttgcat  540
tgctctgaag gcgagcttcg gggaggaggt cctgcagctt tgatacaagg tcgctgatct  600
gctcctcagt gatcctcgac gaaccagact gcctggaccg tgacctccgg ttcgacatct  660
cggtnggtgt ggctgtctgg gccggagata ttggtgaacg aagncttgcn agagaccgag  720
aaagaaactn ngatggtagg agtgagngna agcaatgcaa gcaagtttga ganacacaga  780
tgatgatgaa atggnnntca annac                                        805
```

|  |  |  |
|---|---|---|
| SEQ ID NO: 3 | moltype = DNA   length = 842 | |
| FEATURE | Location/Qualifiers | |
| misc_difference | 2..21 | |
| | note = n is a, c, g, or t | |
| misc_difference | 137 | |
| | note = n is a, c, g, or t | |
| misc_difference | 204 | |
| | note = n is a, c, g, or t | |
| misc_difference | 252 | |
| | note = n is a, c, g, or t | |
| misc_difference | 298..305 | |
| | note = n is a, c, g, or t | |
| misc_difference | 310 | |
| | note = n is a, c, g, or t | |
| misc_difference | 318 | |
| | note = n is a, c, g, or t | |
| misc_difference | 345 | |
| | note = n is a, c, g, or t | |
| misc_difference | 354..360 | |
| | note = n is a, c, g, or t | |
| misc_difference | 400..401 | |
| | note = n is a, c, g, or t | |
| misc_difference | 614 | |
| | note = n is a, c, g, or t | |
| misc_difference | 762..763 | |
| | note = n is a, c, g, or t | |
| misc_difference | 766 | |
| | note = n is a, c, g, or t | |
| misc_difference | 831..837 | |
| | note = n is a, c, g, or t | |
| source | 1..842 | |
| | mol_type = unassigned DNA | |
| | organism = Zea mays | |

SEQUENCE: 3
```
tnnnnnnnnn nnnnnnnnnn naaatgcctg gcaatctcaa ggtaaaagta ctgtctgtct   60
gggtgcagtc ataacacgca ccatttcatt tatgttttg gatcctgcag gttgcgtatt  120
ttgtgaattc tgggacngaa gcgaatgagt tggcaatgtt gatggcccgg ctgtatagtg  180
ggaatctcag tatggttgcg ctcngaaatg catatcatgg cggaagtgcc ggtacgattg  240
gattgactgg tntgcagacg tggaaatacc caattcctca ggtatgtgta cagtgtannn  300
nnnnnttgcn ctttcatnaa attatttgac tggttatgtt ttcanagtca catnnnnnnn  360
gtttgctgca gtagattctt agttatcaat aattatctcn ncgttctacc cagcaaaaat  420
gtatccattt ctttattaca tctatcatag cctcataaga attttgcag gtgaaatac    480
atcatgtcat gaaccctgat ccttatcggg ggactttcgg gtctgatgct gcagcttatg  540
ctaaggaagt cgaagaacac ataacttatg gaagttcagg aagggttgca ggcttcattg  600
cagaaacatt ccangtataa acttgaaca gaccatttat aaaatgctag aactaattga   660
aataatatgt atcttttgtt tataaaccca attcaaaata acttatccctt gtcgcaatct  720
tgttgataca ccatctctgc tgtagggtgt gggaggtgct gnnaantagc tcctggatac  780
ctaaagttag cttatgacat tgtgcgcaag gctggtggcg tttgtattgc nnnnnnngtc  840
ca                                                                 842
```

|  |  |  |
|---|---|---|
| SEQ ID NO: 4 | moltype = DNA   length = 428 | |
| FEATURE | Location/Qualifiers | |
| misc_difference | 73 | |
| | note = n is a, c, g, or t | |
| misc_difference | 293 | |

```
                          note         = n is a, c, g, or t
misc_difference           299
                          note         = n is a, c, g, or t
misc_difference           306
                          note         = n is a, c, g, or t
source                    1..428
                          mol_type     = unassigned DNA
                          organism     = Zea mays
SEQUENCE: 4
ctccttgaaa ccgtcctccc gggcccattc cgtcttctca ctgccctggg caccttcggg    60
attcttagct gtntcgcgtg tgccagcttt gttctggtga tgatgagatg cagaagcttt   120
cctcgacggt ttttccttct ccggtcgaga ttctttgcta ggctcaggag tgtaagcttt   180
ccagacagca ctttgctgaa cgataagcct gtgcagctcg aaaaacttgg tgattgcagc   240
ttgtggatct acttcagaag attcccttat ctcagaaaaa attctgtaaa agnacgtana   300
gattanattt atttgtccag ttcatgagct aaagtaaaca atgtagctcc ctagagaaaa   360
aaaaactaga cataaaagaa aaggtaaagc atgtgcgttg caataaggaa acaagatcct   420
gggatgca                                                            428

SEQ ID NO: 5              moltype = DNA  length = 331
FEATURE                   Location/Qualifiers
misc_difference           1
                          note         = n is a, c, g, or t
misc_difference           82
                          note         = n is a, c, g, or t
source                    1..331
                          mol_type     = unassigned DNA
                          organism     = Zea mays
SEQUENCE: 5
ngtgaccata caaaaatcat gcaatgaact ctacaagcca gtatgtcact ggcatttctt    60
ggcttcatct ggtagatagc anttcttatc ctcactgtcg ggtggtgggg gcacaccaaa   120
tacccagtcc agcacattca ggtacttgga ccggaagact tctcttcct gcgcatagca    180
gtgcataatg atagaggtag ctatgctgaa cacaaccaca tcagctcgct ttatctgaag   240
tattggaggg cagagtcctg catcggtcat ccatgtgaaa aaactctcga tagctctggc   300
aagacagtac agggatatct caatcctcct g                                  331

SEQ ID NO: 6              moltype = DNA  length = 390
FEATURE                   Location/Qualifiers
misc_difference           47
                          note         = n is a, c, g, or t
misc_difference           51..98
                          note         = n is a, c, g, or t
misc_difference           159..160
                          note         = n is a, c, g, or t
misc_difference           162
                          note         = n is a, c, g, or t
misc_difference           174
                          note         = n is a, c, g, or t
misc_difference           253..254
                          note         = n is a, c, g, or t
misc_difference           264
                          note         = n is a, c, g, or t
source                    1..390
                          mol_type     = unassigned DNA
                          organism     = Zea mays
SEQUENCE: 6
tcggagaagg acgcgacgtt gctgaagtca cgagccgcct cccgaangct nnnnnnnnnn    60
nnnnnnnnnn nnnnnnnnnn nnnnnnnnnn nnnnnnnnca tgcaggcagg tgtggagcga   120
gcgagggagg tagcttggct tggctaggta cagaactann cntcttctcg tgtntctctg   180
cggagtagtt ttcagtaccg ccaccagtac gtaccaagaa ggaagtagcc ggggtgtctc   240
atagctggtg tgnngctagt aggnaacgag ggtgcatggg aaagcctcct cagcacccctt  300
ccttcgcgat cgatggatgg taaggactga ggagagcgag gagctgaagg aagcaatgga   360
gaggagagac cagggaatat aagcaagggc                                    390

SEQ ID NO: 7              moltype = DNA  length = 553
FEATURE                   Location/Qualifiers
misc_difference           328
                          note         = n is a, c, g, or t
source                    1..553
                          mol_type     = unassigned DNA
                          organism     = Zea mays
SEQUENCE: 7
tataaatgct taaacttaac ctggtaaatt catctacagg ctctttcaaa tggcaaaccc    60
actgttgttg agttttatgc aaactgatgt gaagtctgca gggaactagc tccagatatc   120
tacaaagttg aacaacaata caagtaattt gtttacacac cactttttcac atttctgaac   180
tttaagcctt gattgagaat aacaattgtg attcatttaa taaatcaat gcttgtcgat   240
gctttgttgc gttgcctatc ctattaacca cgttgattga accttgctat gggcatgaca   300
gttgggatcc aagttgctgc acgacagnca gaaccagcga acaccacgga caacgacgac   360
gacgaaccag agcaggtccg cttctcgctc ttgggtggca agaactgcag caacgttggt   420
gtcacgaccg ccattaggcc catgaacaac gccaggctga ggtccaggga tggaggcaac   480
```

```
gccacgccca cgaccatcac ccacagtgac tctgcatcgg ggagcatgag gacgatttgt   540
acgccatcac aat                                                     553

SEQ ID NO: 8           moltype = DNA  length = 511
FEATURE                Location/Qualifiers
misc_difference        29
                       note = n is a, c, g, or t
misc_difference        126
                       note = n is a, c, g, or t
misc_difference        152
                       note = n is a, c, g, or t
misc_difference        377
                       note = n is a, c, g, or t
misc_difference        401
                       note = n is a, c, g, or t
misc_difference        404
                       note = n is a, c, g, or t
source                 1..511
                       mol_type = unassigned DNA
                       organism = Zea mays
SEQUENCE: 8
tcacctggga gctctgggta tcacgggang cactcgatca gccactcgag gctctgcatg    60
aaacagattg catagaataa tggatgtaag gttagcagac ctgcaaactg tagcatgcat   120
gaatcntgat tcatggcaac cagtgtcttt cnaaaaacaa aagagaaaaa aagaagagga   180
gaagcgtacc attaggcatt ctggtagatc atcgtcctgc gtcctcatgt gagtctgcat   240
atatgtaaag agctactcat taggcatttc cagtctaact cgaatctgag catgtaaatt   300
tggagtctga tatctgtttt gaagctaacc gacttgagct tctgctagtt acagttcata   360
ctttgattta tatatgnata ccaagttcta aacaatagca natntgacaa aatttataac   420
gagaaatgca ggacttgggg ggtgttcacc tccatcacca aatggcatga gggctccttg   480
cctgtggcaa ggcaagcaag agctaccact g                                 511

SEQ ID NO: 9           moltype = DNA  length = 410
FEATURE                Location/Qualifiers
misc_difference        177
                       note = n is a, c, g, or t
source                 1..410
                       mol_type = unassigned DNA
                       organism = Zea mays
SEQUENCE: 9
tcgttgctcg gcggcggcga cagcatccgc tcaaccccag ccatgttgtt gcccaggagc    60
tcgttggcca gctcatcctc gagatcgttc tccaccagcc gcttgacacc gcggagcaca   120
tggagtgcca atccgtcggc gagcctgagc actatgatct tccagtacgc ggtcagncgt   180
gccctcaagt cgaatgcctg cgctgctaag tcagggtcg tcctaagatg acccacgttc   240
acttccccga agcattccag ggtaaactta gatggctcgg acttgttctc cacagaaccc   300
atgaacttct tctgccctac cattatggct tcccaagtct tcatgtagtc agggctcgcc   360
gtgtagcctg ccaccagctc catctctatc atctccttgg acgtgctgag              410

SEQ ID NO: 10          moltype = DNA  length = 812
FEATURE                Location/Qualifiers
misc_difference        39
                       note = n is a, c, g, or t
misc_difference        710..712
                       note = n is a, c, g, or t
misc_difference        717..720
                       note = n is a, c, g, or t
misc_difference        750..757
                       note = n is a, c, g, or t
misc_difference        775..791
                       note = n is a, c, g, or t
source                 1..812
                       mol_type = unassigned DNA
                       organism = Zea mays
SEQUENCE: 10
gtgctcagtg gtcagtgcga ggtgtccacg agtcaattna agttggtttc ttattcgtac    60
aaagcatgca actcttgaac agtttaataa ctacatattt gtcggatgat cctttcttct   120
ctcttagctt tggcttgtct tgggagtctt cctaatggcc acgagcctca gaatgtatgc   180
cacgtgccag cagcttgctc atgctgcagc tgccaacagt tttctcggcc acactgagct   240
gcgtgtgcat gtaccgccgt ccattaccct tgctacgaga ggccggttac agagccttag   300
acttcaactg gctccttcttg atcgtgaatt tgacgattta ggtgtgccaa tacattccat   360
tcgactcatt tgatggttta tagtgtttcc tgaaaactta gtgccatgga aatttttgt    420
ttcagattat gacactctga gagcattgga tgctgacaat agcccacatg ctccatctat   480
gagtgaagaa gaaataaatt ctcttcctgt cttcaaatat aaagttcagg cacaacagag   540
gcatccccct gcccgaaaaa ggtaaagccg aattgtcctt tgggttgatt tgttcatatc   600
accatatcga gttggttcca gtatttccca tcaacacatg accaacatt aattctgaaa   660
tggagacatg aagtaatttt ttctaatgtt tgttttccaa tagtgatggn nnatctnnnn   720
tatcagtttc ttcaactggg tccggcaatn nnnnnnntga taaatactga cttgnnnnnn   780
nnnnnnnnnn nttgaaaagt atcttattat ca                                 812

SEQ ID NO: 11          moltype = DNA  length = 817
```

```
FEATURE                 Location/Qualifiers
misc_difference         160
                        note = n is a, c, g, or t
misc_difference         681..682
                        note = n is a, c, g, or t
source                  1..817
                        mol_type = unassigned DNA
                        organism = Zea mays
SEQUENCE: 11
cggctaccgc gacggctccg agctgcggtt cgacgccacg gtgtcgggca cgctgggcga    60
gggccgcctc acggaggtgg aagggatcaa gaccaaggtg ctcgtctggg ccagggtcac   120
cgccgtcaag gccgacgccg ccaaggtcca cttcaccgcn gggatcaaga ggtcgcgcag   180
ccgggacgcc tacgaggtcg tcaggggcgg catcaccgtc gacgagttct agcttagttt   240
tgctttcgcg gctcacatgg atggacgggc ttcctcttgc tcgctgcacg ctgagatgca   300
caagattgtt gctttcagtt gcaagaataa attctacacc cattagctat gtgcagggc    360
ggagccagga ttacgatata aggggggcca atcaactaat caatattata tgataaaaaa   420
tattatataa tgttataaag tttaagcact cgctatggaa taagaattct aaatctttat   480
aaattatttt ggtccatgag tccattttct agctaattga tatattgaac taaagttatg   540
acgtaagaca ataccaaaaa ataaagacga taaaatgatg aatatccgac taatgagatt   600
caactttta ataatggatc tagtattcat gagacaacta acaaatgtat gagagaattc   660
aaaaatccaa ctagccttaa nnatccatga aaattcgtca acctatgcag gtacatgtta   720
aaatttgttg tgtacacacc aactatcaga tgacaacttt agttgaaatt tgtagattta   780
ttatctacga gatctaatgg agtatgtata aagttg                             817

SEQ ID NO: 12           moltype = DNA    length = 392
FEATURE                 Location/Qualifiers
misc_difference         34
                        note = n is a, c, g, or t
source                  1..392
                        mol_type = unassigned DNA
                        organism = Zea mays
SEQUENCE: 12
gccacccgca agcacccaac cagtcgagtc tgcngccgct gctgtagacg ttgattcggt    60
cgagaaaggc ccaggtacga caccagagca accggcgaag cgaagggcac ccaacgttcg   120
acgaggacag agaagggtgc tgcgaagcgc aacgagagaa ggagagcga cgtaggggg    180
ggatattgtt gctgtatact aaatattaac ggcccaaatt aaaggggca acacatgatc    240
cctagctagg ttaactagag ctatagcaat gactggccgt ttccacgcgt acgagatgcg   300
tagtgtgcat catcaacctg tatccatgtt gtattatcgt aggagtcgta ggccttacag   360
tgaccacgcg tactggttag agttggtcgt tc                                 392

SEQ ID NO: 13           moltype = DNA    length = 1674
FEATURE                 Location/Qualifiers
misc_difference         562..576
                        note = n is a, c, g, or t
misc_difference         674
                        note = n is a, c, g, or t
source                  1..1674
                        mol_type = unassigned DNA
                        organism = Zea mays
SEQUENCE: 13
cctgccccgt cccgtccgtc tccgtcccaa tcggatccac ccgccgtcg tcgcctataa    60
actctccctc ccatccgtct cttgaggggg gccggcttc ctcccaactg ccaccgattt   120
gtttgttcgg cttcggcccc atctccagtc acccgttccc acttcattgg tcgctgctcc   180
ctccctccac ggccgatccc gtgccggcga gaggggaccat ggcggggaaa gggaaggagg   240
tgtacgctggc cgccatcgac cagggcacca caagcaccg gttcatcgtc tacgaccgcc   300
acgccaaacc cgtcgcatcg caccagctcg agttcaagca acactacccg gaggcagggt   360
gggttgagca tgatcctatg gagattatag agactgttaa ggtgtgtatg aaagaggcag   420
ttggcaaagc caaagctggt aaacacaatg tggttgctgg tttgaaggcc attgggatca   480
caaatcagag ggaaaccact gttatgtgga gtaaatccac tggccgtcca ctgtataatg   540
ccattgtgtg gatgatgct cnnnnnnnnn nnnnnncag gagattgaa aatgagctgt   600
caggcggtag aacccacttc gtggagacat gtgggttgcc aatcagtacc tatttcagtg   660
ctctgaaatt attntggttg atggaaaatg tggatgctgt caaggatgca gtccggactg   720
gtgacgcctt attcggcacg atcgacacct ggttgatttg gaaccttaca ggaggtgttg   780
ctggtgggca gcatgtcacg gattgctcaa atgcatctcg tacaatgctt atgaatctaa   840
agacacttga ctgggataag ccaacacttg ctgtgttagg agttcctgtt gagatttgtc   900
caaagattat cagtaattca gagaaaatcg gtgtggtcgc caaagagttc ccgtttgcag   960
gagttcccat ctcggggtgt cttggagatc agcatgctgc tatgcttggg cagctgtgcc  1020
agaagggtga agcgaaaagc acctatgaaa ctggtgcctt catccttctt aacacagggg  1080
aagagcctac ccaatcctcc catggcctc ttagtaccat tgcttacaag cttggtccag  1140
ctgcacccac taactatgct cttgaagggt ccattgcaat tgcaggcgca gcagttcagt  1200
ggctgaggga cagccttgga atcattcagt cagcagctga gatcgaaaag ttggctgaaa  1260
cagtgccaga ttcaggtgga gtgtactttg tgccagcatt taatggttg tttgcaccat  1320
ggtggagaga tgatgcgagg ggaatttgca tcggaatcac aaggttcaca aataaggggc  1380
acattgctcg agcagtgctc gagagtatgt gttttcaggt gaatgatgtc ctcagctcca  1440
tgcacaagga tgctgagag gcaggagaag taaagagcgc agaaggagag ttcttattgc  1500
gtgttgatgg tggtgctact gttaataatc ttctaatgca gatccaggct gatttattag  1560
gcagccctgt tgtcagacca gctgacatag agaccacagc cctcggagct gcatatgctg  1620
ctgggttggc tgcaggagtt tggaccaagg agaaggtttt tgcaggtttg caca        1674
```

```
SEQ ID NO: 14              moltype = DNA   length = 459
FEATURE                    Location/Qualifiers
misc_difference            44
                           note = n is a, c, g, or t
source                     1..459
                           mol_type = unassigned DNA
                           organism = Zea mays
SEQUENCE: 14
cacagatctc caaaaacttt gtggcctcaa atcaattgga gtantgaatt cccactccct    60
tatctgttat cttctttctt gccagggttt ggtgcaggat cctcgcgttc cagggcagct   120
gttgccaggg ctgctccagc aatcaacaat tctcagactc ttgataatgc tcctccacat   180
cctgctgatg gagatgcccc tccacatgct gccgatggag gtgctcctcc acatgctgca   240
gatggagatg ctcctccaat gaacaatgaa gaaattgcaa accaagatga aatttatgatt   300
ggtgaagtag ctgtagatga tgaagatgaa gacgcaaact ctcatccagt tccagccagg   360
gatgcgtcga tggaaagtga gcttgccaat gaactgaagg gggatgcctt ggatgactac   420
gatattgatg tcagtaacga aggacaggct atcgcagag                          459

SEQ ID NO: 15              moltype = DNA   length = 678
FEATURE                    Location/Qualifiers
misc_difference            254
                           note = n is a, c, g, or t
misc_difference            354
                           note = n is a, c, g, or t
misc_difference            577..578
                           note = n is a, c, g, or t
misc_difference            603
                           note = n is a, c, g, or t
misc_difference            637
                           note = n is a, c, g, or t
misc_difference            639
                           note = n is a, c, g, or t
misc_difference            641..651
                           note = n is a, c, g, or t
misc_difference            655..658
                           note = n is a, c, g, or t
misc_difference            664
                           note = n is a, c, g, or t
misc_difference            671..673
                           note = n is a, c, g, or t
source                     1..678
                           mol_type = unassigned DNA
                           organism = Zea mays
SEQUENCE: 15
atttagcatt acaccaaaat gcaaagaaat gtccattgtt caaaaacttt ttcctatatc    60
atcatagtaa ttgaactttt tcttggaatc aagtataaat gaacagataa tgcttgaata   120
ccttaaaata tacgccttt ttccttccag tgccatcata gcgtattcca ataagcttct    180
gtacaacaaa ttcatccttg tcaagagtgt cagcatcctc ttgatcctct gaacctgcta   240
aattcgaatc cacntcttga tgaacatatt tttcacataa gactgcccat tccttaagga   300
gagcaagaaa ctcatcagct ttctcatttc gcacctacat tcaaaggtcc aaanaaactt   360
tttgagagca gctggacaga acagatggaa tccaagatgc agcttaatat gcatacctca   420
gtctgttggat gattgtattt taaactttgg cacgcaaaact tgttaagatc aacagcccat   480
cgctgcaatc atagccataa cagtagaatc agtggtaagt aagaaacatgt tctatccaac   540
agataactag gtagaatatt acagtttcaa gtttcannc agaaagagca gcacccaagc    600
aangaccagt ggacatgccc ccacagcccg aatacangnc nnnnnnnnnn nctgnnnnct   660
ctgncatatt nnntgacg                                                 678

SEQ ID NO: 16              moltype = DNA   length = 590
FEATURE                    Location/Qualifiers
misc_difference            4
                           note = n is a, c, g, or t
misc_difference            14
                           note = n is a, c, g, or t
misc_difference            17..19
                           note = n is a, c, g, or t
misc_difference            44
                           note = n is a, c, g, or t
misc_difference            48
                           note = n is a, c, g, or t
misc_difference            196
                           note = n is a, c, g, or t
misc_difference            267
                           note = n is a, c, g, or t
misc_difference            364
                           note = n is a, c, g, or t
misc_difference            383..385
                           note = n is a, c, g, or t
misc_difference            401..402
                           note = n is a, c, g, or t
misc_difference            418
```

```
                          note = n is a, c, g, or t
misc_difference           433..434
                          note = n is a, c, g, or t
misc_difference           489..497
                          note = n is a, c, g, or t
misc_difference           501..503
                          note = n is a, c, g, or t
misc_difference           505..511
                          note = n is a, c, g, or t
misc_difference           528..535
                          note = n is a, c, g, or t
misc_difference           551
                          note = n is a, c, g, or t
misc_difference           553
                          note = n is a, c, g, or t
misc_difference           557..565
                          note = n is a, c, g, or t
misc_difference           568
                          note = n is a, c, g, or t
misc_difference           576..579
                          note = n is a, c, g, or t
misc_difference           583..586
                          note = n is a, c, g, or t
source                    1..590
                          mol_type = unassigned DNA
                          organism = Zea mays
SEQUENCE: 16
tacnttttcc cccnagnnnc agtaagttca ttgaactttt gggnagcnat gatcagtgaa    60
gagtaaagac ttccccaggt atgcaaaccc tagcccctag gcgacagtat ataacatgac   120
tagatgttta gaatctagat gtagaaatat ttaggtgcaa attagttaaa ttgattgatg   180
ggtacattgt tgatgnatta tgtacttcct tggattgtga agaaggattg agatatgaaa   240
agacagtaaa gtttccgcgg ttccacngac gtcgtgtgtc acccttccac ttcccgcttt   300
atgcagcaaa aataaggtaa aattgcttta tgcagcaaaa ataaggtaaa attgtgcaca   360
actnaggatt caaaacttgg tgnnnggctc cacattcaca nntatctaac caacaganca   420
acacatattt ttnngtttta ttaaaacaaa gtctactcat gtgatatata aaaatcatag   480
caatgtacnn nnnnnnnact nnnannnnnn natttattag tactcccnnn nnnnnaaact   540
ataaactttc ntngatnnnn nnnnnttntt atgcannnnc atnnnncact               590

SEQ ID NO: 17             moltype = DNA  length = 721
FEATURE                   Location/Qualifiers
misc_difference           365
                          note = n is a, c, g, or t
source                    1..721
                          mol_type = unassigned DNA
                          organism = Zea mays
SEQUENCE: 17
ggatgcgccc cacgacctcc cgtgactctc ccagtcccag gctcccagcc ccgccttcct    60
cccgcctccg cgagaccgcg atggcagtct tgctgtggcg gtgcatatgc gggcccaac   120
aatccttcag taagaatcga ggcgcatcca cccttctcc tcctggtaag ccttcgaacc   180
actccctctc ctcccgtcct ccgtatgcct ccttcatttc ttcttgctgc ctctcgaatt   240
ctcagctcct atgcattttt ttcttttcttt ctctaagtta tgttcagttc ttggatatcc   300
ttataactcg ctgaggattc cgatcccgaa catcgacaat tcttgctctt gcttcatgca   360
cagcnggcag gagatccaaa tactcgggac aatctgtggt aaggagcgca cgcattgagc   420
tttccctgct acaccgatgc atttggttca tttctcctga aaaaaagta cactggaggc   480
aaaagcttga aaaaaaaaca tgtcttgtga aaccaagagc ttgtgtgctc cggttctact   540
aataattcgt gtagcctcag ctttctgatc ctgatgtctg tatttccatg tccgcagaaa   600
gcaatgccca tgcgtttgtt aacggttgga aagaagaggt ctcgggggac acaactcctg   660
gttgaagaat acaaggagaa gctcggtcac tattgcgagt cgaggacacg tcttatcagg   720
c                                                                  721

SEQ ID NO: 18             moltype = DNA  length = 1100
FEATURE                   Location/Qualifiers
misc_difference           67
                          note = n is a, c, g, or t
misc_difference           92
                          note = n is a, c, g, or t
misc_difference           195
                          note = n is a, c, g, or t
misc_difference           502
                          note = n is a, c, g, or t
misc_difference           529
                          note = n is a, c, g, or t
misc_difference           538..556
                          note = n is a, c, g, or t
misc_difference           597
                          note = n is a, c, g, or t
misc_difference           657
                          note = n is a, c, g, or t
misc_difference           662
```

|   |   |
|---|---|
| misc_difference | 673 |
|  | note = n is a, c, g, or t |
| source | 1..1100 |
|  | mol_type = unassigned DNA |
|  | organism = Zea mays |

SEQUENCE: 18

```
cgacggcacg aagatgagcg cggcagcgac ggcgagagag acggccaccc atggcgacgg   60
gaagaantgc agcacgaacc ctccgcacca cncgctgaca agccggcccc ggtggcccgc  120
tacggcgtca agcatctcgc cgtagtcgtc aggaagccgc gccccgacgg tctcctcacc  180
tagctcccgg aacanggcca ccagctcggt gtccgtgcgc cgcgtgctgg caaggacccc  240
tcgcttgcgg agcatggccg cgtcctgtgg gcaacgaatc aggccctcca tccgcgctac  300
gtgcgccgtc acgcatgcgc cgtgcgccca gtagaagtgt ttctcgaagg ccaggaggtt  360
gtggagcaca gccgcgctgt actcgtggac gtggaagcac gggacggtca tcacggccac  420
cgggctcgcc gggtgtcgcc agaaccacat gtccaggtcg ccgcagctcg acgacggcctc  480
gcggaaccac accgctgacc tncgaagctc catggagcag gggaacagnc gctccgannn  540
nnnnnnnnnn nnnnnnagct tccgtggcgt cgagaggacg aagtacttgt ccttggncac  600
gcgggaccag tggaagaggt gcaggacgtg gtggaactca ccggcggcag cgctgtnggc  660
gncgcgacgc gcncgcttgg ggcagatgtc gtcgaaacat ccgagcacga gctcctcgac  720
ggagttccgg agcttgagcc cagggcacga agcggcgaga agcttgatgg ctctgaacgg  780
gacctggttc tcgagcacga gcatgtcgag cttgatgtcg tcggcgtgct cgccacggc   840
catgtgcagt atgaagtagt ccttgctgat ggacgccgcc gcgtcacgc tgtcggcgtc   900
gtcgcctgtg ccggccttgc tgagcatcaa gctccaccacc aggatgaagc agctgtccag  960
cagcagcatc tccagcagct tcgcctcgtc gtctagaatc tccacggcgg gcccgtccga 1020
gccgtcgtcg gcgaactcac agcggaggcg gtcgcgctcc aggcagagcg cctcgacgta 1080
cccgtccacg tcgaggccgc                                              1100
```

|   |   |
|---|---|
| SEQ ID NO: 19 | moltype = DNA length = 660 |
| FEATURE | Location/Qualifiers |
| misc_difference | 141 |
|  | note = n is a, c, g, or t |
| misc_difference | 160 |
|  | note = n is a, c, g, or t |
| misc_difference | 167 |
|  | note = n is a, c, g, or t |
| misc_difference | 170 |
|  | note = n is a, c, g, or t |
| misc_difference | 192 |
|  | note = n is a, c, g, or t |
| misc_difference | 213 |
|  | note = n is a, c, g, or t |
| misc_difference | 321 |
|  | note = n is a, c, g, or t |
| misc_difference | 415 |
|  | note = n is a, c, g, or t |
| misc_difference | 458 |
|  | note = n is a, c, g, or t |
| misc_difference | 464 |
|  | note = n is a, c, g, or t |
| misc_difference | 565 |
|  | note = n is a, c, g, or t |
| misc_difference | 570..571 |
|  | note = n is a, c, g, or t |
| misc_difference | 596 |
|  | note = n is a, c, g, or t |
| misc_difference | 608..612 |
|  | note = n is a, c, g, or t |
| misc_difference | 624..625 |
|  | note = n is a, c, g, or t |
| misc_difference | 637..645 |
|  | note = n is a, c, g, or t |
| misc_difference | 647..649 |
|  | note = n is a, c, g, or t |
| misc_difference | 651..653 |
|  | note = n is a, c, g, or t |
| source | 1..660 |
|  | mol_type = unassigned DNA |
|  | organism = Zea mays |

SEQUENCE: 19

```
ttttgcaagg acctttctg gtttacatgc tagaggaatc gagcctggtg ttctttatcc   60
agctgtctct gttgagcagt ttcacgaacc ccatgcttat aagtaacttc atgcttgcat  120
atctccttac atttaggtct nacttattca gtttatagan taaacanatn tttttaccat  180
tatcatatta anatttagct aaagtagaca acnatctttt gtacaggttg aatttcctat  240
caatcaaccg gtttgagagg aaaaagaatc ttgatctcac catttcagca tttgctttgc  300
tccgttctgc tgcttggact ntacctggtg atgctctaca agaagcaaca ttaacagtgg  360
caggtgttta tatttatttt ttccttctag ttgcatgttc aatgttacaa cacncccggt  420
tttaaaccat atgaaatatt gactgctgat ttcctacnat gccnattatt taggtggcta  480
tgataagcgt ctcaaggaaa atgttgaata ccttgaggaa ctcaaaagac tcgcattgac  540
ggaagggggtt tctggacagg ttaantttgn nacatcttgc tcaacatctg aagananacga 600
```

```
gcttctcnnn nnctgcctct gcgnnttata cactccnnnn nnnntnnnt nnngcttaca    660

SEQ ID NO: 20          moltype = DNA  length = 358
FEATURE                Location/Qualifiers
misc_difference        61..62
                       note = n is a, c, g, or t
misc_difference        65..66
                       note = n is a, c, g, or t
misc_difference        227
                       note = n is a, c, g, or t
source                 1..358
                       mol_type = unassigned DNA
                       organism = Zea mays
SEQUENCE: 20
ccaataaaca tgccactaga ttatccaata tcaatggacc aaactaaact cttgcaaaag    60
nnggnnaaca tgcactggtt aacaccaatt caccccatag ccagcaacag agctagttta   120
cagtaaagag aaattgacat tattcttcta taaatgaacc ttatttatat tcatgtgtgc   180
ttgatttgtt tttaacatac actatggaat atgcacgtcc ttaaaancat gcatgtgtgc   240
ctataaccca ataaacatga cagcattaaa gaaattattc atatccgaat tacattgaat   300
cctaactgtg aaaatctgga aatggagatg tgaaggaaag agcaaaaggc acacctca     358

SEQ ID NO: 21          moltype = DNA  length = 773
FEATURE                Location/Qualifiers
misc_difference        4
                       note = n is a, c, g, or t
misc_difference        122
                       note = n is a, c, g, or t
misc_difference        224
                       note = n is a, c, g, or t
misc_difference        244
                       note = n is a, c, g, or t
misc_difference        290
                       note = n is a, c, g, or t
misc_difference        310
                       note = n is a, c, g, or t
misc_difference        428
                       note = n is a, c, g, or t
misc_difference        471
                       note = n is a, c, g, or t
misc_difference        512
                       note = n is a, c, g, or t
misc_difference        521
                       note = n is a, c, g, or t
misc_difference        601
                       note = n is a, c, g, or t
misc_difference        641
                       note = n is a, c, g, or t
misc_difference        644
                       note = n is a, c, g, or t
misc_difference        650..651
                       note = n is a, c, g, or t
misc_difference        666..668
                       note = n is a, c, g, or t
misc_difference        672..680
                       note = n is a, c, g, or t
misc_difference        691..692
                       note = n is a, c, g, or t
misc_difference        695..696
                       note = n is a, c, g, or t
misc_difference        698..700
                       note = n is a, c, g, or t
misc_difference        703..707
                       note = n is a, c, g, or t
misc_difference        721..725
                       note = n is a, c, g, or t
misc_difference        731..761
                       note = n is a, c, g, or t
misc_difference        763..772
                       note = n is a, c, g, or t
source                 1..773
                       mol_type = unassigned DNA
                       organism = Zea mays
SEQUENCE: 21
catncctgca gtgtaagctt gaatctgtct ttacaatcgt gaaccataag ctgagtcctg    60
ttacagggca actctccttt ggcagagggt tgaagagagc agagagctat ggcatctcat   120
gnttccctgc caagaaagag aagccctgaa actggacagc ttaggcattc catttcctga   180
tcatgtaaac aatgagttct ttcctctctt atcttgacct cacngttttc tgctcactgt   240
gggnctgcgg cactgcaata tttatatagt gaacatatcc ttgataagan gtgtacttct   300
tgattttttn cgaagggttt taaaccatgg atatcctctt ggcatccaac atctcccttt   360
```

```
cccttttgcc ctcatggttt tgtctctctg aagttctcac cccactatcg gattccctttt    420
ctcgttcnag atcgagaccc ttctttggca attggcacta gccacagaac ngtagctgct    480
ggtgattttc actttactaa gacaaaccga tngttcagta ntttgactac acagtaaagt    540
tagtgatgct gccacactta ctgctggcga tttccatttt cttaagagaa aacaattgtc    600
nagtacagca tttgtctatt tgaccacaca gtaaaattag ntgntgctgn ntcactaatg    660
tttctnnnct gnnnnnnnnn acatgatctg nngcnnannn gcnnnnntca ctcataatag    720
nnnnnatagt nnnnnnnnnn nnnnnnnnnn nnnnnnnnnn ngnnnnnnnn nnc           773
```

```
SEQ ID NO: 22             moltype = DNA   length = 372
FEATURE                   Location/Qualifiers
misc_difference           29..32
                          note = n is a, c, g, or t
misc_difference           58
                          note = n is a, c, g, or t
misc_difference           86
                          note = n is a, c, g, or t
misc_difference           88
                          note = n is a, c, g, or t
misc_difference           105
                          note = n is a, c, g, or t
misc_difference           170
                          note = n is a, c, g, or t
misc_difference           197
                          note = n is a, c, g, or t
source                    1..372
                          mol_type = unassigned DNA
                          organism = Zea mays
SEQUENCE: 22
ggttgtttgg ttcttgctac ttctgtaann nncatagtgc ttaatcctct tccagccntt     60
atcctcttcg atcttagcca taatananat ttgccaatca atatnttggc caataatggg    120
gagcaacgta cacaaacaag tagctagcag aacatggaga atattttccn ctttctcaca    180
tttgtgcgcg catgaanttg acaaacaatt ggcagtccgt acgtgcgagt agtattattt    240
tgtgtgctga gattagttca tggaataatc atccacgtgt cgccgtggtc atcattatcg    300
tcattcaaca aattggagtg gacgggcata cgatataatt ttctaactat accaagataa    360
ttatcagcgg ca                                                        372
```

```
SEQ ID NO: 23             moltype = DNA   length = 736
FEATURE                   Location/Qualifiers
misc_difference           406
                          note = n is a, c, g, or t
misc_difference           694..698
                          note = n is a, c, g, or t
misc_difference           715..728
                          note = n is a, c, g, or t
source                    1..736
                          mol_type = unassigned DNA
                          organism = Zea mays
SEQUENCE: 23
acctacctct ttatgccact gtcgccagaa tgtgctaaaa aaagaaaag tacataccta      60
ttatgttaat gttcccatat ggcgattaga atctagaagc ttcattcccc ctttttctaat   120
gttctgtgca ttggtgcccc agtcctggtt ggtttgactt tgatcgatag caaagaacaa    180
catgaatcca tgcgcaatta ttagatatat atcgctacaa atgcagaact gctctctgga    240
tttatttctt tgcatatcag tactgcatgg atatatacct gtttaaaact tggtcacatc    300
tgtcaaatgc ttgctcatta cacaggagct tgaagatgaa agtgttctcc ttcggtttgc    360
tcatctatat gaggttttgc actgctaccc ttactctcac ttgttncagg tgaggtaaat    420
cctaatttc ttttctatgt cttgccctgt gctgtcgtgc acataggccg gggaggacaa     480
ggatctttcg tctttagcga gtatcgacct caagagagtg ttcccggaga agaaggttcc    540
ctccgtcact ctgttgtttt acttacgctt attctagtct tcagcattcc taactcagat    600
tcttgatccc tcgctctaga ttggcaaggt catcgagaca agcttatcgg caaaccaaga    660
acgcgcagcc atgagaaga agcgtttgaa atgnnnnncg caaggttctg cggcnnnnnn     720
nnnnnnnttt cggggt                                                    736
```

```
SEQ ID NO: 24             moltype = DNA   length = 1210
FEATURE                   Location/Qualifiers
misc_difference           6..10
                          note = n is a, c, g, or t
misc_difference           404
                          note = n is a, c, g, or t
source                    1..1210
                          mol_type = unassigned DNA
                          organism = Zea mays
SEQUENCE: 24
tgcctnnnnn accttactca aacagtatgg aaaagtatta ggcctagatc ctaaaaggat     60
tccacagaat tgggcagcca ctcaatttgc tgaagcattg ggcagagcat gggccgagta    120
taacaatgac aggtcagcgc ttttctatgc agcatgagtt gtattattca gaatttctag    180
aaaatgtaag tgtcaattaa catgtttttgt tctcttttgt cgctcagtgc tgttgttttg   240
atggttgtcc aacctgaaga aagaaatatg tacgaccagt actgtcttgt caatcatctg    300
aaggaatcat atccttttttt atgtttgctt tcttttcagt tttcactcct attgtcagat   360
tttcaatatc tgggttgtga aaaacttcat ttagttattg actnattcct atcgtgatag    420
```

```
tgtttcctta tctgtggttt ggcggctcgt ctccacaaca aactaataag atgttgattt    480
cttgtatgta cactgctgta ttattctttc aacatattgc ctgcctgata taacttcaga    540
gaaccattaa agtgtgcggc aagcatctgc ttttttttg ggtctggtat taagagcatc    600
caacagcatg aaaaatgtgg ctttccttaa ctagccatca catatggtgt ggcaactata    660
aggaaaacat tggcacaagt agaggctcaa gggcaggttc ttacagatgg aacacttgtg    720
gtgtaagtat cttatataga catggaaaaa ggcttattat tactatcaga atttagtatg    780
taaatttatg aattgcagag atggtcggac agtggctgtt gtgtatttca gagccgggta    840
tgcaccaact gattacccct cggaagcggt atgcaatcaa atatctatta attcaaaatc    900
tttatataga ataagagtaa attctgtttt ttgagtgaaa gaaactgttc ctgtaattgt    960
tttaaaaaaa tcatatgtct ggtgcaatgc cgcttagtct cattttcctg aaacagtcat   1020
cttcttttgt gcatgcattt ctgtctctgt tggaaagcaa tccttagcca aatggtttta   1080
ttgctttggt tgaggatgtg tagtaattca ttttgttatg attatgatat ggcaccactg   1140
ttccaccttg acataacgct atcatattcc aggagtggga agcgaggctt ctgatggaac   1200
aatcatctgc                                                           1210

SEQ ID NO: 25           moltype = DNA   length = 379
FEATURE                 Location/Qualifiers
misc_difference         342
                        note = n is a, c, g, or t
source                  1..379
                        mol_type = unassigned DNA
                        organism = Zea mays
SEQUENCE: 25
ctaccaccac tgggccagtt accaacacta caaaagctag ttatgggagg aatggacagc     60
actttgacag ttgatgaggg tttctgctgc gccggcccgg gagcctttcc tctattcag    120
gaacttcaac tatgccaaat ggagaacctg gaagtgtgga acacaacata ctcctgtggc    180
cagagcaatg aggatgtgca ggaattcatg ttcccaaacc ttagggaact gttaattcgt    240
gattgcccca agttgagact gaaaccatgc ccacctaaaa ctgtgggatg aagatagag    300
aacagcgaca atgtactgtc gtcatgggat gaggaggag anatcgacct tgcagcattg    360
ttcccatcaa ggaaagagt                                                 379

SEQ ID NO: 26           moltype = DNA   length = 829
FEATURE                 Location/Qualifiers
misc_difference         198
                        note = n is a, c, g, or t
misc_difference         630
                        note = n is a, c, g, or t
misc_difference         633
                        note = n is a, c, g, or t
misc_difference         642
                        note = n is a, c, g, or t
source                  1..829
                        mol_type = unassigned DNA
                        organism = Zea mays
SEQUENCE: 26
agtatgggaa ttttgtgtgt aagccagaca caagtcgcta tgctggtgtg ccattgttgg     60
ttcgacattt atgtgtattt cagtggagct ttgcatctca agttcagttg gcgcataaat    120
atgaaccgtg ctatttggcg taatcaaaat agccaacttg tgtggtggca tgcatttctg    180
aaagttgaaa atttgccncc aacataggtc ttgtttggta gagctctcaa cggctcttat    240
agtagaaatt tagaaatgcc catgttcata tgttttcgtt tttaacctct tgagctcacc    300
tctgttcaga tatatgctcc ctcgttttta acctcttgaa tctcacttct gttcagatac    360
atgctcgact tcattttacc aacctatcga tgtggtaaaa tttgttgccg attgtctcca    420
gctgacaaac cctggccaac ctttttggga cagggatcgt ttaaaggtac aatttgtgga    480
taaaagttgt cacatgcaat ttaactcagt gaccaactaa tctgttccta tctacaattt    540
tttagcttaa gagagccctg cgcggagttc ttgttggagc tgaacaccag cagggaaaga    600
gaagcatcta caggataact gggattactn ctnttccatt gnctcaactg aggtaccac    660
cggttcatat ctcttccctc cttgcctgtt tggtctagta ccaagaagac gaacttattc    720
atttccattt cttgtcttca gcttttcttg taacgaaggc cctcagctga ctgttgttga    780
gtactttgca caacggtaca atgtccagct gcgctacact gcttggccc                829

SEQ ID NO: 27           moltype = DNA   length = 379
FEATURE                 Location/Qualifiers
misc_difference         102
                        note = n is a, c, g, or t
source                  1..379
                        mol_type = unassigned DNA
                        organism = Zea mays
SEQUENCE: 27
agtttcatca tctgggtaca acatcagacc gatgacactg ctacagtgga gacgaaatgc     60
aagaatgaat taacatctct ggactttggc attctatgat gnggggtcct agaagcacca    120
aactgtacag cggaaactca acaccgtacc cacccataga atcattactc actttcataa    180
tcatcttcat ctccgaacga gaacaccgag gcatctgcgg caatcgcctt gaattcgctc    240
atgctggaag agtcagcagc tggaggaggt ggtgctgtgg tggagctggc cttgctgctg    300
acttcagttt tgagagatgt accatcaggt gcctttgtgg ttccctgttc gctgcttata    360
gccactttgt ccagtaaaa                                                 379

SEQ ID NO: 28           moltype = DNA   length = 532
FEATURE                 Location/Qualifiers
misc_difference         10
```

|                  |                                                    |
|------------------|----------------------------------------------------|
| misc_difference  | 19                                                 |
|                  | note = n is a, c, g, or t                          |
| misc_difference  | 92                                                 |
|                  | note = n is a, c, g, or t                          |
| misc_difference  | 209                                                |
|                  | note = n is a, c, g, or t                          |
| misc_difference  | 215                                                |
|                  | note = n is a, c, g, or t                          |
| misc_difference  | 232..237                                           |
|                  | note = n is a, c, g, or t                          |
| source           | 1..532                                             |
|                  | mol_type = unassigned DNA                          |
|                  | organism = Zea mays                                |

SEQUENCE: 28

```
atttataacn aggaatctnt tcttctgttt gctctatagc caatgcttgt gttactgctc   60
taaatggttt gctgctgtaa gattgggtac tnacaacaag atccattttt tggatgtgca  120
gagccacctt atggccgagt ctattctga gctacagaag aaggtaacta aagctgaaaa  180
aactttcaag gcagttgcac tcaggcttnc aaaanaaaac agcacttgag tnnnnnnggc  240
catttacctg ctgatgattt gtggttcaga atgctctgca tctgaacagc catcaacagt  300
agattgatca ttgcagaaat gactgttggt actgctgtgg tgtgcaggag aggtcactgc  360
aggaggagaa caaggctctg cagaaggaag taagctgact gcaccctaaa  420
ccattgcatt ggcaacagaa gggtttgatg tgtgtctcct cttttgtgt agcttgcgga  480
gaggcagaag ccgtcgcga ccggcagca gcaggtgcag tgggaccagc ag           532
```

| SEQ ID NO: 29   | moltype = DNA   length = 356 |
|-----------------|------------------------------|
| FEATURE         | Location/Qualifiers          |
| misc_difference | 49                           |
|                 | note = n is a, c, g, or t    |
| source          | 1..356                       |
|                 | mol_type = unassigned DNA    |
|                 | organism = Zea mays          |

SEQUENCE: 29

```
catatataat aactactgta ggcagcggca tctcctgctg ggacgaagnt tcaagaagct   60
agctaagaga gaagggcata acgagataat aagcagcgcg cgaagatgca agactgggcg  120
ccggtgttcg tctcgctggt gctcttcatc ctgctgtcgc cgggcctgct gttccagatg  180
ccgggcaagt gccggatcat cgagttcggc aacttccaga ccagcgccat ctccatcctc  240
gtccacgcca tcctcttctt cgccctcgcc gccatcttcc tcgtcgccgt cggggtgcac  300
atgtacctcg gctcctaggc ggcggcgcgg ggcgccgtac cttctctccc tctcta      356
```

| SEQ ID NO: 30   | moltype = DNA   length = 382 |
|-----------------|------------------------------|
| FEATURE         | Location/Qualifiers          |
| misc_difference | 118                          |
|                 | note = n is a, c, g, or t    |
| misc_difference | 177..179                     |
|                 | note = n is a, c, g, or t    |
| misc_difference | 185                          |
|                 | note = n is a, c, g, or t    |
| misc_difference | 363                          |
|                 | note = n is a, c, g, or t    |
| misc_difference | 381                          |
|                 | note = n is a, c, g, or t    |
| source          | 1..382                       |
|                 | mol_type = unassigned DNA    |
|                 | organism = Zea mays          |

SEQUENCE: 30

```
tgtacatctg tatgtgatgt gtcatgtgca catgctttgc cattttgcat tggcaataat   60
aggttgtgca tcccttcagc gctacaagga gcaaggatgt ccgcttcaga ttaaatcnga  120
ctgtttagac tgctgcaact gtaatcatag agataaatac actatagaaa cagtagnnng  180
agccnatacg aattaaaaac aacgaacagg ctgaaagatg cagcgcttgt ctgcacaaca  240
tccccaaagt atcttcgagt cgaatacaac agggtaactg agtgtaacca cagttcgtac  300
agaatttgta gagaaaatga attgtccaaa ccaccggata aattcatctt gttacaatgt  360
ttnctggcag aatagctcgc nc                                           382
```

| SEQ ID NO: 31   | moltype = DNA   length = 1263 |
|-----------------|-------------------------------|
| FEATURE         | Location/Qualifiers           |
| misc_difference | 291                           |
|                 | note = n is a, c, g, or t     |
| misc_difference | 602..605                      |
|                 | note = n is a, c, g, or t     |
| misc_difference | 782..783                      |
|                 | note = n is a, c, g, or t     |
| misc_difference | 808..809                      |
|                 | note = n is a, c, g, or t     |
| misc_difference | 814..817                      |
|                 | note = n is a, c, g, or t     |
| misc_difference | 842..847                      |
|                 | note = n is a, c, g, or t     |
| misc_difference | 850..853                      |

-continued

| | | |
|---|---|---|
| misc_difference | 870 | note = n is a, c, g, or t |
| misc_difference | 873..875 | note = n is a, c, g, or t |
| misc_difference | 901..903 | note = n is a, c, g, or t |
| misc_difference | 911..913 | note = n is a, c, g, or t |
| misc_difference | 919..920 | note = n is a, c, g, or t |
| misc_difference | 922..927 | note = n is a, c, g, or t |
| misc_difference | 929..932 | note = n is a, c, g, or t |
| misc_difference | 934..935 | note = n is a, c, g, or t |
| misc_difference | 941 | note = n is a, c, g, or t |
| misc_difference | 948..951 | note = n is a, c, g, or t |
| misc_difference | 955..956 | note = n is a, c, g, or t |
| misc_difference | 959..961 | note = n is a, c, g, or t |
| misc_difference | 963 | note = n is a, c, g, or t |
| misc_difference | 971..973 | note = n is a, c, g, or t |
| misc_difference | 975..979 | note = n is a, c, g, or t |
| misc_difference | 981 | note = n is a, c, g, or t |
| misc_difference | 983..988 | note = n is a, c, g, or t |
| misc_difference | 993..994 | note = n is a, c, g, or t |
| misc_difference | 998..1007 | note = n is a, c, g, or t |
| misc_difference | 1009 | note = n is a, c, g, or t |
| misc_difference | 1011..1037 | note = n is a, c, g, or t |
| misc_difference | 1039..1051 | note = n is a, c, g, or t |
| misc_difference | 1053..1057 | note = n is a, c, g, or t |
| misc_difference | 1062..1065 | note = n is a, c, g, or t |
| misc_difference | 1067..1076 | note = n is a, c, g, or t |
| misc_difference | 1078..1081 | note = n is a, c, g, or t |
| misc_difference | 1083..1118 | note = n is a, c, g, or t |
| misc_difference | 1121..1125 | note = n is a, c, g, or t |
| misc_difference | 1127 | note = n is a, c, g, or t |
| misc_difference | 1129..1131 | note = n is a, c, g, or t |
| misc_difference | 1133..1146 | note = n is a, c, g, or t |
| misc_difference | 1151..1170 | note = n is a, c, g, or t |
| misc_difference | 1172..1174 | note = n is a, c, g, or t |
| misc_difference | 1178..1186 | note = n is a, c, g, or t |
| misc_difference | 1188..1202 | note = n is a, c, g, or t |
| misc_difference | 1204..1217 | note = n is a, c, g, or t |
| misc_difference | 1223..1230 | note = n is a, c, g, or t |
| misc_difference | 1235..1240 | note = n is a, c, g, or t |
| misc_difference | 1247..1255 | note = n is a, c, g, or t |

| | |
|---|---|
| misc_difference | 1259 |
| | note = n is a, c, g, or t |
| source | 1..1263 |
| | mol_type = unassigned DNA |
| | organism = Zea mays |

SEQUENCE: 31

```
catatctctt atagtagtgg cctactacaa aatagggtc cgtgatgtac atgccgaagt    60
gaataagtac tgctcattca ttgttggcat gggtataatt actgtactag ccaacttctt   120
gcagcacttc tactttggta taatgggaga gaaaatgacc gagcgtgtca gaaggatgat   180
gttttctggt atgaccgtct tttcctttat gttacttttg tagtcccata tttaatggtg   240
caacctcagc tcttataaac tatctagttt aacatccata aataaagcac ntattcatga   300
gtattgaaca caagaaacaa tgctgctgtg ctaagttcta ttgtgtatag attatagtaa   360
accattgttg aaatatcaga gttctcacat tctgtttact gtattccagc aattctgcgc   420
aatgaagttg gttggtttga cgacgaagaa aatagcgcag acatattatc aatgagactt   480
gcaaatgatg caacatttgt ccgcgctgct ttcagtaaca gactttctat attcattcag   540
gatacatcgg ccattcttgt tgcacttctt cttggtatgt tactacaatg gcgtgttgct   600
cnnnnttgtt tccgaatcca taccgaagtt tatatctatt atttgagaaa atgtaggatg   660
aatttaagat ttatcttta tgaatcttaa caagctggat gttaaaaaca agaatacaaa   720
tttatattgt atattctata tcatatttat tcgcaatcaa agaaaaaact gattaccgaa   780
tnnataccgt ttccgaccgt tttcatcnnt aatnnnngca attctgcgca atgaagttgg   840
tnnnnnngan nnngaagaaa atagcgcagn cannntatca atgagacttg caaatgatgc   900
nnnatttgtc nnngctgcnn tnnnnnncnn nnnnctata ntcattcnnn ntacnncgnn   960
ncntcttgtt nnncnnnnnc ntnnnnnnta ctnnaatnnn nnnnnncnc nnnnnnnnnn  1020
nnnnnnnnnn nnnnnnncnn nnnnnnnnnn ntnnnnnccc cnnnntnnnn nnnnnncnnn  1080
ncnnnnnnnn nnnnnnnnnn nnnnnnnnnn nnnnnnncc nnnngncnn ntnnnnnnnn   1140
nnnnnnccct nnnnnnnnnn nnnnnnnnnn cnnnctcnnn nnnnnctnnn nnnnnnnnnn  1200
nncnnnnnnn nnnnnnctt ccnnnnnnnn cttcnnnnnn tcttctnnnn nnnntccnc   1260
ccc                                                                1263
```

| | |
|---|---|
| SEQ ID NO: 32 | moltype = DNA   length = 254 |
| FEATURE | Location/Qualifiers |
| misc_difference | 46 |
| | note = n is a, c, g, or t |
| source | 1..254 |
| | mol_type = unassigned DNA |
| | organism = Zea mays |

SEQUENCE: 32

```
agggtagtat atgtgcattc atcgtttttc attagccttg attagnccaa agtgatagtt    60
tatgcttggt catcgagagt ttggtgatca gacgatgaag attgtgagtg gcacaactta   120
agaggtaaac agttgtgtga ttcaacatag tagagtgaca aatgatcgac tcatagagag   180
ccctcgtatg agacgtgagc gacactcctt cataggtgtt ctaataagga ttagttagaa   240
gtgtcaactc ttga                                                     254
```

| | |
|---|---|
| SEQ ID NO: 33 | moltype = DNA   length = 1049 |
| FEATURE | Location/Qualifiers |
| misc_difference | 353 |
| | note = n is a, c, g, or t |
| misc_difference | 554 |
| | note = n is a, c, g, or t |
| misc_difference | 592 |
| | note = n is a, c, g, or t |
| misc_difference | 1038..1044 |
| | note = n is a, c, g, or t |
| source | 1..1049 |
| | mol_type = unassigned DNA |
| | organism = Zea mays |

SEQUENCE: 33

```
atagtggtgt aacccatgcc gagcatccgg aggagggcaa gtgctcctta gctgatgatg    60
gaaatatcca gaagtctggg gttatggtca aagaaaaaga gacacatgga caaaacgctg   120
gggctagttt ggatttaact gaaagagttg agaatgttga cactggtgaa aaggcgagcg   180
gaggtaaaat cggtgatatt ggcactagtc aactgagcat gacactgtat gagaaaagtc   240
aggctgctca cagggaggag aggccacgca ggtatgaagg cgtgcatgtt gagtctcaca   300
aagctctgat cgaagagttg gagaggtctc tttcgttcag cagtgaggat gantacttct   360
cggacgaagc agaaagcagt ggcctcagtg atgctctgca taaccaaatg ggtagccgca   420
ggtttatgct aggggggcaga gtgaatgatg cgccccgaag cgatccacat ggtcgattga   480
ttgaagaact agagatgtct ttcagcgatg cagaagagcc attggagcag catgctatgt   540
gttcagagag agtncatgga aatgtgcttg acaaggatcc acagatcctg antgataaaa   600
gtgcacatcc atgtgaagaa agcctctcat catttgagag tggacacctc aaatctgaac   660
aaaactcctca ccaggaaagc agggcaatag gggcaatagg caatggcaat caaggaaatg   720
agcgtattga agataacaat aatactgccg actctgttca tgggagtgag catattgtga   780
ttgacgatga caaaattgca gatatattcc acgagaaaga acatgataag gattgccagc   840
ttgcaaacat agaaagtgca taccccttctg aaggaagcac ctctgctgtc gatgattgca   900
gtattgaagt tcagcaaagt tttcaaccaa atgacctgac agcagtcgat gagtgcagta   960
ttgaagttca gcaaagtttt caaccaaatg acctgacagc agatgtcaat caagaaatgg  1020
aagatgataa gataaccnnn nnnnacata                                    1049
```

| | |
|---|---|
| SEQ ID NO: 34 | moltype = DNA   length = 576 |
| FEATURE | Location/Qualifiers |
| misc_difference | 379 |

```
                        note = n is a, c, g, or t
source                  1..576
                        mol_type = unassigned DNA
                        organism = Zea mays
SEQUENCE: 34
ttggatctcg tctcggcctc cggcacagag tttgcgcaag aagacgacaa cggcgatgag   60
gacgatgacg gctccgacga tgatgaggaa agcgactttg acgaggactt caacgacgtg  120
gttaggatga accctcaatt gtctagaccc cagagaggtt gctggtttca gttgtctaga  180
ctccagagag gttgacctag atgatgtatg taaaaacatg caggagggtg tgttttcggt  240
tgatgaggac gacgaagatg acggagagga agaggaggag gacgacg acgacga        300
cgatgacgag gacctaccaa gctggtccaa ccttgagacc gtgaattcct gccatccact  360
gtactttgca aggatgatng tagaggtaca cgatcgaagt ttggcagcat gtcttgtcag  420
caactgcact cttaactaaa tccattattc ccagactgca accaagtcta gcatagactg  480
gctggaccgg ccacctgcaa gccttgtcgt cgagggccag ctgaggcctg cctttgctga  540
ggagagcacc atggttgcca agcatatatc aagtga                            576

SEQ ID NO: 35           moltype = DNA  length = 594
FEATURE                 Location/Qualifiers
misc_difference         362
                        note = n is a, c, g, or t
source                  1..594
                        mol_type = unassigned DNA
                        organism = Zea mays
SEQUENCE: 35
tatatcacga tcaagtgatg gctgtgttgg aaaaatgagg tggagtatct tacctgacta   60
cactatttct gtctaacctc aaatgatttt tgagctgttt tctgtttgga cctgacattg  120
taatggcaac aggtcaaatt ttcttggcac taaattcatc gtgcatgaca ctcgagcacc  180
acacaatgct gggagccttg tctcctgtga gcgcggcagc cgcagaatct cctctaggag  240
ggtttccccc aaggtaccca ctgccagcta ccccattgcc cgggtgaact atgagctaaa  300
cctgcttggc acaaggggc ccaggcgtat gaattgcacg atgcattcca tcccagcctc  360
ancgctggac cctcaaggca tggtgcctga gcctggccaa cccaagcagc tcttcatccc  420
tggctcgtcg tccttcgaag aatcctttcg cagtgcaaac aacacccctt ccagctcaag  480
gttctcggtc gcagaccgct ccttggactg gagctcctct cgattctcag agacgagcgg  540
attggctcag caggacgaca atgacagtga ccaggctaag aagaggcctt ggt         594

SEQ ID NO: 36           moltype = DNA  length = 1474
FEATURE                 Location/Qualifiers
misc_difference         999
                        note = n is a, c, g, or t
source                  1..1474
                        mol_type = unassigned DNA
                        organism = Zea mays
SEQUENCE: 36
tgtatgacat gttcatcgag gtcgattgca taacaatcaa gatgtagctg tcaaggttca   60
atatcctgga ttggagcagc gaatgaagat agacattatg acaatgtcat tcttgtcaaa  120
aatggtctct tgggtttttc ctgattataa atttgacaga atactaattg aatttgagaa  180
atccatgaca atggagcttg attttacgcg ggaggctaga aattctgaga gaacagccag  240
ctgcttcagg aaaaatagtg ttgttaaagt gccttatgtg ttctggcaac ttacaaccag  300
ggaggttttg acgatggagt tttgttatgg acacaaggtt aacgacttgg acttcctgcg  360
gaaaacagat attagcccta caaaggtagc taaggctttg attgaactct ttggtgaaat  420
gatatttgta catggttttg ttcacggtga tccacatcct ggaaatatat tagttttctcc 480
tgaaggccat gggaaatttt cactagttct gttggatcat ggaatttata gagaattaga  540
ccaaaagttc agattggact attgtcggct atggaaagca ctgatattgt tggattcaaa  600
caaaattctg gaattaggcg aacagtttgg cgttggcaaa tatgcgaagt actttcctgt  660
aatattcaca gggagaacta tagaaagcaa gtcagctctt ggcacacaaa tgtctggtga  720
agagcagagg cgtctgaagg aggacttaaa ctctccttggg atggatgata tctcttcatt  780
tatggaatcc ttgccaccgg acttctatgt catactacga acagacggac tattgaggtc  840
catttttaggg aatcttgggg caccacgcca tgttcggctt ctcacttatg caagatgtgc  900
tatacaggt cttgagaagc agcacaaaat ggagtctgat gttcaattgt gttcaggtgc  960
aatcagacgt atgttcttga atgtcaaaac aaatgtcanc tatctccgtc tgagagtgat 1020
tattgaaata gcggtattat tagctaaagc aaatggtgcc aagcagaaag tcctgaacac 1080
actcagacag atgttactgg agatcagtca aggttttcac cgcctatttt gatgcccaga 1140
agtcagcgac gtggtgaaat taaggctacg agaaaggtgg gggaagttgg aagtacgtca 1200
ggactccgga gtagaatcat aactgtgatt gttctgtttc aacttgtaaa ttggaggttg 1260
tattgtgtca aggagtccaa tcataactgt gattgctctg ttgtaacttg taaattgtac 1320
ttctacgtcg agtctgcgct cgagagtcca ggtgtttttt ttgttggacc aagtacgcat 1380
cccaaaataa gtctacatct caaaattcga ggagtcaaac aaatcttaat ttgaagtttg 1440
gctaaattta taaaattggt attaacatta aaaa                              1474

SEQ ID NO: 37           moltype = DNA  length = 669
FEATURE                 Location/Qualifiers
misc_difference         41
                        note = n is a, c, g, or t
misc_difference         115
                        note = n is a, c, g, or t
misc_difference         299
                        note = n is a, c, g, or t
misc_difference         332
                        note = n is a, c, g, or t
```

| | |
|---|---|
| misc_difference | 336 |
| | note = n is a, c, g, or t |
| misc_difference | 348 |
| | note = n is a, c, g, or t |
| misc_difference | 350 |
| | note = n is a, c, g, or t |
| misc_difference | 370 |
| | note = n is a, c, g, or t |
| misc_difference | 491 |
| | note = n is a, c, g, or t |
| misc_difference | 495 |
| | note = n is a, c, g, or t |
| misc_difference | 527 |
| | note = n is a, c, g, or t |
| misc_difference | 534 |
| | note = n is a, c, g, or t |
| misc_difference | 576 |
| | note = n is a, c, g, or t |
| misc_difference | 643..644 |
| | note = n is a, c, g, or t |
| misc_difference | 646..647 |
| | note = n is a, c, g, or t |
| misc_difference | 649..650 |
| | note = n is a, c, g, or t |
| misc_difference | 664..666 |
| | note = n is a, c, g, or t |
| source | 1..669 |
| | mol_type = unassigned DNA |
| | organism = Zea mays |

SEQUENCE: 37

```
acaaatcact cgctactctt gcctacaccc tcacaatcat ntacgaatac tagtgactgc    60
tttcctctcc tcagcatttt tggcaagtgt tgtgctggcg tgccgtgtgt ggagnggaac   120
gctatataaa gcaacgtcta aaaagaaaa aaaatactat atattagcat actagtatat    180
aaataagaa gtaactccaa tagttttcta aaagactatc taaattaata atttaagtaa    240
ctaaactaaa agctcctctc caacggttct ctaaatgaac ttcataaatt tagctactnc   300
tcatctaacc ttattttctc tctacatttt gnaacnattt accaactncn taaacaaaaa   360
aaaattgacn gtaattttg tatttcgctg cctttttcac tttatagtaa cgatatatta    420
acatagccca tgcgtcgaac aacgacagtc agctagagat taaataattg ccaatacaat   480
agccgcacgt ncacntgtcg gaaataaata aataaacaat tgcaacngta aatnaaaaga   540
tcaacacaac tcaccaagtt gaatatgcca tcgatnatgg tcccactcag atgagtgaca   600
tgttaaattt taacatattt agaaagtaat atatatataa ctnntnnann agatgcgttt   660
tttnnntat                                                           669
```

| | |
|---|---|
| SEQ ID NO: 38 | moltype = DNA  length = 1115 |
| FEATURE | Location/Qualifiers |
| misc_difference | 207 |
| | note = n is a, c, g, or t |
| misc_difference | 758 |
| | note = n is a, c, g, or t |
| misc_difference | 1101 |
| | note = n is a, c, g, or t |
| misc_difference | 1108..1109 |
| | note = n is a, c, g, or t |
| source | 1..1115 |
| | mol_type = unassigned DNA |
| | organism = Zea mays |

SEQUENCE: 38

```
ggcttctttt gctaaagagg gcctatgatt aacagttgga aacgaccata acaaaataga    60
cacaagttct ggcctggcac acagagatac ctatgcaaat catcagcatc aacacttctc   120
tggttgaacc taaatagagg attagatcat aggagaacat tcaagaacaa acgcagaaaa   180
cagatttagt tggccaacag cgaaggncta agaagtcag caaatttagt agtaggcctg    240
aagccagcaa ttcattagcg tagacctaaa gaagccaaca aatccatcat cagaggccaa   300
gttttgagtt acattgacta atgactatga ggtaagaaac agggcatgga tctcaagcag   360
cggcaggctt gcgcagctca ctctcaccat gggcaaagtg gcatttgccg ccataagagc   420
atgaccctt tgcgaagttc tcacacatct tggtcttgaa gttgcttcct atgccactga    480
tgctaacaat cagctcgatg accatagcac tagcgttcct gatctgatca aggtgccct    540
caaactcaat gttttcaag ctggtgtctg attcatggcg gtcctcctga atgaccacct    600
tggccctgt gacggaagat atttgctttta tgttagctcc acccttccca atgatgccac   660
ctgcaaggga cgcatcgaca ctgatcttgg ccgtggcata agcgccgaag ctagctggag   720
tggccaaacc agggttggcc ataggtggag gcgccatngg tggaggcgcc atgggtggag   780
gcgccatagg tagaggtgcc ataggtggag gcgccatagg tggaggtgcc atgggtggag   840
gcgccatagg tggaggcgcc ataggtagag gtgccatagg tggaggcgcc ataggtggag   900
gtgccatggg tagaggtgcc ataggtggag gcgccatagg tagaggtgcc atagttggag   960
gtgccatggg tggaggtgcc ataggtggag gtgccatagg tggaggtgca aaataaccgg  1020
ttggtggtgg tccgatgggg ggtggcatat agttgtccat catagacttg ccaagctccc  1080
tttcaccatg tgcaaagtgg natctgtnnc cccat                              1115
```

| | |
|---|---|
| SEQ ID NO: 39 | moltype = DNA  length = 583 |
| FEATURE | Location/Qualifiers |

```
misc_difference         22..24
                        note = n is a, c, g, or t
misc_difference         27..37
                        note = n is a, c, g, or t
misc_difference         39
                        note = n is a, c, g, or t
misc_difference         43..46
                        note = n is a, c, g, or t
misc_difference         48..51
                        note = n is a, c, g, or t
misc_difference         53..55
                        note = n is a, c, g, or t
misc_difference         280
                        note = n is a, c, g, or t
misc_difference         492..494
                        note = n is a, c, g, or t
misc_difference         498
                        note = n is a, c, g, or t
misc_difference         530..535
                        note = n is a, c, g, or t
misc_difference         539..548
                        note = n is a, c, g, or t
misc_difference         568..580
                        note = n is a, c, g, or t
misc_difference         582
                        note = n is a, c, g, or t
source                  1..583
                        mol_type = unassigned DNA
                        organism = Zea mays
SEQUENCE: 39
ttttcttgta ctggatgaag tnnncnnnn nnnnnnntnt aannnncnnn nannnatgca    60
tagaattttg gagcatgttg gaaggagacc tggaggcaca tctagggata ttcttggccc   120
acttgcgaga cgatctgagc gtcagactat cctggtttct gcaacaatac cattttcagt   180
tatacgagca gcaaggagtt ggggtcatga tccagttctc attagagcta aaagtgtagt   240
tccacttgat tcaatcactg tgccaagacc tgcgttatcn caaagtgacg ctaaccccag   300
ttcgtcatcg cagtcagtga accaagctgc tgttggcagc ttgccgccat cttttggaaca  360
ctactattgt acgccaaggc gcagcacaa ggttgacaca ttacggaggt gcatccatgc   420
tctggaagca cagacagtga ttgcatttat gaacaacacc aagccactga aggatgttgt    480
gtttaagttg gnnncccntg gtatcaaagc cactgagcta catggagacn nnnnnaagnn   540
nnnnnnncg acagttttga aaaagttnnn nnnnnnnnn tnc                       583

SEQ ID NO: 40           moltype = DNA   length = 839
FEATURE                 Location/Qualifiers
misc_difference         281
                        note = n is a, c, g, or t
misc_difference         771..777
                        note = n is a, c, g, or t
misc_difference         787..795
                        note = n is a, c, g, or t
misc_difference         804..833
                        note = n is a, c, g, or t
source                  1..839
                        mol_type = unassigned DNA
                        organism = Zea mays
SEQUENCE: 40
ctcgatcgcc atgtctttca ccggcacgca ggacaagtgc aaagcctgcg acaagacggt    60
ccacatcatc gacctcctca ccgccgacgg cgtctcgtac cacaagacat gcttcaagtg   120
cagccactgc aagggcgtcc tctcggtatg catgcgtggc ctgagctcaa ctccgcatgc   180
gcattcgccc tgcttgcgat gtgtgcggca atgcgctaat gctcatttgc atcgaaagaa   240
acgaagcttt gtttgattcg gttcagatca tctcgacaga ngaacatgta gaaatacggt   300
ctcatttttt catttctgca tgcgtctcct ccagattagc agctactctt ccatggacgg   360
cgtcctgtac tgcaagacgc actttgaaca gctcttcaag gagacaggga ccttctcaaa   420
gaactttcaa ggtaatctac agctgaatac tgtgccccct atgtttctga acccgtccac   480
agcgcgtgat gctgtaacgc tcaactctgg tgcctgatgc aatgcaatgc aattcggacc   540
cttaatttc gttgtgttaa ttactcaggt ggagcatctt caaacaagaa cgaccaggtg    600
cggttcctca aatcttctac acaaatatgg ctcaaatgct caataagttc taaaacttta   660
ttggccatgc catcatcggt aatagctgac tacttacgca cgatgccaat ctgaaaatct   720
ctgcaggcaa aggctccaag caagctatca tctgcattct ctggaactca nnnnnnntgc   780
gcggccnnnn nnnnacagt gtannnnnnn nnnnnnnnn nnnnnnnnn nnnctctgc       839

SEQ ID NO: 41           moltype = DNA   length = 163
FEATURE                 Location/Qualifiers
misc_difference         81
                        note = n is a, c, g, or t
source                  1..163
                        mol_type = unassigned DNA
                        organism = Zea mays
SEQUENCE: 41
tcatgaagaa tgagtacttt aacactgaaa ttgtactgga agactagagt tatgttattt    60
```

```
acctagaatg gctagctacc nctgttgagg aataccttga tgcaataatg tggcatcctt    120
tttcaacgtt ttccacatta attgattgtt tacttgactc aat                     163

SEQ ID NO: 42           moltype = DNA   length = 475
FEATURE                 Location/Qualifiers
misc_difference         151
                        note = n is a, c, g, or t
misc_difference         241
                        note = n is a, c, g, or t
misc_difference         429..435
                        note = n is a, c, g, or t
misc_difference         438..443
                        note = n is a, c, g, or t
source                  1..475
                        mol_type = unassigned DNA
                        organism = Zea mays
SEQUENCE: 42
atcttcggag tcgcttaggc cgagcgaccg aagcaggaac tcgacagcct ttcccttgtc    60
ccagtcgatc accgggcgaa cctctaaaac ctgcagcgta gcaaaagaat ttttttttc    120
gttgagtctt ggagcaagta tcaagatcaa nggcagtcgc agtagaacag tctaggctcc   180
taccattcgc ccgttggtta ctttgagacg agggaaggcc tccaagactt gtttcacgag   240
nctgcgacc actttccagt cctgaaaaaa acaatagcat aaagctctca gtctcaggta    300
aattcgctac tgcttccctg taataggcgc ggtctgaatc tgatgcatcc tagtaaaaat   360
aaaaggatgt ctgaagccgt aatttcatcc atttctctac cgacaaaaaa aaggaaagat   420
aaacagatnn nnnnnatnnn nnntgaaagt ttcaggggca cgcaatctca ccttc         475

SEQ ID NO: 43           moltype = DNA   length = 365
FEATURE                 Location/Qualifiers
misc_difference         299
                        note = n is a, c, g, or t
source                  1..365
                        mol_type = unassigned DNA
                        organism = Zea mays
SEQUENCE: 43
ctgatatttg gatggagaca ttacactgcg agtggtacca aactgtagga aatgaaagt     60
tggttagagg ggaatcgaga gtagttccac tcacatggtc gttccaggcg tgatccctgt   120
tgtagatgat ggcagcgcca aggctcctag ctgggttgat gccagtgcca gtaatgggga   180
tggtggcaag gtgaccagg aacaccgcga acccaattgg cagtgggca aggatctgtt     240
ttcaccaaat aagggtttca ttcatcgtaa gtcttaacac aatatgaaaa atatgtatng   300
aagagtatgc atacatttc aatttgttga aacacaagat taaggaatca gctaaattcc    360
agtcc                                                                365

SEQ ID NO: 44           moltype = DNA   length = 666
FEATURE                 Location/Qualifiers
misc_difference         17..19
                        note = n is a, c, g, or t
misc_difference         336
                        note = n is a, c, g, or t
misc_difference         410
                        note = n is a, c, g, or t
misc_difference         469
                        note = n is a, c, g, or t
misc_difference         485..486
                        note = n is a, c, g, or t
misc_difference         496
                        note = n is a, c, g, or t
misc_difference         501..505
                        note = n is a, c, g, or t
misc_difference         515..528
                        note = n is a, c, g, or t
misc_difference         543..554
                        note = n is a, c, g, or t
misc_difference         566..579
                        note = n is a, c, g, or t
misc_difference         581..586
                        note = n is a, c, g, or t
misc_difference         588..600
                        note = n is a, c, g, or t
misc_difference         603..634
                        note = n is a, c, g, or t
misc_difference         641..663
                        note = n is a, c, g, or t
misc_difference         665
                        note = n is a, c, g, or t
source                  1..666
                        mol_type = unassigned DNA
                        organism = Zea mays
SEQUENCE: 44
ccctgcaaat gcacttnnnc atgcaattgg attgtccacc ttgccccgcc caagcaccga   60
```

```
atcctcaatt cttggctgaa tcaggaactt ctcaatcttg caggcagaat cagcatcaat    120
gccagcagca tcaagcgaat caaggaggaa catgcaagac tgaaagcagt ttaagaagta    180
ctgtgagaag ggaagatcag cgcgatcagc gccatggtct atggctatca caatcttagg    240
agctagctgt ttcaccaacc caaggatcgc tggcagtggt ggtgcacgag cagagcaacc    300
agtcgggagg acaacaacta catcttcatc atcagnggca gaaatgaatt ctgcagggtt    360
gatcatatca gcactgatag cactgaactc aaagggaatt ccaaggtcan cagcaaactg    420
tgcaatgttg tcacgcgcaa gacacagctc cagtggatgg tgggaagcng tgttacagcg    480
cttannacac tgaagnaaca nnnnntcacc ggcannnnnn nnnnnnnngt ctttatgcac    540
cannnnnnnn nnnntctgat gactcnnnnn nnnnnnnnnc nnnnnnncnnn nnnnnnnnnn    600
gannnnnnnn nnnnnnnnnn nnnnnnnnnn nnnntgtctg nnnnnnnnnn nnnnnnnnnn    660
nnnanc                                                                666

SEQ ID NO: 45           moltype = DNA   length = 520
FEATURE                 Location/Qualifiers
misc_difference         44
                        note = n is a, c, g, or t
misc_difference         228
                        note = n is a, c, g, or t
misc_difference         468
                        note = n is a, c, g, or t
source                  1..520
                        mol_type = unassigned DNA
                        organism = Zea mays
SEQUENCE: 45
ttgaagcatg tacattgcaa agatactact attaggttta gatnacaatt aatagatttg     60
tttgtgacaa accgtgtttt ttgcatatcc atacacatga cattccgtag taaacatctc    120
tttagttttt ccattcctac agctactaac tatactactg caatcagata gatggtccta    180
ctctagttac gcaggattaa gtgatgcata gtattaatag caaatagntg gaacttggaa    240
ggttttgaac actcagctat gggtatggag aaaacatctt ttcaaactga tgcttttgta    300
tattcttatg tgacttgctt aaaatgcatg tcttatgcct tattagtgat ctcacaagat    360
acctgatgca aaaggtttcc accacaggtc atcatagatg aagctatcac caaattggat    420
gaggatttct tctggttggg tggcggagaa gttgacctca agctcggnat gcgaacctca    480
caattcttaa gtgtctttag tccattcgtg gtgaaatgca                           520

SEQ ID NO: 46           moltype = DNA   length = 866
FEATURE                 Location/Qualifiers
misc_difference         7..13
                        note = n is a, c, g, or t
misc_difference         16..18
                        note = n is a, c, g, or t
misc_difference         284
                        note = n is a, c, g, or t
misc_difference         394
                        note = n is a, c, g, or t
source                  1..866
                        mol_type = unassigned DNA
                        organism = Zea mays
SEQUENCE: 46
gcctgcnnnn nnncannnac tggtttttcc aggccaccat ctcttagttc agatgatagt     60
gcctgggctt ggcatgaggc tgatgttata cgagttgttg atgatgtagc taatggtatt    120
ccatctacat acacaaatgg tgtatcatca ccacccctcc ctccatcttg ttctcaaaat    180
gaatctttgg atccagctgc tcacttgata acagggaatg agatcaataa tgaagctctg    240
acttctccat cttcggtgca agatagtcct gaagataaaa taangcaagt tgcaaaggct    300
gtgtcttgtg gcagtgaagt agttaaggca gatacattgc catatgccat gctgcggccg    360
atagttgttc ctagtatatc acgaaggtca tcangatctg aagattaaggg tgctcatgat    420
cacaggagga gcccatgtgt accatcaaca aggagggaca tacctattct aagaagacct    480
ccatcaccag tagtacttag tgttcctcgc gtacctaggc caccacctcc ttcacctgct    540
ggagagtcaa gaaaacgagg gttccctatc gttagatccg gcagctcaag tcctcgacat    600
tgggggatga gaggttttatt ttctgaagac aaaattttttc ataggctca gttttgctg    660
gatggtcctg aagttgtatg gccttcatgg ggtaacaagg gtacttctgg tacattggtg    720
caaacaattg aggatactgt tttgcaggac caccttgtta agatttcaca gctatccttgt    780
gatcaacatg taagggtgta gttcaaatc atccctcaat agtgagaatg attgtttatt    840
caactttttct gtctttctaa aatata                                         866

SEQ ID NO: 47           moltype = DNA   length = 788
FEATURE                 Location/Qualifiers
misc_difference         69
                        note = n is a, c, g, or t
misc_difference         250
                        note = n is a, c, g, or t
misc_difference         324
                        note = n is a, c, g, or t
misc_difference         345
                        note = n is a, c, g, or t
misc_difference         456
                        note = n is a, c, g, or t
misc_difference         493
                        note = n is a, c, g, or t
misc_difference         778..779
```

```
                        note = n is a, c, g, or t
source                  1..788
                        mol_type = unassigned DNA
                        organism = Zea mays
SEQUENCE: 47
actatcgcgg acacactccc ttttgtaatc cagcacaatg ctggccagct catgattctc    60
aaaaatagna atcggtgcac tctgaggcaa agataaaagt aaggttaatt gcatatgtgg   120
gcaaagtctt tgtatacaag gcacttatta atatgctaat ctgtctcata tttttttggat  180
tctatctgat ccagttttgg tttagaatca gttgaccaaa tagcagagct aaccccaccc   240
ccaacacacn cattaataca gggaagaaga gctgccaatt gatgaagcag gaaggaaaac   300
caaatgacaa ctgtctccaa acangtagcc aaaaataagt gaatnatgga ccagccaaca   360
tgtagccaaa aataagtgaa tgacggacca gccaacaaca cgcggcatat catcaatcaa   420
gcaaatataa gcattatctc tacccatct tatttntgtg tagtttagag caaagaaaga    480
ctaagttgat ttntacacag gctgctcttg cacaaaagca acacaagtca gtgacattgt   540
taggtgccta ggtggccaac caaatatact aaaatctcag agatgtattc cttgtccaac   600
ttgtgcattt gttgtcatga ataagttaaa aaagatacct cctaaataaa taatatatat   660
catgagatga gccattgtat ttgctaatct gatgaataaa taagtgggca cctaatcatt   720
atcaatggca gaaataagca acccccccc ccaccccac ccaaccaggg acccacannc    780
caatggcc                                                             788

SEQ ID NO: 48           moltype = DNA  length = 397
FEATURE                 Location/Qualifiers
misc_difference         262
                        note = n is a, c, g, or t
source                  1..397
                        mol_type = unassigned DNA
                        organism = Zea mays
SEQUENCE: 48
ctagagattg atctctggtc gcttggatgc attttggcag aactgatgaa actggaggct    60
ttgttcccgg ggatatctga tattgatcag attagtagaa tcatcaatgt cctgggcgat   120
ataacagaag aaaccttcc aggctgttca aacttgccag attacaacaa gatttccttt    180
aacaaagttg agaaaccgac aggccttgaa gcatgtctgc ctaacagatc tcctactgag   240
gttagcatca taaagcagct antttgctat gacacagcaa agaggaccag tgctgttgat   300
ctgctgaatg atcggtactt taccgaagag ccattgccgg cacctataga aggattacat   360
gtcccggcat caaaggacga ggatgatgac agctcaa                             397

SEQ ID NO: 49           moltype = DNA  length = 1049
FEATURE                 Location/Qualifiers
misc_difference         46..47
                        note = n is a, c, g, or t
misc_difference         496
                        note = n is a, c, g, or t
misc_difference         558..563
                        note = n is a, c, g, or t
misc_difference         653
                        note = n is a, c, g, or t
misc_difference         687..796
                        note = n is a, c, g, or t
misc_difference         809..851
                        note = n is a, c, g, or t
misc_difference         868..903
                        note = n is a, c, g, or t
misc_difference         1015..1020
                        note = n is a, c, g, or t
misc_difference         1035..1038
                        note = n is a, c, g, or t
misc_difference         1047..1048
                        note = n is a, c, g, or t
source                  1..1049
                        mol_type = unassigned DNA
                        organism = Zea mays
SEQUENCE: 49
ttgcagctgt gctttagcta aagcgaacgc cgtgtatgtt ttttnntct ggtcaactaa     60
acattgttgt gtatacatac ataaacagca atcgaagcag acaataggca acaaaataac   120
gaattaatgc tgttatcaaa tgagccagca acgdataaac ttgagatgct gccctagtag   180
ccgttctcaa actgaagccc tcaaggcttc aaacccatca attgcttgca actccagcca   240
caatcatact aataattaca cttgagcgca gccaaaatag caataaaaaa gttgagcaaa   300
gagtgcacct gctttgctta attgctctgc acgctcacga cgtccaaccg acgctacagc   360
ctacacgcgc gtgaaaaaag aagagctgtt ttaactcc acacacggca caggaattac    420
caaccgaccg acccagtgta cccgattcgg accagatctt cgtggaattc accagatcta   480
tctagagaag aaacanggaa acaggaaacc agtaccttcc cgccggtcga tgagctgata   540
cgtagcgcgc tcaggcgnnn nnnccatggg cggctggcc tcaggcgggg caagctaaaa    600
agagccctcc cgccgccgc ggttcgggct ctccttcctg aacaaggtcg agntcggctc    660
cggatccggc tgggccacgg ggaagtnnnn nnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnnnacgg gtgaggccnn nnnnnnnnnn nnnnnnnnnn nnnnnnnnnn    840
nnnnnnnnnn ngtggagttt gacccgannn nnnnnnnnnn nnnnnnnnnn nnnnnnnnnn   900
nnnagtgtat ggcgcggtgg cgtcgagggg aagggtgcgg cgcggtgggt ggcggccagc   960
ctcgggatcc gggtccagca cgggcgcacg cgcacctggc gatcggatgg gcgtnnnnnn  1020
```

```
atacgaatat gcacnnnnac ctggcgnnc                                      1049

SEQ ID NO: 50           moltype = DNA  length = 798
FEATURE                 Location/Qualifiers
misc_difference         44
                        note = n is a, c, g, or t
misc_difference         606..607
                        note = n is a, c, g, or t
misc_difference         625..627
                        note = n is a, c, g, or t
misc_difference         677..678
                        note = n is a, c, g, or t
misc_difference         681
                        note = n is a, c, g, or t
misc_difference         685..687
                        note = n is a, c, g, or t
misc_difference         704..705
                        note = n is a, c, g, or t
misc_difference         708..795
                        note = n is a, c, g, or t
source                  1..798
                        mol_type = unassigned DNA
                        organism = Zea mays
SEQUENCE: 50
agaaacagta gttcgaggta gcacaggcag ttgagatgga gtantttgga cccatgaaac    60
caatgtccat tccaagcagg gcagaaccca tgtttgtgat agcatatggg atgaagaaag   120
gagttatctt tctgtatccc ttctcaatga gattctggac accatccgaa aacaccgtga   180
ggccacccat accagtgccc acaagcacac cggcccgggt cttgtcaatc tgccagagag   240
aatattttac caattagcat caaatgtagc attaacagtg aaaaaatctt atagtactag   300
taaaaatatc aaactaccag atgaaactac tatcaataca gtacaaacca tagtttgatg   360
tgctagaaga caatttgatt taatccaaaa atgctactcc ctctgacctg tagggcgtgt   420
ttattttgaa gaaaccaaac tcgtaaaccc aaccaacaat tagtcaaatt atgtgtgttt   480
ggagtacaaa agctatatca acagatttat actcaaacaa cttttaatgc gacattgatt   540
ttgcagagac tagcaatatt ataaaacaat aatggttaaa atatgcttct aatgacacta   600
tccgtnnaca atatgcctgg aaaannntag tactttgcta gaaaaatcac cataatgcaa   660
gtgaatcatc aaacgannca ncagnnnttc gcagagctat gttnntannn nnnnnnnnn    720
nnnnnnnnnn nnnnnnnnnn nnnnnnnnnn nnnnnnnnnn nnnnnnnnnn nnnnnnnnnn   780
nnnnnnnnnn nnnnncga                                                 798

SEQ ID NO: 51           moltype = DNA  length = 544
FEATURE                 Location/Qualifiers
misc_difference         1..4
                        note = n is a, c, g, or t
misc_difference         6..10
                        note = n is a, c, g, or t
misc_difference         14..17
                        note = n is a, c, g, or t
misc_difference         19
                        note = n is a, c, g, or t
misc_difference         28
                        note = n is a, c, g, or t
misc_difference         82
                        note = n is a, c, g, or t
misc_difference         159
                        note = n is a, c, g, or t
misc_difference         214
                        note = n is a, c, g, or t
misc_difference         216
                        note = n is a, c, g, or t
misc_difference         221
                        note = n is a, c, g, or t
misc_difference         264..271
                        note = n is a, c, g, or t
misc_difference         337
                        note = n is a, c, g, or t
misc_difference         358
                        note = n is a, c, g, or t
misc_difference         451..452
                        note = n is a, c, g, or t
misc_difference         455..457
                        note = n is a, c, g, or t
misc_difference         464..466
                        note = n is a, c, g, or t
misc_difference         468..470
                        note = n is a, c, g, or t
misc_difference         472..474
                        note = n is a, c, g, or t
misc_difference         476..477
                        note = n is a, c, g, or t
```

| | | |
|---|---|---|
| misc_difference | 493..512 | |
| | note = n is a, c, g, or t | |
| misc_difference | 514..518 | |
| | note = n is a, c, g, or t | |
| misc_difference | 526..528 | |
| | note = n is a, c, g, or t | |
| misc_difference | 534..538 | |
| | note = n is a, c, g, or t | |
| misc_difference | 540..542 | |
| | note = n is a, c, g, or t | |
| source | 1..544 | |
| | mol_type = unassigned DNA | |
| | organism = Zea mays | |

SEQUENCE: 51

```
nnnnannnnn tctnnnnang tcttcgcnct cgtcgttgct gttttcatgt acattgtcgt    60
tcacatcttg ctgtccttcg anaaaatggc acgggtcatg aagaggactg gagaacagtg   120
ggttccatgt ctgaagaaga tgtgggcact cattgaaant gaacctccaa accatcagcc   180
atcttcagag gaaccatgag aggctgaccc ttgncngtat ncttgtattg tgattacatg   240
aattgttcaa ttgatatgta cctnnnnnnn ntagaatcaa tatttgtttt ccccacttgt   300
ttaaggttga agtgttgtaa tcttttatg cacttanaga taagatgcat tcatccanga    360
gggttagctt caagtacttc gttcttggtt ttaactttct cagtatattg gacggccgga   420
actacttatt tgtagctacc tctagcagtc nntcnnntta ttcnnnannn annncnntct   480
aaagtgtata atnnnnnnnn nnnnnnnnnn nnannnnnat atacannntc tacnnnnnan   540
nncc                                                                544
```

| | | |
|---|---|---|
| SEQ ID NO: 52 | moltype = DNA length = 276 | |
| FEATURE | Location/Qualifiers | |
| misc_difference | 52 | |
| | note = n is a, c, g, or t | |
| source | 1..276 | |
| | mol_type = unassigned DNA | |
| | organism = Zea mays | |

SEQUENCE: 52

```
gctggatgcc aaggtcctga gcaaaatccc caggggtgcg gtcaaatcca anaagcagaa    60
ctagttagga taagccgcag attgtgaatg cccgtatcat gagtatcggg cttgtggttt   120
tgcatggcat atgtcaatct gtctgttggc ttcagcttgg ttcttctgcg actactttgt   180
tgatgttatt atagtcctat gtatgtcact gtgtacatga cagagatgtt cggatgctac   240
gtctagacta ctgctgtgct gtagcttgta aattcc                             276
```

| | | |
|---|---|---|
| SEQ ID NO: 53 | moltype = DNA length = 733 | |
| FEATURE | Location/Qualifiers | |
| misc_difference | 350 | |
| | note = n is a, c, g, or t | |
| misc_difference | 409 | |
| | note = n is a, c, g, or t | |
| misc_difference | 571 | |
| | note = n is a, c, g, or t | |
| misc_difference | 582..584 | |
| | note = n is a, c, g, or t | |
| misc_difference | 586..594 | |
| | note = n is a, c, g, or t | |
| misc_difference | 598 | |
| | note = n is a, c, g, or t | |
| misc_difference | 605 | |
| | note = n is a, c, g, or t | |
| misc_difference | 615..618 | |
| | note = n is a, c, g, or t | |
| misc_difference | 625..632 | |
| | note = n is a, c, g, or t | |
| misc_difference | 634..652 | |
| | note = n is a, c, g, or t | |
| misc_difference | 656..659 | |
| | note = n is a, c, g, or t | |
| misc_difference | 663..665 | |
| | note = n is a, c, g, or t | |
| misc_difference | 671..672 | |
| | note = n is a, c, g, or t | |
| misc_difference | 676 | |
| | note = n is a, c, g, or t | |
| misc_difference | 679 | |
| | note = n is a, c, g, or t | |
| misc_difference | 681..691 | |
| | note = n is a, c, g, or t | |
| misc_difference | 693..696 | |
| | note = n is a, c, g, or t | |
| misc_difference | 698..708 | |
| | note = n is a, c, g, or t | |
| misc_difference | 710..712 | |
| | note = n is a, c, g, or t | |

```
misc_difference          716
                         note = n is a, c, g, or t
misc_difference          718..722
                         note = n is a, c, g, or t
misc_difference          725
                         note = n is a, c, g, or t
misc_difference          727..732
                         note = n is a, c, g, or t
source                   1..733
                         mol_type = unassigned DNA
                         organism = Zea mays
SEQUENCE: 53
caagttctga gtttctctct tgtcagtcaa tggcttgggt aaaaattgtg aacagagaat    60
atgaaagcct gacaaactag caatgagtcc attttctgaa gataaacagc aaggaaaatt   120
ctgaatccca tgtgtagaaa catgtaggaa acacctttct tgtttatgag tgataggcaa   180
aattttggtc attgcatcct agggttaact tacagtcttc ttttgcaggt caaggacact   240
cccacgaagt gttctgatca tagggaccca agcggtgatg ataattactt acctgctctt   300
tgcattgggc cggctcgcca cactttacgt ctctgtcgcc ttactcgggn tatgttttgg   360
tatctcgctc tccgtgataa tctcaacctc ctcagagctc ttcggactna agcactttgg   420
aaagatattc aacttcatcg cattggcgaa tccggtaggc gcgttcctgt ttaacaccct   480
cgcgggatat gtctacgatc tcgaagtgga aaagcagcac gccacaacat cagggtcgga   540
cgttgcatgt catggcccta attgcttcag nctaacattc tnnntnnnnn nnnncgtngc   600
atgcntgggc acacnnnnga gcacnnnnnn nncnnnnnnn nnnnnnnnnn nntatnnnnt   660
gcnnnatgca nncggntcnt nnnnnnnnnn nannnncnnn nnnnnnnnan nnatgncnnn   720
nnagntnnnn nnt                                                     733

SEQ ID NO: 54            moltype = DNA  length = 385
FEATURE                  Location/Qualifiers
misc_difference          115
                         note = n is a, c, g, or t
source                   1..385
                         mol_type = unassigned DNA
                         organism = Zea mays
SEQUENCE: 54
agctggcgtc tgtaagggaa gtacttaaaa agtcagaagg agaactcgag atcacctcga    60
agcagttagt tttggtttca gaagcacata gtgaccttaa taaagaattg ctggntgcat   120
ataagcagtt agagtccacg caaagtgagc tagtgaaaga gcgtaaaatc aatgctactc   180
ttaacatgga gcttgaggct ttggtgaaac aatcagtgat agagtccgaa gcaagaaaaa   240
ctcttcaagt cgacttggat gaggccacta gatcactaaa tgaggtgaat aagagtacac   300
tctgtctgtc taagcagctg gaaacaacta attccaagat ttctgctatt aaagaggaga   360
aagatatgct gtcaatgttc cttga                                        385

SEQ ID NO: 55            moltype = DNA  length = 553
FEATURE                  Location/Qualifiers
misc_difference          29
                         note = n is a, c, g, or t
misc_difference          73..78
                         note = n is a, c, g, or t
misc_difference          103
                         note = n is a, c, g, or t
misc_difference          107
                         note = n is a, c, g, or t
misc_difference          175
                         note = n is a, c, g, or t
misc_difference          211
                         note = n is a, c, g, or t
misc_difference          256
                         note = n is a, c, g, or t
misc_difference          330
                         note = n is a, c, g, or t
misc_difference          345..347
                         note = n is a, c, g, or t
misc_difference          368
                         note = n is a, c, g, or t
source                   1..553
                         mol_type = unassigned DNA
                         organism = Zea mays
SEQUENCE: 55
tgaatgtgtc gagggcctgc aaaatttant tttggtaaag cttaggacag aagcaaaatg    60
catagatatc cannnnnnaa atagcaaatg tttttatacg atntaancat taagtaaatc   120
catttctctt gacacaacta caggttattg tatatgagca tagcgttgat catanattct   180
taccttgttt agatagttca tctgtgttac natgcacaag attacaacaa atgagaacac   240
ccatgttttgt gaatanacaa gctggttcat ccctgaaaat gtcaccttca aggctatccc   300
aagagctttg acactcatga cctggcaaan caaagacaat acagnnngag agtatttatg   360
tcctagcntt cttgagaata gttatgtgaa ttcacatgga aagaactgtt aatcatgaga   420
agcataccga taaagatcca acaagagaac atatgccaat atataccatg atatgtgtct   480
gcccatactg agggacaaaa tggcatatga gcacaaaagc tgctgcaaat acaacagctg   540
catagaatag gaa                                                     553
```

| SEQ ID NO: 56 | moltype = DNA   length = 608 |
|---|---|
| FEATURE | Location/Qualifiers |
| misc_difference | 91 |
| | note = n is a, c, g, or t |
| source | 1..608 |
| | mol_type = unassigned DNA |
| | organism = Zea mays |

SEQUENCE: 56
```
tgtccgtcag ctccgccgcc tcatccagcg tcaggttgtg gttgcacccg gtgaaggcca    60
gcatgtcctt ctcgtatctg acgacgatca nggcaaacca atgcaagttc atccattgat   120
tgatctgcag ataatagccg gccaccgaac gctgtgaact ctcagctacc tcaggtgaag   180
cgcgatgtaa tgctgggact cgtttctcag ccgatcaacc agcgtgttgc cgagctcttc   240
gatctccttc ctgtactgga gcgcctcgta gttcgcgcgg caccgaagct tttgcagcga   300
aggagcgagg ccgttgttca cgatccgtga atccgtgtgt gtaaacctca ccactttgaa   360
cttcctcagg attttcgcaa agtctctgta gaaggaagcc tggaaaacgg agctggcgat   420
gcatcagcct attcagtacg tattcggtta tcctctaagc tgctgcaact gcaatgcaat   480
ccagtagagc aaacaagttg ttgactcgta ccctggacca ggaggtgggc gctctcacgt   540
acggtttcac ccttctgtaa tgtggtggga gggaatccac gatcacaatg tcttccttca   600
acgactcc                                                            608
```

| SEQ ID NO: 57 | moltype = DNA   length = 602 |
|---|---|
| FEATURE | Location/Qualifiers |
| misc_difference | 8..13 |
| | note = n is a, c, g, or t |
| misc_difference | 15 |
| | note = n is a, c, g, or t |
| misc_difference | 47 |
| | note = n is a, c, g, or t |
| misc_difference | 384 |
| | note = n is a, c, g, or t |
| source | 1..602 |
| | mol_type = unassigned DNA |
| | organism = Zea mays |

SEQUENCE: 57
```
aggatccnnn nnngnagcaa tttcgaccag ggaagctcat taacagnaaa tgatgccaca    60
gccagtgaaa ttgaatgtca cagactccaa atggctgcaa taatgatta tggatttggt   120
aaacctgaga ttccttctag ttcctcaatg ccattttct tggctgttga tcctcaacaa   180
ctgaaattga gaaatgagac aaatgttcct tcaacatctt ccaacattcc ttcagattct   240
gcatcaccaa acttgaaaaa tggcacggat cctcttttga tgccatttaa ttcctacatg   300
gcagattgga gcagcgataa gataacttac accactctga acactccaaa aataagcaca   360
gaacttccag gtcagtatgc atcnctttct tctattatta gctaaatcaa tttagctgac   420
aacaaaaact taaccatgca gtcaagttac accatgacaa aagtagtagc tttgaagcac   480
caaacctgaa ggagcatgaa tcagtctttg caacacatga aatgacggta gaagcaacaa   540
gaaaagaaga cgaacacaca tcaaaatcta gttttacttc ctacaatgga gtaccagata   600
ca                                                                  602
```

| SEQ ID NO: 58 | moltype = DNA   length = 880 |
|---|---|
| FEATURE | Location/Qualifiers |
| misc_difference | 346 |
| | note = n is a, c, g, or t |
| misc_difference | 446 |
| | note = n is a, c, g, or t |
| misc_difference | 525 |
| | note = n is a, c, g, or t |
| misc_difference | 816..817 |
| | note = n is a, c, g, or t |
| misc_difference | 876..878 |
| | note = n is a, c, g, or t |
| source | 1..880 |
| | mol_type = unassigned DNA |
| | organism = Zea mays |

SEQUENCE: 58
```
cctccaatcc atgaccagac accttttcag ctatctctct tccttctgtt tcaagtacaa    60
tcctgtgtaa tcattcaaga aaattaggta taatgccaca aataattaca tactaatgtg   120
ggacgttatt catctctaag cttgagaatg atcctattgc taaacctttg aatccagtga   180
ttaaaaccat tacaaaatag acgctcggat attactctat tgccatggcc cccagttcaa   240
aaaaaaaaca tgcggcagat gacagtcaga ttatttcaga gcaaaggaag aataataaat   300
gtacacaata aagggaacaa gaaaagaagc cctaatatca tgtatntagt aagataagga   360
tttacccctcc atcaacaatt tcatcaaggc acaataggat catatccaaa ttctcgagtg   420
ctgtccttttt gtcaaccatg tttctnaaac caccaagatt ggaaacacat tcatatacaa   480
tcagcattaa cacaacaaca tgtaacagaa caaaacagtg gttgnaaaga taagttaaa    540
tagagggaaa ataacttgag aagtcgttcg acagcatcag agaatccctg aagaactgat   600
gctaaaataa gctcattctc ttcttctcct ccagtaacaa aaaagtgcag gtcttggatg   660
aacttgtata ccacaatttg accgtcaaac attacaatct caactgttaa agagaaacaa   720
agaaaaatat gaaatacttg aagagaagaa caaaaactca aacagtcata tctgcatgtt   780
taaggagaaa tcaaggtcag tcagaaggaa aactannccca ggctcattta cagatttgtg   840
gcatgagtgg gagctcgtac aaacagtgtt atgacnnngg                         880
```

| SEQ ID NO: 59 | moltype = DNA   length = 461 |
|---|---|

| FEATURE | Location/Qualifiers |
|---|---|
| misc_difference | 253 |
| | note = n is a, c, g, or t |
| source | 1..461 |
| | mol_type = unassigned DNA |
| | organism = Zea mays |

SEQUENCE: 59

```
acgcggcttg ttcttattga atccatcaag gacgcaggaa agataggatc ttcggctccg   60
attctcggag caacagcgcg accgcagcgg gttttggtgc ttcctttctt tagggttgtg  120
tccttgcaga agttgctctg tggaatgggg acctgtcgga ggagagttct ggggtatgg   180
tttttcttct ggttccttgt tgacacttgag cagtgcacat ccctgaatcg tgaaggtatc  240
tatcgtgttg tgntttgaat cgcttgcgtg gatggttgtt gcccgaccctt tgttttttgac 300
tctgtttagg gttgtttctt tgctgaactg caggtgctgc tctgctgaga tttaaggcgg  360
cgatcgaggc agacccatat ggtgctttgt tggactgaa tcaagagagt ttgagcccct   420
gtacttggtt tggtgtggaa tgctccgatg atggactagt c                      461
```

| SEQ ID NO: 60 | moltype = DNA length = 544 |
|---|---|
| FEATURE | Location/Qualifiers |
| misc_difference | 1..10 |
| | note = n is a, c, g, or t |
| misc_difference | 18..49 |
| | note = n is a, c, g, or t |
| misc_difference | 149..150 |
| | note = n is a, c, g, or t |
| misc_difference | 174 |
| | note = n is a, c, g, or t |
| misc_difference | 205 |
| | note = n is a, c, g, or t |
| misc_difference | 281 |
| | note = n is a, c, g, or t |
| misc_difference | 331..333 |
| | note = n is a, c, g, or t |
| misc_difference | 487..492 |
| | note = n is a, c, g, or t |
| misc_difference | 519..542 |
| | note = n is a, c, g, or t |
| source | 1..544 |
| | mol_type = unassigned DNA |
| | organism = Zea mays |

SEQUENCE: 60

```
nnnnnnnnnn gctagccnnn nnnnnnnnnn nnnnnnnnnn nnnnnnnnna acagaagcta   60
ccactgccgg tgctcatcgt cctgcacctg aagcagcagc agcagctgat ctgatcgaca  120
tacagttcgt gttcggcagc tagcccctnn agccatgctc ggagaggttt aatnaattac  180
gcagcggact ccttcgatgg gggtngattt ttggtgatca ttctgggggt atgtataaac  240
ctgcaaccta cccttgcaag gattagtttt tcttcttctg nttttcttct ttcaagtttc  300
accgaggtgg agtggaggtt gaccgacatt nnnctgttct tcccgcatat tcttgtgaga  360
ttttgattcc aatcagtgtc tatcaattca atttcgatct ccctctctgt aaccacatgt  420
cgtgtggcgt gcgtgcgtgt aaaaaatcga gaaaaccgag cctgccctgt ccgggcttca  480
gcttgtnnnn nntagctagc tcgatctagc ggaaacgann nnnnnnnnnn nnnnnnnnnn  540
nntt                                                               544
```

| SEQ ID NO: 61 | moltype = DNA length = 1249 |
|---|---|
| FEATURE | Location/Qualifiers |
| misc_difference | 4..7 |
| | note = n is a, c, g, or t |
| misc_difference | 250 |
| | note = n is a, c, g, or t |
| misc_difference | 411..417 |
| | note = n is a, c, g, or t |
| misc_difference | 432 |
| | note = n is a, c, g, or t |
| misc_difference | 440 |
| | note = n is a, c, g, or t |
| misc_difference | 461..466 |
| | note = n is a, c, g, or t |
| misc_difference | 474..478 |
| | note = n is a, c, g, or t |
| misc_difference | 500..504 |
| | note = n is a, c, g, or t |
| misc_difference | 506..514 |
| | note = n is a, c, g, or t |
| misc_difference | 517..524 |
| | note = n is a, c, g, or t |
| misc_difference | 541..542 |
| | note = n is a, c, g, or t |
| misc_difference | 548..644 |
| | note = n is a, c, g, or t |
| misc_difference | 646..701 |
| | note = n is a, c, g, or t |

```
misc_difference        703..743
                       note = n is a, c, g, or t
misc_difference        746
                       note = n is a, c, g, or t
misc_difference        749..754
                       note = n is a, c, g, or t
misc_difference        756
                       note = n is a, c, g, or t
misc_difference        760..763
                       note = n is a, c, g, or t
misc_difference        765..769
                       note = n is a, c, g, or t
misc_difference        772..774
                       note = n is a, c, g, or t
misc_difference        776..780
                       note = n is a, c, g, or t
misc_difference        782
                       note = n is a, c, g, or t
misc_difference        784..790
                       note = n is a, c, g, or t
misc_difference        792..797
                       note = n is a, c, g, or t
misc_difference        818..819
                       note = n is a, c, g, or t
misc_difference        821..822
                       note = n is a, c, g, or t
misc_difference        826..828
                       note = n is a, c, g, or t
misc_difference        832..835
                       note = n is a, c, g, or t
source                 1..1249
                       mol_type = unassigned DNA
                       organism = Zea mays
SEQUENCE: 61
ttcnnnnatc ttcctctatt gatactgtag gttcaattgc ttcagcagtt ggcattgttt    60
tagacaattt ttgtttgatt ctgcattgac aacaaaggtt ttcccaaatg gtttcccact   120
taggttgaaa atgatgattt gattgcctac ggcctgatcc cagaatttat tggaaggttg   180
ccaataacag ttggcctgac caatcttagt gaagagcaat tggttcaagt agtaaatttc   240
tttgattttn taatttaaag caatatttct taaaattacc atctcaaata tttccaccac   300
ctcaaaatat tagaaattct ctttgcaggt gctcatggag cccaaaaacg caataggaaa   360
gcaatacaag aagctattca aaatgaatga tgttagtttg tgattcgttt nnnnnnncga   420
aataattgca anatttggcn gattttttt tactttaaac nnnnnnttat aacnnnnnaa    480
gttatttatg ttcatgtttn nnnnannnnn nnnngcnnnn nnnnactgat aatgctttga   540
nnatgatnnn nnnnnnnnnn nnnnnnnnnn nnnnnnnnnn nnnnnnnnnn nnnnnnnnnn   600
nnnnnnnnnn nnnnnnnnnn nnnnnnnnnn nnnnnnnnnn nnnntnnnnn nnnnnnnnnn   660
nnnnnnnnnn nnnnnnnnnn nnnnnnnnnn nnnnnnnnnn ncnnnnnnnn nnnnnnnnnn   720
nnnnnnnnnn nnnnnnnnnn nnnggntann nnnntncttn nnnannnnna gnnngnnnnn   780
cnannnnnnn cnnnnnngtg tcgagcaaaa atttttcnng nngatnnngc cnnnnaactg   840
tatgtttacc agaacaatat caaactgccc gggctgattc agagcaaccc cagacgcaga   900
cgcatttttc ggctctgcct tctagtcgca ttatcggcaa caaagctttg gatttaccag   960
acaattcctt gtttttcatc gatatatgaa tggattgcat ggatactatg caaggtctac  1020
aattttacac aataaaatat gatgaggttg attttcgtgt taaactgttc acacagcaaa  1080
agaatggctg gaccccacgt tctgctttct tcggtagctt gcaatgattt tgcaacaaca  1140
attcgtatca tttacacgct actggtagca aacagacagt tgttttgata ctgaacctga  1200
acaaatggaa aatggtttcc aatggttaca catcaaaatt atgtttgta              1249

SEQ ID NO: 62          moltype = DNA   length = 372
FEATURE                Location/Qualifiers
misc_difference        148
                       note = n is a, c, g, or t
source                 1..372
                       mol_type = unassigned DNA
                       organism = Zea mays
SEQUENCE: 62
tgtatgatca aggaatggtc tacaccaatg tgtttgatgc caactttgat actcttgtct    60
ggtcattaag gaaagctggt gtgcccgaca tgagaatcat tgttggtgaa gttggctggc   120
catctgatgg tgataagaat gctaacanca aatatgcaca gaggttctat aatggttttc   180
tgaagaaaat gacaaaaaat gtcggcacgc ctctgagacc tggtcgtatg gaagtttacc   240
tgtttgcgct gattgatgag aaccagaaga gtgtcctgcc tggacgcttt gagcgtcact   300
ggggactatt cacatgatga ggaaaaccaa agttctctat ggatctcagt ggaaatggca   360
agggcagtgt ag                                                      372

SEQ ID NO: 63          moltype = DNA   length = 442
FEATURE                Location/Qualifiers
misc_difference        130
                       note = n is a, c, g, or t
source                 1..442
                       mol_type = unassigned DNA
                       organism = Zea mays
```

SEQUENCE: 63
gtgcacactg gcgccagatg ggtatgtgtg cagcccttga tagcctgagc tttggcaaa    60
actaatggtc tgtgacagac taaccgatct ttggtttttt gctcttggac agttcaatga   120
catgatcaan gtgccattca cgtcgaagcc gttcgtcgct gggttggtag cctatatcct   180
ggacaacacc ctccaggtaa aggagagcgc ggtgcggaag dacagggca accactggtg    240
ggagaagttc aggagcttca agaaagacgc gaggagccaa gagttctact cgctgccgtt   300
caatctgaac aagttcttcc cgtcggtctg atctcaaatg gcgccgccgc tgaatcaatt   360
ctggaagcaa cccttgttca tatgggcctt aatgaggaac ataattctgc tggtctggcc   420
agtggaagct tctgtgtctc ca                                             442

SEQ ID NO: 64              moltype = DNA  length = 523
FEATURE                    Location/Qualifiers
misc_difference            258
                           note = n is a, c, g, or t
source                     1..523
                           mol_type = unassigned DNA
                           organism = Zea mays
SEQUENCE: 64
tcctttgaaa tgcaggaagt ctagaggaat atacaggaat ttcacaagaa tcagtctatt    60
ttcacagaaa aaatgcagga aactgaaaaa aaatccccgc attccaaagg gggcctcatc   120
taggattttct tcataccgaa ttatcgattg acttcgacca cataccgtgc ttttgttcat   180
gtctttgaac acaggcacac ccaaatttcg aggtagcaac tttgcccac atacactgta    240
tataaagtag ttacagtnca agaacaatgc taactgatca ggtgatgtct cgtcctcccc   300
ccggttctat tattgttact gtatagctgt aattagtcca agtgtacagc tgaatctact   360
aaggtttaca aggaaaatcg ccaggctgta aaccttcaat tcttatggct aggttttcat   420
tctgaaagtc atgtcttccg cgtcagcata atcctgtgtt cctgtataac ctctcttcgg   480
acttagtagt gctcatttga gttctaattc ggccgggcac cta                      523

SEQ ID NO: 65              moltype = DNA  length = 687
FEATURE                    Location/Qualifiers
misc_difference            6
                           note = n is a, c, g, or t
misc_difference            44
                           note = n is a, c, g, or t
misc_difference            74
                           note = n is a, c, g, or t
misc_difference            145
                           note = n is a, c, g, or t
misc_difference            236
                           note = n is a, c, g, or t
misc_difference            324
                           note = n is a, c, g, or t
misc_difference            443..445
                           note = n is a, c, g, or t
misc_difference            501..506
                           note = n is a, c, g, or t
misc_difference            509
                           note = n is a, c, g, or t
misc_difference            518..520
                           note = n is a, c, g, or t
misc_difference            527..528
                           note = n is a, c, g, or t
misc_difference            530..532
                           note = n is a, c, g, or t
misc_difference            537
                           note = n is a, c, g, or t
misc_difference            543
                           note = n is a, c, g, or t
misc_difference            549
                           note = n is a, c, g, or t
misc_difference            553
                           note = n is a, c, g, or t
misc_difference            561..565
                           note = n is a, c, g, or t
misc_difference            570..575
                           note = n is a, c, g, or t
misc_difference            578..586
                           note = n is a, c, g, or t
misc_difference            588..604
                           note = n is a, c, g, or t
misc_difference            608..612
                           note = n is a, c, g, or t
misc_difference            614..654
                           note = n is a, c, g, or t
misc_difference            658..686
                           note = n is a, c, g, or t
source                     1..687
                           mol_type = unassigned DNA
                           organism = Zea mays

```
SEQUENCE: 65
ggtagncagc tgcgcttacc cgactgtctg cggcgcgtac ggcntctgcg tcagcgggca      60
gtgcacgtgc ccanccgcga cgtacttcag gcaggtcgac gaccgccgga ccgacctcgg     120
ctgcgtgccc gtggcccgga tctcntgtgc ctcgacgcag gaccaccggc tcctcgctct     180
gagcaacgtt tcttacttca actacgtgga taccaaggcc tgctgcctc ggatgntcga      240
cgaagagagc tgcaagaagg catgcttgca gaactgctcc tgcaaagccg cgttcttcca     300
gtacggcgga aacgcacct cccngggctc ctgttacctg ccgacgcagg tcttctcgat      360
gcaggtgaac cagtggcaag aaactcacta cagctcttct gcgtacctca aggtgcaggt     420
cacaaggtct cctcctcctc ctnnngtccc tggtccctcg aattcgaatg ggacggccat     480
acccgcaggg aaaggaagga nnnnnnctng tgaagctnnn atcgttnncn nngcacntgc     540
ggnggccant gcnttactag nnnnnnatcgn nnnnnccnnn nnnnnncnnn nnnnnnnnnn     600
nnnncgtnnn nntnnnnnnn nnnnnnnnnn nnnnnnnnnn nnnnnnnnnn nnnngatnnn     660
nnnnnnnnnn nnnnnnnnnn nnnnnng                                         687

SEQ ID NO: 66           moltype = DNA   length = 477
FEATURE                 Location/Qualifiers
misc_difference         66
                        note = n is a, c, g, or t
misc_difference         360..402
                        note = n is a, c, g, or t
source                  1..477
                        mol_type = unassigned DNA
                        organism = Zea mays
SEQUENCE: 66
ccttggcctt ctctattgcc tccttcgaat taggatcaac caatttcttg atttcgatgt      60
ccttgncagc aaagtccctt acctcagtga tctgttgatg catgtgaaag tacaagttaa     120
gcgttctcac attaaagctg acaaacatat tgcaaaacca gtagagtaag tttgccatct     180
atatccacaa ttatgatgcc agagagtggc aatatttctg tgctactata agcttattgg     240
cgttttgaac ttttcaacaa gttgcagtta aaatgattta aataaaatga acttagatgg     300
caatagacat gtgaaaaaga catttggtta cagataagcc gtgctgttac atttttttccn    360
nnnnnnnnnn nnnnnnnnnn nnnnnnnnnn nnnnnnnnnn nngttttgtg atactgacag     420
ttcagattta cctccacttt ccctcgtcca gatgccacag cagcggcatt tttggca        477

SEQ ID NO: 67           moltype = DNA   length = 1253
FEATURE                 Location/Qualifiers
misc_difference         621
                        note = n is a, c, g, or t
misc_difference         1241..1250
                        note = n is a, c, g, or t
source                  1..1253
                        mol_type = unassigned DNA
                        organism = Zea mays
SEQUENCE: 67
atgagatgat gactgcgtcc agaacaataa aaaataagga aagatgcaat tccaatcttc      60
ctatccttac agatgtcaat tctgggttga tagaccttaa ggtcacatga aaaatagtaa     120
atctgttaat agattgtttt agtcgtggtg agttattggt tttaatagag aagcatgata     180
gtgatgatat agtaattact gtgcagtctt acttcctcag catcaggtag gcaagaacaa     240
cagtcgcact tcgactttt ccctcaaagc aatgcacaag tactttgcca cgcaagtgat      300
ccacataact gatgaaatca gaaccatctt gaaagagatc accaatgtct gcattgtcat     360
catcgtttat ctacatagag aagcaattca acactgaaag atatctaaac tgagtcttct     420
gccttatgct aaaggcaaat gattttccat ccatgcaagt attatgtaga actcaccgag     480
aaattcctat actcaaaaag gtcaggcttc tgcgattctg actgtccaat ttcatttgca     540
cacaagcaca atatatgggt gatgccaagg tgtttaagtg tgtgtgttga ccgagcagca     600
agagcaccac caatatacag ntaatctgtg atctgtgatg gacgctcagt acttgcagca     660
tcagagatca aagatatcct ctcgagaatg tgctcaagtc gaacctaaca acagaattgc     720
tcgataggtt caattaatgt gtacacgtag ttagtacaga gtgtacattt agatttacct     780
tcaactcgta agcatcaaca acagtgctat tatcagtgcc ttcaaaaaaa cctgtttgaa     840
aattgttgtc ttgacacaac tttactactt cagtcctcag catgtcattc cattgttcta     900
tctcttttgct taattcactg tctatctgta aaaatgtgtt caatgactaa tagaatcaca     960
tgataaacttt gccttgtttg tttaccctct agattatata atccagctta aataagttaa    1020
aagacaaaca aacaacacaa attattaggt gaattatata atctagatac ttaaatttatg    1080
ataatccata agcaggtcat gaggcccttc ttacgtaaaa aaaatcatga agccatttag     1140
ctatttggct tcctgcaact aaatagtggg acaatctata agagtgaaaa aaacaactag     1200
aaacctacgt cagacagttt ataatagaca atttatcaat nnnnnnnnnn aag            1253

SEQ ID NO: 68           moltype = DNA   length = 491
FEATURE                 Location/Qualifiers
misc_difference         39
                        note = n is a, c, g, or t
source                  1..491
                        mol_type = unassigned DNA
                        organism = Zea mays
SEQUENCE: 68
ttctttgtgg ggctggacat agtggactgc ctcctggtna acaagaacgg gcgcttcacc      60
ggcgaggctt tcgtggtctt cccaacagcc atgcaggcag agtttgcgct gcatcgcgac     120
aggcagaaca tggggcggag gtatgtcgag gtgttcaggt gcaagaagca cgagtactac     180
tgtgcaatag ccaatgaggt gaaccagggc ggttattttg agccggagta ccgccgctcc     240
cgcctcctc cgaggcctag gaagccgtct gaagataagg gcagcatgga gtacacagag     300
gttctgaagc tccgcgggct tccctactct gccaccactg aggacatcat caagttcttc     360
```

```
ctggagtacg agctggcaga ggagaacgtg catatcgcct accgctccga tgggaaggcc    420
acgggtgaag ccttcgttga gtttccgaca gctgaagtcg cgaagacggc catgtgcaag    480
gataagatga c                                                         491
```

| SEQ ID NO: 69 | moltype = DNA length = 1013 |
|---|---|
| FEATURE | Location/Qualifiers |
| misc_difference | 1..4 |
| | note = n is a, c, g, or t |
| misc_difference | 7..9 |
| | note = n is a, c, g, or t |
| misc_difference | 20..23 |
| | note = n is a, c, g, or t |
| misc_difference | 28 |
| | note = n is a, c, g, or t |
| misc_difference | 30 |
| | note = n is a, c, g, or t |
| misc_difference | 149 |
| | note = n is a, c, g, or t |
| misc_difference | 271 |
| | note = n is a, c, g, or t |
| misc_difference | 390 |
| | note = n is a, c, g, or t |
| misc_difference | 547 |
| | note = n is a, c, g, or t |
| misc_difference | 675 |
| | note = n is a, c, g, or t |
| misc_difference | 791 |
| | note = n is a, c, g, or t |
| misc_difference | 994..999 |
| | note = n is a, c, g, or t |
| misc_difference | 1003 |
| | note = n is a, c, g, or t |
| misc_difference | 1010 |
| | note = n is a, c, g, or t |
| source | 1..1013 |
| | mol_type = unassigned DNA |
| | organism = Zea mays |

SEQUENCE: 69

```
nnnntgnnng agcctaagan nnntatantn agcatgatca gtgtgataga acaaattaag    60
caaaacagga tgaaaatgtt tactgtgcat atataaggaa caagcatgca tatatcactc    120
gtattatcta gcatctcata tggaaagcnt ggggatgttc acagatctat atgagctcta    180
tagccctctt tacttcaggt ggcaatttca aagcattgag gctggcaact agcacgtggt    240
aattatgtat gttttgggca aacaagttca ntctatttcc tgtcgggtag gttcagtact    300
gaacgctaga tctgcaccaa atccaaccac cggccgctgc aactgccaaa agtagggtag    360
ctacctaagt tgtagatcta cagtggcaan ggggcgcgac gcttacgttg gggcagtgct    420
tggcgatggc agtgcacagc gccttaacga tgccggcgtt gatgttgaag aggtcgtccc    480
tggtcatgcc gggcttcctg ggcactcctg cgggatgat gacgatgtcg gagccctcca    540
gcgcctncccgagctggtcg tcccccatga accccttcac ctgcaggagc agaaaccagt    600
gagctcggat ccagtccagt tccgtccgag ccaagccaga ggagcgcgcc gagcagggag    660
gtaccagggc ggggnagttg atgtgggaga cgtcggccgc gacgccgggg gtgccggcga    720
tatcgtagag ggagagggag gaaacgagcg ggttgagctt catgaggagc gagagcggct    780
gcccgatgcc nccgccgcg cccaggatgg ccaccttccg ctccggattg gccgaggacg    840
cgtagccgcg gctgcggcgg aggagctcgg ccgtggactt cagcagcgac ggcctcatgg    900
cggcggctgg gtcggggatc actcgctcgg gcgtgtctcg ctgtgattg gtgggggag     960
cggcagtggg cggcggcgag aagtgagggg agcnnnnnng ganaggatcn aaa          1013
```

| SEQ ID NO: 70 | moltype = DNA length = 608 |
|---|---|
| FEATURE | Location/Qualifiers |
| misc_difference | 73 |
| | note = n is a, c, g, or t |
| misc_difference | 89 |
| | note = n is a, c, g, or t |
| misc_difference | 119 |
| | note = n is a, c, g, or t |
| misc_difference | 158 |
| | note = n is a, c, g, or t |
| misc_difference | 230 |
| | note = n is a, c, g, or t |
| misc_difference | 393 |
| | note = n is a, c, g, or t |
| misc_difference | 443..444 |
| | note = n is a, c, g, or t |
| misc_difference | 469 |
| | note = n is a, c, g, or t |
| misc_difference | 492 |
| | note = n is a, c, g, or t |
| misc_difference | 494..497 |
| | note = n is a, c, g, or t |
| misc_difference | 507..509 |

|                  | note = n is a, c, g, or t |
| --- | --- |
| misc_difference  | 511 |
|                  | note = n is a, c, g, or t |
| misc_difference  | 522 |
|                  | note = n is a, c, g, or t |
| misc_difference  | 558 |
|                  | note = n is a, c, g, or t |
| misc_difference  | 561..563 |
|                  | note = n is a, c, g, or t |
| misc_difference  | 569..570 |
|                  | note = n is a, c, g, or t |
| misc_difference  | 572..577 |
|                  | note = n is a, c, g, or t |
| misc_difference  | 579..596 |
|                  | note = n is a, c, g, or t |
| misc_difference  | 602..606 |
|                  | note = n is a, c, g, or t |
| source           | 1..608 |
|                  | mol_type = unassigned DNA |
|                  | organism = Zea mays |

SEQUENCE: 70

```
ctaagtggtg tcaatggcat tctattttat gctgcgagca tcttcaaagc tgctggtaca   60
ttcttcaaaa cangatcaat ctctgatgnt agattctaat gcaattgaga tatgcttttnt  120
ggcttgcgta ttcttgaact tgtccaggaa atgaaagnta cctgttttg gttcgattca    180
tgctttgcat ggagacactg tgacaatgat tcatttacta tgtaaaaaan gggaagagtt   240
ctagaaccta ggcttcatca aagtctgata tcttcctgct ttctcttcct caacaggtat   300
tacaaacagt aatctagcaa catttggttt aggggctgtt caggtacatt tgtttttaaag 360
ttgttacatc ccttgtttct cagacaaatt ttnggcagat gtgggcttgg cactgcatac   420
ttaatgggat cttgtcgttt canntgattg ctactggagt gacaacctng ttgactgaca   480
aagctggtcg angnnnnctt ctcattnnna ntttccaact tnccatcaca attgtttatt   540
ggacatgctt ttccagtntt nnnaattgnn cnnnnnntnn nnnnnnnnn nnnnnnaatg    600
gnnnnnac                                                            608
```

| SEQ ID NO: 71 | moltype = DNA length = 472 |
| --- | --- |
| FEATURE | Location/Qualifiers |
| misc_difference | 263 |
|  | note = n is a, c, g, or t |
| source | 1..472 |
|  | mol_type = unassigned DNA |
|  | organism = Zea mays |

SEQUENCE: 71

```
ggttgcatca acatcggctg gcgagtagta gttggtacag cttccaaaag aatgcgctga   60
ttgcctactt gttgtataca tacagcagag tgttttgaac caacaaagag atcaaaaaat  120
cggatttctg tatatgcagc ctctggcaat tgaatctctc agttcccgt atatgttcga   180
atcctaccaa gcaaaaggga atccaggcca gagctggaaa catcctatca agcaaacact  240
ttacaagaaa ccttctacta tcnagattgc ttggtgtatg ttcatccctg cagatgcaat  300
aggctgtgct tggttacatg agttacagag agattactgc aaacactgta agtttcgggt  360
gtttacctat acaacaggaa tcttcagaag aataagtgag cagagataca ggcacactga  420
gatggcgatc ccagcaacga aattttggta cagacggcta ttatccctac tg           472
```

| SEQ ID NO: 72 | moltype = DNA length = 679 |
| --- | --- |
| FEATURE | Location/Qualifiers |
| misc_difference | 538 |
|  | note = n is a, c, g, or t |
| source | 1..679 |
|  | mol_type = unassigned DNA |
|  | organism = Zea mays |

SEQUENCE: 72

```
ttttgtaccc agcagaccag aagagtccaa acgggaaact acggtataac aaaggcaaca   60
atctttttt tacttactat tattactatt cccggaactg tagtttagct tcctgtcctc   120
acattggttg ttctatgtg gaattgcagc gttctgtatg aagtcttccc gatgtcattc   180
ctgatggaac aagctggagg ccaggctttc acaggcaaac aacgggtgtg tttcagtttc   240
cctttctcag accccaatcc ccaactgaaa aatcttgatg ctagagctat cacatttgcc   300
tgagatatca gggggatttt tcaacacttt tacaggttga aattattgag aaaagggcac   360
tattttaaca tgccatgttt ttttttacca gtggttggca ttgcatataa ctgaaaatgc   420
tcctgctaaa tttataatgc aggcccttga acttgctccc gctaaacttc acgacagatc   480
cccagtgttc tcgggagct acgatgacgt tgaggagatc aaagcactgt acgcttcnat    540
gtcaaacagc ggttgacctt tctgcctgag gaaacgagcg agatcaaaag caccgtacgc   600
ttcagagtca actgcttgat ctttatagat tgtaataaaa taataaaga gtttgtaaaa    660
aaaacaacaa cactgcttg                                                679
```

| SEQ ID NO: 73 | moltype = DNA length = 397 |
| --- | --- |
| FEATURE | Location/Qualifiers |
| misc_difference | 49 |
|  | note = n is a, c, g, or t |
| source | 1..397 |
|  | mol_type = unassigned DNA |
|  | organism = Zea mays |

SEQUENCE: 73

```
cctagaggtg gtccgcttac cagtttacta tccttctgag caagaaaang atgatcctaa    60
gctctatgca aacaatgtac ggaaactgat ggcagtggag gtatcttaaa cacttgaaaa   120
tgattaatta cattgaatgg tattgctgta caagtgtttg gtattattgt aaccatgtgg   180
taatcttgat ttcttttcag ggaaacttga ttctttcaga ccttgggctg gcggagaagc   240
gagtgtacca tgccgcactg aatggtaata gtctagctcg tgctttacat cagaaagatg   300
attgaaatgc catgctatcg tgcttccata atactggctt gcttgtaact gtgtgcttgc   360
ttgtgcatcg tcatggttga gaggaatgtc gtgaata                            397

SEQ ID NO: 74           moltype = DNA   length = 648
FEATURE                 Location/Qualifiers
misc_difference         1
                        note = n is a, c, g, or t
misc_difference         8..12
                        note = n is a, c, g, or t
misc_difference         499
                        note = n is a, c, g, or t
misc_difference         581..587
                        note = n is a, c, g, or t
misc_difference         589..593
                        note = n is a, c, g, or t
misc_difference         595
                        note = n is a, c, g, or t
misc_difference         603
                        note = n is a, c, g, or t
misc_difference         605
                        note = n is a, c, g, or t
misc_difference         611..638
                        note = n is a, c, g, or t
misc_difference         640..646
                        note = n is a, c, g, or t
source                  1..648
                        mol_type = unassigned DNA
                        organism = Zea mays
SEQUENCE: 74
ntgcctgnnn nnggacatga gtactctgaa tccttggatc caatgggtgc agtacttttg    60
gcgttcgcct caaatgcaag aaaaatggat gggataataa cagaaccaat cagtacacca   120
tatatgtgcc cagccactac agctctcggg gaggtcgaag tcatatagcc agtcttaagg   180
tcttgcatgg cttgtgaaga cacattcaga gctgcaacag acaccccaca ggctgcaagg   240
ctagcgatga ccgcaccagg cacggcaacc catgctgcta tgacgaactg tatgaacctg   300
ccataagatt gtgcaactga ccagtctgtg agtcctgttc cgtacgtgtt gcagaaggtg   360
aaaacgggaa gaatggtgaa cagaagggcc atgtggtaga gtttaatgtg ttggaagatc   420
caagggatga cgactgagca tactattgca catccgatat atccagcaac cggcacatgg   480
agcgggattc tctgaccang aaacacatca agccttctac gatcatcata gctaaggctg   540
gggcttgtca acatgtattt gatcttccct gaatcatttt nnnnnnncnn nnngnatagg   600
tcnantgagc nnnnnnnnnn nnnnnnnnnn nnnnnnnncn nnnnnnca                648

SEQ ID NO: 75           moltype = DNA   length = 381
FEATURE                 Location/Qualifiers
misc_difference         139
                        note = n is a, c, g, or t
source                  1..381
                        mol_type = unassigned DNA
                        organism = Zea mays
SEQUENCE: 75
agactctggc tgggtacctt cccaaccgcg gaggatgcag ctagggccta tgatgaggca    60
gccagagcga tgtatggaga cttggcacgg actaacttcc ccggacagga tgcaacaacc   120
tctgcccaag ctgctctanc atcgacctct gcccaggctg ctccaacagc tgttgaagct   180
cttcagactg gcacgtcatg cgagtcgaca acgacatcaa atcactcgga catcgcatcc   240
acctcacaca agcctgagcc tgaagcctct gacatctcga gctccctaaa ggaaaaatgt   300
ccagctggat catgtggtat ccaagagggt acacccagtg tagctgacaa ggaggtcttt   360
gggccgttgg agcctatcac a                                             381

SEQ ID NO: 76           moltype = DNA   length = 692
FEATURE                 Location/Qualifiers
misc_difference         159
                        note = n is a, c, g, or t
misc_difference         369..376
                        note = n is a, c, g, or t
misc_difference         381..382
                        note = n is a, c, g, or t
misc_difference         398..399
                        note = n is a, c, g, or t
misc_difference         404
                        note = n is a, c, g, or t
misc_difference         455..457
                        note = n is a, c, g, or t
misc_difference         635..639
                        note = n is a, c, g, or t
misc_difference         662..689
```

```
                        note = n is a, c, g, or t
source                  1..692
                        mol_type = unassigned DNA
                        organism = Zea mays
SEQUENCE: 76
tgtctttcgg ttgaacttgt ttgaagccct gcccaacctg gacatttttt agtttaggtc   60
taaaaagaga aaccctaggg ttgtttgaaa gggcttgttt ctaggcttgg catttttggg  120
tcagtgaagc aattagtatg gttgtggatt tgcatttgnt actcggcatt aggtcttatt  180
tttcgcgagc gctaactcta attgtattgc tgaaactttaa gtgttgctta tatattccgt  240
tggtaacgga tactattctg cttcaattcc cttctacatt gtagattcgc tacaggcttg  300
gctcttggct agccaagcct gcagtttagg actttgccaa aactgcattt gccatttaac  360
aggcttctnn nnnnnncatt nnctctggag gtctaggnng tggnagacgt cgcagcagga  420
gcaggagccg cagtcgcagc cctagatacc gcagnnntcc gagctataat agaaggtaac  480
catttttttg acttcttaga tttcatcagt tgtaaattaa tctctcaaatt ttgtcgctca  540
acctcaaatg ctgcttatat cttttccttgg taactgatac tattctgctt taatgccctt  600
ctattgtcga ttcattatgg gctttacttt tggcnnnnna agcctgcaat ttgctacttt  660
gnnnnnnnnn nnnnnnnnnn nnnnnnnnnt tc                                692

SEQ ID NO: 77           moltype = DNA   length = 672
FEATURE                 Location/Qualifiers
misc_difference         3..6
                        note = n is a, c, g, or t
misc_difference         9..17
                        note = n is a, c, g, or t
misc_difference         33
                        note = n is a, c, g, or t
misc_difference         36
                        note = n is a, c, g, or t
misc_difference         38
                        note = n is a, c, g, or t
misc_difference         91
                        note = n is a, c, g, or t
misc_difference         342
                        note = n is a, c, g, or t
misc_difference         475..486
                        note = n is a, c, g, or t
misc_difference         511..513
                        note = n is a, c, g, or t
misc_difference         518..523
                        note = n is a, c, g, or t
misc_difference         547..548
                        note = n is a, c, g, or t
misc_difference         552..554
                        note = n is a, c, g, or t
misc_difference         558..560
                        note = n is a, c, g, or t
misc_difference         575..577
                        note = n is a, c, g, or t
misc_difference         582..583
                        note = n is a, c, g, or t
misc_difference         587..589
                        note = n is a, c, g, or t
misc_difference         591..599
                        note = n is a, c, g, or t
misc_difference         606..628
                        note = n is a, c, g, or t
misc_difference         630..632
                        note = n is a, c, g, or t
misc_difference         634..636
                        note = n is a, c, g, or t
misc_difference         639..657
                        note = n is a, c, g, or t
source                  1..672
                        mol_type = unassigned DNA
                        organism = Zea mays
SEQUENCE: 77
tcnnnnagnn nnnnnnnaag ttactagaac ctngtntngt tgatcgcatt gttgtttcaa   60
ataaatcagt agcgaaggtc tacatcagga nttcacctca tccaaagagc caaggccaag  120
atagtgatat ccatattact accactgatg ctccaggcaa gcctgctccc agcagatgca  180
agtattactt caatattggt agtgttgatt tgtttgaaga gaagttagag gaagcccagg  240
aagctttggg aatagatcca catgattttg tcccagtaac ttatgttgct gaagtaaatt  300
ggttccaaga agttatgagg tttgcccccaa cagcattgat tnttggtcta ttatatttca  360
cgggaaaaag gatgcagagt ggtttcaata ttggaggtgg tgctggcaaa ggaagaggag  420
gtattttcaa cattggaaaa gctacagtga tgaagatgga caagaactcc aaaannnnnn  480
nnnnnnatta cttttcttat gttactcaat nnntgacnnn nnctatatt tgatggatga  540
taaaaannat cnnncccnnn acccaaatga ttttnnncac annctannnc nnnnnnnnng  600
atgacnnnnn nnnnnnnnnn nnnnnnnngn nncnnntgnn nnnnnnnnnn nnnnnnnagc  660
atactacatg aa                                                     672
```

```
SEQ ID NO: 78           moltype = DNA  length = 557
FEATURE                 Location/Qualifiers
misc_difference         422
                        note = n is a, c, g, or t
source                  1..557
                        mol_type = unassigned DNA
                        organism = Zea mays
SEQUENCE: 78
cgttggcaca gtcacgtcaa tcgatgaaca tcattcagaa acattaccca gggctgatag    60
cagccgcgat cctttcgac cctccaaaga tctttgaatc cttttggaag gtacggtgtt    120
ccatagtgca attctgtttc taagtttaac agcaggttta ctagttctgg catcggttgt    180
caagcatcct gaactttaag ccatggactt tgtctgaacc agtacaagct tggtcctgta    240
gaaattgtga catgccattt cattaactgc agtgtcaatg tataatgctt aaacctcctt    300
ttttttagat gctaagttac ttcatcgagc cggagctgga aaagaaggtg aaattcgtgt    360
acactgacaa tcctgagagc cagaggataa tggccgacat gtttgacatg gagaagctgg    420
antccgcatt tggtggccgc agcgcgtctg gcatcgacgt tgccaagtat tccgagagaa    480
tgcgaacagg agatcagatt aggggtcttc gctaacggca aatggaatac tgctatctca    540
cagttcgtca agaaact                                                   557

SEQ ID NO: 79           moltype = DNA  length = 807
FEATURE                 Location/Qualifiers
misc_difference         34
                        note = n is a, c, g, or t
misc_difference         54
                        note = n is a, c, g, or t
misc_difference         103
                        note = n is a, c, g, or t
misc_difference         198
                        note = n is a, c, g, or t
misc_difference         207
                        note = n is a, c, g, or t
misc_difference         263
                        note = n is a, c, g, or t
misc_difference         283..287
                        note = n is a, c, g, or t
misc_difference         299
                        note = n is a, c, g, or t
misc_difference         351
                        note = n is a, c, g, or t
misc_difference         358
                        note = n is a, c, g, or t
misc_difference         365
                        note = n is a, c, g, or t
misc_difference         380
                        note = n is a, c, g, or t
misc_difference         413
                        note = n is a, c, g, or t
misc_difference         470
                        note = n is a, c, g, or t
misc_difference         523..524
                        note = n is a, c, g, or t
misc_difference         617..623
                        note = n is a, c, g, or t
misc_difference         672..678
                        note = n is a, c, g, or t
misc_difference         694..700
                        note = n is a, c, g, or t
misc_difference         702..706
                        note = n is a, c, g, or t
misc_difference         710..717
                        note = n is a, c, g, or t
misc_difference         720..739
                        note = n is a, c, g, or t
misc_difference         743..745
                        note = n is a, c, g, or t
misc_difference         750..806
                        note = n is a, c, g, or t
source                  1..807
                        mol_type = unassigned DNA
                        organism = Zea mays
SEQUENCE: 79
gcctgcagtg gtgaagtcgg agctgctttg gttntgaggg tgcaacaaag ctcnacaacg    60
atggcaaatt gttcttttc tcaagaggtc gtggcttgtt gcnagtgagt ggcagcttag    120
tatgggcttt gactgaggtt ttttgtggga agtcggagtt gcttatcact atcttgggat    180
taagctcggc aacgatgncg cacggtnggc tacattggtt gtgtgacact tttgtgtatt    240
tgtgggttgc ttaggttag ctntctgggc tgttatgttt agnnnnngta tttttggtng    300
gtttcccttt aataaactgt gccattgtga ggtttttagg cttggtttcc ntcataanct    360
gggtnaattc tatctctcan tctctccttt aattgaaagg caaagatcct gcnattgcgt    420
taaaaaagaa atatgagagt ctctaaccaa ggatagaaat aaaacatgan ggagaaatgc    480
```

```
ttattagcta tcaagtaggg tcactgaatt atgagctgga gtnnaagacg tggacgagtg    540
gctgtggcat gtatttaagt caaattgaag gggttcataa aggtgttctc tagctggctt    600
ctatctataa gaaagannnn nnngatttct agtgccgaac ttctgtatct attcccagga    660
ctcatatcat gnnnnnnnat ttcaatttca tcannnnnnn annnnntatn nnnnnnntgn    720
nnnnnnnnnn nnnnnnnnna atnnntcgtn nnnnnnnnnn nnnnnnnnnn nnnnnnnnnn    780
nnnnnnnnnn nnnnnnnnnn nnnnnna                                       807

SEQ ID NO: 80            moltype = DNA   length = 1415
FEATURE                  Location/Qualifiers
misc_difference          5..6
                         note = n is a, c, g, or t
misc_difference          19..25
                         note = n is a, c, g, or t
misc_difference          364
                         note = n is a, c, g, or t
misc_difference          367
                         note = n is a, c, g, or t
misc_difference          454
                         note = n is a, c, g, or t
misc_difference          539
                         note = n is a, c, g, or t
misc_difference          816
                         note = n is a, c, g, or t
misc_difference          832
                         note = n is a, c, g, or t
misc_difference          902
                         note = n is a, c, g, or t
misc_difference          937..938
                         note = n is a, c, g, or t
misc_difference          958
                         note = n is a, c, g, or t
misc_difference          1021..1026
                         note = n is a, c, g, or t
misc_difference          1042
                         note = n is a, c, g, or t
misc_difference          1094
                         note = n is a, c, g, or t
misc_difference          1155..1156
                         note = n is a, c, g, or t
misc_difference          1170
                         note = n is a, c, g, or t
misc_difference          1211
                         note = n is a, c, g, or t
misc_difference          1401..1402
                         note = n is a, c, g, or t
source                   1..1415
                         mol_type = unassigned DNA
                         organism = Zea mays
SEQUENCE: 80
ggganncgcg tcgccgtgnn nnnnncagcg atggctggcc tactctctcc gcgaagctgg     60
ccttcgagaa gtcggtcttc gccaaaaccc agaaagcgaa tgctggaacg gatggtaatt    120
tacatctgat ttctcttaat acggaagaat tgttttcgac tgatggtgag cgttgttgtg    180
ctcccttgag gtagtccgga gtacttgatt aacattatca tctcataatg aactcatgag    240
tgtgatgtat tgatgtgcct gtttgcgtgt tttttctttt cttcaagtat ttcatatgtt    300
tatttgtttc tctttaacag cagagattgt aatgtttgat ggtcaaattg tggtatacaa    360
gttnatncaa gacctgcact ttttttgttac tggaggagaa gaggagaatg agcttatttt    420
agcatcagtt cttcagggat tctctgatgc tgtngaacga cttctcaagt tatcttccct    480
ctattgaagt ttatctttc aaccattgtt tgttctgtta catgttattg tgttaatgnt    540
gattgtatat gaatgtgttt ccaaccttgg tggtttcagg aacatggttg acaaaaggac    600
agcactcgag aatttggacc tgatcctatt gtgtcttgat gaattgttg atggagggta    660
aagccttttc ttactacgta catgatatta agggcttctt ttcttgttct ctttattgtg    720
tacatttatt atcctttgat ctgaaatcac ctgactcatc tgggccatgg caatagagct    780
ctattagggc ctctatttgt aatggttgta ttcacnggat tcaaggtttt antctggtgt    840
tctgcttctg tacctcaagc ccaagcatgc ctaaccttt aatggggtta cacaattga    900
tntgtgaaac aatggcttag tttgctaaag acatcannaa aataaacagc ccattccntt    960
ttttttgaaa tggaacaaaa ctgattatcc acatgaagaa ttgtatctat ttgatttga   1020
nnnnnngttt gagatcttga angactgcag gtaccacaac tatgcactcg cctcaatgtg   1080
tctttgataa cccnattgat gtctaaactc tgaaatgtgg aagtgatagg atcaagcata   1140
gagatgaata gaatnncaca ttgtaagcan catgtaattg tttggtgcat taaacataat   1200
tttctgaatg nttacacagg attgtacttg aaacagaagg aagagagata gctgaaaagg   1260
tgtctggtca cggatcggag ggtgcttcat cggctgagca ggtaggctgc aggctgtatc   1320
tatttcaaat tttaactgaa gaaactggtt tcttttaact tactagctat cgttatttgc   1380
gtgcagactt tagtcaatgc nntaacgcaa gcaag                              1415

SEQ ID NO: 81            moltype = DNA   length = 364
FEATURE                  Location/Qualifiers
misc_difference          100
                         note = n is a, c, g, or t
source                   1..364
```

```
                        mol_type = unassigned DNA
                        organism = Zea mays
SEQUENCE: 81
tgaggaactg caggaaggcc atccctccga gggaaggagg agggaaggtg ataatcatcg    60
acatggtggt cggggctggg ccggcggacc cgaggcacan ggagatgcag gccctgttcg   120
acctctacat catggtcgtc aacggcatgg agcgggacga gcaggagtgg aagcagatct   180
tcgtcgaggc cggggttcacc gactacagag tcacgccggt cctcggcgtc cgctccatca   240
tcgaggtgta cccttgaacg aacgaacgaa cgaacgtcgt ctggtgccat gtgtgtgtgt   300
ttgtgtggag ggagggtcat cctctatttt cttttttgtt ttgtttctgc attctgaaga   360
cacg                                                                364

SEQ ID NO: 82           moltype = DNA  length = 426
FEATURE                 Location/Qualifiers
misc_difference         232
                        note = n is a, c, g, or t
source                  1..426
                        mol_type = unassigned DNA
                        organism = Zea mays
SEQUENCE: 82
tggagagggt gagatcacaa aagctttcaa ccgccgggac tcaaagctag aaaagccatc    60
gccgccaact ccaagaccgg cccgtccaac ttccaggcat tccccttga cgccctctgc   120
tagagtggca ccgataccctg cgaggagaaa atctgtcacg cccaagaacg ggcttttcaca  180
ggtggacgat gacgcgagga gcgtgctcag tgtgcagtct gagcggccaa gnaggcacag   240
tatagccacc tcgactgtgc gggacgacga gagcctcacg agctcccgt cgctcccaag   300
ctacatggtt cccacagaat ctgcaagggc caaatctcgc ctccagggtt cagcaatggc   360
caatggcgca gagacacctg agaaaggagg ctcaactgga ccagccaaga agaggttatc   420
cttcca                                                              426

SEQ ID NO: 83           moltype = DNA  length = 1289
FEATURE                 Location/Qualifiers
misc_difference         2..17
                        note = n is a, c, g, or t
misc_difference         79..86
                        note = n is a, c, g, or t
misc_difference         89
                        note = n is a, c, g, or t
misc_difference         92
                        note = n is a, c, g, or t
misc_difference         95
                        note = n is a, c, g, or t
misc_difference         99..105
                        note = n is a, c, g, or t
misc_difference         107..109
                        note = n is a, c, g, or t
misc_difference         111
                        note = n is a, c, g, or t
misc_difference         114..118
                        note = n is a, c, g, or t
misc_difference         123..125
                        note = n is a, c, g, or t
misc_difference         127
                        note = n is a, c, g, or t
misc_difference         134
                        note = n is a, c, g, or t
misc_difference         137
                        note = n is a, c, g, or t
misc_difference         140
                        note = n is a, c, g, or t
misc_difference         142
                        note = n is a, c, g, or t
misc_difference         146
                        note = n is a, c, g, or t
misc_difference         151
                        note = n is a, c, g, or t
misc_difference         312
                        note = n is a, c, g, or t
misc_difference         352
                        note = n is a, c, g, or t
misc_difference         354
                        note = n is a, c, g, or t
misc_difference         377
                        note = n is a, c, g, or t
misc_difference         434
                        note = n is a, c, g, or t
misc_difference         650..651
                        note = n is a, c, g, or t
misc_difference         1171..1173
                        note = n is a, c, g, or t
misc_difference         1231..1235
```

|  |  |
|---|---|
|  | note = n is a, c, g, or t |
| misc_difference | 1261..1266 |
|  | note = n is a, c, g, or t |
| source | 1..1289 |
|  | mol_type = unassigned DNA |
|  | organism = Zea mays |

SEQUENCE: 83

```
gnnnnnnnnn nnnnnnntcc taaatggact gggttactgc ctaaatctgg aaagatggtt  60
agtgcttgaa ttctttatnn nnnnnntang gnctnacann nnnnnnannna nacnnnnnat 120
tcnnngntat ggtnttnacn ancatnagaa ncgtgtaacc atgaaatatt attcttggtg 180
ctctaggtaa ttaatacaga gtggggagc ttcaaatcca acaaacttcc tctttcagaa 240
tatgacaaag ccatggactt tgaaagtttg aaccctggag agcaggtatt gttgctctgg 300
cggttgactt tnccatttca ggtgactgca tgaatatatg tggataactt angngtggct 360
tctgcagat atacganaaa atgatttctg gtatgtatct cggagagatt gttcgaagaa 420
ttttactgaa gttngcacat gaagcttctc tatttgggga tgttgttcca cctaagctgg 480
agctgccatt tatattgagg tatgctttct tgtcctatgg acatccagct gttcaagctt 540
gtttgctaca ttgttggtat ggaaaagttg tttatgtctc tttaataggc taagttagat 600
gtcacatcag taagtaatcc aaagaaggcg acatgataca atattttttn nggtcaactc 660
tgtttatttc aattggttgc aataaacatg gtctctgata tgctgcaatt ttactttga 720
ataactatct tgatggcatg agaaaatgtg tgcctagaaa cagcttgctt cagggagctt 780
tatattgat tagatttcag ggctaataaa gtatttacct ggagctaaaa caaacggtca 840
ccttgtaact ctcgttagtc tattaacagg tacatgtatt gggtttgagg catgttgatg 900
cttaacatct ttgtgtgatg cttaacattt tctttggcac cagctctttc tgtgcccttt 960
ttatgcttat tagtaagttg aaacctatgt atcaattagt acatgttcga tgaatacatt 1020
cgttgtggta tcacaggacg ccagatatgt cagccatgca tcatgactcc tcacatgacc 1080
tcaaaactct tggagctaaa ctgaaggaca tagtcggggc acggcttgcc tgtgccaaat 1140
tggcttgttg ttcataaata gtcagtcagt nnnctctcgg tcccttacgg catatacatt 1200
tgttctcatg ttcaggtcgc ggacacttcc nnnnnagtaa ggtacatcac tcgtcacatc 1260
nnnnnncttg tcgcagagcg tgcagcacg                                    1289
```

| SEQ ID NO: 84 | moltype = DNA   length = 665 |
|---|---|
| FEATURE | Location/Qualifiers |
| misc_difference | 473 |
|  | note = n is a, c, g, or t |
| source | 1..665 |
|  | mol_type = unassigned DNA |
|  | organism = Zea mays |

SEQUENCE: 84

```
tcaaaaccca gtgcatccga gttcaggtct tcaggcttgg caggtgaaga tttctcgaga  60
aaccctgga aacaactggc ttccgttttcc ggaccttgat tcccacacct gccatgcccc 120
tcaaatgcct ggtggttctg ctttacgtca tcctgatgaa cttccttggt ttttcggact 180
gtaaacatgc cttcgcatcc agaaacctaa caaagataaa ttactgattg catcgtatca 240
gggacaatat tgtttctaag ttactgagtg tttcttcttg gtccaaatcg gagcttcagg 300
ttgtccaaaa cacgggtaac attgagaagt cgtggatcgt cagaaggaat ctctcgcgcc 360
tgaatttgaa aaacaaggga gcatgagcag aacacgaatc aagaacagcc agatgaacca 420
gttcgtttta attcttcaga gcttaattgc tgacaggtga cagcagacaa atnatttcag 480
tgtacaaaca gttgagaccc aaatgaatat gtacatcaag gaccaatata gtaagttagc 540
aactcattct atagttagga agtactcaat tattcataga tgttttcaag gtgaagaaag 600
tgtaccaagt cacaagttca agatactaaa gcttaccgtc agacccttgt ggtatgcctc 660
aacac                                                              665
```

| SEQ ID NO: 85 | moltype = DNA   length = 1302 |
|---|---|
| FEATURE | Location/Qualifiers |
| misc_difference | 3..9 |
|  | note = n is a, c, g, or t |
| misc_difference | 14..18 |
|  | note = n is a, c, g, or t |
| misc_difference | 81..87 |
|  | note = n is a, c, g, or t |
| misc_difference | 90 |
|  | note = n is a, c, g, or t |
| misc_difference | 93 |
|  | note = n is a, c, g, or t |
| misc_difference | 100..102 |
|  | note = n is a, c, g, or t |
| misc_difference | 105..106 |
|  | note = n is a, c, g, or t |
| misc_difference | 108..110 |
|  | note = n is a, c, g, or t |
| misc_difference | 112 |
|  | note = n is a, c, g, or t |
| misc_difference | 124..126 |
|  | note = n is a, c, g, or t |
| misc_difference | 129 |
|  | note = n is a, c, g, or t |
| misc_difference | 135 |
|  | note = n is a, c, g, or t |
| misc_difference | 138 |
|  | note = n is a, c, g, or t |

| | |
|---|---|
| misc_difference | 141 |
| | note = n is a, c, g, or t |
| misc_difference | 143 |
| | note = n is a, c, g, or t |
| misc_difference | 147 |
| | note = n is a, c, g, or t |
| misc_difference | 152 |
| | note = n is a, c, g, or t |
| misc_difference | 313 |
| | note = n is a, c, g, or t |
| misc_difference | 353 |
| | note = n is a, c, g, or t |
| misc_difference | 355 |
| | note = n is a, c, g, or t |
| misc_difference | 378 |
| | note = n is a, c, g, or t |
| misc_difference | 435 |
| | note = n is a, c, g, or t |
| misc_difference | 1159..1161 |
| | note = n is a, c, g, or t |
| misc_difference | 1174 |
| | note = n is a, c, g, or t |
| misc_difference | 1232..1234 |
| | note = n is a, c, g, or t |
| misc_difference | 1262..1266 |
| | note = n is a, c, g, or t |
| misc_difference | 1279..1282 |
| | note = n is a, c, g, or t |
| misc_difference | 1289..1295 |
| | note = n is a, c, g, or t |
| source | 1..1302 |
| | mol_type = unassigned DNA |
| | organism = Zea mays |

SEQUENCE: 85

```
ggnnnnnna aatnnnnntc ctaaatggac tgggttactg cctaaatctg gaaagatggt    60
tagtgcttga attctttata nnnnnnntan ggncttacan nnttnnannn anactttta   120
ttcnnngtna tggtnttnac nancatnaga ancgtgtaac catgaaatat tattcttggt   180
gctctaggta attaatacag agtggggggag cttcaaatcc aacaaacttc ctctttcaga   240
atatgacaaa gccatggact tgaaagttt gaaccctgga gagcaggtat tgttgctctg   300
gcggttgact ttnccatttc aggtgactgc atgaatatat gtggataact tangngtggc   360
ttctgacaga tatacganaa aatgattct ggtatgtatc tcggagagat tgttcgaaga   420
attttactga agttngcaca tgaagcttct ctatttgggg atgttgttcc acctaagctg   480
gagctgccat ttatattgag gtatgctttc ttgtcctatg gacatccagc tgttcaagct   540
tgtttgctac attgttggta tggaaaagtt gtttatgtct ctttaatagg ctaagttaga   600
tgtcacatca gtaagtaatc caaagaaggc gacatgatac aatattttt ttggtcaact   660
ctgttatttt caattggttg caataaacat ggtctctgat atgctgcaat tttacttttg   720
aataactatc ttgatggcat gagaaaatgt gtgcctagaa acagcttgct tcagggagct   780
ttatattaga ttagatttca gggctaataa agtatttacc tggagctaaa acaaacggtc   840
accttgtaac tctcgttagt ctattaacag gtacatgtat tgggtttgag gcatgttgat   900
gcttaacatc tttgtgtgat gcttaacatt ttctttggca ccagctcttt ctgtgccctt   960
tttatgctta ttagtaagtt gaaacctatg tatcaattag tacatgttcg atgaatacat  1020
tcgttgtggt atcacaggac gccagatatg tcagccatgc atcatgactc ctcacatgac  1080
ctcaaaactc ttggagctaa actgaaggac atagtcgggg tacggcttgc ctgtgccaaa  1140
ttggcttgtt gttcataann ngtcagtcag tgtnctctcg gtcccttacg gcatatacat  1200
ttgttctcat gttcaggtcg cggacacttc cnnaagtaa ggtacatcac tcgtcacatc  1260
tnnnnncttg tcgcagagnn nncagcacnn nnnncgccg ca                     1302
```

| | |
|---|---|
| SEQ ID NO: 86 | moltype = DNA    length = 726 |
| FEATURE | Location/Qualifiers |
| misc_difference | 140 |
| | note = n is a, c, g, or t |
| source | 1..726 |
| | mol_type = unassigned DNA |
| | organism = Zea mays |

SEQUENCE: 86

```
tcatcttcta ctgaaaaaac caggagaagt ggccatcgca tggcatgaca cacaactttg    60
tccatccctt ttactctggc atccagcctc tgtgacctgg acgagctacc ggcgcgtgga   120
gcccagaaag aacggagtgn cattctctta cgccactgtg accgccctca accccccca   180
aagccaatga aaggcggttt agtcgcttcc tacctcactt ggtgatcgtt ctctcttcc   240
ggttgatggt tggcgctgtt tatttttagc atcggttgga ctatcagact aggctaaggg   300
ccccttggt agggcttatt tttcagcttc ggctctggct catgcaaaag ttgtgccaaa   360
cacctctttt tcaaatggct tcaccaatga agtgcttttc caaaatgaac tagagggcat   420
gagccaaaaa agtggctca cccggcttca gctcacgtca ttttgcaca atagccctcc   480
caccagtcca aattaattt tttggtcatg ccctcaatcc ctagccacgc acaatagccc   540
tcccaccagt cccaactata caagggtctt tctaaaaaac aacttataag ccgttttgcc   600
aaatgatttt tcagaatggc tttggctcat ctaaagaagt ggcttcacct cgtgagtcag   660
agccaaagcc gttttgtag aagccagagc cctgccaaag gggccctaaa ccttgcctta   720
gtttaa                                                             726
```

```
SEQ ID NO: 87              moltype = DNA   length = 710
FEATURE                    Location/Qualifiers
misc_difference            366
                           note = n is a, c, g, or t
misc_difference            590
                           note = n is a, c, g, or t
misc_difference            608
                           note = n is a, c, g, or t
misc_difference            627..628
                           note = n is a, c, g, or t
misc_difference            643..644
                           note = n is a, c, g, or t
misc_difference            648..650
                           note = n is a, c, g, or t
misc_difference            670..672
                           note = n is a, c, g, or t
misc_difference            689..698
                           note = n is a, c, g, or t
source                     1..710
                           mol_type = unassigned DNA
                           organism = Zea mays
SEQUENCE: 87
gtttgggtct acaaacattg ggttgacaga tctcgatgta ctcttccact gtaaacaaca    60
cattttgaga catttttaagc tttaccatca tagagcaagg aggatcaagt atatatagat  120
gttctgagag caagagttcc tacctggtgt gaaaatgcat atgcaagcgc tctttctctt   180
cttatcgccg cctcttgcct gcttatcagg cttgcctcga tttgctcctt ggattgggtg   240
ctgtcatccc agttctcacc catctgatat atcattattc acagacagaa tatgtttagt   300
tctctcaata atatcttata actatctcaa ggctttaagc agattagagc tttgagaagg   360
tttgcntact ctgaaattct ccagttcctg tttaagtagg agctggcgtt ggagagcctg   420
gttctcctcg gacatctttg ctctcctgga agatatctgt gactgcaccc gtgatagagt   480
ttgcatgcag cgcagagtgc ttgcagattg acgctttact gaattaccct caaccaatga   540
cttcaatcga acaaggcctc gcagtgctcg tagtgccctc cttgcctacn ttatcacaat   600
gaccgaaaac tctcagcata acattgnntt gtaaaagtaa ganncttnnn ttttcttc     660
cttttttttn nngcaaagtg taaaagtann nnnnnnnntt actatgaaac              710

SEQ ID NO: 88              moltype = DNA   length = 614
FEATURE                    Location/Qualifiers
misc_difference            249
                           note = n is a, c, g, or t
misc_difference            412..416
                           note = n is a, c, g, or t
misc_difference            424..440
                           note = n is a, c, g, or t
misc_difference            442..447
                           note = n is a, c, g, or t
misc_difference            465..474
                           note = n is a, c, g, or t
misc_difference            481..485
                           note = n is a, c, g, or t
misc_difference            492..505
                           note = n is a, c, g, or t
misc_difference            518..519
                           note = n is a, c, g, or t
misc_difference            530..546
                           note = n is a, c, g, or t
misc_difference            549..558
                           note = n is a, c, g, or t
misc_difference            564..576
                           note = n is a, c, g, or t
misc_difference            587..605
                           note = n is a, c, g, or t
source                     1..614
                           mol_type = unassigned DNA
                           organism = Zea mays
SEQUENCE: 88
gtcggagaag ttggctgtgt tgccaggatg taatagaaaa gggctcagaa tgttgctgat    60
ccttgttaac tggataatat ggcggaaaag gaacgcaagg acttttgatc gtaggttttt   120
gaccagtcag cagagcataa cttcggttaa gtgtgaggcg tcagcctgga tggcggccgg   180
ggctaggcaa ttggctactc tcttaccttc gtcaacttag ttgggttact acttgtgggt   240
tgttttctna gtgggctagt ggcggaggga tgcttaataa gccctgacg cacttctcat    300
cataattgta ttgactttct tgccttagag cattcctctc tttattaata tataagggtt   360
tcaaaaaaaa tgcatagcag ataatttctg gacagtatgt aggagatctg gnnnnntgat   420
ctcnnnnnnn nnnnnnnnn annnnnngct atgcattttt tttgnnnnnn nnnatatta    480
nnnngagag gnnnnnnnn gtcaatanna ttatgatgan nnnnnnnnn               540
nnnnntann nnnnnnnnct ccgnnnnnnn nnnnaaga aaacaannnn nnnnnnnnn       600
nnnnnctaag ttga                                                     614

SEQ ID NO: 89              moltype = DNA   length = 1028
FEATURE                    Location/Qualifiers
```

| | | |
|---|---|---|
| misc_difference | 574 | |
| | note = n is a, c, g, or t | |
| misc_difference | 960..962 | |
| | note = n is a, c, g, or t | |
| misc_difference | 994 | |
| | note = n is a, c, g, or t | |
| misc_difference | 997..1003 | |
| | note = n is a, c, g, or t | |
| source | 1..1028 | |
| | mol_type = unassigned DNA | |
| | organism = Zea mays | |

SEQUENCE: 89
```
caatccaata ccaaatcaga aggaatatta gaaaaggctt cacttgttaa atatgtcaag   60
gcattcatgt actgcaagaa tagagggggc agagaatccc atcagatagg tgctgtagaa  120
tgtggataaa gcctgaacaa gatggtctac ttgcaaaact gaagcagaga aagtgtaaaa  180
tatacagttc agaccactga ggctaaaaga acaaatctac attgggtaaa tgtcaacatt  240
cagattttaa aacataccat tttaacattg ttatggcagt ccagaagtgg tctacgagca  300
accagattgt aagccaaaca tccaaagcta aacatatcac aagcagagcc aactttagaa  360
tctctacttt ggaccaattc tggtgcagta tagttcaacg atggttgaag aggtaaagct  420
gtatcctcga catcatagtc ctagaaagaa acaagcagaa taaattgtta acaggtcagg  480
gcattggaag caacaaaaaa aatcacaaaa cgtatcttga agacacaaat cacagaagat  540
gtcaccaaag tacttaggaa tgggtatgat gaancgtcaa atatgcttag ttgaccattg  600
ataacttaac aatgtagcgg tctaataatg actaacatag gttcgtggtg cacatcgtat  660
atgccattac aaatcccagc agtagcaatg tgctaaacac aatcgccagt tcgccacatc  720
acagtagtgg tatattctta acttttatat gaaaagatca gttcaagaca agaagaaact  780
ctgccagaaa aatatgtatc atgcaaaact gtgtgcaaat ttagaaatta aatgattgca  840
aaaaaagaa caatataagt tcagtggaat attttctgtt acagcaaact tcaaagggat  900
aatacagatt agtaatattc ccaaaatatg gtagaagaat ctgcaaatta aagccaccan  960
nntgacaaac taaatgtata tcacttacta accnaannnn nnnatagttg tgatgaagtc 1020
aaactcaa                                                         1028
```

| | | |
|---|---|---|
| SEQ ID NO: 90 | moltype = DNA   length = 663 | |
| FEATURE | Location/Qualifiers | |
| misc_difference | 218 | |
| | note = n is a, c, g, or t | |
| source | 1..663 | |
| | mol_type = unassigned DNA | |
| | organism = Zea mays | |

SEQUENCE: 90
```
agttctgcaa gcctgtgtct gagggtacta gtatctttct tcggttgttc accttcattc   60
ttaccaacat atacaaggac acagataaag cgaaaaatgc caggagcgaa ggtaataaaa  120
ctttttatcaa caagttcttt gatcgtgaat gattactgat attgtagcac tgtgctatac  180
ctaggcgagg aaggccacac agcgcattgt tccccatnaa tgatttgagt gtgatatttg  240
agaacactcc tccttctggt atctgtccat ccaatctgtt aaaagaaagg ttcaagttgg  300
caaggtaagt gagattggtc aaggattttg ggatggcacc ggagagtgca ttggaggata  360
ggtccaattc ctgatatta agtatattgc tgaatgaacc tggtattgat ccttggaata  420
aatttctgga cagattgaga tatatcatca tgtggagttc accaaaggag actgggatgt  480
cacctgacag cttgtttcct gataaatcca tcatgtaat tgctgtcaat tttccaacat  540
cagcaggcag gaacccactt aaagagttct gtgacaagtc aagctcaata agtttctgaa  600
gatcccacag acttgttggt atggttgaag acaatgagtt ttgggataac gtcataattt  660
gca                                                                663
```

| | | |
|---|---|---|
| SEQ ID NO: 91 | moltype = DNA   length = 785 | |
| FEATURE | Location/Qualifiers | |
| misc_difference | 701 | |
| | note = n is a, c, g, or t | |
| source | 1..785 | |
| | mol_type = unassigned DNA | |
| | organism = Zea mays | |

SEQUENCE: 91
```
gtgaggcttt gaatattcta cttactacgt ccccgaaaaa caaatctact tacatatccc   60
atctatggtt tatttcttct ggctctgttt tgcatcagat ggtgtcacta ttaacgttac  120
atgcatgcct atgattcact cttatctgca atataagctc ttgtttaatc aatgatgatg  180
tattcgtgaa ttcaggaaca tttcaagaaa aacaagatga ccattaatct gaagtacata  240
ggtcagtggt tttcttcggt gtcatatttc agggccagaa ctgctagtta cacacatctc  300
agatgttgtt cttctactgc agatccaacg tacatgatac gtgccatccc aagcaatgct  360
tctgataacg tctattgcac actgctggct cacagcgtgg tccatggagc catggctgga  420
tatactggtt ttaccattgg ccaagtgaat ggtcggcact gctacatcca attctatga  480
agtcgcaccc ctgccggagc aggacacgga attcttttta ccgcattcat catctcagca  540
tctgagacct acttatcctg cttgaaccaa tgccctccgt actaattgtt ttgcattcgc  600
gtcactcact tcagaggata acagagaagc agaacagagt ttcgataacc gacaggatgt  660
gggcaaggct tctctcgtcg acgaaccagc caagcttcct ntgcaacaaa gtcgtcgagg  720
aggcaaagaa ggaacatgaa agagcaacgc gactttaga tggctcgcct tcccatcgaa  780
aagt                                                              785
```

| | | |
|---|---|---|
| SEQ ID NO: 92 | moltype = DNA   length = 638 | |
| FEATURE | Location/Qualifiers | |
| misc_difference | 182 | |
| | note = n is a, c, g, or t | |

| | |
|---|---|
| misc_difference | 559 |
| | note = n is a, c, g, or t |
| misc_difference | 566 |
| | note = n is a, c, g, or t |
| misc_difference | 579 |
| | note = n is a, c, g, or t |
| misc_difference | 585 |
| | note = n is a, c, g, or t |
| misc_difference | 589..590 |
| | note = n is a, c, g, or t |
| misc_difference | 594 |
| | note = n is a, c, g, or t |
| misc_difference | 597..598 |
| | note = n is a, c, g, or t |
| misc_difference | 607..637 |
| | note = n is a, c, g, or t |
| source | 1..638 |
| | mol_type = unassigned DNA |
| | organism = Zea mays |

SEQUENCE: 92
```
ccttctgctg gaaatggtcg gtgctgagcc tgctatcaga aacctccagc gagcttccga    60
tcttctgttt ctgccggcgg taccaggaga acgcaaataa accgcaaaat gcagcaccga   120
tcaccgccgc gacaacagcg acgataagaa ctccttggga cgcgtttgcg gactttgagc   180
anctagcgcc tgagcagccg tctggatttg ctgattgagg cacctgcctt gtcttgacag   240
taccgtctgt tccaaaaggc tcgggcttgc tgggcttcag gccatcctct gaagaaaggc   300
aaagctctag caaactgaag ccagcgccac aaagcccttt gttattcata tactgaagc   360
caccattcag tctcctcaat cctagcatcc aacacagaat tgtagtggtt aaaataccat   420
gaagactaac aaaaaaaagt acaagtttca gaaaggctat gagattatta ccaacaggga   480
cactcccaga aagggtgttg ttgcgaacat caaagacctc aagcaatgga acctcagcaa   540
tcttggatgg gattgaacna aacagnctgt gaagctcna atcangccnn ctcngcnntg   600
ttagctnnnn nnnnnnnnnn nnnnnnnnnn nnnnnnnc                          638
```

| | |
|---|---|
| SEQ ID NO: 93 | moltype = DNA length = 764 |
| FEATURE | Location/Qualifiers |
| misc_difference | 108..129 |
| | note = n is a, c, g, or t |
| misc_difference | 444 |
| | note = n is a, c, g, or t |
| source | 1..764 |
| | mol_type = unassigned DNA |
| | organism = Zea mays |

SEQUENCE: 93
```
tgggtacctc gcctcgagcc ggaattcggc acgaggatcc aatcgaacca ccagtccacc    60
acctgattga ctagagcaaa agcacaagcc gcccacgcat ctcgattnnn nnnnnnnnn   120
nnnnnnnnng gcgcgcagag ctcgtgacga gagcaacctt ccttccgttc ctcgatcgcc   180
atggacaagt gctggccttt ctcgatcctg agcgcgtcgc cggccgacct ctcctccacg   240
ggcgccggct tcggcgggag ctgggcgcgg ctgtcgtggc ggcggggggc ggacgaccag   300
cgtgcgccgt ggtggtagca ctataatcag caccaggagg aggacaggga gaagcgagac   360
ttgcgctccc gcgacggcgg agcgcacgcg agcggagggg gagcggcggc ggcgccaccg   420
cggttcgcgc ggagtttgac ggnatcgac tggttcggaa ccatcgtgtc gcgctgatca   480
acaatccggg ctcggccgac gcgccccccg agttaaccac gtgaccaatc ctgtctacta   540
tgttttttt accttatggt ggattaattg tcccaacaca gataattggg actccgcgtg   600
ttgtacatac agggaactgc tcaattacca ggtgggatgg gaacattta tttgttcctg   660
tcctctgcat ttttttctg taccgaaatg gatggatggt ctccaacttg aaattgagtc   720
cctcagcccc aggtaatctg gcggtggatg aacccaagcc gaac                  764
```

| | |
|---|---|
| SEQ ID NO: 94 | moltype = DNA length = 536 |
| FEATURE | Location/Qualifiers |
| misc_difference | 49 |
| | note = n is a, c, g, or t |
| misc_difference | 242..243 |
| | note = n is a, c, g, or t |
| misc_difference | 288 |
| | note = n is a, c, g, or t |
| source | 1..536 |
| | mol_type = unassigned DNA |
| | organism = Zea mays |

SEQUENCE: 94
```
tgcagtactc accaaatctg cgttgcacta ctgtaagaac aaatttgana ttgtaactga    60
cgaattagtg aatccaaact cttctctagg tctgtaatat tatgtgtact ataatgttta   120
tctactctac aaccatcatt ggcagcttaa ttgtgatcat accacagtat ccaaacactc   180
caacgttgta caattcactc tgatttacta tgcaacacag ttgtacaatt cactctaatt   240
tnnactatgc aacacacgcg catgtgcgcg cagtcgcaga gcacactngt ttcatatata   300
ctccctccaa ccatagatgc aagaccatta gatttgacct aaacagttag gcaatcccga   360
gcagatagag aaatcatgtg tagccgtata tctacttgaa ctatctatct atgtatggat   420
ttgagcgcca aatctctcgt ttggttgtaa ccggtggact gaaaagtggg tggaaataat   480
gtgtgaaatg acaaaaattcg atgtggtctc tagctggagt atttattagt ttctgt     536
```

| | |
|---|---|
| SEQ ID NO: 95 | moltype = DNA length = 640 |

| FEATURE | Location/Qualifiers |
|---|---|
| misc_difference | 295 |
| | note = n is a, c, g, or t |
| misc_difference | 418 |
| | note = n is a, c, g, or t |
| misc_difference | 423 |
| | note = n is a, c, g, or t |
| misc_difference | 479..480 |
| | note = n is a, c, g, or t |
| misc_difference | 482..484 |
| | note = n is a, c, g, or t |
| misc_difference | 574 |
| | note = n is a, c, g, or t |
| source | 1..640 |
| | mol_type = unassigned DNA |
| | organism = Zea mays |

SEQUENCE: 95

```
ggcgcatcat cttccagtca gctctgcacg tgccacactg ccactgccaa atctccgtga   60
tggtggtggg ctgcatgttt gcgcaaactt tctgccgagg ccgaatacca acgagtcgag  120
tagacgaagg aatcaccggc gagttcgatc ggccccaatg caaggttctc tgtgtgtgcg  180
tgggtgtgtg gacggtggtg gagaggtaga tggcgaggcg gaggagatgg agatggggag  240
atctatttat acatgatgat gacgcgtgcg gaggctgcga tcaccagtcg gtcgncaaac  300
gagagcgttt cccacagcgt cgtttccaag cgacccttgg cacctgttca gttgcttcct  360
tcagtcggaa ggtccctctg cttccgacgt gaatcgcacg cagggtttag aggttcantc  420
tcngtacgca gcctaatctc tcacaataag gagaagacgc caatttgatc tctctcatnn  480
cnnntatacc gtttgacaaa catggtaatg ctcttgccaa acccgtgaca tatctttgcc  540
tttatctttt atgttcggtc ggttacgaga ttcntcgcta ctcacattca cacgactgac  600
tacgactaca cgagaggcgg ttggccttga tcagacagac                        640
```

| SEQ ID NO: 96 | moltype = DNA length = 714 |
|---|---|
| FEATURE | Location/Qualifiers |
| misc_difference | 96 |
| | note = n is a, c, g, or t |
| misc_difference | 134 |
| | note = n is a, c, g, or t |
| misc_difference | 220 |
| | note = n is a, c, g, or t |
| misc_difference | 225 |
| | note = n is a, c, g, or t |
| misc_difference | 257 |
| | note = n is a, c, g, or t |
| misc_difference | 327 |
| | note = n is a, c, g, or t |
| misc_difference | 370 |
| | note = n is a, c, g, or t |
| misc_difference | 401 |
| | note = n is a, c, g, or t |
| misc_difference | 533 |
| | note = n is a, c, g, or t |
| misc_difference | 622..627 |
| | note = n is a, c, g, or t |
| misc_difference | 633..640 |
| | note = n is a, c, g, or t |
| misc_difference | 656 |
| | note = n is a, c, g, or t |
| misc_difference | 668 |
| | note = n is a, c, g, or t |
| misc_difference | 670..673 |
| | note = n is a, c, g, or t |
| misc_difference | 677..682 |
| | note = n is a, c, g, or t |
| misc_difference | 685 |
| | note = n is a, c, g, or t |
| misc_difference | 690..692 |
| | note = n is a, c, g, or t |
| misc_difference | 697..698 |
| | note = n is a, c, g, or t |
| misc_difference | 702..706 |
| | note = n is a, c, g, or t |
| misc_difference | 708..709 |
| | note = n is a, c, g, or t |
| misc_difference | 711 |
| | note = n is a, c, g, or t |
| misc_difference | 713 |
| | note = n is a, c, g, or t |
| source | 1..714 |
| | mol_type = unassigned DNA |
| | organism = Zea mays |

SEQUENCE: 96

```
tactgtcaat cctgttgttt atccttgtgt atgcttgtta gtcaaaccat atttcagtaa    60
ctaattcctt gattgtgagt tactgctgat ctcatnatgg aatgggtttt catgtagttc   120
agatgtgttt tttnactcaa ctatttctct attagtttct aggttactta cgtggatgct   180
atttatctgt ctggactttg gatagtgcaa tgttggctcn aaaangaaaa aaagatagac   240
ctggtgctga aggctcnggg gtctgggaaa gggataaaca gaggcaagcc ttcttcccac   300
aattgcggag aggctgcttt caacacncga cttagtggga cagctctcac cactgcacga   360
gacgtgtccn tctaaaacta ctaactcaca aaattataaa ntttgtgatt ttgtagccat   420
tgtgatcttg tatttgtatc aacaaatggt tgatgctgca tgtttgcagg gaatatgaga   480
attcattaca acatatcatt tattttttact actgagttat agtatggatt ganttgtatc   540
ttttgtgagt tacttctctt tgtacttgtt gagcttgtgc attgtagatt tgaactgaag   600
tcatgtggca tttgatttac tnnnnnnttt tannnnnnnn ttcatgtggc gtatangtga   660
gggatgangn nnnaagnnnn nnatntcatn nngcatnnac tnnnnnannc ncng         714
```

| SEQ ID NO: 97 | moltype = DNA  length = 353 |
|---|---|
| FEATURE | Location/Qualifiers |
| misc_difference | 100 |
| | note = n is a, c, g, or t |
| source | 1..353 |
| | mol_type = unassigned DNA |
| | organism = Zea mays |

SEQUENCE: 97
```
tcaccagcca tgtagttgct gggttttcct gcttgcatgc tgcaacagct tcacattatt    60
gaagaaaccg atgaggcttc tgtggaatta tgagctgagn tgaacctggc aagcattgga   120
atctggtttc agaatgctct aattttgaag attaacttgt gttccatttt aagcgtgtag   180
taagatgcaa ggaagccctt tacttctgtt cataggttgc aatcagtttt gtgtgctcca   240
aaggtaatat ttgattgcca cagttgcagg gattcaataa atccacgagt tagaaatgac   300
catttgatga tgaataagaa tgaatgtctg ccttgtgcta ttgatatgg ata           353
```

| SEQ ID NO: 98 | moltype = DNA  length = 1097 |
|---|---|
| FEATURE | Location/Qualifiers |
| misc_difference | 517..518 |
| | note = n is a, c, g, or t |
| misc_difference | 521..524 |
| | note = n is a, c, g, or t |
| misc_difference | 530..532 |
| | note = n is a, c, g, or t |
| misc_difference | 534..538 |
| | note = n is a, c, g, or t |
| misc_difference | 555..558 |
| | note = n is a, c, g, or t |
| misc_difference | 561..565 |
| | note = n is a, c, g, or t |
| misc_difference | 569 |
| | note = n is a, c, g, or t |
| misc_difference | 592..593 |
| | note = n is a, c, g, or t |
| misc_difference | 1052 |
| | note = n is a, c, g, or t |
| misc_difference | 1091..1095 |
| | note = n is a, c, g, or t |
| source | 1..1097 |
| | mol_type = unassigned DNA |
| | organism = Zea mays |

SEQUENCE: 98
```
tataatatga atggtctaaa aagataatat agaagtattt cagcataata ttgaggatta    60
agataagaac atattaggtt cacaggaaaa aaaaatgagg gtgcttttga aactcaactt   120
ggtgatggac aataaaataa gattatttat agttttttaga ataattgtgc caactggttg   180
caaatggatg cctcaaatgt ttacacttca atttaatcat gccacaggaa aatttgtgaa   240
agtttagttc cacactgaga aaaacaatcc aacttttattt attgatacct ttatttttag   300
gtgcaaacat caaataacca aaattctaac atgtcagtat ttacctgata aaggaagct    360
aatctaacat agccagtctt gcactcatgg ccatcgtctg ttctatgaga gataattgca   420
gttgacagag gtgaaaggtt gataatttca cgagacagct ggaccttttgg aaacaaaagg   480
tagtggacat aattaggaaa cactcgatca ctgtctnngt nnnnaaatgn nncnnnnntg   540
gttaatgaat ttttnnnnga nnnnntacng caatttgatg agctctgtag gnncagatca   600
tacatttcaa attacacata taaaaatctt aagatttac aattcttcgt tcagcaagtt    660
aggcattacc tccttttgtc ttaaaccccc acacctttca tcgtcagttc cctggatata    720
aatatgcatc ggtaagaaag taaatacaaa gacgaggagc aacgtttcca tggctgagtt   780
caccaaatta cataaagggg attcaggata tgatataata taatagaagc ctagtatgcc    840
agacttcggt gaaccaaaaa aacgcgatgt ttttttagtt ctataaacca aaaccttggc   900
cacttattca atctctgaat gttttttttta aacaagtgcc ttaatgttga actggacat    960
ctcaagttga agtatacttc acaaccagca aaatagattt aactgaagct aagtatctac  1020
tatgaagctc aaggtaagga aatacatcta anaacttcac tttcactgtt gttcctacac  1080
ggcctctaag nnnnnga                                                 1097
```

| SEQ ID NO: 99 | moltype = DNA  length = 458 |
|---|---|
| FEATURE | Location/Qualifiers |
| misc_difference | 204 |
| | note = n is a, c, g, or t |
| source | 1..458 |

```
                          mol_type = unassigned DNA
                          organism = Zea mays
SEQUENCE: 99
cggcggcaat caagcagcag cgggatgatg gagggaccgt tccgattctt gccggccgaa    60
gtgaaagaga tggaggagcg cctgttcccg gtcaccaatc gcaggctgga tcacatcctc   120
atggatgagc tcgctctgaa atttagctgc ttccggcgcc gtgctggcat ggttcccgtc   180
aagccaaagc aggtatgtgc atcnacgatg ttccgttcca catatcaatt tcaaattccc   240
tctcccatga acctgcggtt tcattccgat ctggacatgc atgcatccag gtgctcaact   300
ggttttataa caaccgtaac aagacttctg ccaaggtagc agccagggaa gcacatgctc   360
catgggagtt ttgggccaac catcacgcaag ctagagctag aggaggctca tccatcagca   420
agctgaagcc aaagaaggcg actacgcacg caggatct                           458

SEQ ID NO: 100          moltype = DNA  length = 1025
FEATURE                 Location/Qualifiers
misc_difference         23..26
                          note = n is a, c, g, or t
misc_difference         32
                          note = n is a, c, g, or t
misc_difference         89..92
                          note = n is a, c, g, or t
misc_difference         100..102
                          note = n is a, c, g, or t
misc_difference         128
                          note = n is a, c, g, or t
misc_difference         161
                          note = n is a, c, g, or t
misc_difference         174
                          note = n is a, c, g, or t
misc_difference         211
                          note = n is a, c, g, or t
misc_difference         217
                          note = n is a, c, g, or t
misc_difference         262
                          note = n is a, c, g, or t
misc_difference         402
                          note = n is a, c, g, or t
misc_difference         429
                          note = n is a, c, g, or t
misc_difference         435
                          note = n is a, c, g, or t
misc_difference         550
                          note = n is a, c, g, or t
misc_difference         582
                          note = n is a, c, g, or t
misc_difference         660
                          note = n is a, c, g, or t
misc_difference         682..687
                          note = n is a, c, g, or t
misc_difference         699
                          note = n is a, c, g, or t
misc_difference         704
                          note = n is a, c, g, or t
misc_difference         883
                          note = n is a, c, g, or t
misc_difference         902..912
                          note = n is a, c, g, or t
misc_difference         914
                          note = n is a, c, g, or t
misc_difference         916..925
                          note = n is a, c, g, or t
misc_difference         930..934
                          note = n is a, c, g, or t
misc_difference         949..951
                          note = n is a, c, g, or t
misc_difference         965
                          note = n is a, c, g, or t
misc_difference         970..975
                          note = n is a, c, g, or t
misc_difference         977..988
                          note = n is a, c, g, or t
misc_difference         994..1002
                          note = n is a, c, g, or t
misc_difference         1005..1020
                          note = n is a, c, g, or t
source                  1..1025
                          mol_type = unassigned DNA
                          organism = Zea mays
SEQUENCE: 100
tgtcttcctt tatttgtgtc tcnnnngact gntctctgtc ctgtcatgaa atttgtactg    60
```

```
atctcatgtc catctgcagc actgggagnn nnattttctn nncagacacc gtgtgcacgt   120
tgcaggtntg ctgcattctg aatccttaac actttgtccc ncttccatct gctnaacaca   180
cggagctgaa acgcaggtca taaaccaaga ngagacncca aggctgtaca gcctggtgtt   240
tggagaagga gttgtcaacg angcaacggc ggtcgttctt ttcaatgcca tcaaggatct   300
cgatatcagt cggctcaagg gtggggttgt gctaaaagtg atatttgact tcctctatct   360
ctttgcaacc agcactgtcc tcggaatctc agtaagaact gnttttttct tccatatata   420
tgcattagng ccatntcttt gtacacccta aactctttac cgcaaatttg tcagatcggt   480
ctagtaactg catatgttct caaagctctg tattttggta ggtgagtaat cgttgttacc   540
gatcggtttn gtttgtgttc atctgctact cttttatctt tnaaatctct tccccatatt   600
ttgttcaggc attcgaccga tagagaggtt gccttgatgg ctctcatggc ctatctatcn   660
tatatgctgg cagaggtaag annnnnntta ccaaatttna tctnctagta cttacattat   720
gcacttccac aattcatccc aagatgctgc atgttctgca gttgctagag ctgagtggaa   780
ttttgaccgt gttcttttgc ggcattgtca tgtcccatta tgcatggcac aacgtgacag   840
agagctcaag gattacaaca aagtgagctc aataatcaat gtncaaacat ttcttaagaa   900
tnnnnnnnnn nntncnnnnn nnnnnttcgn nnnnattctc agcaatgtnn ntgctgttgc   960
gaagncatcn nnnncnnnn nnnnnnnngc aggnnnnnnn nnaannnnnn nnnnnnnnnn  1020
agaca                                                             1025

SEQ ID NO: 101           moltype = DNA   length = 529
FEATURE                  Location/Qualifiers
misc_difference          125..126
                         note = n is a, c, g, or t
misc_difference          130..131
                         note = n is a, c, g, or t
misc_difference          135..136
                         note = n is a, c, g, or t
misc_difference          139
                         note = n is a, c, g, or t
misc_difference          141..142
                         note = n is a, c, g, or t
misc_difference          144
                         note = n is a, c, g, or t
misc_difference          146
                         note = n is a, c, g, or t
misc_difference          148
                         note = n is a, c, g, or t
misc_difference          151..153
                         note = n is a, c, g, or t
misc_difference          157
                         note = n is a, c, g, or t
misc_difference          159..160
                         note = n is a, c, g, or t
misc_difference          162
                         note = n is a, c, g, or t
misc_difference          165
                         note = n is a, c, g, or t
misc_difference          191
                         note = n is a, c, g, or t
misc_difference          242
                         note = n is a, c, g, or t
misc_difference          389
                         note = n is a, c, g, or t
misc_difference          503
                         note = n is a, c, g, or t
misc_difference          510..511
                         note = n is a, c, g, or t
source                   1..529
                         mol_type = unassigned DNA
                         organism = Zea mays
SEQUENCE: 101
gtaagcgaac gcgatgttgc caagagcttg aagcgcgagc cagaccttct gggctgaatc    60
aacgtcgact ccgatctcag tgccggtcag agtggtcgta ccactacggc ctgcagtgac   120
aacanncacn naatnnatnc nntnanancg nnntgtngnn angancttta tggagtaaaa   180
tttatctact ngctagttca cctgaaatgg tccgcgccaa cgagaggccg acggcgatgc   240
tngagtaaga gaacgacatg atggcggcga cgatggacag ccacgaaagg tcgctgaagt   300
tagggagctg agagaagaag atctgaacga tcccaaatac gaccatgtac atggtgtcgt   360
aggtgctgca gtcggccgcg tggcccttnt tgtggaagca gtttgccttg tgcacggccc   420
tgctcatcgc cattcagcca aaagggggttt ctcaatcgac gatgagactg aatctgccaa   480
acattcact actaaatgag ccntttttn ngcaagaatt actcacgct                  529

SEQ ID NO: 102           moltype = DNA   length = 1328
FEATURE                  Location/Qualifiers
misc_difference          1..2
                         note = n is a, c, g, or t
misc_difference          21..22
                         note = n is a, c, g, or t
misc_difference          74..84
                         note = n is a, c, g, or t
misc_difference          149
```

| | | |
|---|---|---|
| misc_difference | 280..281 | |
| | note = n is a, c, g, or t | |
| misc_difference | 329 | |
| | note = n is a, c, g, or t | |
| misc_difference | 337 | |
| | note = n is a, c, g, or t | |
| misc_difference | 448 | |
| | note = n is a, c, g, or t | |
| misc_difference | 559 | |
| | note = n is a, c, g, or t | |
| misc_difference | 722 | |
| | note = n is a, c, g, or t | |
| misc_difference | 748 | |
| | note = n is a, c, g, or t | |
| misc_difference | 978 | |
| | note = n is a, c, g, or t | |
| misc_difference | 1010 | |
| | note = n is a, c, g, or t | |
| misc_difference | 1029..1030 | |
| | note = n is a, c, g, or t | |
| misc_difference | 1037 | |
| | note = n is a, c, g, or t | |
| misc_difference | 1058 | |
| | note = n is a, c, g, or t | |
| misc_difference | 1077 | |
| | note = n is a, c, g, or t | |
| misc_difference | 1093 | |
| | note = n is a, c, g, or t | |
| misc_difference | 1107..1108 | |
| | note = n is a, c, g, or t | |
| misc_difference | 1119..1121 | |
| | note = n is a, c, g, or t | |
| misc_difference | 1137..1139 | |
| | note = n is a, c, g, or t | |
| misc_difference | 1145 | |
| | note = n is a, c, g, or t | |
| misc_difference | 1153 | |
| | note = n is a, c, g, or t | |
| misc_difference | 1281 | |
| | note = n is a, c, g, or t | |
| misc_difference | 1301..1305 | |
| | note = n is a, c, g, or t | |
| misc_difference | 1322..1327 | |
| | note = n is a, c, g, or t | |
| source | 1..1328 | |
| | mol_type = unassigned DNA | |
| | organism = Zea mays | |

SEQUENCE: 102

```
nncatgcatg cacgacagta nngtgatttt ttttgttagt tgcagtgctg atgtcatact    60
atgaatatat atannnnnnn nnnntgacga tatttaccte ttcgatactg gtaaatgacg   120
attccgctga aatttcagaa actccagang ccagcagatg gcgagcacgc tcgcgtgtgt   180
tgtacagctt gtcccttaca tggcctagta tcacccggta gggctcgttt ggaggaattt   240
gcttccagaa ttctgcgcca gcaaatacac ttcagaaaan ntgccaaaag agccctcaaa   300
ttaatttgaa aacactagtg gagactttng caaaagnctg tacggcaggc aaaaattaag   360
caaacataaa tgcttctgtt tgtggttacc tatgtaatac ttggtaactt tggaaccaga   420
cgaactgtgg agctcttcgg cacgaacncg aagctcatcg ttgcagcgcc acatagagag   480
ctacagatat atcagacgat gcatgcatga gagttctggt atggaccgga dacagcaaaa   540
aacagggcaa gcaaaaaant catagagcat tcaatcaaac aaatctgcag tatggatgta   600
cagtacctca aacatcagct cttcaatctg atcgatgtac aagtttgcag ccatcattct   660
ggccagcaag catacatctc ttgtcacctc cggggtaact cttggatttc ctatatagcg   720
anagattgca aagatataca ggcttagnaa aaacatataa ttctgtatat ataattttct   780
ggcgagaaaa gaaaaacgtt agccttgaat attgacagga caagtactga tataaataa    840
gcactctttg atatataaaa taatactaca cgtataattc tgtgatataa aaaattcaac   900
aagttaggtt ccaggttgca atataaagat ttgattaaat tatgcttata tgttgtgcta   960
gcatgtatgg atgataantt tttattagtg aggtgtacta aataaatttcn attttaaaat  1020
tctagctcnn gagagcncga aatgatagac tagtttttnct gaacatctat tgcagtnaga  1080
gtaaagcagg aangttctc tcaagcnnaa agacagagnn nagctcctgc cactttnnng    1140
aaaanggtag gcngaaatgt accatcgcgg tcaccaccca tccaagaaga gaaccgaatg   1200
agagaaacat tgtagggaag gcgctcattg atgccgatat tcttcagggc tgtatccaca   1260
cggcgcaaga acttaggcac nccttccat acagtctcat nnnnnagctc atcccatagc    1320
gnnnnnng                                                            1328
```

| | | |
|---|---|---|
| SEQ ID NO: 103 | moltype = DNA length = 619 | |
| FEATURE | Location/Qualifiers | |
| misc_difference | 560 | |
| | note = n is a, c, g, or t | |
| source | 1..619 | |
| | mol_type = unassigned DNA | |

```
                        organism = Zea mays
SEQUENCE: 103
tggggtggac ctcgccactt cagctcgtct ttgcagttgc cacgctcttc tgggcactca    60
agcttggggc tcttcctggt ctagtccgc tagtcatctt tggtttcctc aacgtgccat    120
tcgcgaaaat gctgcagggg taccaggcca agttcatggt tgcacaggac gagaggctcc   180
ggtccacgtc ggagatactc aacagcatga agatcatcaa gctgcagtcg tgggaagaca   240
agttccgcag cacgatcgag tcgctcaggg acggcgagtt caaatggctg agggagaccc   300
agatgaagaa ggcctatggt gcagtcatgt actggatgtc cccgacggtc gtctctgctg   360
tcatgtacac agcaacggcc atcatgggga gtgctcccct gaatgctagc acgctcttca   420
cggtcttggc caccctgagg gtaatgtctg agccagtgag gatgcttccg gaggtcctca   480
caatgatgat ccagtacaag gtgtcattag atcgaattga gaagttcctt ctcgaagacg   540
agatcagaga ggaggatgtn aaaagggtac cttcagatga ctctggtgtc agagttcgag   600
tccaagccgg aaatttcag                                                 619

SEQ ID NO: 104        moltype = DNA   length = 543
FEATURE               Location/Qualifiers
misc_difference       309
                      note = n is a, c, g, or t
misc_difference       470..472
                      note = n is a, c, g, or t
misc_difference       474..479
                      note = n is a, c, g, or t
misc_difference       487..493
                      note = n is a, c, g, or t
misc_difference       495..499
                      note = n is a, c, g, or t
misc_difference       502..509
                      note = n is a, c, g, or t
misc_difference       511..517
                      note = n is a, c, g, or t
misc_difference       522..531
                      note = n is a, c, g, or t
misc_difference       535..539
                      note = n is a, c, g, or t
source                1..543
                      mol_type = unassigned DNA
                      organism = Zea mays
SEQUENCE: 104
ctgcagtacc tttaccaaca tgatgctttt gttttctat aagcatgtgt ggcacactag    60
ttatcagctc cgcaggaact acatcagcat tgtgaaattc atcggtagtg gactgcctag   120
ttgaagtcat atcgttgttt tcaaaattag cagccttgct tctggaaaca ttcgactcag   180
tgctagacaa gcttcttctc aagaagcccc ttcccttcat cttgaggaca ccaccaccct   240
tttggtccat tgatggctgg agaatcttcc atgtctcttc ccaatagttg ggtgtagaca   300
agagagaant tcctctcgat gaggatgaag gaagatttgc ttcaagggca aaagattgca   360
gtaacttggc tttctcaatt aagctcttta agtcaatatc ttctggaaaa tttaacaacc   420
tcactaggca agaagtcgca tgttcactcc ctaataagga ggatctgagn nngnnnnnna   480
ttgatannnn nnncnnnnna annnnnnnnc nnnnnnnaga annnnnnnnn ntaannnnnt   540
aat                                                                  543

SEQ ID NO: 105        moltype = DNA   length = 393
FEATURE               Location/Qualifiers
misc_difference       58
                      note = n is a, c, g, or t
source                1..393
                      mol_type = unassigned DNA
                      organism = Zea mays
SEQUENCE: 105
tgctgagtta agatgctctg tgggatattt gaagtccatt attgcagtga cagagggntt    60
ggtgttcagt gaagacagta aagttgctgg aaattgcagt gcctgtctct ctgtgatttt   120
gggatgggag aaatttggaa gccaagaaaa ggtggcagtc agagaatcta aatggtttag   180
gctaataatg gaggaatttg ttgtggcctt gactgctcct ggtttgacgt cgaaatcttt   240
ctccagtcag cagaagtttg ctgcgaatat agctgtttcg ttgctcaggc tgagccaagt   300
gccagattgg ctgacatcgt tgtttgatgg gcatctgata tctggcatcg tggctaatct   360
ttctgctagg atcccacaga gcatcttaac tca                                393

SEQ ID NO: 106        moltype = DNA   length = 572
FEATURE               Location/Qualifiers
misc_difference       466
                      note = n is a, c, g, or t
misc_difference       503
                      note = n is a, c, g, or t
misc_difference       517..518
                      note = n is a, c, g, or t
misc_difference       520..521
                      note = n is a, c, g, or t
misc_difference       538..539
                      note = n is a, c, g, or t
misc_difference       550
                      note = n is a, c, g, or t
```

```
misc_difference        560..564
                       note = n is a, c, g, or t
misc_difference        566
                       note = n is a, c, g, or t
misc_difference        569..571
                       note = n is a, c, g, or t
source                 1..572
                       mol_type = unassigned DNA
                       organism = Zea mays
SEQUENCE: 106
tctaggggtt ttgggtgaat tgtaagtagg gtaacgcgaa ggaaaaccac taaatttaca    60
tttattcctt ctcattacat cacggagtct gcaaattgag atccttcact gacgatccat   120
gttttcctac atgaaaatgt gatgcgttca gttacatggc tctgatattt ggtattatcg   180
aatagtactt ttggatttta atatatattt gtttctctca aggttctgca aagagcattg   240
gattttagtc gataatttga cattccattt agtagttatt tttatattgg aaaggtgtgt   300
gtaggatgca gcattgaatg ttagtttaat ttaattgtta taaacattga acacaaccag   360
gacaacatga ggaaaccaga gtactatagt agatggtaat gtttgattaa ggttttcaac   420
cagtgatatg atacccaatt tctcttggta atctgtttcg accatncaac atatggatgg   480
tttttgatga aatctggatc tcnttttttt ttgaaanngn natctagatc taggactnna   540
ttgatttacn tcctagttcn nnnntnttnn na                                 572

SEQ ID NO: 107         moltype = DNA   length = 658
FEATURE                Location/Qualifiers
misc_difference        202
                       note = n is a, c, g, or t
misc_difference        223..226
                       note = n is a, c, g, or t
misc_difference        229
                       note = n is a, c, g, or t
misc_difference        245
                       note = n is a, c, g, or t
misc_difference        282
                       note = n is a, c, g, or t
misc_difference        333..334
                       note = n is a, c, g, or t
misc_difference        363
                       note = n is a, c, g, or t
misc_difference        445
                       note = n is a, c, g, or t
misc_difference        453
                       note = n is a, c, g, or t
misc_difference        465..466
                       note = n is a, c, g, or t
misc_difference        534
                       note = n is a, c, g, or t
misc_difference        591
                       note = n is a, c, g, or t
misc_difference        606
                       note = n is a, c, g, or t
misc_difference        647..653
                       note = n is a, c, g, or t
source                 1..658
                       mol_type = unassigned DNA
                       organism = Zea mays
SEQUENCE: 107
cctaccttct gatcctccgg ctagctagct acttcaaatc cccgccgctg cgctgcgcat    60
gtgttcacgc tctaaatacg atggcatatg catgcatgca gaacggagtc cgggcgctga   120
tgctcgacac gtacgacttc aagggagacg tgtggctgtg ccattcgagc ggagggaaat   180
gcaacgactt caccgcgttc gngagtacgc tggctcgctc tgnnnnaant gaacagggcg   240
tgcgnccgta cgtctcaaag ctgagcattt gttttgggg gntcattgta ggaacctgca   300
ctggacactt tcaaggagat cgaggcgttc ctnncagcaa accgtccga aatcgtcacg   360
ctnatcctag aggactacgt ccacgcgccg aacgggctga cgaacgtgtt caacgcgtct   420
ggcctgctca agtactggtt cccgntgtcg agnatgccgc cgagnngcca ggactggcct   480
ctcgtcagcg acatggtcgc gaccaaccag cgcctcctgg tgttcaccct cgtnagctcc   540
aaacagagcg cggaaggcat cgcttaccag tggaacttca tggtcgagaa naactgtgag   600
gcatcncgat tggttcctgc tttctatcta tcttttttt ttctcnnnn nnntgcag     658

SEQ ID NO: 108         moltype = DNA   length = 444
FEATURE                Location/Qualifiers
misc_difference        155
                       note = n is a, c, g, or t
misc_difference        440
                       note = n is a, c, g, or t
source                 1..444
                       mol_type = unassigned DNA
                       organism = Zea mays
SEQUENCE: 108
acatgaagta cggtaactat aaaatgacac cagtggaaat agcatacaac gccatttcct    60
tcgtcatcgc tatcgccctc acggtcgcct tcacggtgta cgcgaagaga gctctggggtg  120
```

```
acataaaaag tccggacgat ggcatcggta aagangaaga agatcacggc ccaaatggct    180
caggggggt gcgtatgaat cgtcgtcagg agcgtgcgcg tgccgatgca cgttacatag    240
aactagatga tatgtgatgg tgtgttgacc cggatcttgc ttggaaggag gcaccagtag   300
gtcattaggt gcacggctac ggtaggtagc tagctatagt ttacaagagg aggctacaat   360
aatccacacc cagctgacgt ggtttgcgtg attcgtttcg tactttcgtg tgctttgcct   420
actgcactgc catactgtcn gaat                                          444

SEQ ID NO: 109           moltype = DNA   length = 476
FEATURE                  Location/Qualifiers
misc_difference          436
                         note = n is a, c, g, or t
source                   1..476
                         mol_type = unassigned DNA
                         organism = Zea mays
SEQUENCE: 109
agcccgaatt tgcatatttg actacgaact agcaaggcaa atcctttcga gcaagtctgg    60
gcatttcgtg aagaacgatg cgcaccctac tttgttggct ctggtcggca agggactcgg   120
gttcatggaa ggctctgact gggtgcgcca tcgcagggtg atcaaccctg ctttcaccat   180
tgacaagctt aaggtacacg caatgcctag ctctctctct ctctctcgct ttaaaaaaga   240
agttcgtttg cagtatgcac gcgagcagca agaacaatgg ccgtgctcat tgcataaaca   300
gattgtgacc gagacgatgc tggacttcgc cgatagcatg gcaggtgagt tggaagctga   360
agcatcccag aacgagaacg gagaaacaca agtggatata tacaaacatt tcagcgatct   420
gacagttgac aatatngcct acgccatctt tggaagcagc tacaagttag aaatgg       476

SEQ ID NO: 110           moltype = DNA   length = 720
FEATURE                  Location/Qualifiers
misc_difference          2
                         note = n is a, c, g, or t
misc_difference          600
                         note = n is a, c, g, or t
misc_difference          658
                         note = n is a, c, g, or t
source                   1..720
                         mol_type = unassigned DNA
                         organism = Zea mays
SEQUENCE: 110
cntgagtttt tctcagagtg ttcgtgatgt tgtgttgggc agcggtgaaa tcgtatgctt    60
ctcacactcg agttgcttca tcctgacata ttcaatccat cctaactatt gactcgtttg   120
tttatgttgc aactttcag atggttgatg atgttaaata tacagtttca catgtcgtgg   180
agcctatgga gcggagtttt acaaagataa ataagacaat tcatcaaatc tcagaaaacg   240
tcaagcagct tgaagaagcaa aagaggaagg caaaggacga cagtcatctt attcccctag   300
aaccatggtc agaggaattt tcagaagctc atgaccatgt tgcgggcggt agtgccagtg   360
acagcggatt agctaagaca aggtacaaca ggatcttaaa taggccccgg aggtcattcg   420
agtccagatt gcgcagatgg ttctagcagc cagccggtgc tagtgggtta attgattttg   480
atcaaaagag gcggttaacc ttttcgctcc ggttgtttga caaaatgata gcaatttctga   540
caaactagtt ctccctccgt tcttttcttc tttatttgct ggtgacaaat attcgagaan   600
ggagtttgga gtttggcacg gggtggaggc agtagccagc agctcttcat tattttgngg   660
gtgacaaata ttcatgaacg gagtttggag tttggcacgg ggtggaggca gtagccagca   720

SEQ ID NO: 111           moltype = DNA   length = 639
FEATURE                  Location/Qualifiers
misc_difference          418
                         note = n is a, c, g, or t
misc_difference          449
                         note = n is a, c, g, or t
misc_difference          634
                         note = n is a, c, g, or t
source                   1..639
                         mol_type = unassigned DNA
                         organism = Zea mays
SEQUENCE: 111
tttgttacct aaacatggag cagctaacaa aatgcctgct ttctctgtat gatatgtatc    60
atgtacttca taagtgtgat tcacacagca aaaggaggc tgagtattat tccttctatg   120
tgcttctaca tttgggatgc aagatacaca aaatgttaat ttgttttccc tttctcactt   180
cttccatgtt caaatttgtt cttaatcctt tcaagagct ttatgcttta ccttactcca   240
acttgtatcc aaaattaact ttctatttat cttcagatag attcactctc tttgtggtat   300
ggtcaattgg ctactccagt cagacggtca aaggaaatga tatttgctag atctttatta   360
aggtaacatc tagacgaatt gattgccaac atgaaccttc attctttgca tgctcctntt   420
tctgttcaca tagttaagcc cagagtctnt atgtgttttc atttttctcta tcctgaccca   480
cttgtatgat ttggtcataa gtacttattg ttgattcata gttggctact tcagtgctga   540
gccatgttgt tttaaatctt agataattgt atatatctta tgtagatgct atcgcctagg   600
aaacttcaag cgtttctttt gcatggtagc aggngtacc                          639

SEQ ID NO: 112           moltype = DNA   length = 711
FEATURE                  Location/Qualifiers
misc_difference          539
                         note = n is a, c, g, or t
misc_difference          595
                         note = n is a, c, g, or t
```

| | |
|---|---|
| misc_difference | 613..614 |
| | note = n is a, c, g, or t |
| misc_difference | 628..630 |
| | note = n is a, c, g, or t |
| misc_difference | 639..643 |
| | note = n is a, c, g, or t |
| misc_difference | 655 |
| | note = n is a, c, g, or t |
| misc_difference | 657..660 |
| | note = n is a, c, g, or t |
| misc_difference | 666 |
| | note = n is a, c, g, or t |
| misc_difference | 686..690 |
| | note = n is a, c, g, or t |
| misc_difference | 693..699 |
| | note = n is a, c, g, or t |
| misc_difference | 706..708 |
| | note = n is a, c, g, or t |
| misc_difference | 710 |
| | note = n is a, c, g, or t |
| source | 1..711 |
| | mol_type = unassigned DNA |
| | organism = Zea mays |

SEQUENCE: 112

```
aatgatgggc aaatcagtat taagttcttg tatcaaagga tgaggagcaa ttggttgtct   60
aggaccattg aactcagaag tacgagcaaa tcccaggaac agtttcttgg cccaaggatc  120
atacatctca tcggtgaact tataggcaaa atttcgatca gcacaccaaa catttatctg  180
gtgaagggga aagggctgtt aatgaacact gacaatatat gtgataaaaa cagatagatg  240
taaaagaaca actcttacaa tacttggagg ttccaaactc ttttaacatt tagagcaaaa  300
aatgtactca gatgactata gacactgatg gcctcatgca atgcaatata caaaagaaac  360
ccacatggac aagacaaatg gactcacagg tggtgctcta gctggcggaa taaaagcata  420
tgctgaacga agaagcctaa tgtttgaagc gagcctgtcg cgatgagaaa gcaccagtgc  480
ttcatatggg ccatcaattg gcccagtccc aatctttgtc ctaagcaaac tgggcttgnc  540
ctttgtagaa gaaagcaaca aacgggcaac tgcacgaact tttgtggaat cattntgact  600
ggactggatg ccnntatctt ctgaatcnnn gaattcatnn nnnatttcag cagtntnnnn  660
catatnccat tgcattactg aaaagnnnnn tcnnnnnnnc aatgannnan t           711
```

| | |
|---|---|
| SEQ ID NO: 113 | moltype = DNA   length = 1441 |
| FEATURE | Location/Qualifiers |
| misc_difference | 10 |
| | note = n is a, c, g, or t |
| misc_difference | 23 |
| | note = n is a, c, g, or t |
| misc_difference | 56 |
| | note = n is a, c, g, or t |
| misc_difference | 75 |
| | note = n is a, c, g, or t |
| misc_difference | 382 |
| | note = n is a, c, g, or t |
| misc_difference | 548 |
| | note = n is a, c, g, or t |
| misc_difference | 556..560 |
| | note = n is a, c, g, or t |
| misc_difference | 604..611 |
| | note = n is a, c, g, or t |
| misc_difference | 619..626 |
| | note = n is a, c, g, or t |
| misc_difference | 629..631 |
| | note = n is a, c, g, or t |
| misc_difference | 634..758 |
| | note = n is a, c, g, or t |
| misc_difference | 763..769 |
| | note = n is a, c, g, or t |
| misc_difference | 775..784 |
| | note = n is a, c, g, or t |
| misc_difference | 786..792 |
| | note = n is a, c, g, or t |
| misc_difference | 799..808 |
| | note = n is a, c, g, or t |
| misc_difference | 811..813 |
| | note = n is a, c, g, or t |
| misc_difference | 816..829 |
| | note = n is a, c, g, or t |
| misc_difference | 836..839 |
| | note = n is a, c, g, or t |
| misc_difference | 841..845 |
| | note = n is a, c, g, or t |
| misc_difference | 847 |
| | note = n is a, c, g, or t |

```
misc_difference        853
                       note = n is a, c, g, or t
misc_difference        855
                       note = n is a, c, g, or t
misc_difference        869..872
                       note = n is a, c, g, or t
misc_difference        874..878
                       note = n is a, c, g, or t
misc_difference        890..898
                       note = n is a, c, g, or t
misc_difference        934
                       note = n is a, c, g, or t
misc_difference        1308
                       note = n is a, c, g, or t
misc_difference        1391
                       note = n is a, c, g, or t
source                 1..1441
                       mol_type = unassigned DNA
                       organism = Zea mays
SEQUENCE: 113
tagtgctccn aaacggccaa gcntcaagcc agattagtag aaaacatact aatgancaat    60
agtgcaaaaa aatantacaa atacacccag cactaaaatg agatgagtgt atgtacctgt   120
gcagcttgaa ggtattaggc ccataccggt gagtggtatc cttttccaag tcttttggaa   180
ggttgatgat ttcaatggca tcaaatgggc atttctgcaa cagagattac agaagcaaga   240
agtgcattac atcaaatagg cacatctatc acagttacct ggagtaagtt agaaatctac   300
ctttacacag ataccacaac cgatgcacag ttcctcagca atgaaagcga gtttcgacgc   360
cgaagtcact tcaatgcaaa gnttccctaa acagtaaaac agaatattgt cataaaagtg   420
atccatgcca agccagaaac tagatgatgt gcagaacaac aaagggaaga gaacaatata   480
ctgtatctat ttcagcgaaa tggatgatat tgtatttgga cactgggacct tcacaagtta   540
cagtacgnac tatacnnnnn gcagcatgtg agaattctat tcaattcact aaacaagaga   600
tatnnnnnnn ntttctacnn nnnnnnaann nacnnnnnnn nnnnnnnnnn nnnnnnnnnn   660
nnnnnnnnnn nnnnnnnnnn nnnnnnnnnn nnnnnnnnnn nnnnnnnnnn nnnnnnnnnn   720
nnnnnnnnnn nnnnnnnnnn nnnnnnnnnn nnnnnnnncc tcnnnnnnna aaatnnnnnn   780
nnnntnnnnn nntgacgtnn nnnnnnnnnt g nnncannnnn nnnnnnnnnt catgannnna   840
nnnnncntac tgnangtagc atttggttnn nnannnnnta tattttttgan nnnnnnnntt   900
ggttgtatga aggaatgatc acggagcacg gtancttctc tagtgctcga cataactgat   960
gagttgcact atggttgtct gacttccctc gtccttgatg tcaaagaagg atttgggat   1020
gcactttgat tgttgggcaa gaactgtggt gaagatgcag tagctatacg gattatgcat  1080
ctgtggccac cacctaaaat tgttgaggtg aagcagtgt atggagctat cgtcagtaaa  1140
ttggccaacc tttagagatt gttagtgtca taacagacta tgattgtgtt aggacatttc  1200
ttatgcgaga agtcactcag cctcgcattc agtcaatact gtatgttgaa aagccctatg  1260
tttttttacag tgaacattga tgtgaagctt cttcctggga aatggctnga accatatttt  1320
aatgtgagat gttgctgatc ttctactcaa aggctattgc aattttctga tatgaattta  1380
caagggaatg ntgtcctcgc actaaacaaa agtcaactgt gcaatatata tgaagaatgt  1440
a                                                                  1441

SEQ ID NO: 114          moltype = DNA  length = 570
FEATURE                 Location/Qualifiers
misc_difference         26
                        note = n is a, c, g, or t
misc_difference         83
                        note = n is a, c, g, or t
misc_difference         113
                        note = n is a, c, g, or t
misc_difference         251..252
                        note = n is a, c, g, or t
misc_difference         293
                        note = n is a, c, g, or t
source                  1..570
                        mol_type = unassigned DNA
                        organism = Zea mays
SEQUENCE: 114
cgtaagcact ccccatgtca cagccnctca gtttgttgac ccaaaccttc tttcccttat     60
agacacccct gaatgaattc gcnccaaacc aatcaacgaa ctcgatctcc tcngaacgca    120
gcatccagcg accaagctcc tcgccaccgg agcgaatggt ttgccattca tctactgaga    180
cgaagactga tgcctgtggt aggggagtgg gaagctgtgg tctgtgcgcc ggctcattgt    240
cgagtacccg nncatcatct ggatcaaaca tcgactcctc atcgaagttt ctngatcctt    300
cttcttgaca accgcacagc ccaaatggta gcttcacacc accactgttc tttctttgct    360
tctttactac cgatttcagc gcggactcaa cctggttctt gaagacgcgc tcgttcccag    420
tctgcacaag tatcatgacg acgccaagtc tcagccctct cttctcaaag atctcggatct   480
tcttgcaaca gaacgaaggg ctgtctagtg atcctgacat tgactgccat gagagcgggg    540
ctgtgcaagc aaatgttagc tggaaaacag                                    570

SEQ ID NO: 115          moltype = DNA  length = 22
FEATURE                 Location/Qualifiers
source                  1..22
                        mol_type = unassigned DNA
                        organism = Zea mays
SEQUENCE: 115
```

```
cgtctccttt catctccggt at                                                22

SEQ ID NO: 116          moltype = DNA   length = 18
FEATURE                 Location/Qualifiers
source                  1..18
                        mol_type = unassigned DNA
                        organism = Zea mays
SEQUENCE: 116
gcaacaccct cgcagatg                                                     18

SEQ ID NO: 117          moltype = DNA   length = 21
FEATURE                 Location/Qualifiers
source                  1..21
                        mol_type = unassigned DNA
                        organism = Zea mays
SEQUENCE: 117
tgcaggttgc gtattttgtg a                                                 21

SEQ ID NO: 118          moltype = DNA   length = 18
FEATURE                 Location/Qualifiers
source                  1..18
                        mol_type = unassigned DNA
                        organism = Zea mays
SEQUENCE: 118
ctgggcacct tcgggatt                                                     18

SEQ ID NO: 119          moltype = DNA   length = 22
FEATURE                 Location/Qualifiers
source                  1..22
                        mol_type = unassigned DNA
                        organism = Zea mays
SEQUENCE: 119
actggcattt cttggcttca tc                                                22

SEQ ID NO: 120          moltype = DNA   length = 25
FEATURE                 Location/Qualifiers
source                  1..25
                        mol_type = unassigned DNA
                        organism = Zea mays
SEQUENCE: 120
cttggcttgg ctaggtacag aacta                                             25

SEQ ID NO: 121          moltype = DNA   length = 20
FEATURE                 Location/Qualifiers
source                  1..20
                        mol_type = unassigned DNA
                        organism = Zea mays
SEQUENCE: 121
ggcatgacag ttgggatcca                                                   20

SEQ ID NO: 122          moltype = DNA   length = 21
FEATURE                 Location/Qualifiers
source                  1..21
                        mol_type = unassigned DNA
                        organism = Zea mays
SEQUENCE: 122
cacctgggag ctctgggtat c                                                 21

SEQ ID NO: 123          moltype = DNA   length = 25
FEATURE                 Location/Qualifiers
source                  1..25
                        mol_type = unassigned DNA
                        organism = Zea mays
SEQUENCE: 123
cctgagcact atgatcttcc agtac                                             25

SEQ ID NO: 124          moltype = DNA   length = 18
FEATURE                 Location/Qualifiers
source                  1..18
                        mol_type = unassigned DNA
                        organism = Zea mays
SEQUENCE: 124
ggtcagtgcg aggtgtcc                                                     18

SEQ ID NO: 125          moltype = DNA   length = 17
FEATURE                 Location/Qualifiers
source                  1..17
                        mol_type = unassigned DNA
                        organism = Zea mays
```

```
SEQUENCE: 125
gccgccaagg tccactt                                                        17

SEQ ID NO: 126          moltype = DNA  length = 16
FEATURE                 Location/Qualifiers
source                  1..16
                        mol_type = unassigned DNA
                        organism = Zea mays
SEQUENCE: 126
cgcaagcacc caacca                                                         16

SEQ ID NO: 127          moltype = DNA  length = 25
FEATURE                 Location/Qualifiers
source                  1..25
                        mol_type = unassigned DNA
                        organism = Zea mays
SEQUENCE: 127
ggttgccaat cagtacctat ttcag                                               25

SEQ ID NO: 128          moltype = DNA  length = 25
FEATURE                 Location/Qualifiers
source                  1..25
                        mol_type = unassigned DNA
                        organism = Zea mays
SEQUENCE: 128
ctccaaaaac tttgtggcct caaat                                               25

SEQ ID NO: 129          moltype = DNA  length = 24
FEATURE                 Location/Qualifiers
source                  1..24
                        mol_type = unassigned DNA
                        organism = Zea mays
SEQUENCE: 129
cctcttgatc ctctgaacct gcta                                                24

SEQ ID NO: 130          moltype = DNA  length = 28
FEATURE                 Location/Qualifiers
source                  1..28
                        mol_type = unassigned DNA
                        organism = Zea mays
SEQUENCE: 130
tgaagaagga ttgagatatg aaaagaca                                            28

SEQ ID NO: 131          moltype = DNA  length = 23
FEATURE                 Location/Qualifiers
source                  1..23
                        mol_type = unassigned DNA
                        organism = Zea mays
SEQUENCE: 131
ctgaggattc cgatccctaa cat                                                 23

SEQ ID NO: 132          moltype = DNA  length = 21
FEATURE                 Location/Qualifiers
source                  1..21
                        mol_type = unassigned DNA
                        organism = Zea mays
SEQUENCE: 132
cgacggtctc ctcacctagc t                                                   21

SEQ ID NO: 133          moltype = DNA  length = 21
FEATURE                 Location/Qualifiers
source                  1..21
                        mol_type = unassigned DNA
                        organism = Zea mays
SEQUENCE: 133
catttgcttt gctccgttct g                                                   21

SEQ ID NO: 134          moltype = DNA  length = 29
FEATURE                 Location/Qualifiers
source                  1..29
                        mol_type = unassigned DNA
                        organism = Zea mays
SEQUENCE: 134
gcttgatttg tttttaacat acactatgg                                           29

SEQ ID NO: 135          moltype = DNA  length = 21
FEATURE                 Location/Qualifiers
source                  1..21
                        mol_type = unassigned DNA
```

```
                                organism = Zea mays
SEQUENCE: 135
ctcaccccac tatcggattc c                                               21

SEQ ID NO: 136          moltype = DNA   length = 26
FEATURE                 Location/Qualifiers
source                  1..26
                        mol_type = unassigned DNA
                        organism = Zea mays
SEQUENCE: 136
acaagtagct agcagaacat ggagaa                                          26

SEQ ID NO: 137          moltype = DNA   length = 25
FEATURE                 Location/Qualifiers
source                  1..25
                        mol_type = unassigned DNA
                        organism = Zea mays
SEQUENCE: 137
gttctccttc ggtttgctca tctat                                           25

SEQ ID NO: 138          moltype = DNA   length = 27
FEATURE                 Location/Qualifiers
source                  1..27
                        mol_type = unassigned DNA
                        organism = Zea mays
SEQUENCE: 138
ctgggttgtg aaaaacttca tttagtt                                         27

SEQ ID NO: 139          moltype = DNA   length = 25
FEATURE                 Location/Qualifiers
source                  1..25
                        mol_type = unassigned DNA
                        organism = Zea mays
SEQUENCE: 139
ggaagataga gaacagcgac aatgt                                           25

SEQ ID NO: 140          moltype = DNA   length = 20
FEATURE                 Location/Qualifiers
source                  1..20
                        mol_type = unassigned DNA
                        organism = Zea mays
SEQUENCE: 140
ccagcaggga aagagaagca                                                 20

SEQ ID NO: 141          moltype = DNA   length = 27
FEATURE                 Location/Qualifiers
source                  1..27
                        mol_type = unassigned DNA
                        organism = Zea mays
SEQUENCE: 141
attaacatct ctggactttg gcattct                                         27

SEQ ID NO: 142          moltype = DNA   length = 25
FEATURE                 Location/Qualifiers
source                  1..25
                        mol_type = unassigned DNA
                        organism = Zea mays
SEQUENCE: 142
gctctaaatg gtttgctgct gtaag                                           25

SEQ ID NO: 143          moltype = DNA   length = 18
FEATURE                 Location/Qualifiers
source                  1..18
                        mol_type = unassigned DNA
                        organism = Zea mays
SEQUENCE: 143
tgtaggcagc ggcatctc                                                   18

SEQ ID NO: 144          moltype = DNA   length = 20
FEATURE                 Location/Qualifiers
source                  1..20
                        mol_type = unassigned DNA
                        organism = Zea mays
SEQUENCE: 144
agcaaggatg tccgcttcag                                                 20

SEQ ID NO: 145          moltype = DNA   length = 25
FEATURE                 Location/Qualifiers
source                  1..25
```

-continued

```
                        mol_type = unassigned DNA
                        organism = Zea mays
SEQUENCE: 145
ggtgcaacct cagctcttat aaact                                 25

SEQ ID NO: 146          moltype = DNA  length = 29
FEATURE                 Location/Qualifiers
source                  1..29
                        mol_type = unassigned DNA
                        organism = Zea mays
SEQUENCE: 146
ggtagtatat gtgcattcat cgtttttca                             29

SEQ ID NO: 147          moltype = DNA  length = 23
FEATURE                 Location/Qualifiers
source                  1..23
                        mol_type = unassigned DNA
                        organism = Zea mays
SEQUENCE: 147
ttggagaggt ctctttcgtt cag                                   23

SEQ ID NO: 148          moltype = DNA  length = 21
FEATURE                 Location/Qualifiers
source                  1..21
                        mol_type = unassigned DNA
                        organism = Zea mays
SEQUENCE: 148
tgccatccac tgtactttgc a                                     21

SEQ ID NO: 149          moltype = DNA  length = 21
FEATURE                 Location/Qualifiers
source                  1..21
                        mol_type = unassigned DNA
                        organism = Zea mays
SEQUENCE: 149
caggcgtatg aattgcacga t                                     21

SEQ ID NO: 150          moltype = DNA  length = 25
FEATURE                 Location/Qualifiers
source                  1..25
                        mol_type = unassigned DNA
                        organism = Zea mays
SEQUENCE: 150
gcaatcagac gtatgttctt gaatg                                 25

SEQ ID NO: 151          moltype = DNA  length = 21
FEATURE                 Location/Qualifiers
source                  1..21
                        mol_type = unassigned DNA
                        organism = Zea mays
SEQUENCE: 151
cctcagcatt tttggcaagt g                                     21

SEQ ID NO: 152          moltype = DNA  length = 25
FEATURE                 Location/Qualifiers
source                  1..25
                        mol_type = unassigned DNA
                        organism = Zea mays
SEQUENCE: 152
aagaacaaac gcagaaaaca gattt                                 25

SEQ ID NO: 153          moltype = DNA  length = 23
FEATURE                 Location/Qualifiers
source                  1..23
                        mol_type = unassigned DNA
                        organism = Zea mays
SEQUENCE: 153
tgattcaatc actgtgccaa gac                                   23

SEQ ID NO: 154          moltype = DNA  length = 25
FEATURE                 Location/Qualifiers
source                  1..25
                        mol_type = unassigned DNA
                        organism = Zea mays
SEQUENCE: 154
gaagctttgt ttgattcggt tcaga                                 25

SEQ ID NO: 155          moltype = DNA  length = 31
FEATURE                 Location/Qualifiers
```

```
source                  1..31
                        mol_type = unassigned DNA
                        organism = Zea mays
SEQUENCE: 155
ctgaaattgt actggaagac tagagttatg t                              31

SEQ ID NO: 156          moltype = DNA   length = 22
FEATURE                 Location/Qualifiers
source                  1..22
                        mol_type = unassigned DNA
                        organism = Zea mays
SEQUENCE: 156
ggaaggcctc caagacttgt tt                                        22

SEQ ID NO: 157          moltype = DNA   length = 25
FEATURE                 Location/Qualifiers
source                  1..25
                        mol_type = unassigned DNA
                        organism = Zea mays
SEQUENCE: 157
ggcaaggatc tgttttcacc aaata                                     25

SEQ ID NO: 158          moltype = DNA   length = 24
FEATURE                 Location/Qualifiers
source                  1..24
                        mol_type = unassigned DNA
                        organism = Zea mays
SEQUENCE: 158
gggaggacaa caactacatc ttca                                      24

SEQ ID NO: 159          moltype = DNA   length = 19
FEATURE                 Location/Qualifiers
source                  1..19
                        mol_type = unassigned DNA
                        organism = Zea mays
SEQUENCE: 159
gggtggcgga gaagttgac                                            19

SEQ ID NO: 160          moltype = DNA   length = 23
FEATURE                 Location/Qualifiers
source                  1..23
                        mol_type = unassigned DNA
                        organism = Zea mays
SEQUENCE: 160
cttcggtgca agatagtcct gaa                                       23

SEQ ID NO: 161          moltype = DNA   length = 25
FEATURE                 Location/Qualifiers
source                  1..25
                        mol_type = unassigned DNA
                        organism = Zea mays
SEQUENCE: 161
agttgaccaa atagcagagc taacc                                     25

SEQ ID NO: 162          moltype = DNA   length = 25
FEATURE                 Location/Qualifiers
source                  1..25
                        mol_type = unassigned DNA
                        organism = Zea mays
SEQUENCE: 162
gcctaacaga tctcctactg aggtt                                     25

SEQ ID NO: 163          moltype = DNA   length = 25
FEATURE                 Location/Qualifiers
source                  1..25
                        mol_type = unassigned DNA
                        organism = Zea mays
SEQUENCE: 163
ttcgtggaat tcaccagatc tatct                                     25

SEQ ID NO: 164          moltype = DNA   length = 20
FEATURE                 Location/Qualifiers
source                  1..20
                        mol_type = unassigned DNA
                        organism = Zea mays
SEQUENCE: 164
cgaggtagca caggcagttg                                           20

SEQ ID NO: 165          moltype = DNA   length = 25
```

```
FEATURE                 Location/Qualifiers
source                  1..25
                        mol_type = unassigned DNA
                        organism = Zea mays
SEQUENCE: 165
tgtacattgt cgttcacatc ttgct                                              25

SEQ ID NO: 166          moltype = DNA  length = 21
FEATURE                 Location/Qualifiers
source                  1..21
                        mol_type = unassigned DNA
                        organism = Zea mays
SEQUENCE: 166
gccaaggtcc tgagcaaaat c                                                  21

SEQ ID NO: 167          moltype = DNA  length = 24
FEATURE                 Location/Qualifiers
source                  1..24
                        mol_type = unassigned DNA
                        organism = Zea mays
SEQUENCE: 167
cgtgataatc tcaacctcct caga                                               24

SEQ ID NO: 168          moltype = DNA  length = 25
FEATURE                 Location/Qualifiers
source                  1..25
                        mol_type = unassigned DNA
                        organism = Zea mays
SEQUENCE: 168
ggtttcagaa gcacatagtg acctt                                              25

SEQ ID NO: 169          moltype = DNA  length = 26
FEATURE                 Location/Qualifiers
source                  1..26
                        mol_type = unassigned DNA
                        organism = Zea mays
SEQUENCE: 169
attacaacaa atgagaacac ccatgt                                             26

SEQ ID NO: 170          moltype = DNA  length = 23
FEATURE                 Location/Qualifiers
source                  1..23
                        mol_type = unassigned DNA
                        organism = Zea mays
SEQUENCE: 170
cagcatgtcc ttctcgtatc tga                                                23

SEQ ID NO: 171          moltype = DNA  length = 19
FEATURE                 Location/Qualifiers
source                  1..19
                        mol_type = unassigned DNA
                        organism = Zea mays
SEQUENCE: 171
ccctgggaag caatttcga                                                     19

SEQ ID NO: 172          moltype = DNA  length = 26
FEATURE                 Location/Qualifiers
source                  1..26
                        mol_type = unassigned DNA
                        organism = Zea mays
SEQUENCE: 172
caatcagcat taacacaaca acatgt                                             26

SEQ ID NO: 173          moltype = DNA  length = 26
FEATURE                 Location/Qualifiers
source                  1..26
                        mol_type = unassigned DNA
                        organism = Zea mays
SEQUENCE: 173
tcttctggtt cttgttgaca cttgag                                             26

SEQ ID NO: 174          moltype = DNA  length = 20
FEATURE                 Location/Qualifiers
source                  1..20
                        mol_type = unassigned DNA
                        organism = Zea mays
SEQUENCE: 174
cagttcgtgt tcggcagcta                                                    20
```

```
SEQ ID NO: 175         moltype = DNA   length = 28
FEATURE                Location/Qualifiers
source                 1..28
                       mol_type = unassigned DNA
                       organism = Zea mays
SEQUENCE: 175
gtgaagagca attggttcaa gtagtaaa                                            28

SEQ ID NO: 176         moltype = DNA   length = 20
FEATURE                Location/Qualifiers
source                 1..20
                       mol_type = unassigned DNA
                       organism = Zea mays
SEQUENCE: 176
agttggctgg ccatctgatg                                                     20

SEQ ID NO: 177         moltype = DNA   length = 23
FEATURE                Location/Qualifiers
source                 1..23
                       mol_type = unassigned DNA
                       organism = Zea mays
SEQUENCE: 177
tgctcttgga cagttcaatg aca                                                 23

SEQ ID NO: 178         moltype = DNA   length = 25
FEATURE                Location/Qualifiers
source                 1..25
                       mol_type = unassigned DNA
                       organism = Zea mays
SEQUENCE: 178
gcaaattttg cccacataca ctgta                                               25

SEQ ID NO: 179         moltype = DNA   length = 17
FEATURE                Location/Qualifiers
source                 1..17
                       mol_type = unassigned DNA
                       organism = Zea mays
SEQUENCE: 179
cagtacggcg gcaacga                                                        17

SEQ ID NO: 180         moltype = DNA   length = 25
FEATURE                Location/Qualifiers
source                 1..25
                       mol_type = unassigned DNA
                       organism = Zea mays
SEQUENCE: 180
tcaaccaatt tcttgatttc gatgt                                               25

SEQ ID NO: 181         moltype = DNA   length = 20
FEATURE                Location/Qualifiers
source                 1..20
                       mol_type = unassigned DNA
                       organism = Zea mays
SEQUENCE: 181
tgttgaccga gcagcaagag                                                     20

SEQ ID NO: 182         moltype = DNA   length = 20
FEATURE                Location/Qualifiers
source                 1..20
                       mol_type = unassigned DNA
                       organism = Zea mays
SEQUENCE: 182
ggctggacat agtggactgc                                                     20

SEQ ID NO: 183         moltype = DNA   length = 26
FEATURE                Location/Qualifiers
source                 1..26
                       mol_type = unassigned DNA
                       organism = Zea mays
SEQUENCE: 183
gaacaagcat gcatatatca ctcgta                                              26

SEQ ID NO: 184         moltype = DNA   length = 23
FEATURE                Location/Qualifiers
source                 1..23
                       mol_type = unassigned DNA
                       organism = Zea mays
SEQUENCE: 184
ggcttgcgta ttcttgaact tgt                                                 23
```

| SEQ ID NO: 185 | moltype = DNA  length = 25 | |
|---|---|---|
| FEATURE | Location/Qualifiers | |
| source | 1..25 | |
| | mol_type = unassigned DNA | |
| | organism = Zea mays | |
| SEQUENCE: 185 | | |
| ccagagctgg aaacatccta tcaag | | 25 |

| SEQ ID NO: 186 | moltype = DNA  length = 23 | |
|---|---|---|
| FEATURE | Location/Qualifiers | |
| source | 1..23 | |
| | mol_type = unassigned DNA | |
| | organism = Zea mays | |
| SEQUENCE: 186 | | |
| ctacgatgac gttgaggaga tca | | 23 |

| SEQ ID NO: 187 | moltype = DNA  length = 25 | |
|---|---|---|
| FEATURE | Location/Qualifiers | |
| source | 1..25 | |
| | mol_type = unassigned DNA | |
| | organism = Zea mays | |
| SEQUENCE: 187 | | |
| gtccgcttac cagtttacta tcctt | | 25 |

| SEQ ID NO: 188 | moltype = DNA  length = 17 | |
|---|---|---|
| FEATURE | Location/Qualifiers | |
| source | 1..17 | |
| | mol_type = unassigned DNA | |
| | organism = Zea mays | |
| SEQUENCE: 188 | | |
| agcaaccggc acatgga | | 17 |

| SEQ ID NO: 189 | moltype = DNA  length = 20 | |
|---|---|---|
| FEATURE | Location/Qualifiers | |
| source | 1..20 | |
| | mol_type = unassigned DNA | |
| | organism = Zea mays | |
| SEQUENCE: 189 | | |
| cggacaggat gcaacaacct | | 20 |

| SEQ ID NO: 190 | moltype = DNA  length = 22 | |
|---|---|---|
| FEATURE | Location/Qualifiers | |
| source | 1..22 | |
| | mol_type = unassigned DNA | |
| | organism = Zea mays | |
| SEQUENCE: 190 | | |
| gcatttttgg gtcagtgaag ca | | 22 |

| SEQ ID NO: 191 | moltype = DNA  length = 22 | |
|---|---|---|
| FEATURE | Location/Qualifiers | |
| source | 1..22 | |
| | mol_type = unassigned DNA | |
| | organism = Zea mays | |
| SEQUENCE: 191 | | |
| agttatgagg tttgccccaa ca | | 22 |

| SEQ ID NO: 192 | moltype = DNA  length = 24 | |
|---|---|---|
| FEATURE | Location/Qualifiers | |
| source | 1..24 | |
| | mol_type = unassigned DNA | |
| | organism = Zea mays | |
| SEQUENCE: 192 | | |
| ggataatggc cgacatgttt gaca | | 24 |

| SEQ ID NO: 193 | moltype = DNA  length = 20 | |
|---|---|---|
| FEATURE | Location/Qualifiers | |
| source | 1..20 | |
| | mol_type = unassigned DNA | |
| | organism = Zea mays | |
| SEQUENCE: 193 | | |
| gaagtcggag ctgctttggt | | 20 |

| SEQ ID NO: 194 | moltype = DNA  length = 26 | |
|---|---|---|
| FEATURE | Location/Qualifiers | |
| source | 1..26 | |
| | mol_type = unassigned DNA | |
| | organism = Zea mays | |
| SEQUENCE: 194 | | |

```
gggcctctat ttgtaatggt tgtatt                                          26

SEQ ID NO: 195           moltype = DNA   length = 25
FEATURE                  Location/Qualifiers
source                   1..25
                         mol_type = unassigned DNA
                         organism = Zea mays
SEQUENCE: 195
gagggaaggt gataatcatc gacat                                           25

SEQ ID NO: 196           moltype = DNA   length = 19
FEATURE                  Location/Qualifiers
source                   1..19
                         mol_type = unassigned DNA
                         organism = Zea mays
SEQUENCE: 196
cgtgctcagt gtgcagtct                                                  19

SEQ ID NO: 197           moltype = DNA   length = 25
FEATURE                  Location/Qualifiers
source                   1..25
                         mol_type = unassigned DNA
                         organism = Zea mays
SEQUENCE: 197
cggagagatt gttcgaagaa tttta                                           25

SEQ ID NO: 198           moltype = DNA   length = 22
FEATURE                  Location/Qualifiers
source                   1..22
                         mol_type = unassigned DNA
                         organism = Zea mays
SEQUENCE: 198
agcatgagca gaacacgaat ca                                              22

SEQ ID NO: 199           moltype = DNA   length = 25
FEATURE                  Location/Qualifiers
source                   1..25
                         mol_type = unassigned DNA
                         organism = Zea mays
SEQUENCE: 199
cggagagatt gttcgaagaa tttta                                           25

SEQ ID NO: 200           moltype = DNA   length = 18
FEATURE                  Location/Qualifiers
source                   1..18
                         mol_type = unassigned DNA
                         organism = Zea mays
SEQUENCE: 200
gcgtggagcc cagaaaga                                                   18

SEQ ID NO: 201           moltype = DNA   length = 26
FEATURE                  Location/Qualifiers
source                   1..26
                         mol_type = unassigned DNA
                         organism = Zea mays
SEQUENCE: 201
ggctttaagc agattagagc tttgag                                          26

SEQ ID NO: 202           moltype = DNA   length = 25
FEATURE                  Location/Qualifiers
source                   1..25
                         mol_type = unassigned DNA
                         organism = Zea mays
SEQUENCE: 202
ccttcgtcaa cttagttggg ttact                                           25

SEQ ID NO: 203           moltype = DNA   length = 26
FEATURE                  Location/Qualifiers
source                   1..26
                         mol_type = unassigned DNA
                         organism = Zea mays
SEQUENCE: 203
cacaaatcac agaagatgtc accaaa                                          26

SEQ ID NO: 204           moltype = DNA   length = 24
FEATURE                  Location/Qualifiers
source                   1..24
                         mol_type = unassigned DNA
                         organism = Zea mays
```

-continued

```
SEQUENCE: 204
actgtgctat acctaggcga ggaa                                           24

SEQ ID NO: 205          moltype = DNA  length = 20
FEATURE                 Location/Qualifiers
source                  1..20
                        mol_type = unassigned DNA
                        organism = Zea mays
SEQUENCE: 205
gatgtgggca aggcttctct                                                20

SEQ ID NO: 206          moltype = DNA  length = 19
FEATURE                 Location/Qualifiers
source                  1..19
                        mol_type = unassigned DNA
                        organism = Zea mays
SEQUENCE: 206
aactccttgg gacgcgttt                                                 19

SEQ ID NO: 207          moltype = DNA  length = 16
FEATURE                 Location/Qualifiers
source                  1..16
                        mol_type = unassigned DNA
                        organism = Zea mays
SEQUENCE: 207
ggttcgcgcc ggagtt                                                    16

SEQ ID NO: 208          moltype = DNA  length = 18
FEATURE                 Location/Qualifiers
source                  1..18
                        mol_type = unassigned DNA
                        organism = Zea mays
SEQUENCE: 208
tgcaacacac gcgcatgt                                                  18

SEQ ID NO: 209          moltype = DNA  length = 16
FEATURE                 Location/Qualifiers
source                  1..16
                        mol_type = unassigned DNA
                        organism = Zea mays
SEQUENCE: 209
gcggaggctg cgatca                                                    16

SEQ ID NO: 210          moltype = DNA  length = 19
FEATURE                 Location/Qualifiers
source                  1..19
                        mol_type = unassigned DNA
                        organism = Zea mays
SEQUENCE: 210
attgcggaga ggctgcttt                                                 19

SEQ ID NO: 211          moltype = DNA  length = 23
FEATURE                 Location/Qualifiers
source                  1..23
                        mol_type = unassigned DNA
                        organism = Zea mays
SEQUENCE: 211
ccgatgaggc ttctgtggaa tta                                            23

SEQ ID NO: 212          moltype = DNA  length = 32
FEATURE                 Location/Qualifiers
source                  1..32
                        mol_type = unassigned DNA
                        organism = Zea mays
SEQUENCE: 212
gctaagtatc tactatgaag ctcaaggtaa gg                                  32

SEQ ID NO: 213          moltype = DNA  length = 18
FEATURE                 Location/Qualifiers
source                  1..18
                        mol_type = unassigned DNA
                        organism = Zea mays
SEQUENCE: 213
tcccgtcaag ccaaagca                                                  18

SEQ ID NO: 214          moltype = DNA  length = 20
FEATURE                 Location/Qualifiers
source                  1..20
                        mol_type = unassigned DNA
```

```
                               organism = Zea mays
SEQUENCE: 214
acagacaccg tgtgcacgtt                                                    20

SEQ ID NO: 215          moltype = DNA  length = 15
FEATURE                 Location/Qualifiers
source                  1..15
                        mol_type = unassigned DNA
                        organism = Zea mays
SEQUENCE: 215
ggtccgcgcc aacga                                                         15

SEQ ID NO: 216          moltype = DNA  length = 22
FEATURE                 Location/Qualifiers
source                  1..22
                        mol_type = unassigned DNA
                        organism = Zea mays
SEQUENCE: 216
ccagacgaac tgtggagctc tt                                                 22

SEQ ID NO: 217          moltype = DNA  length = 23
FEATURE                 Location/Qualifiers
source                  1..23
                        mol_type = unassigned DNA
                        organism = Zea mays
SEQUENCE: 217
gttccttctc gaagacgaga tca                                                23

SEQ ID NO: 218          moltype = DNA  length = 25
FEATURE                 Location/Qualifiers
source                  1..25
                        mol_type = unassigned DNA
                        organism = Zea mays
SEQUENCE: 218
cttccatgtc tcttcccaat agttg                                              25

SEQ ID NO: 219          moltype = DNA  length = 25
FEATURE                 Location/Qualifiers
source                  1..25
                        mol_type = unassigned DNA
                        organism = Zea mays
SEQUENCE: 219
gctctgtggg atatttgaag tccat                                              25

SEQ ID NO: 220          moltype = DNA  length = 28
FEATURE                 Location/Qualifiers
source                  1..28
                        mol_type = unassigned DNA
                        organism = Zea mays
SEQUENCE: 220
tgatatgata cccaatttct cttggtaa                                           28

SEQ ID NO: 221          moltype = DNA  length = 19
FEATURE                 Location/Qualifiers
source                  1..19
                        mol_type = unassigned DNA
                        organism = Zea mays
SEQUENCE: 221
caaacccgtc cgaaatcgt                                                     19

SEQ ID NO: 222          moltype = DNA  length = 25
FEATURE                 Location/Qualifiers
source                  1..25
                        mol_type = unassigned DNA
                        organism = Zea mays
SEQUENCE: 222
gaagagagct ctgggtgaca taaaa                                              25

SEQ ID NO: 223          moltype = DNA  length = 29
FEATURE                 Location/Qualifiers
source                  1..29
                        mol_type = unassigned DNA
                        organism = Zea mays
SEQUENCE: 223
gaacggagaa acacaagtgg atatataca                                          29

SEQ ID NO: 224          moltype = DNA  length = 26
FEATURE                 Location/Qualifiers
source                  1..26
```

```
                        mol_type = unassigned DNA
                        organism = Zea mays
SEQUENCE: 224
ttttcttctt tatttgctgg tgacaa                                          26

SEQ ID NO: 225          moltype = DNA   length = 22
FEATURE                 Location/Qualifiers
source                  1..22
                        mol_type = unassigned DNA
                        organism = Zea mays
SEQUENCE: 225
tgattgccaa catgaacctt ca                                              22

SEQ ID NO: 226          moltype = DNA   length = 24
FEATURE                 Location/Qualifiers
source                  1..24
                        mol_type = unassigned DNA
                        organism = Zea mays
SEQUENCE: 226
agtcccaatc tttgtcctaa gcaa                                            24

SEQ ID NO: 227          moltype = DNA   length = 19
FEATURE                 Location/Qualifiers
source                  1..19
                        mol_type = unassigned DNA
                        organism = Zea mays
SEQUENCE: 227
cgacgccgaa gtcacttca                                                  19

SEQ ID NO: 228          moltype = DNA   length = 24
FEATURE                 Location/Qualifiers
source                  1..24
                        mol_type = unassigned DNA
                        organism = Zea mays
SEQUENCE: 228
cccttataga cacccctgaa tgaa                                            24

SEQ ID NO: 229          moltype = DNA   length = 27
FEATURE                 Location/Qualifiers
source                  1..27
                        mol_type = unassigned DNA
                        organism = Zea mays
SEQUENCE: 229
agtgatgcga tctgtataga tgtgtgt                                         27

SEQ ID NO: 230          moltype = DNA   length = 22
FEATURE                 Location/Qualifiers
source                  1..22
                        mol_type = unassigned DNA
                        organism = Zea mays
SEQUENCE: 230
cgacggtccg gtaaattgtt ct                                              22

SEQ ID NO: 231          moltype = DNA   length = 20
FEATURE                 Location/Qualifiers
source                  1..20
                        mol_type = unassigned DNA
                        organism = Zea mays
SEQUENCE: 231
ggccatcaac attgccaact                                                 20

SEQ ID NO: 232          moltype = DNA   length = 24
FEATURE                 Location/Qualifiers
source                  1..24
                        mol_type = unassigned DNA
                        organism = Zea mays
SEQUENCE: 232
tctcatcatc accagaacaa agct                                            24

SEQ ID NO: 233          moltype = DNA   length = 17
FEATURE                 Location/Qualifiers
source                  1..17
                        mol_type = unassigned DNA
                        organism = Zea mays
SEQUENCE: 233
cgccaccacc cgacagt                                                    17

SEQ ID NO: 234          moltype = DNA   length = 23
FEATURE                 Location/Qualifiers
```

```
source                   1..23
                         mol_type = unassigned DNA
                         organism = Zea mays
SEQUENCE: 234
tggtggcggt actgaaaact act                                               23

SEQ ID NO: 235           moltype = DNA   length = 19
FEATURE                  Location/Qualifiers
source                   1..19
                         mol_type = unassigned DNA
                         organism = Zea mays
SEQUENCE: 235
gtcgttgtcc gtggtgttc                                                    19

SEQ ID NO: 236           moltype = DNA   length = 20
FEATURE                  Location/Qualifiers
source                   1..20
                         mol_type = unassigned DNA
                         organism = Zea mays
SEQUENCE: 236
cagagcctcg agtggctgat                                                   20

SEQ ID NO: 237           moltype = DNA   length = 19
FEATURE                  Location/Qualifiers
source                   1..19
                         mol_type = unassigned DNA
                         organism = Zea mays
SEQUENCE: 237
cgcaggcatt cgacttgag                                                    19

SEQ ID NO: 238           moltype = DNA   length = 25
FEATURE                  Location/Qualifiers
source                   1..25
                         mol_type = unassigned DNA
                         organism = Zea mays
SEQUENCE: 238
caagagttgc atgctttgta cgaat                                             25

SEQ ID NO: 239           moltype = DNA   length = 18
FEATURE                  Location/Qualifiers
source                   1..18
                         mol_type = unassigned DNA
                         organism = Zea mays
SEQUENCE: 239
gcccctgacg acctcgta                                                     18

SEQ ID NO: 240           moltype = DNA   length = 22
FEATURE                  Location/Qualifiers
source                   1..22
                         mol_type = unassigned DNA
                         organism = Zea mays
SEQUENCE: 240
ctcgaccgaa tcaacgtcta ca                                                22

SEQ ID NO: 241           moltype = DNA   length = 23
FEATURE                  Location/Qualifiers
source                   1..23
                         mol_type = unassigned DNA
                         organism = Zea mays
SEQUENCE: 241
atccttgaca gcatccacat ttt                                               23

SEQ ID NO: 242           moltype = DNA   length = 22
FEATURE                  Location/Qualifiers
source                   1..22
                         mol_type = unassigned DNA
                         organism = Zea mays
SEQUENCE: 242
accaaaccct ggcaagaaag aa                                                22

SEQ ID NO: 243           moltype = DNA   length = 24
FEATURE                  Location/Qualifiers
source                   1..24
                         mol_type = unassigned DNA
                         organism = Zea mays
SEQUENCE: 243
gaatgggcag tcttatgtga aaaa                                              24

SEQ ID NO: 244           moltype = DNA   length = 20
```

```
FEATURE                 Location/Qualifiers
source                  1..20
                        mol_type = unassigned DNA
                        organism = Zea mays
SEQUENCE: 244
gcataaagcg ggaagtggaa                                                   20

SEQ ID NO: 245          moltype = DNA   length = 24
FEATURE                 Location/Qualifiers
source                  1..24
                        mol_type = unassigned DNA
                        organism = Zea mays
SEQUENCE: 245
accacagatt gtcccgagta tttg                                              24

SEQ ID NO: 246          moltype = DNA   length = 17
FEATURE                 Location/Qualifiers
source                  1..17
                        mol_type = unassigned DNA
                        organism = Zea mays
SEQUENCE: 246
gcacggacac cgagctg                                                      17

SEQ ID NO: 247          moltype = DNA   length = 25
FEATURE                 Location/Qualifiers
source                  1..25
                        mol_type = unassigned DNA
                        organism = Zea mays
SEQUENCE: 247
gccactgtta atgttgcttc ttgta                                             25

SEQ ID NO: 248          moltype = DNA   length = 26
FEATURE                 Location/Qualifiers
source                  1..26
                        mol_type = unassigned DNA
                        organism = Zea mays
SEQUENCE: 248
tgctgtcatg tttattgggt tatagg                                            26

SEQ ID NO: 249          moltype = DNA   length = 20
FEATURE                 Location/Qualifiers
source                  1..20
                        mol_type = unassigned DNA
                        organism = Zea mays
SEQUENCE: 249
ggctagtgcc aattgccaaa                                                   20

SEQ ID NO: 250          moltype = DNA   length = 21
FEATURE                 Location/Qualifiers
source                  1..21
                        mol_type = unassigned DNA
                        organism = Zea mays
SEQUENCE: 250
cgtacggact gccaattgtt t                                                 21

SEQ ID NO: 251          moltype = DNA   length = 17
FEATURE                 Location/Qualifiers
source                  1..17
                        mol_type = unassigned DNA
                        organism = Zea mays
SEQUENCE: 251
cctccccggc ctatgtg                                                      17

SEQ ID NO: 252          moltype = DNA   length = 24
FEATURE                 Location/Qualifiers
source                  1..24
                        mol_type = unassigned DNA
                        organism = Zea mays
SEQUENCE: 252
gccaaaccac agataaggaa acac                                              24

SEQ ID NO: 253          moltype = DNA   length = 24
FEATURE                 Location/Qualifiers
source                  1..24
                        mol_type = unassigned DNA
                        organism = Zea mays
SEQUENCE: 253
tctttccttg atgggaacaa tgct                                              24
```

```
SEQ ID NO: 254          moltype = DNA   length = 20
FEATURE                 Location/Qualifiers
source                  1..20
                        mol_type = unassigned DNA
                        organism = Zea mays
SEQUENCE: 254
ccggtgggta cctcagttga                                                      20

SEQ ID NO: 255          moltype = DNA   length = 22
FEATURE                 Location/Qualifiers
source                  1..22
                        mol_type = unassigned DNA
                        organism = Zea mays
SEQUENCE: 255
agtttccgct gtacagtttg gt                                                   22

SEQ ID NO: 256          moltype = DNA   length = 20
FEATURE                 Location/Qualifiers
source                  1..20
                        mol_type = unassigned DNA
                        organism = Zea mays
SEQUENCE: 256
tggctctgca catccaaaaa                                                      20

SEQ ID NO: 257          moltype = DNA   length = 24
FEATURE                 Location/Qualifiers
source                  1..24
                        mol_type = unassigned DNA
                        organism = Zea mays
SEQUENCE: 257
tcgttatgcc cttctctctt agct                                                 24

SEQ ID NO: 258          moltype = DNA   length = 26
FEATURE                 Location/Qualifiers
source                  1..26
                        mol_type = unassigned DNA
                        organism = Zea mays
SEQUENCE: 258
ctgttcgttg tttttaattc gtatcg                                               26

SEQ ID NO: 259          moltype = DNA   length = 27
FEATURE                 Location/Qualifiers
source                  1..27
                        mol_type = unassigned DNA
                        organism = Zea mays
SEQUENCE: 259
agcagcattg tttcttgtgt tcaatac                                              27

SEQ ID NO: 260          moltype = DNA   length = 25
FEATURE                 Location/Qualifiers
source                  1..25
                        mol_type = unassigned DNA
                        organism = Zea mays
SEQUENCE: 260
ccaaactctc gatgaccaag cataa                                                25

SEQ ID NO: 261          moltype = DNA   length = 20
FEATURE                 Location/Qualifiers
source                  1..20
                        mol_type = unassigned DNA
                        organism = Zea mays
SEQUENCE: 261
gccactgctt tctgcttcgt                                                      20

SEQ ID NO: 262          moltype = DNA   length = 20
FEATURE                 Location/Qualifiers
source                  1..20
                        mol_type = unassigned DNA
                        organism = Zea mays
SEQUENCE: 262
tgctgccaaa cttcgatcgt                                                      20

SEQ ID NO: 263          moltype = DNA   length = 17
FEATURE                 Location/Qualifiers
source                  1..17
                        mol_type = unassigned DNA
                        organism = Zea mays
SEQUENCE: 263
ccaggctcag gcaccat                                                         17
```

```
SEQ ID NO: 264          moltype = DNA   length = 26
FEATURE                 Location/Qualifiers
source                  1..26
                        mol_type = unassigned DNA
                        organism = Zea mays
SEQUENCE: 264
ccgctatttc aataatcact ctcaga                                              26

SEQ ID NO: 265          moltype = DNA   length = 30
FEATURE                 Location/Qualifiers
source                  1..30
                        mol_type = unassigned DNA
                        organism = Zea mays
SEQUENCE: 265
gtattttttt tcttttttag acgttgcttt                                          30

SEQ ID NO: 266          moltype = DNA   length = 24
FEATURE                 Location/Qualifiers
source                  1..24
                        mol_type = unassigned DNA
                        organism = Zea mays
SEQUENCE: 266
gctggcttca ggcctactac taaa                                                24

SEQ ID NO: 267          moltype = DNA   length = 21
FEATURE                 Location/Qualifiers
source                  1..21
                        mol_type = unassigned DNA
                        organism = Zea mays
SEQUENCE: 267
ttcactgact gcgatgacga a                                                   21

SEQ ID NO: 268          moltype = DNA   length = 20
FEATURE                 Location/Qualifiers
source                  1..20
                        mol_type = unassigned DNA
                        organism = Zea mays
SEQUENCE: 268
ggaggagacg catgcagaaa                                                     20

SEQ ID NO: 269          moltype = DNA   length = 24
FEATURE                 Location/Qualifiers
source                  1..24
                        mol_type = unassigned DNA
                        organism = Zea mays
SEQUENCE: 269
aaaacgttga aaaggatgc caca                                                 24

SEQ ID NO: 270          moltype = DNA   length = 24
FEATURE                 Location/Qualifiers
source                  1..24
                        mol_type = unassigned DNA
                        organism = Zea mays
SEQUENCE: 270
gcagtagcga atttacctga gact                                                24

SEQ ID NO: 271          moltype = DNA   length = 28
FEATURE                 Location/Qualifiers
source                  1..28
                        mol_type = unassigned DNA
                        organism = Zea mays
SEQUENCE: 271
gctgattcct taatcttgtg tttcaaca                                            28

SEQ ID NO: 272          moltype = DNA   length = 24
FEATURE                 Location/Qualifiers
source                  1..24
                        mol_type = unassigned DNA
                        organism = Zea mays
SEQUENCE: 272
atatgatcaa ccctgcagaa ttca                                                24

SEQ ID NO: 273          moltype = DNA   length = 27
FEATURE                 Location/Qualifiers
source                  1..27
                        mol_type = unassigned DNA
                        organism = Zea mays
SEQUENCE: 273
```

-continued

```
cacgaatgga ctaaagacac ttaagaa                                               27

SEQ ID NO: 274          moltype = DNA   length = 21
FEATURE                 Location/Qualifiers
source                  1..21
                        mol_type = unassigned DNA
                        organism = Zea mays
SEQUENCE: 274
ctgccacaag acacagcctt t                                                     21

SEQ ID NO: 275          moltype = DNA   length = 22
FEATURE                 Location/Qualifiers
source                  1..22
                        mol_type = unassigned DNA
                        organism = Zea mays
SEQUENCE: 275
gcttcatcaa ttggcagctc tt                                                    22

SEQ ID NO: 276          moltype = DNA   length = 21
FEATURE                 Location/Qualifiers
source                  1..21
                        mol_type = unassigned DNA
                        organism = Zea mays
SEQUENCE: 276
ctggtcctct ttgctgtgtc a                                                     21

SEQ ID NO: 277          moltype = DNA   length = 20
FEATURE                 Location/Qualifiers
source                  1..20
                        mol_type = unassigned DNA
                        organism = Zea mays
SEQUENCE: 277
ggcgggaagg tactggtttc                                                       20

SEQ ID NO: 278          moltype = DNA   length = 20
FEATURE                 Location/Qualifiers
source                  1..20
                        mol_type = unassigned DNA
                        organism = Zea mays
SEQUENCE: 278
ccctgcttgg aatggacatt                                                       20

SEQ ID NO: 279          moltype = DNA   length = 23
FEATURE                 Location/Qualifiers
source                  1..23
                        mol_type = unassigned DNA
                        organism = Zea mays
SEQUENCE: 279
ccactgttct ccagtcctct tca                                                   23

SEQ ID NO: 280          moltype = DNA   length = 25
FEATURE                 Location/Qualifiers
source                  1..25
                        mol_type = unassigned DNA
                        organism = Zea mays
SEQUENCE: 280
acaatctgcg gcttatccta actag                                                 25

SEQ ID NO: 281          moltype = DNA   length = 20
FEATURE                 Location/Qualifiers
source                  1..20
                        mol_type = unassigned DNA
                        organism = Zea mays
SEQUENCE: 281
gccaatgcga tgaagttgaa                                                       20

SEQ ID NO: 282          moltype = DNA   length = 24
FEATURE                 Location/Qualifiers
source                  1..24
                        mol_type = unassigned DNA
                        organism = Zea mays
SEQUENCE: 282
tttgcgtgga ctctaactgc ttat                                                  24

SEQ ID NO: 283          moltype = DNA   length = 23
FEATURE                 Location/Qualifiers
source                  1..23
                        mol_type = unassigned DNA
                        organism = Zea mays
```

```
SEQUENCE: 283
gaaggtgaca ttttcaggga tga                                               23

SEQ ID NO: 284          moltype = DNA   length = 19
FEATURE                 Location/Qualifiers
source                  1..19
                        mol_type = unassigned DNA
                        organism = Zea mays
SEQUENCE: 284
cgcttcacct gaggtagct                                                    19

SEQ ID NO: 285          moltype = DNA   length = 25
FEATURE                 Location/Qualifiers
source                  1..25
                        mol_type = unassigned DNA
                        organism = Zea mays
SEQUENCE: 285
ttggagtctg tgacattcaa tttca                                             25

SEQ ID NO: 286          moltype = DNA   length = 25
FEATURE                 Location/Qualifiers
source                  1..25
                        mol_type = unassigned DNA
                        organism = Zea mays
SEQUENCE: 286
gctgtcgaac gacttctcaa gttat                                             25

SEQ ID NO: 287          moltype = DNA   length = 18
FEATURE                 Location/Qualifiers
source                  1..18
                        mol_type = unassigned DNA
                        organism = Zea mays
SEQUENCE: 287
tcgggcaaca accatcca                                                     18

SEQ ID NO: 288          moltype = DNA   length = 20
FEATURE                 Location/Qualifiers
source                  1..20
                        mol_type = unassigned DNA
                        organism = Zea mays
SEQUENCE: 288
cccccagaat gatcaccaaa                                                   20

SEQ ID NO: 289          moltype = DNA   length = 26
FEATURE                 Location/Qualifiers
source                  1..26
                        mol_type = unassigned DNA
                        organism = Zea mays
SEQUENCE: 289
ggtggtggaa atatttgaga tggtaa                                            26

SEQ ID NO: 290          moltype = DNA   length = 22
FEATURE                 Location/Qualifiers
source                  1..22
                        mol_type = unassigned DNA
                        organism = Zea mays
SEQUENCE: 290
acttccatac gaccaggtct ca                                                22

SEQ ID NO: 291          moltype = DNA   length = 19
FEATURE                 Location/Qualifiers
source                  1..19
                        mol_type = unassigned DNA
                        organism = Zea mays
SEQUENCE: 291
ctaccaaccc agcgacgaa                                                    19

SEQ ID NO: 292          moltype = DNA   length = 24
FEATURE                 Location/Qualifiers
source                  1..24
                        mol_type = unassigned DNA
                        organism = Zea mays
SEQUENCE: 292
gagacatcac ctgatcagtt agca                                              24

SEQ ID NO: 293          moltype = DNA   length = 21
FEATURE                 Location/Qualifiers
source                  1..21
                        mol_type = unassigned DNA
```

```
                        organism = Zea mays
SEQUENCE: 293
ggttcacctg catcgagaag a                                              21

SEQ ID NO: 294          moltype = DNA  length = 25
FEATURE                 Location/Qualifiers
source                  1..25
                        mol_type = unassigned DNA
                        organism = Zea mays
SEQUENCE: 294
gatccaacag atcactgagg taagg                                          25

SEQ ID NO: 295          moltype = DNA  length = 21
FEATURE                 Location/Qualifiers
source                  1..21
                        mol_type = unassigned DNA
                        organism = Zea mays
SEQUENCE: 295
ctgagcgtcc atcacagatc a                                              21

SEQ ID NO: 296          moltype = DNA  length = 16
FEATURE                 Location/Qualifiers
source                  1..16
                        mol_type = unassigned DNA
                        organism = Zea mays
SEQUENCE: 296
agcctcgccg gtgaag                                                    16

SEQ ID NO: 297          moltype = DNA  length = 26
FEATURE                 Location/Qualifiers
source                  1..26
                        mol_type = unassigned DNA
                        organism = Zea mays
SEQUENCE: 297
ccacctgaag taaagagggc tataga                                         26

SEQ ID NO: 298          moltype = DNA  length = 20
FEATURE                 Location/Qualifiers
source                  1..20
                        mol_type = unassigned DNA
                        organism = Zea mays
SEQUENCE: 298
ccatgcaaag catgaatcga                                                20

SEQ ID NO: 299          moltype = DNA  length = 23
FEATURE                 Location/Qualifiers
source                  1..23
                        mol_type = unassigned DNA
                        organism = Zea mays
SEQUENCE: 299
ctgcagggat gaacatacac caa                                            23

SEQ ID NO: 300          moltype = DNA  length = 22
FEATURE                 Location/Qualifiers
source                  1..22
                        mol_type = unassigned DNA
                        organism = Zea mays
SEQUENCE: 300
cagaaaggtc aaccgctgtt tg                                             22

SEQ ID NO: 301          moltype = DNA  length = 25
FEATURE                 Location/Qualifiers
source                  1..25
                        mol_type = unassigned DNA
                        organism = Zea mays
SEQUENCE: 301
catcagtttc cgtacattgt ttgca                                          25

SEQ ID NO: 302          moltype = DNA  length = 25
FEATURE                 Location/Qualifiers
source                  1..25
                        mol_type = unassigned DNA
                        organism = Zea mays
SEQUENCE: 302
atgatgatcg tagaaggctt gatgt                                          25

SEQ ID NO: 303          moltype = DNA  length = 20
FEATURE                 Location/Qualifiers
source                  1..20
```

```
                        mol_type = unassigned DNA
                        organism = Zea mays
SEQUENCE: 303
cgtgccagtc tgaagagctt                                               20

SEQ ID NO: 304          moltype = DNA   length = 28
FEATURE                 Location/Qualifiers
source                  1..28
                        mol_type = unassigned DNA
                        organism = Zea mays
SEQUENCE: 304
cgttaccaac ggaatatata agcaacac                                      28

SEQ ID NO: 305          moltype = DNA   length = 20
FEATURE                 Location/Qualifiers
source                  1..20
                        mol_type = unassigned DNA
                        organism = Zea mays
SEQUENCE: 305
tgcatccttt ttcccgtgaa                                               20

SEQ ID NO: 306          moltype = DNA   length = 22
FEATURE                 Location/Qualifiers
source                  1..22
                        mol_type = unassigned DNA
                        organism = Zea mays
SEQUENCE: 306
cggaatactt ggcaacgtcg at                                            22

SEQ ID NO: 307          moltype = DNA   length = 23
FEATURE                 Location/Qualifiers
source                  1..23
                        mol_type = unassigned DNA
                        organism = Zea mays
SEQUENCE: 307
ccacgacctc ttgagaaaaa gaa                                           23

SEQ ID NO: 308          moltype = DNA   length = 22
FEATURE                 Location/Qualifiers
source                  1..22
                        mol_type = unassigned DNA
                        organism = Zea mays
SEQUENCE: 308
gcttgggctt gaggtacaga ag                                            22

SEQ ID NO: 309          moltype = DNA   length = 23
FEATURE                 Location/Qualifiers
source                  1..23
                        mol_type = unassigned DNA
                        organism = Zea mays
SEQUENCE: 309
ccgttgacga ccatgatgta gag                                           23

SEQ ID NO: 310          moltype = DNA   length = 20
FEATURE                 Location/Qualifiers
source                  1..20
                        mol_type = unassigned DNA
                        organism = Zea mays
SEQUENCE: 310
gcacagtcga ggtggctata                                               20

SEQ ID NO: 311          moltype = DNA   length = 24
FEATURE                 Location/Qualifiers
source                  1..24
                        mol_type = unassigned DNA
                        organism = Zea mays
SEQUENCE: 311
ggaacaacat ccccaaatag agaa                                          24

SEQ ID NO: 312          moltype = DNA   length = 29
FEATURE                 Location/Qualifiers
source                  1..29
                        mol_type = unassigned DNA
                        organism = Zea mays
SEQUENCE: 312
ccttgatgta catattcatt tgggtctca                                     29

SEQ ID NO: 313          moltype = DNA   length = 24
FEATURE                 Location/Qualifiers
```

```
source                  1..24
                        mol_type = unassigned DNA
                        organism = Zea mays
SEQUENCE: 313
ggaacaacat ccccaaatag agaa                                          24

SEQ ID NO: 314          moltype = DNA   length = 18
FEATURE                 Location/Qualifiers
source                  1..18
                        mol_type = unassigned DNA
                        organism = Zea mays
SEQUENCE: 314
gcggtcacag tggcgtaa                                                 18

SEQ ID NO: 315          moltype = DNA   length = 25
FEATURE                 Location/Qualifiers
source                  1..25
                        mol_type = unassigned DNA
                        organism = Zea mays
SEQUENCE: 315
ccagctccta cttaaacagg aactg                                         25

SEQ ID NO: 316          moltype = DNA   length = 18
FEATURE                 Location/Qualifiers
source                  1..18
                        mol_type = unassigned DNA
                        organism = Zea mays
SEQUENCE: 316
gcatccctcc gccactag                                                 18

SEQ ID NO: 317          moltype = DNA   length = 28
FEATURE                 Location/Qualifiers
source                  1..28
                        mol_type = unassigned DNA
                        organism = Zea mays
SEQUENCE: 317
accgctacat tgttaagtta tcaatggt                                      28

SEQ ID NO: 318          moltype = DNA   length = 25
FEATURE                 Location/Qualifiers
source                  1..25
                        mol_type = unassigned DNA
                        organism = Zea mays
SEQUENCE: 318
ccagaaggag gagtgttctc aaata                                         25

SEQ ID NO: 319          moltype = DNA   length = 23
FEATURE                 Location/Qualifiers
source                  1..23
                        mol_type = unassigned DNA
                        organism = Zea mays
SEQUENCE: 319
catctaaaag tcgcgttgct ctt                                           23

SEQ ID NO: 320          moltype = DNA   length = 20
FEATURE                 Location/Qualifiers
source                  1..20
                        mol_type = unassigned DNA
                        organism = Zea mays
SEQUENCE: 320
tgcctcaatc agcaaatcca                                               20

SEQ ID NO: 321          moltype = DNA   length = 17
FEATURE                 Location/Qualifiers
source                  1..17
                        mol_type = unassigned DNA
                        organism = Zea mays
SEQUENCE: 321
cagcgcgaca cgatggt                                                  17

SEQ ID NO: 322          moltype = DNA   length = 22
FEATURE                 Location/Qualifiers
source                  1..22
                        mol_type = unassigned DNA
                        organism = Zea mays
SEQUENCE: 322
tggtcttgca tctatggttg ga                                            22

SEQ ID NO: 323          moltype = DNA   length = 18
```

```
FEATURE                 Location/Qualifiers
source                  1..18
                        mol_type = unassigned DNA
                        organism = Zea mays
SEQUENCE: 323
acgacgctgt gggaaacg                                                        18

SEQ ID NO: 324          moltype = DNA   length = 20
FEATURE                 Location/Qualifiers
source                  1..20
                        mol_type = unassigned DNA
                        organism = Zea mays
SEQUENCE: 324
cgtctcgtgc agtggtgaga                                                      20

SEQ ID NO: 325          moltype = DNA   length = 25
FEATURE                 Location/Qualifiers
source                  1..25
                        mol_type = unassigned DNA
                        organism = Zea mays
SEQUENCE: 325
cattctgaaa ccagattcca atgct                                                25

SEQ ID NO: 326          moltype = DNA   length = 22
FEATURE                 Location/Qualifiers
source                  1..22
                        mol_type = unassigned DNA
                        organism = Zea mays
SEQUENCE: 326
gccgtgtagg aacaacagtg aa                                                   22

SEQ ID NO: 327          moltype = DNA   length = 23
FEATURE                 Location/Qualifiers
source                  1..23
                        mol_type = unassigned DNA
                        organism = Zea mays
SEQUENCE: 327
ggttcatggg agagggaatt tga                                                  23

SEQ ID NO: 328          moltype = DNA   length = 20
FEATURE                 Location/Qualifiers
source                  1..20
                        mol_type = unassigned DNA
                        organism = Zea mays
SEQUENCE: 328
gcgtttcagc tccgtgtgtt                                                      20

SEQ ID NO: 329          moltype = DNA   length = 17
FEATURE                 Location/Qualifiers
source                  1..17
                        mol_type = unassigned DNA
                        organism = Zea mays
SEQUENCE: 329
gtcgccgcca tcatgtc                                                         17

SEQ ID NO: 330          moltype = DNA   length = 17
FEATURE                 Location/Qualifiers
source                  1..17
                        mol_type = unassigned DNA
                        organism = Zea mays
SEQUENCE: 330
tgtggcgctg caacgat                                                         17

SEQ ID NO: 331          moltype = DNA   length = 24
FEATURE                 Location/Qualifiers
source                  1..24
                        mol_type = unassigned DNA
                        organism = Zea mays
SEQUENCE: 331
ctgacaccag agtcatctga aggt                                                 24

SEQ ID NO: 332          moltype = DNA   length = 24
FEATURE                 Location/Qualifiers
source                  1..24
                        mol_type = unassigned DNA
                        organism = Zea mays
SEQUENCE: 332
agcaaatctt ccttcatcct catc                                                 24
```

| | | |
|---|---|---|
| SEQ ID NO: 333<br>FEATURE<br>source | moltype = DNA   length = 25<br>Location/Qualifiers<br>1..25<br>mol_type = unassigned DNA<br>organism = Zea mays | |
| SEQUENCE: 333<br>ccagcaactt tactgtcttc actga | | 25 |
| SEQ ID NO: 334<br>FEATURE<br>source | moltype = DNA   length = 25<br>Location/Qualifiers<br>1..25<br>mol_type = unassigned DNA<br>organism = Zea mays | |
| SEQUENCE: 334<br>gagatccaga tttcatcaaa aacca | | 25 |
| SEQ ID NO: 335<br>FEATURE<br>source | moltype = DNA   length = 15<br>Location/Qualifiers<br>1..15<br>mol_type = unassigned DNA<br>organism = Zea mays | |
| SEQUENCE: 335<br>cggcgcgtgg acgta | | 15 |
| SEQ ID NO: 336<br>FEATURE<br>source | moltype = DNA   length = 18<br>Location/Qualifiers<br>1..18<br>mol_type = unassigned DNA<br>organism = Zea mays | |
| SEQUENCE: 336<br>gccatttggg ccgtgatc | | 18 |
| SEQ ID NO: 337<br>FEATURE<br>source | moltype = DNA   length = 27<br>Location/Qualifiers<br>1..27<br>mol_type = unassigned DNA<br>organism = Zea mays | |
| SEQUENCE: 337<br>tctaacttgt agctgcttcc aaagatg | | 27 |
| SEQ ID NO: 338<br>FEATURE<br>source | moltype = DNA   length = 17<br>Location/Qualifiers<br>1..17<br>mol_type = unassigned DNA<br>organism = Zea mays | |
| SEQUENCE: 338<br>ccaccccgtg ccaaact | | 17 |
| SEQ ID NO: 339<br>FEATURE<br>source | moltype = DNA   length = 25<br>Location/Qualifiers<br>1..25<br>mol_type = unassigned DNA<br>organism = Zea mays | |
| SEQUENCE: 339<br>aagtggtcag gcatagagaa aatga | | 25 |
| SEQ ID NO: 340<br>FEATURE<br>source | moltype = DNA   length = 19<br>Location/Qualifiers<br>1..19<br>mol_type = unassigned DNA<br>organism = Zea mays | |
| SEQUENCE: 340<br>gtgcagttgc ccgtttgtt | | 19 |
| SEQ ID NO: 341<br>FEATURE<br>source | moltype = DNA   length = 25<br>Location/Qualifiers<br>1..25<br>mol_type = unassigned DNA<br>organism = Zea mays | |
| SEQUENCE: 341<br>ggcatggatc acttttatga caata | | 25 |
| SEQ ID NO: 342<br>FEATURE<br>source | moltype = DNA   length = 18<br>Location/Qualifiers<br>1..18<br>mol_type = unassigned DNA<br>organism = Zea mays | |
| SEQUENCE: 342<br>gcttggtcgc tggatgct | | 18 |

```
SEQ ID NO: 343            moltype = DNA  length = 16
FEATURE                   Location/Qualifiers
source                    1..16
                          mol_type = unassigned DNA
                          organism = Zea mays SEQUENCE: 343
cttgtccagc tatacg                                                         16

SEQ ID NO: 344            moltype = DNA  length = 14
FEATURE                   Location/Qualifiers
source                    1..14
                          mol_type = unassigned DNA
                          organism = Zea mays SEQUENCE: 344
acggcagatt aaag                                                           14

SEQ ID NO: 345            moltype = DNA  length = 14
FEATURE                   Location/Qualifiers
source                    1..14
                          mol_type = unassigned DNA
                          organism = Zea mays SEQUENCE: 345
tctgggaccg aagc                                                           14

SEQ ID NO: 346            moltype = DNA  length = 14
FEATURE                   Location/Qualifiers
source                    1..14
                          mol_type = unassigned DNA
                          organism = Zea mays SEQUENCE: 346
cacacgcgag acag                                                           14

SEQ ID NO: 347            moltype = DNA  length = 17
FEATURE                   Location/Qualifiers
source                    1..17
                          mol_type = unassigned DNA
                          organism = Zea mays SEQUENCE: 347
tggtagatag cagttct                                                        17

SEQ ID NO: 348            moltype = DNA  length = 14
FEATURE                   Location/Qualifiers
source                    1..14
                          mol_type = unassigned DNA
                          organism = Zea mays SEQUENCE: 348
ctcgtgtatc tctg                                                           14

SEQ ID NO: 349            moltype = DNA  length = 15
FEATURE                   Location/Qualifiers
source                    1..15
                          mol_type = unassigned DNA
                          organism = Zea mays SEQUENCE: 349
cacgacagac agaac                                                          15

SEQ ID NO: 350            moltype = DNA  length = 13
FEATURE                   Location/Qualifiers
source                    1..13
                          mol_type = unassigned DNA
                          organism = Zea mays SEQUENCE: 350
acgggacgca ctc                                                            13

SEQ ID NO: 351            moltype = DNA  length = 14
FEATURE                   Location/Qualifiers
source                    1..14
                          mol_type = unassigned DNA
                          organism = Zea mays SEQUENCE: 351
cggtcagccg tgcc                                                           14

SEQ ID NO: 352            moltype = DNA  length = 17
FEATURE                   Location/Qualifiers
source                    1..17
                          mol_type = unassigned DNA
                          organism = Zea mays

SEQUENCE: 352
```

```
acgagtcaat taaagtt                                                                    17

SEQ ID NO: 353          moltype = DNA  length = 16
FEATURE                 Location/Qualifiers
source                  1..16
                        mol_type = unassigned DNA
                        organism = Zea mays SEQUENCE: 353
cttgatcccg gcggtg                                                                     16

SEQ ID NO: 354          moltype = DNA  length = 14
FEATURE                 Location/Qualifiers
source                  1..14
                        mol_type = unassigned DNA
                        organism = Zea mays SEQUENCE: 354
tctgcagccg ctgc                                                                       14

SEQ ID NO: 355          moltype = DNA  length = 16
FEATURE                 Location/Qualifiers
source                  1..16
                        mol_type = unassigned DNA
                        organism = Zea mays SEQUENCE: 355
ccatcaacca taataa                                                                     16

SEQ ID NO: 356          moltype = DNA  length = 19
FEATURE                 Location/Qualifiers
source                  1..19
                        mol_type = unassigned DNA
                        organism = Zea mays SEQUENCE: 356
caattggagt aatgaattc                                                                  19

SEQ ID NO: 357          moltype = DNA  length = 14
FEATURE                 Location/Qualifiers
source                  1..14
                        mol_type = unassigned DNA
                        organism = Zea mays SEQUENCE: 357
cgaatccaca tctt                                                                       14

SEQ ID NO: 358          moltype = DNA  length = 15
FEATURE                 Location/Qualifiers
source                  1..15
                        mol_type = unassigned DNA
                        organism = Zea mays SEQUENCE: 358
cggttccaca gacgt                                                                      15

SEQ ID NO: 359          moltype = DNA  length = 17
FEATURE                 Location/Qualifiers
source                  1..17
                        mol_type = unassigned DNA
                        organism = Zea mays SEQUENCE: 359
atctcctgcc tgctgtg                                                                    17

SEQ ID NO: 360          moltype = DNA  length = 14
FEATURE                 Location/Qualifiers
source                  1..14
                        mol_type = unassigned DNA
                        organism = Zea mays SEQUENCE: 360
tggccttgtt ccgg                                                                       14

SEQ ID NO: 361          moltype = DNA  length = 15
FEATURE                 Location/Qualifiers
source                  1..15
                        mol_type = unassigned DNA
                        organism = Zea mays SEQUENCE: 361
caccaggtat agtcc                                                                      15

SEQ ID NO: 362          moltype = DNA  length = 16
FEATURE                 Location/Qualifiers
source                  1..16
                        mol_type = unassigned DNA
                        organism = Zea mays
```

-continued

```
SEQUENCE: 362
catgcatgtt tttaag                                                     16

SEQ ID NO: 363         moltype = DNA   length = 14
FEATURE                Location/Qualifiers
source                 1..14
                       mol_type = unassigned DNA
                       organism = Zea mays
SEQUENCE: 363
cgttcgagat cgag                                                       14

SEQ ID NO: 364         moltype = DNA   length = 13
FEATURE                Location/Qualifiers
source                 1..13
                       mol_type = unassigned DNA
                       organism = Zea mays
SEQUENCE: 364
cgcatgaaat tga                                                        13

SEQ ID NO: 365         moltype = DNA   length = 16
FEATURE                Location/Qualifiers
source                 1..16
                       mol_type = unassigned DNA
                       organism = Zea mays
SEQUENCE: 365
cctcacctgt aacaag                                                     16

SEQ ID NO: 366         moltype = DNA   length = 16
FEATURE                Location/Qualifiers
source                 1..16
                       mol_type = unassigned DNA
                       organism = Zea mays
SEQUENCE: 366
cacgatagga attagt                                                     16

SEQ ID NO: 367         moltype = DNA   length = 18
FEATURE                Location/Qualifiers
source                 1..18
                       mol_type = unassigned DNA
                       organism = Zea mays
SEQUENCE: 367
caaggtcgat ctctccct                                                   18

SEQ ID NO: 368         moltype = DNA   length = 15
FEATURE                Location/Qualifiers
source                 1..15
                       mol_type = unassigned DNA
                       organism = Zea mays
SEQUENCE: 368
aactgggatt actcc                                                      15

SEQ ID NO: 369         moltype = DNA   length = 19
FEATURE                Location/Qualifiers
source                 1..19
                       mol_type = unassigned DNA
                       organism = Zea mays
SEQUENCE: 369
ttctaggacc cctcatcat                                                  19

SEQ ID NO: 370         moltype = DNA   length = 17
FEATURE                Location/Qualifiers
source                 1..17
                       mol_type = unassigned DNA
                       organism = Zea mays
SEQUENCE: 370
tgggtactaa caacaag                                                    17

SEQ ID NO: 371         moltype = DNA   length = 15
FEATURE                Location/Qualifiers
source                 1..15
                       mol_type = unassigned DNA
                       organism = Zea mays
SEQUENCE: 371
cttcttgaat cttcg                                                      15

SEQ ID NO: 372         moltype = DNA   length = 15
FEATURE                Location/Qualifiers
source                 1..15
                       mol_type = unassigned DNA
```

```
                            organism = Zea mays
SEQUENCE: 372
acagtcggat ttaat                                                           15

SEQ ID NO: 373          moltype = DNA  length = 21
FEATURE                 Location/Qualifiers
source                  1..21
                        mol_type = unassigned DNA
                        organism = Zea mays
SEQUENCE: 373
cataaataaa gcacatattc a                                                    21

SEQ ID NO: 374          moltype = DNA  length = 18
FEATURE                 Location/Qualifiers
source                  1..18
                        mol_type = unassigned DNA
                        organism = Zea mays
SEQUENCE: 374
cttgattaga ccaaagtg                                                        18

SEQ ID NO: 375          moltype = DNA  length = 16
FEATURE                 Location/Qualifiers
source                  1..16
                        mol_type = unassigned DNA
                        organism = Zea mays
SEQUENCE: 375
aggatgaata cttctc                                                          16

SEQ ID NO: 376          moltype = DNA  length = 15
FEATURE                 Location/Qualifiers
source                  1..15
                        mol_type = unassigned DNA
                        organism = Zea mays
SEQUENCE: 376
cctctacgat catcc                                                           15

SEQ ID NO: 377          moltype = DNA  length = 15
FEATURE                 Location/Qualifiers
source                  1..15
                        mol_type = unassigned DNA
                        organism = Zea mays
SEQUENCE: 377
cagcctcaac gctgg                                                           15

SEQ ID NO: 378          moltype = DNA  length = 14
FEATURE                 Location/Qualifiers
source                  1..14
                        mol_type = unassigned DNA
                        organism = Zea mays
SEQUENCE: 378
tgtcagctat ctcc                                                            14

SEQ ID NO: 379          moltype = DNA  length = 14
FEATURE                 Location/Qualifiers
source                  1..14
                        mol_type = unassigned DNA
                        organism = Zea mays
SEQUENCE: 379
tgtggagagg aacg                                                            14

SEQ ID NO: 380          moltype = DNA  length = 15
FEATURE                 Location/Qualifiers
source                  1..15
                        mol_type = unassigned DNA
                        organism = Zea mays
SEQUENCE: 380
cgaaggacta aagaa                                                           15

SEQ ID NO: 381          moltype = DNA  length = 16
FEATURE                 Location/Qualifiers
source                  1..16
                        mol_type = unassigned DNA
                        organism = Zea mays
SEQUENCE: 381
actttgggat aacgca                                                          16

SEQ ID NO: 382          moltype = DNA  length = 16
FEATURE                 Location/Qualifiers
source                  1..16
```

-continued

```
                    mol_type = unassigned DNA
                    organism = Zea mays
SEQUENCE: 382
ctcgacagaa gaacat                                                   16

SEQ ID NO: 383          moltype = DNA  length = 17
FEATURE                 Location/Qualifiers
source                  1..17
                        mol_type = unassigned DNA
                        organism = Zea mays
SEQUENCE: 383
cctcaacagt ggtagct                                                  17

SEQ ID NO: 384          moltype = DNA  length = 13
FEATURE                 Location/Qualifiers
source                  1..13
                        mol_type = unassigned DNA
                        organism = Zea mays
SEQUENCE: 384
cgcagggctc gtg                                                      13

SEQ ID NO: 385          moltype = DNA  length = 20
FEATURE                 Location/Qualifiers
source                  1..20
                        mol_type = unassigned DNA
                        organism = Zea mays
SEQUENCE: 385
catactcttc gatacatatt                                               20

SEQ ID NO: 386          moltype = DNA  length = 14
FEATURE                 Location/Qualifiers
source                  1..14
                        mol_type = unassigned DNA
                        organism = Zea mays
SEQUENCE: 386
atcagcggca gaaa                                                     14

SEQ ID NO: 387          moltype = DNA  length = 13
FEATURE                 Location/Qualifiers
source                  1..13
                        mol_type = unassigned DNA
                        organism = Zea mays
SEQUENCE: 387
agctcggaat gcg                                                      13

SEQ ID NO: 388          moltype = DNA  length = 16
FEATURE                 Location/Qualifiers
source                  1..16
                        mol_type = unassigned DNA
                        organism = Zea mays
SEQUENCE: 388
caacttgcgt tatttt                                                   16

SEQ ID NO: 389          moltype = DNA  length = 15
FEATURE                 Location/Qualifiers
source                  1..15
                        mol_type = unassigned DNA
                        organism = Zea mays
SEQUENCE: 389
caacacacac attaa                                                    15

SEQ ID NO: 390          moltype = DNA  length = 20
FEATURE                 Location/Qualifiers
source                  1..20
                        mol_type = unassigned DNA
                        organism = Zea mays
SEQUENCE: 390
ataaagcagc taatttgcta                                               20

SEQ ID NO: 391          moltype = DNA  length = 16
FEATURE                 Location/Qualifiers
source                  1..16
                        mol_type = unassigned DNA
                        organism = Zea mays
SEQUENCE: 391
ctgtttcctt gtttct                                                   16

SEQ ID NO: 392          moltype = DNA  length = 16
FEATURE                 Location/Qualifiers
```

```
source                          1..16
                                mol_type = unassigned DNA
                                organism = Zea mays
SEQUENCE: 392
agatggagta atttgg                                                               16

SEQ ID NO: 393                  moltype = DNA   length = 14
FEATURE                         Location/Qualifiers
source                          1..14
                                mol_type = unassigned DNA
                                organism = Zea mays
SEQUENCE: 393
cttcgacaaa atgg                                                                 14

SEQ ID NO: 394                  moltype = DNA   length = 17
FEATURE                         Location/Qualifiers
source                          1..17
                                mol_type = unassigned DNA
                                organism = Zea mays
SEQUENCE: 394
tcaaatccaa aaagcag                                                              17

SEQ ID NO: 395                  moltype = DNA   length = 16
FEATURE                         Location/Qualifiers
source                          1..16
                                mol_type = unassigned DNA
                                organism = Zea mays
SEQUENCE: 395
cggactaaag cacttt                                                               16

SEQ ID NO: 396                  moltype = DNA   length = 17
FEATURE                         Location/Qualifiers
source                          1..17
                                mol_type = unassigned DNA
                                organism = Zea mays
SEQUENCE: 396
agaattgctg gatgcat                                                              17

SEQ ID NO: 397                  moltype = DNA   length = 15
FEATURE                         Location/Qualifiers
source                          1..15
                                mol_type = unassigned DNA
                                organism = Zea mays
SEQUENCE: 397
ccagcttgtt tattc                                                                15

SEQ ID NO: 398                  moltype = DNA   length = 15
FEATURE                         Location/Qualifiers
source                          1..15
                                mol_type = unassigned DNA
                                organism = Zea mays
SEQUENCE: 398
acgatcaagg caaac                                                                15

SEQ ID NO: 399                  moltype = DNA   length = 16
FEATURE                         Location/Qualifiers
source                          1..16
                                mol_type = unassigned DNA
                                organism = Zea mays
SEQUENCE: 399
ctcattaaca gaaaat                                                               16

SEQ ID NO: 400                  moltype = DNA   length = 15
FEATURE                         Location/Qualifiers
source                          1..15
                                mol_type = unassigned DNA
                                organism = Zea mays
SEQUENCE: 400
agtggttgaa aagat                                                                15

SEQ ID NO: 401                  moltype = DNA   length = 18
FEATURE                         Location/Qualifiers
source                          1..18
                                mol_type = unassigned DNA
                                organism = Zea mays
SEQUENCE: 401
aagcgattca agcacaa                                                              18

SEQ ID NO: 402                  moltype = DNA   length = 18
```

```
FEATURE                Location/Qualifiers
source                 1..18
                       mol_type = unassigned DNA
                       organism = Zea mays
SEQUENCE: 402
cgtaattgat taaacctc                                                            18

SEQ ID NO: 403         moltype = DNA  length = 20
FEATURE                Location/Qualifiers
source                 1..20
                       mol_type = unassigned DNA
                       organism = Zea mays
SEQUENCE: 403
ttgctttaaa ttataaaatc                                                          20

SEQ ID NO: 404         moltype = DNA  length = 20
FEATURE                Location/Qualifiers
source                 1..20
                       mol_type = unassigned DNA
                       organism = Zea mays
SEQUENCE: 404
ctgtgcatat ttggtgttag                                                          20

SEQ ID NO: 405         moltype = DNA  length = 15
FEATURE                Location/Qualifiers
source                 1..15
                       mol_type = unassigned DNA
                       organism = Zea mays
SEQUENCE: 405
atggcacgtt gatca                                                               15

SEQ ID NO: 406         moltype = DNA  length = 20
FEATURE                Location/Qualifiers
source                 1..20
                       mol_type = unassigned DNA
                       organism = Zea mays
SEQUENCE: 406
tagttacagt acaagaacaa                                                          20

SEQ ID NO: 407         moltype = DNA  length = 14
FEATURE                Location/Qualifiers
source                 1..14
                       mol_type = unassigned DNA
                       organism = Zea mays
SEQUENCE: 407
aggagccctg ggag                                                                14

SEQ ID NO: 408         moltype = DNA  length = 15
FEATURE                Location/Qualifiers
source                 1..15
                       mol_type = unassigned DNA
                       organism = Zea mays
SEQUENCE: 408
ccttgacagc aaagt                                                               15

SEQ ID NO: 409         moltype = DNA  length = 19
FEATURE                Location/Qualifiers
source                 1..19
                       mol_type = unassigned DNA
                       organism = Zea mays
SEQUENCE: 409
ccaatataca gataatctg                                                           19

SEQ ID NO: 410         moltype = DNA  length = 18
FEATURE                Location/Qualifiers
source                 1..18
                       mol_type = unassigned DNA
                       organism = Zea mays
SEQUENCE: 410
cccgttcttg ttgaccag                                                            18

SEQ ID NO: 411         moltype = DNA  length = 13
FEATURE                Location/Qualifiers
source                 1..13
                       mol_type = unassigned DNA
                       organism = Zea mays
SEQUENCE: 411
tccccatgct ttc                                                                 13
```

| | | |
|---|---|---|
| SEQ ID NO: 412 | moltype = DNA length = 17 | |
| FEATURE | Location/Qualifiers | |
| source | 1..17<br>mol_type = unassigned DNA<br>organism = Zea mays | |
| SEQUENCE: 412 | | |
| aaaacaaggt atctttc | | 17 |
| SEQ ID NO: 413 | moltype = DNA length = 19 | |
| FEATURE | Location/Qualifiers | |
| source | 1..19<br>mol_type = unassigned DNA<br>organism = Zea mays | |
| SEQUENCE: 413 | | |
| cttctactat caagattgc | | 19 |
| SEQ ID NO: 414 | moltype = DNA length = 18 | |
| FEATURE | Location/Qualifiers | |
| source | 1..18<br>mol_type = unassigned DNA<br>organism = Zea mays | |
| SEQUENCE: 414 | | |
| cactgtacgc ttcaatgt | | 18 |
| SEQ ID NO: 415 | moltype = DNA length = 19 | |
| FEATURE | Location/Qualifiers | |
| source | 1..19<br>mol_type = unassigned DNA<br>organism = Zea mays | |
| SEQUENCE: 415 | | |
| cttaggatca tcttttct | | 19 |
| SEQ ID NO: 416 | moltype = DNA length = 14 | |
| FEATURE | Location/Qualifiers | |
| source | 1..14<br>mol_type = unassigned DNA<br>organism = Zea mays | |
| SEQUENCE: 416 | | |
| tctgaccaag aaac | | 14 |
| SEQ ID NO: 417 | moltype = DNA length = 16 | |
| FEATURE | Location/Qualifiers | |
| source | 1..16<br>mol_type = unassigned DNA<br>organism = Zea mays | |
| SEQUENCE: 417 | | |
| ctgctctagc atcgac | | 16 |
| SEQ ID NO: 418 | moltype = DNA length = 18 | |
| FEATURE | Location/Qualifiers | |
| source | 1..18<br>mol_type = unassigned DNA<br>organism = Zea mays | |
| SEQUENCE: 418 | | |
| atttgcattt gctactcg | | 18 |
| SEQ ID NO: 419 | moltype = DNA length = 17 | |
| FEATURE | Location/Qualifiers | |
| source | 1..17<br>mol_type = unassigned DNA<br>organism = Zea mays | |
| SEQUENCE: 419 | | |
| agaccaataa tcaatgc | | 17 |
| SEQ ID NO: 420 | moltype = DNA length = 16 | |
| FEATURE | Location/Qualifiers | |
| source | 1..16<br>mol_type = unassigned DNA<br>organism = Zea mays | |
| SEQUENCE: 420 | | |
| caaatgcgga gtccag | | 16 |
| SEQ ID NO: 421 | moltype = DNA length = 14 | |
| FEATURE | Location/Qualifiers | |
| source | 1..14<br>mol_type = unassigned DNA<br>organism = Zea mays | |
| SEQUENCE: 421 | | |
| agctccacaa cgat | | 14 |

| | | |
|---|---|---|
| SEQ ID NO: 422<br>FEATURE<br>source | moltype = DNA   length = 16<br>Location/Qualifiers<br>1..16<br>mol_type = unassigned DNA<br>organism = Zea mays | |
| SEQUENCE: 422<br>caccagatta aacctt | | 16 |
| SEQ ID NO: 423<br>FEATURE<br>source | moltype = DNA   length = 16<br>Location/Qualifiers<br>1..16<br>mol_type = unassigned DNA<br>organism = Zea mays | |
| SEQUENCE: 423<br>catctccctg tgcctc | | 16 |
| SEQ ID NO: 424<br>FEATURE<br>source | moltype = DNA   length = 15<br>Location/Qualifiers<br>1..15<br>mol_type = unassigned DNA<br>organism = Zea mays | |
| SEQUENCE: 424<br>ctgtgccttc ttggc | | 15 |
| SEQ ID NO: 425<br>FEATURE<br>source | moltype = DNA   length = 14<br>Location/Qualifiers<br>1..14<br>mol_type = unassigned DNA<br>organism = Zea mays | |
| SEQUENCE: 425<br>catgtgctaa cttc | | 14 |
| SEQ ID NO: 426<br>FEATURE<br>source | moltype = DNA   length = 16<br>Location/Qualifiers<br>1..16<br>mol_type = unassigned DNA<br>organism = Zea mays | |
| SEQUENCE: 426<br>cagacaaata atttca | | 16 |
| SEQ ID NO: 427<br>FEATURE<br>source | moltype = DNA   length = 14<br>Location/Qualifiers<br>1..14<br>mol_type = unassigned DNA<br>organism = Zea mays | |
| SEQUENCE: 427<br>catgtgctaa cttc | | 14 |
| SEQ ID NO: 428<br>FEATURE<br>source | moltype = DNA   length = 14<br>Location/Qualifiers<br>1..14<br>mol_type = unassigned DNA<br>organism = Zea mays | |
| SEQUENCE: 428<br>cggagtggca ttct | | 14 |
| SEQ ID NO: 429<br>FEATURE<br>source | moltype = DNA   length = 15<br>Location/Qualifiers<br>1..15<br>mol_type = unassigned DNA<br>organism = Zea mays | |
| SEQUENCE: 429<br>aggtttgcat actct | | 15 |
| SEQ ID NO: 430<br>FEATURE<br>source | moltype = DNA   length = 13<br>Location/Qualifiers<br>1..13<br>mol_type = unassigned DNA<br>organism = Zea mays | |
| SEQUENCE: 430<br>ccactcagaa aac | | 13 |
| SEQ ID NO: 431<br>FEATURE<br>source | moltype = DNA   length = 19<br>Location/Qualifiers<br>1..19<br>mol_type = unassigned DNA<br>organism = Zea mays | |
| SEQUENCE: 431 | | | catatttagc gtttcatca                                               19

SEQ ID NO: 432         moltype = DNA  length = 14
FEATURE                Location/Qualifiers
source                 1..14
                       mol_type = unassigned DNA
                       organism = Zea mays
SEQUENCE: 432
ccccatcaat gatt                                                    14

SEQ ID NO: 433         moltype = DNA  length = 16
FEATURE                Location/Qualifiers
source                 1..16
                       mol_type = unassigned DNA
                       organism = Zea mays
SEQUENCE: 433
tttgttgcag aggaag                                                  16

SEQ ID NO: 434         moltype = DNA  length = 15
FEATURE                Location/Qualifiers
source                 1..15
                       mol_type = unassigned DNA
                       organism = Zea mays
SEQUENCE: 434
tgagcaacta gcgcc                                                   15

SEQ ID NO: 435         moltype = DNA  length = 13
FEATURE                Location/Qualifiers
source                 1..13
                       mol_type = unassigned DNA
                       organism = Zea mays
SEQUENCE: 435
tgacggcatc gac                                                     13

SEQ ID NO: 436         moltype = DNA  length = 16
FEATURE                Location/Qualifiers
source                 1..16
                       mol_type = unassigned DNA
                       organism = Zea mays
SEQUENCE: 436
cagagcacac tagttt                                                  16

SEQ ID NO: 437         moltype = DNA  length = 13
FEATURE                Location/Qualifiers
source                 1..13
                       mol_type = unassigned DNA
                       organism = Zea mays
SEQUENCE: 437
tcggtcgcca aac                                                     13

SEQ ID NO: 438         moltype = DNA  length = 16
FEATURE                Location/Qualifiers
source                 1..16
                       mol_type = unassigned DNA
                       organism = Zea mays
SEQUENCE: 438
caacacacga cttagt                                                  16

SEQ ID NO: 439         moltype = DNA  length = 17
FEATURE                Location/Qualifiers
source                 1..17
                       mol_type = unassigned DNA
                       organism = Zea mays
SEQUENCE: 439
tgagctgaga tgaacct                                                 17

SEQ ID NO: 440         moltype = DNA  length = 20
FEATURE                Location/Qualifiers
source                 1..20
                       mol_type = unassigned DNA
                       organism = Zea mays
SEQUENCE: 440
aaatacatct aaaaacttca                                              20

SEQ ID NO: 441         moltype = DNA  length = 16
FEATURE                Location/Qualifiers
source                 1..16
                       mol_type = unassigned DNA
                       organism = Zea mays -continued

```
SEQUENCE: 441
atgtgcatca acgatg                                                        16

SEQ ID NO: 442         moltype = DNA   length = 14
FEATURE                Location/Qualifiers
source                 1..14
                       mol_type = unassigned DNA
                       organism = Zea mays
SEQUENCE: 442
atgcagcata cctg                                                          14

SEQ ID NO: 443         moltype = DNA   length = 16
FEATURE                Location/Qualifiers
source                 1..16
                       mol_type = unassigned DNA
                       organism = Zea mays
SEQUENCE: 443
ttactctagc atcgcc                                                        16

SEQ ID NO: 444         moltype = DNA   length = 14
FEATURE                Location/Qualifiers
source                 1..14
                       mol_type = unassigned DNA
                       organism = Zea mays
SEQUENCE: 444
cacgaacacg aagc                                                          14

SEQ ID NO: 445         moltype = DNA   length = 16
FEATURE                Location/Qualifiers
source                 1..16
                       mol_type = unassigned DNA
                       organism = Zea mays
SEQUENCE: 445
cctttttaca tcctcc                                                        16

SEQ ID NO: 446         moltype = DNA   length = 15
FEATURE                Location/Qualifiers
source                 1..15
                       mol_type = unassigned DNA
                       organism = Zea mays
SEQUENCE: 446
acaagagaga acttc                                                         15

SEQ ID NO: 447         moltype = DNA   length = 15
FEATURE                Location/Qualifiers
source                 1..15
                       mol_type = unassigned DNA
                       organism = Zea mays
SEQUENCE: 447
acagagggat tggtg                                                         15

SEQ ID NO: 448         moltype = DNA   length = 15
FEATURE                Location/Qualifiers
source                 1..15
                       mol_type = unassigned DNA
                       organism = Zea mays
SEQUENCE: 448
accatgcaac atatg                                                         15

SEQ ID NO: 449         moltype = DNA   length = 15
FEATURE                Location/Qualifiers
source                 1..15
                       mol_type = unassigned DNA
                       organism = Zea mays
SEQUENCE: 449
cctctaggat cagcg                                                         15

SEQ ID NO: 450         moltype = DNA   length = 18
FEATURE                Location/Qualifiers
source                 1..18
                       mol_type = unassigned DNA
                       organism = Zea mays
SEQUENCE: 450
atcggtaaag aagaagaa                                                      18

SEQ ID NO: 451         moltype = DNA   length = 20
FEATURE                Location/Qualifiers
source                 1..20
                       mol_type = unassigned DNA
```

```
                                    organism = Zea mays
SEQUENCE: 451
cagttgacaa tatagcctac                                                    20

SEQ ID NO: 452         moltype = DNA  length = 15
FEATURE                Location/Qualifiers
source                 1..15
                       mol_type = unassigned DNA
                       organism = Zea mays
SEQUENCE: 452
cgagaacgga gtttg                                                         15

SEQ ID NO: 453         moltype = DNA  length = 15
FEATURE                Location/Qualifiers
source                 1..15
                       mol_type = unassigned DNA
                       organism = Zea mays
SEQUENCE: 453
atgctcctat ttctg                                                         15

SEQ ID NO: 454         moltype = DNA  length = 14
FEATURE                Location/Qualifiers
source                 1..14
                       mol_type = unassigned DNA
                       organism = Zea mays
SEQUENCE: 454
tgggcttgac cttt                                                          14

SEQ ID NO: 455         moltype = DNA  length = 13
FEATURE                Location/Qualifiers
source                 1..13
                       mol_type = unassigned DNA
                       organism = Zea mays
SEQUENCE: 455
atgcaaagct tcc                                                           13

SEQ ID NO: 456         moltype = DNA  length = 13
FEATURE                Location/Qualifiers
source                 1..13
                       mol_type = unassigned DNA
                       organism = Zea mays
SEQUENCE: 456
ttcgcaccaa acc                                                           13

SEQ ID NO: 457         moltype = DNA  length = 15
FEATURE                Location/Qualifiers
source                 1..15
                       mol_type = unassigned DNA
                       organism = Zea mays
SEQUENCE: 457
tgtccagcca tacgt                                                         15

SEQ ID NO: 458         moltype = DNA  length = 13
FEATURE                Location/Qualifiers
source                 1..13
                       mol_type = unassigned DNA
                       organism = Zea mays
SEQUENCE: 458
cggcaaatta aag                                                           13

SEQ ID NO: 459         moltype = DNA  length = 14
FEATURE                Location/Qualifiers
source                 1..14
                       mol_type = unassigned DNA
                       organism = Zea mays
SEQUENCE: 459
tgggactgaa gcga                                                          14

SEQ ID NO: 460         moltype = DNA  length = 13
FEATURE                Location/Qualifiers
source                 1..13
                       mol_type = unassigned DNA
                       organism = Zea mays
SEQUENCE: 460
cgcgacacag cta                                                           13

SEQ ID NO: 461         moltype = DNA  length = 19
FEATURE                Location/Qualifiers
source                 1..19
```

```
                            mol_type = unassigned DNA
                            organism = Zea mays
SEQUENCE: 461
agatagcaat tcttatcct                                                     19

SEQ ID NO: 462              moltype = DNA   length = 14
FEATURE                     Location/Qualifiers
source                      1..14
                            mol_type = unassigned DNA
                            organism = Zea mays
SEQUENCE: 462
tcgtgtgtct ctgc                                                          14

SEQ ID NO: 463              moltype = DNA   length = 15
FEATURE                     Location/Qualifiers
source                      1..15
                            mol_type = unassigned DNA
                            organism = Zea mays
SEQUENCE: 463
cacgacaggc agaac                                                         15

SEQ ID NO: 464              moltype = DNA   length = 13
FEATURE                     Location/Qualifiers
source                      1..13
                            mol_type = unassigned DNA
                            organism = Zea mays
SEQUENCE: 464
cgggatgcac tcg                                                           13

SEQ ID NO: 465              moltype = DNA   length = 14
FEATURE                     Location/Qualifiers
source                      1..14
                            mol_type = unassigned DNA
                            organism = Zea mays
SEQUENCE: 465
cggtcagtcg tgcc                                                          14

SEQ ID NO: 466              moltype = DNA   length = 17
FEATURE                     Location/Qualifiers
source                      1..17
                            mol_type = unassigned DNA
                            organism = Zea mays
SEQUENCE: 466
acgagtcaat tgaagtt                                                       17

SEQ ID NO: 467              moltype = DNA   length = 17
FEATURE                     Location/Qualifiers
source                      1..17
                            mol_type = unassigned DNA
                            organism = Zea mays
SEQUENCE: 467
tcttgatccc agcggtg                                                       17

SEQ ID NO: 468              moltype = DNA   length = 14
FEATURE                     Location/Qualifiers
source                      1..14
                            mol_type = unassigned DNA
                            organism = Zea mays
SEQUENCE: 468
tctgctgccg ctgc                                                          14

SEQ ID NO: 469              moltype = DNA   length = 15
FEATURE                     Location/Qualifiers
source                      1..15
                            mol_type = unassigned DNA
                            organism = Zea mays
SEQUENCE: 469
aaccacaata atttc                                                         15

SEQ ID NO: 470              moltype = DNA   length = 16
FEATURE                     Location/Qualifiers
source                      1..16
                            mol_type = unassigned DNA
                            organism = Zea mays
SEQUENCE: 470
ttggagtagt gaattc                                                        16

SEQ ID NO: 471              moltype = DNA   length = 15
FEATURE                     Location/Qualifiers
```

```
source                   1..15
                         mol_type = unassigned DNA
                         organism = Zea mays
SEQUENCE: 471
cgaatccacg tcttg                                                         15

SEQ ID NO: 472           moltype = DNA   length = 15
FEATURE                  Location/Qualifiers
source                   1..15
                         mol_type = unassigned DNA
                         organism = Zea mays
SEQUENCE: 472
ttccacggac gtcgt                                                         15

SEQ ID NO: 473           moltype = DNA   length = 14
FEATURE                  Location/Qualifiers
source                   1..14
                         mol_type = unassigned DNA
                         organism = Zea mays
SEQUENCE: 473
tcctgccagc tgtg                                                          14

SEQ ID NO: 474           moltype = DNA   length = 13
FEATURE                  Location/Qualifiers
source                   1..13
                         mol_type = unassigned DNA
                         organism = Zea mays
SEQUENCE: 474
tggccctgtt ccg                                                           13

SEQ ID NO: 475           moltype = DNA   length = 15
FEATURE                  Location/Qualifiers
source                   1..15
                         mol_type = unassigned DNA
                         organism = Zea mays
SEQUENCE: 475
ccaggtagag tccaa                                                         15

SEQ ID NO: 476           moltype = DNA   length = 15
FEATURE                  Location/Qualifiers
source                   1..15
                         mol_type = unassigned DNA
                         organism = Zea mays
SEQUENCE: 476
atgcatgctt ttaag                                                         15

SEQ ID NO: 477           moltype = DNA   length = 17
FEATURE                  Location/Qualifiers
source                   1..17
                         mol_type = unassigned DNA
                         organism = Zea mays
SEQUENCE: 477
ttctcgttct agatcga                                                       17

SEQ ID NO: 478           moltype = DNA   length = 13
FEATURE                  Location/Qualifiers
source                   1..13
                         mol_type = unassigned DNA
                         organism = Zea mays
SEQUENCE: 478
cgcatgaatt tga                                                           13

SEQ ID NO: 479           moltype = DNA   length = 15
FEATURE                  Location/Qualifiers
source                   1..15
                         mol_type = unassigned DNA
                         organism = Zea mays
SEQUENCE: 479
ctcacctgga acaag                                                         15

SEQ ID NO: 480           moltype = DNA   length = 16
FEATURE                  Location/Qualifiers
source                   1..16
                         mol_type = unassigned DNA
                         organism = Zea mays
SEQUENCE: 480
cacgatagga atgagt                                                        16

SEQ ID NO: 481           moltype = DNA   length = 17
```

```
FEATURE                 Location/Qualifiers
source                  1..17
                        mol_type = unassigned DNA
                        organism = Zea mays SEQUENCE: 481
aaggtcgata tctccct                                                          17

SEQ ID NO: 482          moltype = DNA   length = 18
FEATURE                 Location/Qualifiers
source                  1..18
                        mol_type = unassigned DNA
                        organism = Zea mays SEQUENCE: 482
ataactggga ttacttct                                                         18

SEQ ID NO: 483          moltype = DNA   length = 16
FEATURE                 Location/Qualifiers
source                  1..16
                        mol_type = unassigned DNA
                        organism = Zea mays SEQUENCE: 483
taggaccccc catcat                                                           16

SEQ ID NO: 484          moltype = DNA   length = 16
FEATURE                 Location/Qualifiers
source                  1..16
                        mol_type = unassigned DNA
                        organism = Zea mays SEQUENCE: 484
tgggtactga caacaa                                                           16

SEQ ID NO: 485          moltype = DNA   length = 15
FEATURE                 Location/Qualifiers
source                  1..15
                        mol_type = unassigned DNA
                        organism = Zea mays SEQUENCE: 485
cttcttgaac cttcg                                                            15

SEQ ID NO: 486          moltype = DNA   length = 15
FEATURE                 Location/Qualifiers
source                  1..15
                        mol_type = unassigned DNA
                        organism = Zea mays SEQUENCE: 486
acagtccgat ttaat                                                            15

SEQ ID NO: 487          moltype = DNA   length = 20
FEATURE                 Location/Qualifiers
source                  1..20
                        mol_type = unassigned DNA
                        organism = Zea mays SEQUENCE: 487
ataaataaag cacgtattca                                                       20

SEQ ID NO: 488          moltype = DNA   length = 16
FEATURE                 Location/Qualifiers
source                  1..16
                        mol_type = unassigned DNA
                        organism = Zea mays SEQUENCE: 488
tgattaggcc aaaagtg                                                          16

SEQ ID NO: 489          moltype = DNA   length = 16
FEATURE                 Location/Qualifiers
source                  1..16
                        mol_type = unassigned DNA
                        organism = Zea mays SEQUENCE: 489
aggatgacta cttctc                                                           16

SEQ ID NO: 490          moltype = DNA   length = 15
FEATURE                 Location/Qualifiers
source                  1..15
                        mol_type = unassigned DNA
                        organism = Zea mays SEQUENCE: 490
cctctacaat catcc                                                            15
```

| | | |
|---|---|---|
| SEQ ID NO: 491<br>FEATURE<br>source | moltype = DNA   length = 14<br>Location/Qualifiers<br>1..14<br>mol_type = unassigned DNA<br>organism = Zea mays | |
| SEQUENCE: 491<br>agcctcagcg ctgg | | 14 |
| SEQ ID NO: 492<br>FEATURE<br>source | moltype = DNA   length = 16<br>Location/Qualifiers<br>1..16<br>mol_type = unassigned DNA<br>organism = Zea mays | |
| SEQUENCE: 492<br>atgtcatcta tctccg | | 16 |
| SEQ ID NO: 493<br>FEATURE<br>source | moltype = DNA   length = 14<br>Location/Qualifiers<br>1..14<br>mol_type = unassigned DNA<br>organism = Zea mays | |
| SEQUENCE: 493<br>tggagtggaa cgct | | 14 |
| SEQ ID NO: 494<br>FEATURE<br>source | moltype = DNA   length = 14<br>Location/Qualifiers<br>1..14<br>mol_type = unassigned DNA<br>organism = Zea mays | |
| SEQUENCE: 494<br>agcgaagggc taaa | | 14 |
| SEQ ID NO: 495<br>FEATURE<br>source | moltype = DNA   length = 16<br>Location/Qualifiers<br>1..16<br>mol_type = unassigned DNA<br>organism = Zea mays | |
| SEQUENCE: 495<br>tcactttgag ataacg | | 16 |
| SEQ ID NO: 496<br>FEATURE<br>source | moltype = DNA   length = 17<br>Location/Qualifiers<br>1..17<br>mol_type = unassigned DNA<br>organism = Zea mays | |
| SEQUENCE: 496<br>tctcgacaga tgaacat | | 17 |
| SEQ ID NO: 497<br>FEATURE<br>source | moltype = DNA   length = 17<br>Location/Qualifiers<br>1..17<br>mol_type = unassigned DNA<br>organism = Zea mays | |
| SEQUENCE: 497<br>cctcaacaga ggtagct | | 17 |
| SEQ ID NO: 498<br>FEATURE<br>source | moltype = DNA   length = 14<br>Location/Qualifiers<br>1..14<br>mol_type = unassigned DNA<br>organism = Zea mays | |
| SEQUENCE: 498<br>tcgcaggact cgtg | | 14 |
| SEQ ID NO: 499<br>FEATURE<br>source | moltype = DNA   length = 20<br>Location/Qualifiers<br>1..20<br>mol_type = unassigned DNA<br>organism = Zea mays | |
| SEQUENCE: 499<br>catactcttc aatacatatt | | 20 |
| SEQ ID NO: 500<br>FEATURE<br>source | moltype = DNA   length = 16<br>Location/Qualifiers<br>1..16<br>mol_type = unassigned DNA<br>organism = Zea mays | |
| SEQUENCE: 500<br>tcatcagtgg cagaaa | | 16 |

```
SEQ ID NO: 501          moltype = DNA  length = 14
FEATURE                 Location/Qualifiers
source                  1..14
                        mol_type = unassigned DNA
                        organism = Zea mays
SEQUENCE: 501
ctcgggatgc gaac                                                          14

SEQ ID NO: 502          moltype = DNA  length = 18
FEATURE                 Location/Qualifiers
source                  1..18
                        mol_type = unassigned DNA
                        organism = Zea mays
SEQUENCE: 502
aacttgcatt attttatc                                                      18

SEQ ID NO: 503          moltype = DNA  length = 14
FEATURE                 Location/Qualifiers
source                  1..14
                        mol_type = unassigned DNA
                        organism = Zea mays
SEQUENCE: 503
cacacgcatt aata                                                          14

SEQ ID NO: 504          moltype = DNA  length = 20
FEATURE                 Location/Qualifiers
source                  1..20
                        mol_type = unassigned DNA
                        organism = Zea mays
SEQUENCE: 504
ataaagcagc tagtttgcta                                                    20

SEQ ID NO: 505          moltype = DNA  length = 16
FEATURE                 Location/Qualifiers
source                  1..16
                        mol_type = unassigned DNA
                        organism = Zea mays
SEQUENCE: 505
tgtttccctg tttctt                                                        16

SEQ ID NO: 506          moltype = DNA  length = 17
FEATURE                 Location/Qualifiers
source                  1..17
                        mol_type = unassigned DNA
                        organism = Zea mays
SEQUENCE: 506
atggagtagt ttggacc                                                       17

SEQ ID NO: 507          moltype = DNA  length = 15
FEATURE                 Location/Qualifiers
source                  1..15
                        mol_type = unassigned DNA
                        organism = Zea mays
SEQUENCE: 507
cttcgataaa atggc                                                         15

SEQ ID NO: 508          moltype = DNA  length = 16
FEATURE                 Location/Qualifiers
source                  1..16
                        mol_type = unassigned DNA
                        organism = Zea mays
SEQUENCE: 508
caaatccaag aagcag                                                        16

SEQ ID NO: 509          moltype = DNA  length = 13
FEATURE                 Location/Qualifiers
source                  1..13
                        mol_type = unassigned DNA
                        organism = Zea mays
SEQUENCE: 509
cggactcaag cac                                                           13

SEQ ID NO: 510          moltype = DNA  length = 17
FEATURE                 Location/Qualifiers
source                  1..17
                        mol_type = unassigned DNA
                        organism = Zea mays
SEQUENCE: 510
```

-continued

```
agaattgctg ggtgcat                                                    17

SEQ ID NO: 511        moltype = DNA   length = 16
FEATURE               Location/Qualifiers
source                1..16
                      mol_type = unassigned DNA
                      organism = Zea mays SEQUENCE: 511
cagcttgtct attcac                                                     16

SEQ ID NO: 512        moltype = DNA   length = 14
FEATURE               Location/Qualifiers
source                1..14
                      mol_type = unassigned DNA
                      organism = Zea mays SEQUENCE: 512
cgatcagggc aaac                                                       14

SEQ ID NO: 513        moltype = DNA   length = 18
FEATURE               Location/Qualifiers
source                1..18
                      mol_type = unassigned DNA
                      organism = Zea mays SEQUENCE: 513
attaacagga aatgatgc                                                   18

SEQ ID NO: 514        moltype = DNA   length = 15
FEATURE               Location/Qualifiers
source                1..15
                      mol_type = unassigned DNA
                      organism = Zea mays SEQUENCE: 514
tggttgcaaa gataa                                                      15

SEQ ID NO: 515        moltype = DNA   length = 18
FEATURE               Location/Qualifiers
source                1..18
                      mol_type = unassigned DNA
                      organism = Zea mays SEQUENCE: 515
aagcgattca aaccacaa                                                   18

SEQ ID NO: 516        moltype = DNA   length = 17
FEATURE               Location/Qualifiers
source                1..17
                      mol_type = unassigned DNA
                      organism = Zea mays SEQUENCE: 516
tgcgtaatta attaaac                                                    17

SEQ ID NO: 517        moltype = DNA   length = 18
FEATURE               Location/Qualifiers
source                1..18
                      mol_type = unassigned DNA
                      organism = Zea mays SEQUENCE: 517
tgctttaaat taaaaaat                                                   18

SEQ ID NO: 518        moltype = DNA   length = 19
FEATURE               Location/Qualifiers
source                1..19
                      mol_type = unassigned DNA
                      organism = Zea mays SEQUENCE: 518
tgtgcatatt tgatgttag                                                  19

SEQ ID NO: 519        moltype = DNA   length = 15
FEATURE               Location/Qualifiers
source                1..15
                      mol_type = unassigned DNA
                      organism = Zea mays SEQUENCE: 519
atggcacatt gatca                                                      15

SEQ ID NO: 520        moltype = DNA   length = 15
FEATURE               Location/Qualifiers
source                1..15
                      mol_type = unassigned DNA
                      organism = Zea mays
```

```
SEQUENCE: 520
acagtgcaag aacaa                                                    15

SEQ ID NO: 521         moltype = DNA  length = 14
FEATURE                Location/Qualifiers
source                 1..14
                       mol_type = unassigned DNA
                       organism = Zea mays
SEQUENCE: 521
aggagccccg ggag                                                     14

SEQ ID NO: 522         moltype = DNA  length = 13
FEATURE                Location/Qualifiers
source                 1..13
                       mol_type = unassigned DNA
                       organism = Zea mays
SEQUENCE: 522
ccttgccagc aaa                                                      13

SEQ ID NO: 523         moltype = DNA  length = 18
FEATURE                Location/Qualifiers
source                 1..18
                       mol_type = unassigned DNA
                       organism = Zea mays
SEQUENCE: 523
caatatacag gtaatctg                                                 18

SEQ ID NO: 524         moltype = DNA  length = 17
FEATURE                Location/Qualifiers
source                 1..17
                       mol_type = unassigned DNA
                       organism = Zea mays
SEQUENCE: 524
ccgttcttgt taaccag                                                  17

SEQ ID NO: 525         moltype = DNA  length = 13
FEATURE                Location/Qualifiers
source                 1..13
                       mol_type = unassigned DNA
                       organism = Zea mays
SEQUENCE: 525
catccccaag ctt                                                      13

SEQ ID NO: 526         moltype = DNA  length = 17
FEATURE                Location/Qualifiers
source                 1..17
                       mol_type = unassigned DNA
                       organism = Zea mays
SEQUENCE: 526
aaacaaggta actttca                                                  17

SEQ ID NO: 527         moltype = DNA  length = 16
FEATURE                Location/Qualifiers
source                 1..16
                       mol_type = unassigned DNA
                       organism = Zea mays
SEQUENCE: 527
ctactatcga gattgc                                                   16

SEQ ID NO: 528         moltype = DNA  length = 18
FEATURE                Location/Qualifiers
source                 1..18
                       mol_type = unassigned DNA
                       organism = Zea mays
SEQUENCE: 528
cactgtacgc ttcgatgt                                                 18

SEQ ID NO: 529         moltype = DNA  length = 19
FEATURE                Location/Qualifiers
source                 1..19
                       mol_type = unassigned DNA
                       organism = Zea mays
SEQUENCE: 529
cttaggatca tcctttcct                                                19

SEQ ID NO: 530         moltype = DNA  length = 15
FEATURE                Location/Qualifiers
source                 1..15
                       mol_type = unassigned DNA
```

```
                                organism = Zea mays
SEQUENCE: 530
ctctgaccat gaaac                                                          15

SEQ ID NO: 531                  moltype = DNA  length = 16
FEATURE                         Location/Qualifiers
source                          1..16
                                mol_type = unassigned DNA
                                organism = Zea mays
SEQUENCE: 531
ctgctctatc atcgac                                                         16

SEQ ID NO: 532                  moltype = DNA  length = 17
FEATURE                         Location/Qualifiers
source                          1..17
                                mol_type = unassigned DNA
                                organism = Zea mays
SEQUENCE: 532
tttgcatttg gtactcg                                                        17

SEQ ID NO: 533                  moltype = DNA  length = 15
FEATURE                         Location/Qualifiers
source                          1..15
                                mol_type = unassigned DNA
                                organism = Zea mays
SEQUENCE: 533
accaacaatc aatgc                                                          15

SEQ ID NO: 534                  moltype = DNA  length = 15
FEATURE                         Location/Qualifiers
source                          1..15
                                mol_type = unassigned DNA
                                organism = Zea mays
SEQUENCE: 534
aaatgcggac tccag                                                          15

SEQ ID NO: 535                  moltype = DNA  length = 14
FEATURE                         Location/Qualifiers
source                          1..14
                                mol_type = unassigned DNA
                                organism = Zea mays
SEQUENCE: 535
agctcgacaa cgat                                                           14

SEQ ID NO: 536                  moltype = DNA  length = 16
FEATURE                         Location/Qualifiers
source                          1..16
                                mol_type = unassigned DNA
                                organism = Zea mays
SEQUENCE: 536
accagactaa accttt                                                         16

SEQ ID NO: 537                  moltype = DNA  length = 16
FEATURE                         Location/Qualifiers
source                          1..16
                                mol_type = unassigned DNA
                                organism = Zea mays
SEQUENCE: 537
catctccatg tgcctc                                                         16

SEQ ID NO: 538                  moltype = DNA  length = 14
FEATURE                         Location/Qualifiers
source                          1..14
                                mol_type = unassigned DNA
                                organism = Zea mays
SEQUENCE: 538
tgtgcctcct tggc                                                           14

SEQ ID NO: 539                  moltype = DNA  length = 16
FEATURE                         Location/Qualifiers
source                          1..16
                                mol_type = unassigned DNA
                                organism = Zea mays
SEQUENCE: 539
cttcatgtgc caactt                                                         16

SEQ ID NO: 540                  moltype = DNA  length = 16
FEATURE                         Location/Qualifiers
source                          1..16
```

```
                        mol_type = unassigned DNA
                        organism = Zea mays
SEQUENCE: 540
cagacaaatg atttca                                                   16

SEQ ID NO: 541          moltype = DNA  length = 16
FEATURE                 Location/Qualifiers
source                  1..16
                        mol_type = unassigned DNA
                        organism = Zea mays
SEQUENCE: 541
cttcatgtgc caactt                                                   16

SEQ ID NO: 542          moltype = DNA  length = 15
FEATURE                 Location/Qualifiers
source                  1..15
                        mol_type = unassigned DNA
                        organism = Zea mays
SEQUENCE: 542
acggagtgtc attct                                                    15

SEQ ID NO: 543          moltype = DNA  length = 16
FEATURE                 Location/Qualifiers
source                  1..16
                        mol_type = unassigned DNA
                        organism = Zea mays
SEQUENCE: 543
aaggtttgcg tactct                                                   16

SEQ ID NO: 544          moltype = DNA  length = 14
FEATURE                 Location/Qualifiers
source                  1..14
                        mol_type = unassigned DNA
                        organism = Zea mays
SEQUENCE: 544
cccactaaga aaac                                                     14

SEQ ID NO: 545          moltype = DNA  length = 19
FEATURE                 Location/Qualifiers
source                  1..19
                        mol_type = unassigned DNA
                        organism = Zea mays
SEQUENCE: 545
catatttagc gcttcatca                                                19

SEQ ID NO: 546          moltype = DNA  length = 15
FEATURE                 Location/Qualifiers
source                  1..15
                        mol_type = unassigned DNA
                        organism = Zea mays
SEQUENCE: 546
ttgttcccca ttaat                                                    15

SEQ ID NO: 547          moltype = DNA  length = 15
FEATURE                 Location/Qualifiers
source                  1..15
                        mol_type = unassigned DNA
                        organism = Zea mays
SEQUENCE: 547
ttgttgcaaa ggaag                                                    15

SEQ ID NO: 548          moltype = DNA  length = 15
FEATURE                 Location/Qualifiers
source                  1..15
                        mol_type = unassigned DNA
                        organism = Zea mays
SEQUENCE: 548
ctttgagcag ctagc                                                    15

SEQ ID NO: 549          moltype = DNA  length = 14
FEATURE                 Location/Qualifiers
source                  1..14
                        mol_type = unassigned DNA
                        organism = Zea mays
SEQUENCE: 549
tgacgggatc gact                                                     14

SEQ ID NO: 550          moltype = DNA  length = 14
FEATURE                 Location/Qualifiers
```

```
source                          1..14
                                mol_type = unassigned DNA
                                organism = Zea mays
SEQUENCE: 550
agcacactgg tttc                                                              14

SEQ ID NO: 551                  moltype = DNA  length = 13
FEATURE                         Location/Qualifiers
source                          1..13
                                mol_type = unassigned DNA
                                organism = Zea mays
SEQUENCE: 551
tcggtcggca aac                                                               13

SEQ ID NO: 552                  moltype = DNA  length = 15
FEATURE                         Location/Qualifiers
source                          1..15
                                mol_type = unassigned DNA
                                organism = Zea mays
SEQUENCE: 552
aacacgcgac ttagt                                                             15

SEQ ID NO: 553                  moltype = DNA  length = 15
FEATURE                         Location/Qualifiers
source                          1..15
                                mol_type = unassigned DNA
                                organism = Zea mays
SEQUENCE: 553
agctgaggtg aacct                                                             15

SEQ ID NO: 554                  moltype = DNA  length = 18
FEATURE                         Location/Qualifiers
source                          1..18
                                mol_type = unassigned DNA
                                organism = Zea mays
SEQUENCE: 554
atacatctaa caacttca                                                          18

SEQ ID NO: 555                  moltype = DNA  length = 17
FEATURE                         Location/Qualifiers
source                          1..17
                                mol_type = unassigned DNA
                                organism = Zea mays
SEQUENCE: 555
tatgtgcatc gacgatg                                                           17

SEQ ID NO: 556                  moltype = DNA  length = 13
FEATURE                         Location/Qualifiers
source                          1..13
                                mol_type = unassigned DNA
                                organism = Zea mays
SEQUENCE: 556
tgcagcagac ctg                                                               13

SEQ ID NO: 557                  moltype = DNA  length = 15
FEATURE                         Location/Qualifiers
source                          1..15
                                mol_type = unassigned DNA
                                organism = Zea mays
SEQUENCE: 557
ttactccagc atcgc                                                             15

SEQ ID NO: 558                  moltype = DNA  length = 13
FEATURE                         Location/Qualifiers
source                          1..13
                                mol_type = unassigned DNA
                                organism = Zea mays
SEQUENCE: 558
cgaacgcgaa gct                                                               13

SEQ ID NO: 559                  moltype = DNA  length = 15
FEATURE                         Location/Qualifiers
source                          1..15
                                mol_type = unassigned DNA
                                organism = Zea mays
SEQUENCE: 559
cttttcacat cctcc                                                             15

SEQ ID NO: 560                  moltype = DNA  length = 14
```

```
FEATURE                 Location/Qualifiers
source                  1..14
                        mol_type = unassigned DNA
                        organism = Zea mays SEQUENCE: 560
caagagagaa tttc                                                         14

SEQ ID NO: 561          moltype = DNA  length = 15
FEATURE                 Location/Qualifiers
source                  1..15
                        mol_type = unassigned DNA
                        organism = Zea mays SEQUENCE: 561
acagagggtt tggtg                                                        15

SEQ ID NO: 562          moltype = DNA  length = 16
FEATURE                 Location/Qualifiers
source                  1..16
                        mol_type = unassigned DNA
                        organism = Zea mays SEQUENCE: 562
cgaccattca acatat                                                       16

SEQ ID NO: 563          moltype = DNA  length = 15
FEATURE                 Location/Qualifiers
source                  1..15
                        mol_type = unassigned DNA
                        organism = Zea mays SEQUENCE: 563
cctctaggat aagcg                                                        15

SEQ ID NO: 564          moltype = DNA  length = 18
FEATURE                 Location/Qualifiers
source                  1..18
                        mol_type = unassigned DNA
                        organism = Zea mays SEQUENCE: 564
atcggtaaag acgaagaa                                                     18

SEQ ID NO: 565          moltype = DNA  length = 19
FEATURE                 Location/Qualifiers
source                  1..19
                        mol_type = unassigned DNA
                        organism = Zea mays SEQUENCE: 565
agttgacaat atcgcctac                                                    19

SEQ ID NO: 566          moltype = DNA  length = 16
FEATURE                 Location/Qualifiers
source                  1..16
                        mol_type = unassigned DNA
                        organism = Zea mays SEQUENCE: 566
tcgagaatgg agtttg                                                       16

SEQ ID NO: 567          moltype = DNA  length = 14
FEATURE                 Location/Qualifiers
source                  1..14
                        mol_type = unassigned DNA
                        organism = Zea mays SEQUENCE: 567
tgctcctgtt tctg                                                         14

SEQ ID NO: 568          moltype = DNA  length = 13
FEATURE                 Location/Qualifiers
source                  1..13
                        mol_type = unassigned DNA
                        organism = Zea mays SEQUENCE: 568
tgggcttggc ctt                                                          13

SEQ ID NO: 569          moltype = DNA  length = 13
FEATURE                 Location/Qualifiers
source                  1..13
                        mol_type = unassigned DNA
                        organism = Zea mays SEQUENCE: 569
tgcaaagttt ccc                                                          13
```

```
SEQ ID NO: 570         moltype = DNA   length = 13
FEATURE                Location/Qualifiers
source                 1..13
                       mol_type = unassigned DNA
                       organism = Zea mays
SEQUENCE: 570
ttcgcgccaa acc                                                              13
```